US012397061B2

(12) United States Patent
Stamps et al.

(10) Patent No.: US 12,397,061 B2
(45) Date of Patent: Aug. 26, 2025

(54) SYSTEMS, METHODS, AND COMPOSITIONS FOR THE GENERATION OF WATER-SOLUBLE CANNABINOIDS UTILIZING FATTY-ACID BINDING PROTEINS AND FATTY-ACID BINDING-LIKE PROTEINS AS CANNABINOID-CARRIERS

(71) Applicant: Trait Biosciences, Inc., Los Alamos, NM (US)

(72) Inventors: Jennifer Stamps, Los Alamos, NM (US); Elton Carvalho Goncalves, Los Alamos, NM (US); Richard T. Sayre, Los Alamos, NM (US); Tawanda Zidenga, White Rock, NM (US); Erick Scott LeBrun, White Rock, NM (US); Timothy Travers, Los Alamos, NM (US)

(73) Assignee: Trait Biosciences, Inc., Los Alamos, NM (US)

( * ) Notice: Subject to any disclaimer, the term of this patent is extended or adjusted under 35 U.S.C. 154(b) by 997 days.

(21) Appl. No.: 17/428,537

(22) PCT Filed: Feb. 4, 2020

(86) PCT No.: PCT/US2020/016642
§ 371 (c)(1),
(2) Date: Aug. 4, 2021

(87) PCT Pub. No.: WO2020/163378
PCT Pub. Date: Aug. 13, 2020

(65) Prior Publication Data
US 2022/0152212 A1    May 19, 2022

Related U.S. Application Data

(60) Provisional application No. 62/800,692, filed on Feb. 4, 2019.

(51) Int. Cl.
| | |
|---|---|
| *A61K 47/64* | (2017.01) |
| *A61K 31/00* | (2006.01) |
| *A61K 31/05* | (2006.01) |
| *A61K 31/352* | (2006.01) |
| *C07K 14/415* | (2006.01) |
| *C07K 14/435* | (2006.01) |
| *C12N 15/62* | (2006.01) |

(52) U.S. Cl.
CPC ............ *A61K 47/64* (2017.08); *A61K 31/05* (2013.01); *A61K 31/352* (2013.01); *A61K 31/658* (2023.05); *C07K 14/415* (2013.01); *C07K 14/435* (2013.01); *C12N 15/62* (2013.01); *C07K 2319/036* (2013.01)

(58) Field of Classification Search
CPC ...... A61K 47/64; A61K 31/05; A61K 31/352; A61K 31/658; C07K 14/415; C07K 14/435; C07K 2319/036; C12N 15/62; C12P 7/22; C12P 7/42; C12P 21/02; C12P 17/06; C07D 311/80
See application file for complete search history.

(56) References Cited

U.S. PATENT DOCUMENTS

2009/0123377 A1    5/2009  Jacob et al.

FOREIGN PATENT DOCUMENTS

| WO | 03/025579 A2 | 3/2003 |
| WO | 2019014395 A1 | 1/2019 |

OTHER PUBLICATIONS

Whisstock et al. Quaterly Reviews of Biophysics, 2003, "Prediction of protein function from protein sequence and structure", 36(3): 307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
Martin et al. Human Liver Fatty Acid Binding Protein (L-FABP) T94A Variant Alters Structure, Stability, and Interaction With Fibrates. Biochemistry. Dec. 23, 2013; 52(51): 9347-93570. (Year: 2013).*
Elmes et al. "Fatty acid-binding proteins (FABPS) are intracellular carriers for .delta.9-tetrahydrocannabinol (THC) and cannabidiol (CBD)" J Biol Chem, vol. 290, No. 14, pp. 8711-8721, Apr. 3, 2015; abstract, p. 8713, col. 2, para 2, p. 8713, col. 2, para 4.
Ringom et al. "Substituted benzylamino-6-(triHuoromethyl)pyrimidin-4(1H)-ones: a novel class of selective human A-FABP inhibitors" Bioorganic & Medicinal Chemistry Letters. Sep. 6, 2004, vol. 14, No. 17, pp. 4449-4452; abstract, p. 4449, col. 2, para 2 to p. 4450, col. 1, para 1.
International Search Report and Written Opinion dated Jun. 26, 2020 in PCT/US2020/016642, 18 pages.
Huan Huang et al: "FABP1: A Novel Hepatic Endocannabinoid and Cannabinoid Binding Protein", Biochemistry, vol. 55, No. 37, Sep. 2, 2016 (Sep. 2, 2016), pp. 5243-5255, XP055658406, ISSN: 0006-2960, DOI: 10.1021 /acs.biochem.6b00446.

(Continued)

*Primary Examiner* — Iqbal H Chowdhury
(74) *Attorney, Agent, or Firm* — Berg Hill Greenleaf Ruscitti LLP

(57) ABSTRACT

The inventive technology includes novel systems, methods, and compositions for the generation of water-soluble short-chain fatty acid phenolic compounds, preferably cannabinoids, terpenes, and other volatile compounds produced in *Cannabis* and other cannabinoid producing plants. In particular, the inventive technology includes novel systems and methods to solubilize short-chain fatty acid phenolic compounds, such as cannabinoids, via binding to a water soluble and readily digested carrier protein.

10 Claims, 16 Drawing Sheets

Specification includes a Sequence Listing.

(56) References Cited

OTHER PUBLICATIONS

Deutsch Dale G: "A Personal Retrospective: Elevating Anandamide (AEA) by Targeting Fatty Acid Amide Hydrolase (FAAH) and the Fatty Acid Binding Proteins (FABPs)", Frontiers in Pharmacology, vol. 7, Oct. 13, 2016 (Oct. 13, 2016), XP055980130, DOI: 10.3389/fphar.2016.00370.
Supplemental European Search Report dated Nov. 22, 2022 in EP patent application No. 20753033.8, 7 pages.

\* cited by examiner

SYSTEMS, METHODS, AND COMPOSITIONS FOR THE GENERATION OF WATER-SOLUBLE CANNABINOIDS UTILIZING FATTY-ACID BINDING PROTEINS AND FATTY-ACID BINDING-LIKE PROTEINS AS CANNABINOID-CARRIERS

CROSS REFERENCE TO RELATED APPLICATION

This application is a national stage application under 35 U.S.C. 371 of PCT Application No. PCT/US20/16642 having an international filing date of Feb. 4, 2020, which designated the United States, which PCT application claimed the benefit of U.S. Application Ser. No. 62/800,692, filed Feb. 4, 2019, both of which are incorporated by reference in their entirety.

SEQUENCE LISTING

The instant application contains a Sequence Listing which has been submitted electronically in ASCII format and is hereby incorporated by reference in its entirety. Said ASCII copy, created on Aug. 4, 2021, is named 90425-00162-Sequence-Listing-AF.txt, and is 213 Kbytes in size.

This International PCT Application claims the benefit of and priority to U.S. Provisional Application No. 62/800,692 filed Feb. 4, 2019. The entire specification and figures of the above-referenced application is hereby incorporated, in its entirety by reference.

TECHNICAL FIELD

The inventive technology includes novel systems, methods, and compositions for the generation of water-soluble short-chain fatty acid phenolic compounds, preferably cannabinoids, terpenes, and other volatile compounds produced in *Cannabis* and other cannabinoid producing plants. In particular, the inventive technology includes novel systems and methods to solubilize short-chain fatty acid phenolic compounds, such as cannabinoids, via binding to a water soluble and readily digested carrier protein.

BACKGROUND OF THE INVENTION

Cannabinoids are a class of specialized compounds synthesized by *Cannabis*. They are formed by condensation of terpene and phenol precursors. They include these more abundant forms: $\Delta^9$-tetrahydrocannabinol (THC), cannabidiol (CBD), cannabichromene (CBC), and cannabigerol (CBG). Another cannabinoid, cannabinol (CBN), is formed from THC as a degradation product and can be detected in some plant strains. Typically, THC, CBD, CBC, and CBG occur together in different ratios in the various plant strains. These cannabinoids are generally lipophilic, nitrogen-free, mostly phenolic compounds and are derived biogenetically from a monoterpene and phenol, the acid cannabinoids from a monoterpene and phenol carboxylic acid, and have a C21 base. Cannabinoids also find their corresponding carboxylic acids in plant products. In general, the carboxylic acids have the function of a biosynthetic precursor. For example, these compounds arise in vivo from the THC carboxylic acids by decarboxylation the tetrahydrocannabinols $\Delta^9$- and $\Delta^8$-THC and CBD from the associated cannabidiol.

Importantly, cannabinoids are hydrophobic small molecules and, as a result, are highly insoluble. Due to this insolubility, cannabinoids such as THC and CBD may need to be efficiently solubilized to facilitate transport, storage, and adsorption through certain tissues and organs. As described in, U.S. Pat. No. 8,410,064 by Pandya et al., cannabinoids may be subject to cytochrome P450 oxidation and subsequent UDP-glucuronosyltransferase (UGT)-dependent glucuronidation in the body after consumption. The resulting glucuronide of the oxidized cannabinoid is the main metabolite found in urine, and thus, this solubilization process plays a critical role in the metabolic clearance of cannabinoids. In another embodiments outlined in PCT/US18/24409 and PCT/US18/41710 (both of which are incorporated herein in their entirety by reference), by Sayre et al., cannabinoids may be glycosylated in vivo to form water-soluble glycoside and acetylated cannabinoid glycoside compounds.

As outlined below, cannabinoids may be solubilized by binding to certain carrier proteins. For example, cannabinoids, and other short-chain fatty acid phenolic compounds, may be transported in biological fluids (such as blood) and tissues (including the intracellular milieu) by these so-called carrier proteins. Generally, the binding to these carrier proteins molecules effectively increases the water-solubility of fatty acids and other lipophilic molecules, thereby facilitating their transport through aqueous environments as well as their transfer across cellular membranes. Human and homologous non-human carrier proteins may offer an opportunity for use in the solubilization of cannabinoids among other compounds. One area where water-soluble cannabinoids has seen renewed interest is in the fields of cannabinoid-infused consumer products. However, the ability to effectively solubilize cannabinoids has limited their applicability. To overcome these limitations, many manufacturers of cannabinoid-infused products have adopted the use of traditional pharmaceutical delivery methods of using nanoemulsions of cannabinoids. This nanoemulsion process essentially coats the cannabinoid in a hydrophilic compound, such as oil or other similar compositions. However, the use of nanoemulsions is limited both technically, and from a safety perspective.

First, a large number of surfactants and cosurfactants are required for nanoemulsion stabilization. Moreover, the stability of nanoemulsions is inherently unstable, and may be disturbed by slight fluctuations in temperature and pH, and is further subject to the "oswald ripening effect" or ORE. ORE describes the process whereby molecules on the surface of particles are more energetically unstable than those within. Therefore, the unstable surface molecules often go into solution shrinking the particle over time and increasing the number of free molecules in solution. When the solution is supersaturated with the molecules of the shrinking particles, those free molecules will redeposit on the larger particles. Thus, small particles decrease in size until they disappear and large particles grow even larger. This shrinking and growing of particles will result in a larger mean diameter of a particle size distribution (PSD). Over time, this causes emulsion instability and eventually phase separation.

Second, nanoemulsions may not be safe for human consumption. For example, nanoemulsions were first developed as a method to deliver small quantities of pharmaceutical compounds having poor solubility. However, the ability to "hide" a compound, such as a cannabinoid, in a nanoemulsion may allow the cannabinoid to be delivered to parts of the body were it was previously prevented from entering, as well as accumulating in tissues and organs where cannabinoids and nanoparticles would not typically be found. Additionally, such nanoemulsions, as well as other water-compatible strategies, do not address one of the major-shortcomings of cannabinoid-infused commercial consumables, namely the strong unpleasant smell and taste. Moreover, such water-compatible strategies deliver inconsistent and delayed cannabinoid uptake in the body which may result in user's ingesting a larger that recommended amount of cannabinoid-infused product, as well as delayed and inconsistent medical and/or psychotropic experiences.

As a result, there is a need for more effective strategies to both solubilize cannabinoids, and other associated compounds, such as terpenes and the like, in a way that is both cost-effective, as well as safe to consumers. In one aspect of the invention, members of the Fatty Acid-Binding Protein (FABP) family may be used in novel systems, methods, and compositions to solubilize cannabinoids and other associated compounds. FABPs generally act as intracellular lipid chaperones and help coordinate lipid responses in cells and are also strongly linked to metabolic and inflammatory pathways. FABPs are abundantly expressed 14-15 kDa proteins that reversibly bind hydrophobic ligands, such as saturated and unsaturated long-chain fatty acids, eicosanoids and other lipids, with high affinity. FABPs are found across species, from *Drosophila melanogaster* and *Caenorhabditis elegans* to mice and humans, demonstrating strong evolutionary conservation. However, little is known about their exact biological functions and mechanisms of action. Studies in cultured cells have suggested potential action of FABPs in fatty-acid import, storage and export as well as cholesterol and phospholipid metabolism. FABPs have also been proposed to sequester and/or distribute ligands to regulate signaling processes and enzyme activities. As will be discussed in more detail below, the current inventive technology overcomes the limitations of traditional cannabinoid emulsion systems while meeting the objectives of a truly effective and scalable cannabinoid production, solubilization, and isolation system.

SUMMARY OF THE INVENTION

Generally, the inventive technology relates to systems, methods and compositions to solubilize short-chain fatty acid phenolic compounds, such as cannabinoids, terpenes and other volatile compounds found in cannabinoid-producing plants such as *Cannabis*. In one aspect, human and homologous non-human FABP proteins, sometimes referred to herein as a carrier, or carrier-proteins, may be used to bind to, and solubilization of one or more cannabinoid compounds. In addition aspects, chimeric FABP proteins may be used to bind to, and solubilization of one or more cannabinoid compounds. In another aspect, rationally engineered FABP proteins having one or more directed mutations may exhibit enhanced binding and solubilization of one or more cannabinoid compounds.

Another aspect of the current invention may include novel methods and compositions for increasing the water solubility of one or more cannabinoid compounds via binding to a select FABP. In this embodiment, FABPs may be utilized to solubilize, transport, and store cannabinoid compounds in in vitro, ex vivo, and in vivo systems. In specific preferred aspects, non-human homologs of FABPs, such as plant FABPs, or engineered FABP may be utilized to solubilize, transport, and store, for example, THC, CBD, and other cannabinoids, terpenoids, and volatile compounds produced in *Cannabis* and other cannabinoid producing plants, or even synthetically generated cannabinoids.

Another aspect of the current invention includes novel methods and compositions for increasing the water solubility of one or more cannabinoid compounds via binding to a select chimeric or genetically modified, sometimes referred to as an engineered, FABP. In this aspect, a novel chimeric FABP construct may be rationally designed from homologs of human FABP to allow for enhanced binding of cannabinoid molecules to a single protein chain. In one specific aspect, a novel chimeric FABP construct may be rationally designed from non-human homologs of FABP to allow for enhanced binding of THC, CBD, or other cannabinoid molecules to a single protein chain. In another aspect, one or more FABPs may be subjected to directed evolutionary process, preferably via in silico random mutagenesis, to identify one or more mutations that may increase the binding affinity, and solubility, of one or more target cannabinoids.

Another aspect of the current invention may include the decrease of aggregation propensity and potential antigenicity for the FABP-carrier proteins that may be specific for short-chain fatty acid phenolic compounds, such as cannabinoids. In this embodiment, mutations on the surface of a carrier protein may be rationally designed to reduce aggregate formation in solution and to reduce any elicited antigenic reactions.

Another aspect of the current invention may include the decrease of aggregation propensity and potential antigenicity for a novel wild-type, or engineered FABP-carrier protein, as discussed below, that may be specific for short-chain fatty acid phenolic compounds, such as cannabinoids. In this embodiment, mutations on the surface of a carrier protein may be rationally designed to reduce aggregate formation in solution and to reduce any elicited antigenic reactions.

Another aspect of the current invention may include systems, methods, and compositions for the solubilization of cannabinoids, terpenoids and other short-chain fatty acid phenolic compounds in cell cultures that express one or more FABP-carrier, or engineered FABP proteins. Exemplary cell cultures may include bacterial, yeast, plant, algae and fungi cell cultures. In another aspect, FABP-carrier, or engineered FABP proteins, may be coupled with secretion signals to allow such proteins to be more easily exported from the cell culture into the surrounding supernatant or media. In this aspect of the invention, a FABP-carrier protein, the terms generally encompassing FABP carrier proteins, or engineered FABP proteins that bind to one or more target compounds, and preferably, cannabinoids, may be exported out of a cell through the action of the secretion signal that may direct posttranslational protein translocation into the endoplasmic reticulum (ER), or in alternative embodiments, a secretion signal that may direct cotranslational translocation across the ER membrane where it may assume its three-dimensional form and bind one or more cannabinoid or other compounds as described herein. In one preferred embodiment, a FABP-carrier protein may be generated in a cell culture, preferably a bacterial, yeast, plant or fungi cell culture, and then be exported out of the cell through natural cellular action, or through the action of the secretion signal where it may assume its three dimensional form and bind one or more cannabinoid or other compounds that may be present, preferably by addition of said compound, such as: a quantity of an isolated cannabinoid; a quantity of a plurality of cannabinoids; or *Cannabis* extract, to the culture's supernatant.

In another aspect of the invention, a FABP-carrier protein may be exported out of a cell through the action of the secretion signal after it has assumed a transitory and or final three dimensional form and may further be bound to one or more cannabinoid or other compounds as described herein. In one preferred embodiment, a FABP-carrier protein may be generated in a cell culture, preferably a bacterial, yeast, plant or fungi cell culture, and more preferably a plant suspension culture of a cannabinoid-producing plant such as *Cannabis*, where it may assume a transitory or final three dimensional form and bind one or more cannabinoids or other compounds that may be present or produced in the cell.

Another aspect of the current invention may include systems, methods and compositions for the solubilization of cannabinoids, terpenoids and other short-chain fatty acid phenolic compounds in whole plants and plant cell cultures. In certain embodiments, such plants or cell cultures may be genetically modified to direct cannabinoid synthesis to the cytosol, as opposed to a trichome structure. One or more FABP-carrier proteins may be coupled with a secretion signal, preferable in a plant cell culture, to allow such proteins to be exported from the cell into the surrounding media. Expression of exportable and non-exportable FABP-carrier proteins may be co-expressed with one or more catalase and/or one or more myb transcription factors which may enhance cannabinoid production in a *Cannabis* plant or cell culture.

Another aspect of the current invention may include systems, methods and compositions for the coupled glycosylation and solubilization of cannabinoids, terpenoids and other short-chain fatty acid phenolic compounds in whole cannabinoid-producing plants or cell cultures, preferably a *Cannabis* plant or cell culture. In this embodiment, such *Cannabis* plants or cell cultures may be genetically modified to direct cannabinoid synthesis to the cytosol, as opposed to a trichome structure as generally outlines by the current inventors, Sayre et al. in U.S. Pat. No. 10,378,020, the disclosure of such processes being fully incorporated herein by reference. Such *Cannabis* plant, or *Cannabis* cell culture may be further genetically modified to express one or more heterologous glycosyltransferases having glycosylation activity towards at least one cannabinoid (for example SEQ ID NOs. 32-47, and SEQ ID NOs. 61-62) In additional embodiments, a plant or cell may be further genetically modified to express one or more heterologous glycosyltransferases, wherein in said polynucleotides encoding such glycosyltransferases may be codon-optimized for expression in an exogenous system, such as in yeast (for example SEQ ID NOs. 49-60). In additional embodiments, a heterologous or exogenous, being generally the same term, cytochrome P450 and/or a P450 oxidoreductase may be expressed. In this configuration a heterologous cytochrome P450 (for example SEQ ID NOs. 22-23, and SEQ ID NOs. 26-27) may hydroxylate a cannabinoid to form a hydroxylated cannabinoid and/or oxidize a hydroxylated cannabinoid to form a cannabinoid carboxylic acid. Further, in this embodiment, a heterologous P450 oxidoreductase (for example SEQ ID NOs. 24-25, and SEQ ID NOs. 28-29) may facilitate electron transfer from a nicotinamide adenine dinucleotide phosphate (NADPH) to said cytochrome P450.

As noted above, a heterologous glycosyltransferase may glycosylate a cannabinoid compound and thereby produce a water-soluble cannabinoid glycoside. This glycosylated cannabinoid may bind to a heterologous FABP-carrier also expressed in the *Cannabis* plant or cell that may be coupled with a secretion signal, to allow the carrier proteins to be exported from the cell into the surrounding media. Expression of exportable and non-exportable FABP-carriers may be co-expressed with one or more catalase and/or one or more myb transcription factors. The glycosylated cannabinoids bound to the FABP-carrier, being further coupled with a tag in some embodiments, may be isolated, while in still further embodiments, the FABP-carrier protein may be disrupted by a protease, or other protein disrupting detergent and the like, such that the glycosylated cannabinoid may be released from the FABP-carrier and may be further isolated or reconstituted to their original forms through the action of a glycosidase that may remove the sugar moiety.

Another aspect of the current invention may include systems, methods, and compositions for the coupled glycosylation and solubilization of cannabinoids, terpenoids and other short-chain fatty acid phenolic compounds in non-cannabinoid-producing plants and cell cultures, preferably a tobacco cell culture. In this embodiment, a tobacco cell culture may endogenously express one or more glycosyltransferases having glycosylation activity towards at least one cannabinoid. The tobacco cell culture may optionally be genetically modified to express a heterologous cytochrome P450, and a P450 oxidoreductase. In this configuration a heterologous cytochrome P450 may hydroxylate a cannabinoid added to a tobacco cell culture for example, to form a hydroxylated cannabinoid and/or oxidizes a hydroxylated cannabinoid to form a cannabinoid carboxylic acid. Further, in this embodiment, a heterologous P450 oxidoreductase may facilitate electron transfer from a nicotinamide adenine dinucleotide phosphate (NADPH) to said cytochrome P450. As noted above, the endogenously expressed heterologous glycosyltransferases (fore example, NtGT1, 2, 3, 4 or 5 as identified below) may glycosylate one or more cannabinoids introduced to the tobacco cell culture converting it into a water-soluble cannabinoid-glycoside. This glycosylated cannabinoid may bind to a heterologous FABP-carrier co-expressed or added to the tobacco cell culture. In this aspect, an expression of an exportable FABP-carrier may be co-expressed with one or more catalase and/or one or more myb transcription factors. The glycosylated cannabinoids bound to the FABP-carrier, being further coupled with a tag in some embodiments, may be isolated, while in still further embodiments, the carrier protein may be disrupted by a protease or other protein disrupting detergent and the like such that the glycosylated cannabinoids may be released from the carrier protein and may be further isolated or reconstituted to their original forms through the action of a glycosidase.

Another aspect of the current invention may include systems, methods and compositions for the coupled glycosylation and solubilization of cannabinoids, terpenoids and other short-chain fatty acid phenolic compounds in a cell cultures, preferably a yeast cell culture. In these embodiments, yeast cultures may be genetically modified to biosynthesize one or more cannabinoids. The yeast cell culture may be further genetically modified to express one or more heterologous glycosyltransferases having glycosylation activity towards at least one cannabinoid, as well as in some embodiments, a heterologous cytochrome P450 and/or a P450 oxidoreductase.

As noted above, heterologous glycosyltransferases may glycosylate the cannabinoid making it water-soluble. This glycosylated cannabinoid may bind to a heterologous FABP-carrier protein also expressed in the yeast culture which may further be coupled with a secretion signal, to allow the carrier proteins to be exported from the yeast cell into the surrounding media. Expression of exportable and non-exportable FABP-carrier may be co-expressed with a catalase. The glycosylated cannabinoids bound to the FABP-carrier being further coupled with a tag in some embodiments, may be isolated, while in still further embodiments, the carrier protein may be disrupted by a protease or other protein disrupting detergent and the like such that the glycosylated cannabinoids may be released from the carrier protein and may be further isolated or reconstituted to their original forms through the action of a glycosidase.

Another aspect of the current invention may include systems, methods and compositions for the coupled glycosylation and solubilization of cannabinoids, terpenoids and other short-chain fatty acid phenolic compounds in a cell cultures, preferably yeast, bacteria, fungi or algal cell culture. In these embodiments, a yeast cultures may be genetically modified to express one or more heterologous glycosyltransferases having glycosylation activity towards at least one cannabinoid, as well as in some embodiments, a heterologous cytochrome P450 and/or a P450 oxidoreductase.

As noted above, in one preferred embodiment, a quantity of cannabinoids may be added to the cell culture, and preferably a yeast cell culture, where heterologous glycosyltransferases may glycosylate the cannabinoid making it water-soluble. This glycosylated cannabinoid may bind to a heterologous FABP-carrier co-expressed in the yeast culture which may further be coupled with a secretion signal, to allow the carrier proteins to be exported from the yeast cell into the surrounding media. The glycosylated cannabinoids bound to the FABP-carrier, being further coupled with a tag in some embodiments, may be isolated, while in still further embodiments, the carrier protein may be disrupted by a protease or other protein disrupting detergent and the like such that the glycosylated cannabinoids may be released from the carrier protein and may be further isolated or reconstituted to their original forms through the action of a glycosidase.

Another aspect of the current invention may include one or more heterologous glycosyltransferases coupled with the expression of a FABP-carrier optionally having secretion signal, and in some embodiments a tag, which may be expressed in a plant, yeast or bacterial cell culture. Another aspect of the current invention may include one or more heterologous glycosyltransferases coupled with the addition of a FABP-carrier to a plant, yeast, or bacterial cell culture.

Another aspect of the current invention may include one or more endogenously expressed glycosyltransferases coupled with the expression of a FABP-carrier, and preferable an engineered FABP-carrier having secretion signal, and in some embodiments a tag, that may be expressed in a plant, yeast or bacterial cell culture. Another aspect of the current invention may include one or more endogenously expressed glycosyltransferases coupled with the addition of a FABP-carrier to a plant cell culture.

Another aspect of the current invention may include the increase of CBD water solubility for transport via binding to a FABP-carrier. In this embodiment, plant or other non-human homologs of FABPs may be utilized to solubilize, transport, and/or store CBD and closely-related cannabinoids. Another aspect of the current invention may include the increase of CBD water solubility for transport via binding to a FABP-carrier. In this aspect, a novel engineered FABP-carrier construct may be rationally designed from homologs of FABPs to allow for enhanced binding of CBD molecules to a single protein chain.

Another aspect of the current invention may include the increase of THC water solubility for transport via binding to a FABP-carrier. In this embodiment, plant or other non-human homologs of FABPs may be utilized to solubilize, transport, and/or store THC and closely-related cannabinoids. Another aspect of the current invention may include the increase of THC water solubility for transport via binding to a FABP-carrier. In this aspect, a novel engineered FABP-carrier construct may be rationally designed from homologs of FABPs to allow for enhanced binding of THC molecules to a single protein chain.

Another aspect of the inventive technology may include polynucleotides encoding one or more engineered FABP carrier proteins having enhanced cannabinoid affinity motifs. Another aspect of the inventive technology may include polynucleotides encoding one or more engineered FABP-carrier proteins being heterologously expressed in a genetically modified microorganism, such as yeast, bacteria, fungi, algae and the like.

Another aspect of the inventive technology may include genetically modified bacteria that express at least one polynucleotide encoding one or more heterologous FABP-carrier, and preferably one or more engineered FABP-carrier proteins having enhanced cannabinoid affinity motifs. Another aspect of the inventive technology may include novel engineered FABP-carrier amino acid sequences having enhanced cannabinoid affinity motifs.

Another aspect of the inventive technology provides for a method of enhancing the solubility and stability of cannabinoids, terpenoids and/or other short-chain fatty acid phenolic compounds utilizing FABP-carrier proteins. In a preferred embodiment, a nucleotide sequence encoding a FABP-carrier protein may be genetically engineered to express a rationally designed FABP-carrier protein having cannabinoid affinity or binding sites having enhanced affinity for cannabinoids such that the engineered FABP-carrier carrier protein may bind cannabinoids with a higher affinity thereby increasing the solubility and stability of the cannabinoid in a solution or other form.

Another aspect of the invention includes compositions of novel engineered FABP-carrier polynucleotides and proteins and their method or manufacture. Another aspect of the invention includes compositions of novel engineered FABP-carrier polynucleotides and proteins and their method or manufacture. Another aspect of the invention involves the identification of FABP-carrier proteins that may have endogenous cannabinoid or other affinity sites. Another aspect of the invention involves the rational design of engineered FABP-carrier proteins have enhanced cannabinoid affinity.

Another aspect of the invention includes compositions of novel consumer products that incorporate one or more solubilized cannabinoids or terpenoids bound to FABP-carrier proteins and/or engineered FABP-carrier proteins.

Additional aspects of the invention may include one or more of the following embodiments:

1. A method of solubilizing a cannabinoid comprising the steps of:
   generating a Fatty-Acid Binding Protein (FABP)-carrier protein having affinity towards at least one cannabinoid; and
   introducing said FABP-carrier protein to said at least one cannabinoid, wherein said FABP-carrier protein binds said at least one cannabinoid to form a water-soluble protein-cannabinoid composition.

2. The method of embodiment 1, wherein the FABP-carrier protein comprises a FABP-carrier protein having an amino acid sequence selected from the group of consisting of: SEQ ID NOs. 1-2, 21, and 74-86, or a homolog having affinity towards at least one cannabinoid thereof.

3. The method of embodiment 2, wherein said step of generating a FABP-carrier protein comprises the step of generating a FABP-carrier protein in a protein production system selected from the group consisting of:
   a bacterial cell culture;
   a yeast cell culture;
   a plant cell culture;

a fungi cell culture;
an algae cell culture;
a bioreactor production system;
a plant.

4. The method of embodiment 3, wherein the FABP-carrier protein is coupled with a secretion signal.

5. The method of embodiment 4, wherein said secretion signal comprises a secretion signal selected from the group consisting of: SEQ ID NO. 3, SEQ ID NO. 65, SEQ ID NOs. 69-73.

6. The method of embodiments 3 and 5, wherein the FABP-carrier protein is introduced to said at least one cannabinoid in said protein production system.

7. The method of embodiment 2, wherein the at least one cannabinoid comprises a cannabinoid selected from the group consisting of: cannabidiol (CBD), cannabidiolic acid (CBDA), $\Delta^9$-tetrahydrocannabinol (THC), tetrahydrocannabinolic acid (THCA), and (cannabigerolic acid) CBGA).

8. The method of embodiment 1, and further comprising the of step of genetically modifying the FABP-carrier protein form to an engineered FABP-carrier protein having enhanced affinity for at least one cannabinoid, such genetic modification comprising one or more of the following:
  replacing one or more amino acid residues of the FABP-carrier protein cannabinoid binding pocket with side chains pointing towards orientated toward the binding cavity;
  replacing one or more amino acid residues of the FABP-carrier protein cannabinoid binding pocket having a hydrophilic side chain with amino acid residues having a hydrophobic side chain; and
  replacing one or more small hydrophobic amino acid residues of the FABP-carrier protein cannabinoid binding pocket with larger hydrophobic amino acid residues.

9. The method of embodiment 8, wherein said engineered FABP-carrier protein comprises an engineered FABP-carrier protein having an amino acid sequence selected from the group of consisting of: SEQ ID NOs. 79-86.

10. A method of solubilizing a cannabinoid comprising the steps of:
  genetically modifying a Fatty-Acid Binding Protein (FABP)-carrier protein having affinity towards at least one cannabinoid to produce an engineered FABP-carrier protein having enhanced affinity towards said at least one cannabinoid;
  introducing said engineered FABP-carrier protein to at least one cannabinoid, wherein said engineered FABP-carrier protein binds said at least one cannabinoid forming a water-soluble protein-cannabinoid composition.

11. The method of embodiment 10, wherein the engineered FABP-carrier protein comprises an engineered FABP-carrier protein having an amino acid sequence selected from the group of consisting of: SEQ ID NOs. SEQ ID NOs. 79-86.

12. The method of embodiments 10 and 11, wherein said step of genetically modifying the FABP-carrier protein comprises one or more of the following:
  replacing one or more amino acid residues of the FABP-carrier protein cannabinoid binding pocket with side chains pointing towards orientated toward the binding cavity;
  replacing one or more amino acid residues of the FABP-carrier protein cannabinoid binding pocket having a hydrophilic side chain with amino acid residues having a hydrophobic side chain; and
  replacing one or more small hydrophobic amino acid residues of the FABP-carrier protein cannabinoid binding pocket with larger hydrophobic amino acid residues.

13. The method of embodiment 11, wherein the engineered FABP-carrier protein is expressed in a protein production system selected from the group consisting of:
  a bacterial cell culture;
  a yeast cell culture;
  a plant cell culture;
  a fungi cell culture;
  an algae cell culture;
  a bioreactor production system; and
  a plant.

14. The method of embodiment 13, wherein the engineered FABP-carrier protein is coupled with a secretion signal.

15. The method of embodiment 14, wherein said secretion signal is selected from the group consisting of: SEQ ID NO. 3, SEQ ID NO. 65, SEQ ID NOs. 69-73.

16. The method of embodiments 13-15, wherein the engineered FABP-carrier protein is introduced to said at least one cannabinoid in said protein production system.

17. The method of embodiments 1 and 10, wherein said water-soluble protein-cannabinoid composition undergoes lyophilisation.

18. The method of embodiment 10, and wherein said at least one cannabinoid comprises at least one cannabinoid selected from the group consisting of: cannabidiol (CBD), cannabidiolic acid (CBDA), $\Delta^9$-tetrahydrocannabinol (THC), tetrahydrocannabinolic acid (THCA), and (cannabigerolic acid) CBGA).

19. An isolated polynucleotide that encodes one or more amino acid sequences selected from the group of consisting of: SEQ ID NOs. 1-2, 21, and 74-86, or a homolog having affinity towards at least one cannabinoid thereof.

20. The polynucleotide of embodiment 19, wherein said polynucleotide is operably linked to a promotor forming an expression vector.

21. The polynucleotide of embodiment 19, wherein said polynucleotide is codon optimized for expression in a microorganism, or plant cell, and is further operably linked to a promotor forming an expression vector.

22. A genetically modified organism expressing at least one of the expression vectors of embodiments 20 and 21

23. The genetically modified organism of embodiment 22, wherein said genetically modified organism is selected from the group consisting of:
  a genetically modified bacterial cell
  a genetically modified yeast cell,
  a genetically modified plant cell,
  a genetically modified fungi cell,
  a genetically modified algae cell, and
  a genetically modified plant.

24. A method of solubilizing a cannabinoid comprising the steps of:
  establishing a cell culture of genetically modified yeast, plant, or bacteria cells that express a nucleotide sequence encoding a heterologous Fatty-Acid Binding Protein (FABP)-carrier protein operably linked to a promotor wherein said heterologous FABP-carrier protein exhibits activity towards one or more cannabinoids;
  introducing one or more cannabinoids to the genetically modified yeast or bacteria cell culture; and wherein said FABP-carrier protein binds said one or more cannabinoids to form a water-soluble protein-cannabinoid composition.

25. The method of embodiment 24, wherein the step of introducing comprises the step of introducing one or more cannabinoids to a genetically modified yeast, plant, or bacteria cell culture in a fermenter or suspension cell culture.

26. The method of embodiment 24, wherein the step of introducing comprises the step of biosynthesizing one or more cannabinoids in a genetically modified yeast or bacteria cell culture wherein said heterologous FABP-carrier protein binds said one or more biosynthesized cannabinoids to form a water-soluble protein-cannabinoid composition.

27. The method of embodiment 24, wherein said heterologous FABP-carrier protein comprises a heterologous FABP-carrier protein having an amino acid sequence selected from the group of consisting of: SEQ ID NOs. 1-2, 21, and 74-86, or a homolog having affinity towards at least one cannabinoid thereof.

28. The method of embodiments 24 and 27, wherein said heterologous FABP-carrier protein is coupled with a tag.

29. The method of embodiments 24 and 27, wherein said heterologous FABP-carrier protein is coupled with a secretion signal.

30. The method of embodiment 29, wherein said secretion signal comprises a secretion signal selected from the group consisting of: SEQ ID NO. 3, SEQ ID NO. 65, SEQ ID NOs. 69-73.

31. The method of embodiment 24, wherein the at least one cannabinoid comprises a cannabinoid selected from the group consisting of: cannabidiol (CBD), cannabidiolic acid (CBDA), $\Delta^9$-tetrahydrocannabinol (THC), tetrahydrocannabinolic acid (THCA), and (cannabigerolic acid) CBGA).

32. The method of embodiment 24, and further comprising the of step of genetically modifying the FABP-carrier protein form an engineered FABP-carrier protein having enhanced affinity for at least one cannabinoid, such genetic modification comprising one or more of the following:
replacing one or more amino acid residues of the FABP-carrier protein cannabinoid binding pocket with side chains pointing towards orientated toward the binding cavity;
replacing one or more amino acid residues of the FABP-carrier protein cannabinoid binding pocket having a hydrophilic side chain with amino acid residues having a hydrophobic side chain; and
replacing one or more small hydrophobic amino acid residues of the FABP-carrier protein cannabinoid binding pocket with larger hydrophobic amino acid residues.

33. The method of embodiment 32, wherein said engineered FABP-carrier protein comprises an engineered FABP-carrier protein having an amino acid sequence selected from the group of consisting of: SEQ ID NOs. 79-86.

34. The FABP-carrier protein of embodiments 1, 2, 10-11, 19, 24, and 27, wherein said FABP-carrier protein is further genetically modified to decrease aggregation propensity and potential antigenicity.

35. The FABP-carrier protein of embodiments 34, wherein said FABP-carrier protein comprises a FABP-carrier protein having one or more of the following mutations: V58E, V42R.

36. The water-soluble protein-cannabinoid composition of any of the embodiments above wherein said water-soluble protein-cannabinoid composition is introduced to a consumer product meant for human-consumption, or a pharmaceutical composition for administration of a therapeutically effective dose to a subject in need thereof; or a prodrug for administration of a therapeutically effective dose to a subject in need thereof.

37. An exportable FABP-carrier protein having a first domain having affinity for at least one cannabinoid, and a second domain comprising a eukaryotic or prokaryotic secretion signal.

38. The exportable FABP-carrier protein of embodiment 37, wherein said first domain is selected from the group of amino acid sequences identified as SEQ ID NO. 1-2, 21, and 74-86

39. The exportable FABP-carrier protein of embodiment 37, wherein said second domain is selected from the group of amino acid sequences identified as: SEQ ID NO. 3, SEQ ID NO. 65, SEQ ID NOs. 69-73.

40. The exportable polypeptide of embodiments 37-39, wherein said exportable FABP-carrier protein binds at least one cannabinoid.

41. The exportable polypeptide of embodiments 37-39, wherein said exportable FABP-carrier protein binds at least one cannabinoid introduced, or biosynthesized in a cell culture.

42. The exportable polypeptide of embodiment 41, wherein said cell culture comprises a cell culture selected from the group consisting of: a bacterial cell culture, a yeast cell culture, a plant cell culture.

43. A genetically modified *Cannabis* plant expressing a nucleotide sequence operably linked to a promoter encoding at least one FABP-carrier protein.

44. The *Cannabis* plant of embodiment 43 and wherein said FABP-carrier protein comprises a FABP-carrier protein selected from the group consisting of: an amino acid sequence according to SEQ ID NOs. 1-2, 21, and 74-86.

45. The *Cannabis* plant of embodiments 43 and 44, and further comprising the step of expressing a nucleotide sequence operably linked to a promoter encoding one or more cannabinoid synthases having its trichome targeting sequence disrupted or removed.

46. The *Cannabis* plant of embodiment 45, wherein one or more cannabinoid synthase genes has been disrupted or knocked out.

47. The *Cannabis* plant of embodiment 46, wherein said one or more cannabinoid synthases having its trichome targeting sequence disrupted or removed is selected from the group consisting of: the nucleotide sequence identified as: SEQ ID NO. 13, SEQ ID NO. 14, and SEQ ID NO. 15.

48. The *Cannabis* plant of embodiment 44, and further comprising the step of expressing at least one myb transcription factor.

49. The *Cannabis* plant of embodiment 48, wherein said at least one myb transcription factor is selected from the group consisting of: SEQ ID NOs. 16-20.

50. The *Cannabis* plant of embodiment 44, and further comprising the step of expressing at least one catalase.

51. The *Cannabis* plant of embodiment 50, wherein said at least one catalase is selected from the group consisting of: SEQ ID NOs. 6-10.

52. The *Cannabis* plant of embodiment 44, and further comprising the step of expressing at least one heterologous glycosyltransferase, 53. The *Cannabis* plant of embodiment 52, wherein said at least one at least one heterologous glycosyltransferase is selected from the group consisting of: 32-47, and SEQ ID NOs. 61-62. Additional aspects of the invention may be evident from the specification and figures below.

DETAILED DESCRIPTION OF THE INVENTION

In certain embodiments, the invention may include the use of a FABP as a carrier protein, generally referred to as a FABP-carrier, to solubilize cannabinoids, terpenes/terpenoids, and other short-chain fatty acid phenolic compounds.

In one embodiment, the invention may include systems, methods and compositions to solubilize cannabinoids, terpenes/terpenoids, and other short-chain fatty acid phenolic compounds utilizing FABPs an, preferably non-human homologs of FABPs to solubilize cannabinoids and other compounds generally identified herein. In this embodiment, the use of FABPs compositions to solubilize cannabinoids may facilitate the transport, and/or storage of cannabinoids in in vitro, and in vivo systems, as well as their use in commercial products where enhanced solubility may enhance the product's characteristics or price.

In another embodiment, the current invention may include the rational design of a novel chimeric FABP construct, preferably based on non-human homologs of FABPs, to increase cannabinoid water solubility via binding. In a preferred embodiment, a human homolog of hepatic FABP1 (SEQ ID NO. 21), for example as identified in SEQ ID NO. 1-2, or a homolog thereof, may be used to solubilize cannabinoids and other compounds in both in vitro and in vivo systems generally identified herein. Additional embodiments may include the generation of genetically modified or engineered FABPs that may be used to solubilize cannabinoids.

In a preferred embodiment, such site-directed mutations may be rationally designed such that one or more mutations may be made near a cannabinoid, or other binding site. Such rationally designed mutations may modulate the compounds binding affinity with the FABP-carrier protein. In a preferred embodiment, rationally designed mutations may increase its strength of binding with a cannabinoid, terpene, or other short-chain fatty acid phenolic compound. In some further embodiments, rationally designed mutations may enhance binding affinity for the FABP-carrier protein that is compound specific. In this embodiment, mutations at and/or near the binding site may be rationally designed to increase its strength of binding with THC, CBD or other cannabinoids as identified herein.

Figure 8A:
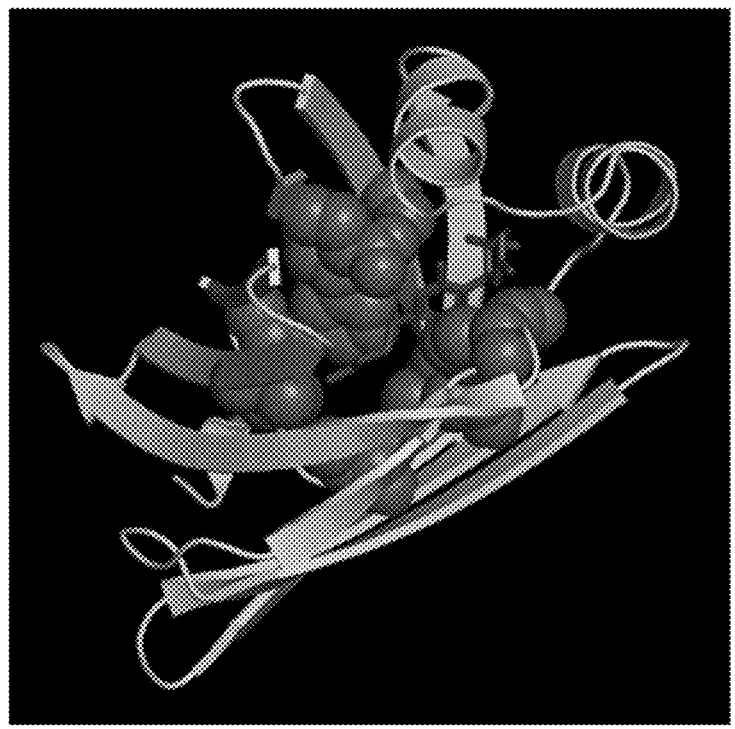
FIG. 8. Structural models of engineered variants of (A) plant FABP (images encompass modified amino acid residues for SEQ ID NOs. 85-86) and (B) horse FABP1 (images encompass modified amino acid residues for both SEQ ID NOs. 83-84) with predicted enhanced binding affinity to CBD relative to the WT proteins. Protein backbones are shown in green or blue cartoons, while bound CBD is shown with magenta sticks. The mutations in each protein that were introduced by the in silico directed evolution procedure are shown as red spheres. Note that all these mutations, which are predicted to help improve each protein's binding affinity to CBD, occur within the binding cavity.
Figure 8B:
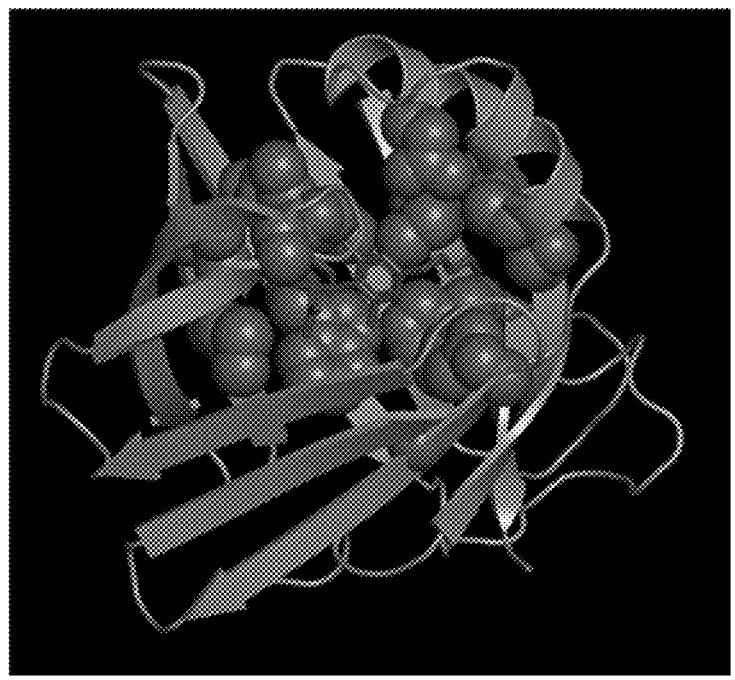

In one example, the directed evolution algorithm may identify amino acid substitution mutations that aid in enhancing the binding affinity to one or more target cannabinoids, such as CBD based quantitatively on the Metropolis criterion. As generally shown in FIG. 8, which shows t 1 three-dimensional models of the FABP-carries according to SEQ ID NOs. 84-85, and 85-86, the specifically identified mutations sites followed a pattern. In these examples, the set of residues at, or near the cannabinoid binding pocket and with side chains pointing towards this cavity were targeted for mutations. Thus, when looking at any two variants (that started from the same WT parent), there is an expected higher chance of seeing a mutation occur at a particular position. For instance, both chicken FABP7 variants (SEQ ID NOs. 79 & 80) have mutations at positions 34 and 54, and both pig FABP1 variants (SEQ ID NOs. 81 & 82) have mutations at positions 100 and 102. Such mutations may induce conformational or other changes that enhance the affinity of the cannabinoid binding pocket on the respective FABP-carrier proteins.

Such mutations may induce conformational or other changes that enhance the affinity of the cannabinoid binding pocket on the respective FABP-carrier proteins for a specific ligand cannabinoid, such as CBD. Since CBD is highly nonpolar or hydrophobic, as generally shown in SEQ ID NOs. 79-86, the specific mutations may: i) replace a residue with a hydrophilic side chain to another residue with a hydrophobic side chain; or ii) replace a small hydrophobic residue with a bulkier/larger hydrophobic residue. These mutations may enhance the overall hydrophobicity of the cannabinoid binding pocket, thereby making it more attractive to the ligand, for example CBD, for binding. In one example, the FABP-carrier identified a chicken FABP7 (SEQ ID NO. 74) for instance, the wild-type Gly at position 34 is mutated to either Ala or Phe in the variants (case B), and the wild-type Thr at position 54 is replaced with either Met or Ile in the variants (case A). In another example, the FABP-carrier identified a pig FABP1 (SEQ ID NO. 75), the wild-type Ser at position 100 is mutated to Ala in both variants and the wild-type Thr at position 102 is replaced with either Phe or Ile in the variants.

In another example, as noted in the SEQUENCING LISTING below, amino acid residues that have been modified from their wild type versions are underlined (see for example the amino acid sequences according to SEQ ID NO. 79-86, compared to wild type amino acid sequences according to SEQ ID NO. 74-78). For example, in one embodiment, the amino acid sequence for a wild type FABP-carrier having affinity for one or more cannabinoids from the plant *Rhodamnia argentea*, being identified as SEQ ID NO. 77, may be engineered to form an engineered FABP-carrier protein through rationally designed mutations derived from the in silico directed evolution of the proteins binding site such that the rationally designed proteins may exhibit enhanced binding affinity for the FABP-carrier protein. For example, in one embodiment, specific rationally designed mutations identified in the FABP-carrier according to SEQ ID NO 85 may include: A34M, G35M, P39A, T41V, F53I, T55V, L77F, Q95I, R107A, V117F, W119E, and R128A. In another example, specific rationally designed mutations identified in the FABP-carrier according to SEQ ID NO. 86 may include: T41I, F53I, T55M, I64V, N74A, R76A, 84GA, Q95I, Q96N, K104T, and A128A.

In certain embodiment, the invention may include an engineered FABP-carrier protein having one or more mutations that enhance the overall hydrophobicity of the cannabinoid binding pocket, thereby making it more attractive to the cannabinoid ligand. In certain embodiment, the invention may include an engineered FABP-carrier protein having at least one mutation that: (i) that replace a residue with a hydrophilic side chain to another residue with a hydrophobic side chain thereby enhancing the overall hydrophobicity of the cannabinoid binding pocket, thereby making it more attractive to the cannabinoid ligand; and/or that replace a small hydrophobic residue with a bulkier/larger hydrophobic residue thereby enhancing the overall hydrophobicity of the cannabinoid binding pocket, thereby making it more attractive to a cannabinoid ligand. As noted above, in certain embodiments the invention may include an engineered FABP-carrier protein having at least one of the substitution mutations identified in SEQ ID NO. 79-86. In alternative embodiments, invention may include an engineered FABP-carrier protein according to SEQ ID NO. 79-86.

Figure 1A:
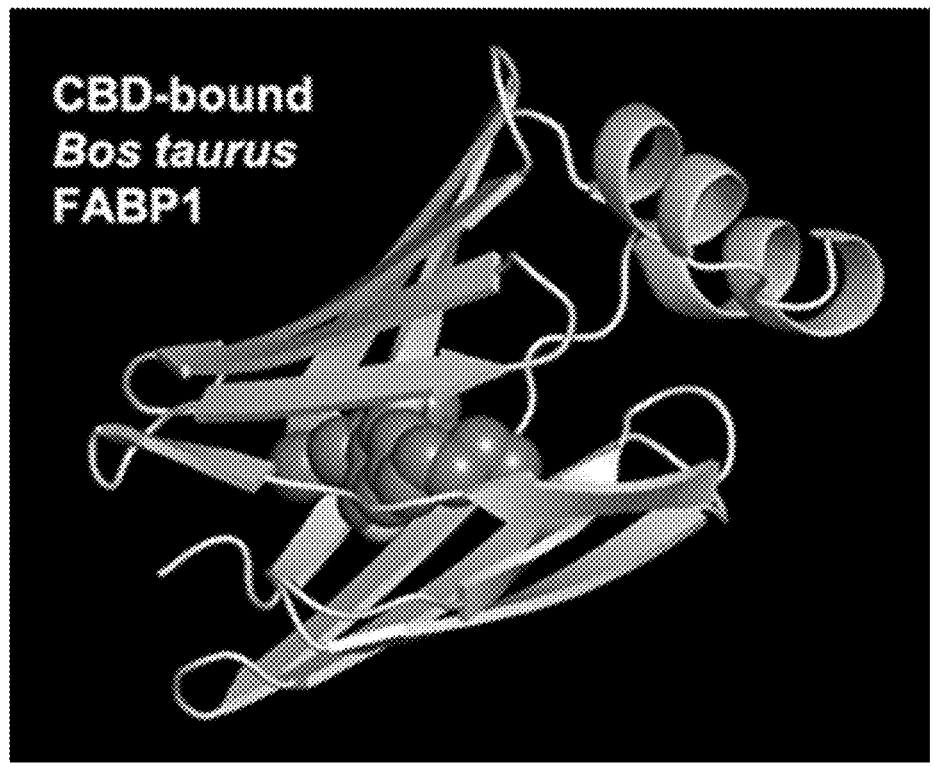
FIG. 1. (A) an exemplary cannabinoid (CBD) molecule (purple spheres) is bound to the predicted micromolar affinity site in Bos taurus FABP1 (white cartoons). (B) an exemplary cannabinoid (THC) molecule (purple spheres) is bound to the predicted micromolar affinity site in Mus musculus FABP1 (white cartoons).
Figure 1B:
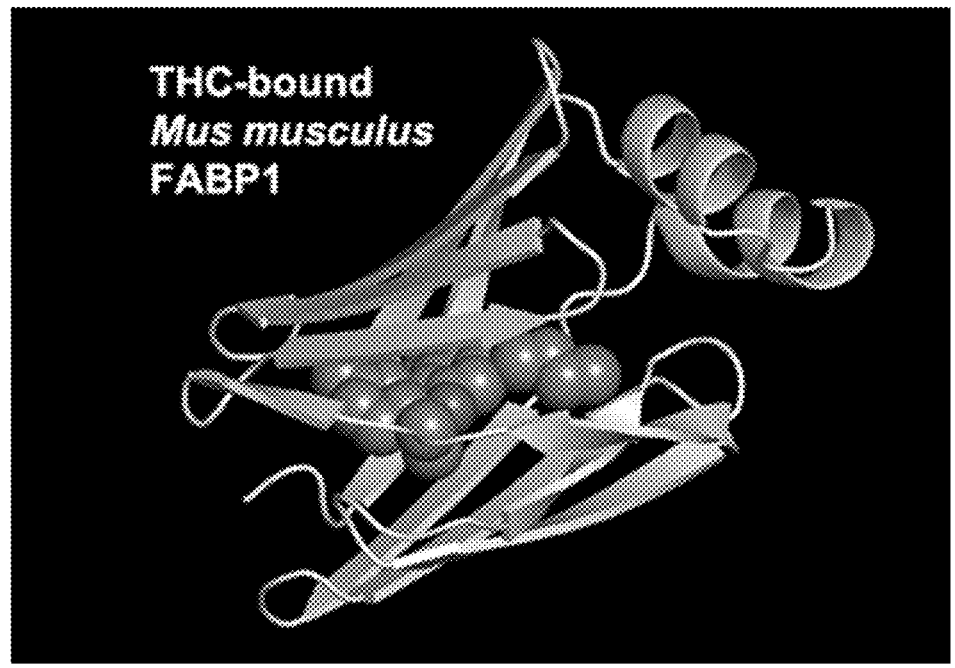

In one embodiment, the current invention may include the increase of THC water solubility for transport via binding to a non-human homolog of an FABP. In a preferred embodiment, the FABP1 (hepatic FABP) homolog from *Mus musculus* may be used due to its sequence homology with *Homo sapiens* FABP1 (high sequence identity of around 84%) and the presence of a site with predicted micromolar affinity for binding the cannabinoid THC. The protein sequence for *Mus musculus* FABP1 is identified as SEQ ID NO. 1. The left panel of FIG. 1 above demonstrates a structural model of a THC molecule bound to *Mus musculus* FABP1.

In another embodiment, the current invention may include the rational design of mutations to the binding site of an FABP-carrier protein to enhance its binding affinity for THC or other related cannabinoids. In one preferred embodiment, these mutations may be designed into wild type FABP-carriers identified by amino acid SEQ ID NO. 1-2, 21, and 74-78, using a combination of in vitro, in vivo studies as well as bioinformatics approaches such as computational docking, binding affinity estimation, and molecular dynamics simulations. Such bioinformatics applications may be further employed to identify additional potential FABP carrier proteins, as well as direct specific point-mutations to modulate or enhance cannabinoid binding affinity.

In another embodiment, the current invention may include the increase of CBD water solubility for transport via binding to a non-human homolog of an FABP. In a preferred embodiment, the FABP1 (hepatic FABP) homolog from *Bos taurus* may be used due to its sequence homology with *Homo sapiens* FABP1 (high sequence identity of around 81%) and the presence of a site with predicted micromolar affinity for binding CBD. The protein sequence for *Bos taurus* FABP1 is identified as amino acid sequence SEQ ID NO. 2. The right panel of FIG. 1 above demonstrates a structural model of a CBD molecule bound to *Bos taurus* FABP1.

In another embodiment, the current invention may include the increase of CBD water solubility for transport via binding to a non-human homolog of an FABP selected from the amino acid sequences according to SEQ ID NO. 1-2, 21, 74-86. In one preferred embodiment, the aforementioned sequences may be coupled with a tag, and/or secretion signal.

In another embodiment, the current invention may include the rational design of mutations at and/or near the binding site of an FABP-based carrier protein to enhance its binding affinity for CBD. In a preferred embodiment, these mutations will be designed into the FABP1 homolog identified as amino acid sequence SEQ ID NO. 1-2, 21, and 74-78 using a combination of in vitro, in vivo studies as well as bioinformatics approaches such as computational docking, binding affinity estimation, and molecular dynamics simulations. Such bioinformatics applications may be further employed to identify additional potential FABP carrier proteins, as well as direct specific point-mutations to modulate or enhance cannabinoid binding affinity.

In another embodiment, the current invention may include the rational design of mutations on the surface of a FABP-carrier protein to decrease its aggregation propensity and potential antigenicity. In a preferred embodiment, one or more of the mutations V58E, or V42R, may be introduced into one or more of the FABP-carriers identified herein. In a preferred embodiment, one or more of the mutations V58E, or V42R, may be introduced into one or more of the FABP-carriers according to SEQ ID NOs. 21, 75-76, 78, and 81-84. Each mutation may reduce the tendency of this protein to form aggregates in solution, without destabilizing its conformational stability. Preliminary analyses of linear epitopes for this FABP1 homolog suggest a high false positive prediction rate, based on a comparison with corresponding predictions for *Homo sapiens* FABP1 (SEQ ID NO. 21).

The above FABP-carrier proteins are provided as exemplary embodiments only. Nor are they limiting as to the number of punitive cannabinoid, or other short-fatty-acid phenolic compound affinity sites that may be engineered in a FABP-carrier. Consideration of which may include the desired type of short-fatty-acid phenolic compound to be bound by the FABP-carrier, as well as steric considerations resulting from the addition of such modified affinity motifs presented in the three-dimensional folded protein. Naturally, certain modifications may be made to a FABP-carrier that may alter the affinity strength of one or more existing cannabinoid affinity sites.

In another embodiment, the current invention may include the rational design of mutations on the surface of a cannabinoid-specific FABP-carrier protein that may decrease its aggregation propensity and potential antigenicity. In a preferred embodiment, the mutation V58K may be introduced into the FABP-carrier which may further include SEQ ID NOs. SEQ ID NOs. 21, 75-76, 78, and 81-84, or a homolog thereof. Such a mutation may reduce the tendency of a FABP-carrier to form aggregates in solution, without destabilizing its conformational stability. Analyses of the linear epitopes for this modified FABP-carrier suggest a high false positive prediction rate, based on a comparison with corresponding predictions for *Homo sapiens* FABP1 (SEQ ID NO. 21).

In another embodiment, the current invention may include the increase of cannabinoid water solubility for transport via binding to an artificial or non-human homolog of FABP. In this embodiment of the current invention may include the increase of CBD water solubility for transport via binding to a non-human homolog of FABP.

In another embodiment, a FABP-carrier protein may be identified an engineered FABP-carrier protein having at least one modified cannabinoid-affinity sites or motifs, such as a THC, or CBD-affinity site or motif, when the protein is in its folded three-dimensional configuration. In one embodiment, a cannabinoid affinity from an engineered FABP-carrier may be modified to have increased or decreased cannabinoid affinity. In one preferred embodiment, a FABP-carrier protein, preferably a non-human homolog such as identified in SEQ ID NO. 74-86, or a homolog thereof may be identified and established as an engineered FABP-carrier protein. This engineered FABP-carrier protein may be genetically modified to construct a FABP-chimera or fusion protein having one or more modified cannabinoid-affinity sites or motifs having, preferable enhanced cannabinoid affinity. For example, as shown in FIG. 1, a FABP-carrier may have a micromolar affinity for a cannabinoid, while an engineered FABP-carrier may be engineered to have a nanomolar or greater affinity for cannabinoids.

As one of ordinary skill in the art would recognize, a ligand, such as a cannabinoid, or other short-chain fatty acid phenolic compound, with nanomolar (nM) dissociation constant may bind more tightly to a particular protein than a ligand with micromolar (μM) dissociation constant. As a result, in certain embodiments of the inventive technology, customized FABP-carrier proteins, and in particular engineered FABP-carrier proteins may be generated that have a customized dissociation constant. This customized dissociation constant may be engineered according to the specifications of a particular application. For example, in one application a FABP-carrier may be engineered to be a fusion, or chimeric protein having one or more cannabinoid affinity sites having nanomolar (nM) or greater dissociation constant. Such FABP-carrier may be useful for long-term storage of cannabinoids in solution, or for applications inclusion in various commercial and other consumer products where the FABP-carrier may be exposed to artificial, or natural environmental conditions or other chemical processes that might degrade the protein structure and prematurely released the cannabinoid. Alternatively, in one application a FABP-carrier may be engineered to have one or more a cannabinoid affinity sites having micromolar (μM) dissociation constant. Such FABP-carrier may allow for one or more cannabinoid compounds to be more easily release from the FABP-carrier. In one preferred embodiment, a FABP-carrier may include one or more a cannabinoid affinity sites having a macro- or micromolar (μM) dissociation that may allow for greater release, as compared for example to a nanomolar (nM) dissociation, and bioavailability of the cannabinoid upon consumption.

As noted above, cannabinoid producing strains of *Cannabis*, as well as other plants may be utilized with the inventive technology. In certain preferred embodiments, *Cannabis* plant material may be harvested and undergo cannabinoid extraction through one or more of the methods generally known in the art. These extracted cannabinoids, terpenoids and other short chain fatty acid phenolic compounds, may be introduced to a quantity of FABP-carrier proteins to be solubilized as described herein.

In one embodiment, cells of a microorganism, such as yeast or bacteria, may be transformed with artificially created expression vectors encoding one or more FABP-carrier proteins. In this preferred embodiment, the nucleotide sequences encoding a FABP-carrier protein may be codon optimized for exogenous expression. Additional embodiments may include genetic control elements such as promotors and/or enhancers as well as post-transcriptional regulatory elements that may also be expressed in the genetically engineered microorganisms, such as yeast or bacteria, such that the presence, quantity and activity of any FABP-carrier proteins present in a culture may be controlled. In a preferred embodiment, the microorganism, such as yeast or bacteria strain, may be further modified to generate high-levels of FABP-carrier proteins. In a preferred embodiment, the bacterial strain may include a high expression strain of bacteria, such as *E. coli* strain BL21(DE3) for optimal protein expression. In another preferred embodiment, the yeast strain may include genetically modified yeast cells selected from the group consisting of: genetically modified *Pichia pastoris* cells, genetically modified *Saccharomyces cerevisiae* cells, and/or genetically modified *Kluyveromyces marxianus* cells.

As noted above, in one embodiment the inventive technology may include individual expression of one or more FABP-carrier proteins each having a selected molecular tag. In a preferred embodiment, an FABP-carrier-protein, for example engineered from the amino acid sequences SEQ ID NO. 1-2, 21, and 74-86, or other homologous sequences, may each be configured to contain a poly-His or His-6 tag, which may be used later for protein purification. In this embodiment, the expressed FABP-carrier-protein may be detected and purified because the string of histidine residues bind to several types of immobilized metal ions, including nickel, cobalt and copper, under appropriate buffer conditions.

In one embodiment of the inventive technology, a cell culture, such as a plant, yeast or bacterial culture, may be genetically modified to express a tagged heterologous FABP-carrier and may further be allowed to grow to a desired level of cell or optical density, or in other instances until a desired level of FABP-carrier proteins have accumulated in the cultured cells and/or media, for example through the addition of a secretion signal that directs the FABP-carrier to be exported from the cell. All, or a portion of the accumulated FABP-carrier proteins may then be harvested from the culture and/or media, which in a preferred embodiment may be an industrial-scale fermenter or other apparatus suitable for the large-scale culturing of microorganisms. Optionally, the harvested cells may be lysed such that the accumulated FABP-carrier proteins may be released to the surrounding lysate. Additional steps may include treating this lysate. Examples of such treatment may include filtering, centrifugation or screening to remove extraneous cellular material as well as chemical treatments to improve later FABP-carrier yields.

The FABP-carrier may be further isolated and purified. In one preferred embodiment, the cell lysate or media may be processed utilizing affinity chromatography or other purification methods. In this preferred embodiment, an affinity column having a ligand configured to bind with one or more of the tags coupled with the FABP-carrier protein, for example, a poly-His or His-6 tag, among others, may be immobilized or coupled to a solid support. The lysate may then be passed over the column such that the tagged FABP-carrier, having specific binding affinity to the ligand becomes bound and immobilized. In some embodiments, non-binding and non-specific binding proteins that may have been present in the lysate may be removed. Finally, the FABP-carrier may be eluted or displaced from the affinity column by, for example, a corresponding protein, tag or other compound that may displace or disrupt the tag-ligand bond. The eluted FABP-carrier proteins may be collected and further purified or processed. Notably, in other embodiments, FABP-carrier proteins may be commercially obtained or synthesized and used consistent with the embodiments described herein.

All FABP and FABP-carrier amino sequences described herein include homologs of said sequences which may have between 75-99% homology, while retaining specific activity towards one or more short-chain fatty-acid phenolic compound, and preferably one or more cannabinoid compounds.

One embodiment of the inventive technology includes the generation of novel genetically modified short-chain fatty-acid phenolic compound-carrier proteins that may have enhanced affinity for short-chain fatty-acid phenolic compounds, and preferably a terpenoid or cannabinoid from *Cannabis*. In one preferred embodiment, the inventive technology includes the generation of novel genetically modified cannabinoid-carrier FABPs engineered from one or more wild type FABP-carriers, for example SEQ ID NO. 1-2, and 74-78, or homologs thereof that may have enhanced affinity for cannabinoids.

Another embodiment of the inventive technology provides for systems and methods of high-capacity cannabinoid solubilization. In this preferred embodiment, a polynucleotide configured to express one or more FABP-carrier proteins, for example the amino acid sequences SEQ ID NO. 1-2, 74-86, or a homolog thereof, which may optionally be coupled with a tag for purification or isolation purposes, and may be operably linked to a promoter forming an expression vector. This expression vector may be used to transform a microorganism which may express one or more tagged FABP-carrier proteins, which may be further isolated, preferably through affinity purification. The isolated tagged FABP-carrier may be placed into a bio-reactor or other suitable environment where they may be introduced to one or more cannabinoids, terpenoids, and/or other short-chain fatty-acid phenolic compounds. The tagged FABP-carrier proteins may solubilize the cannabinoids, terpenoids, and/or other short-chain fatty-acid phenolic compounds through affinity binding to one or more affinity site. The solubilized cannabinoids may be isolated and used for commercial, pharmaceutical and other applications as generally described herein.

Another embodiment of the invention provides for methods of masking the typical unpleasant small and taste of cannabinoid-infused commercial products and beverages. For example, in this embodiment a FABP-carrier, for example as identified in the amino acid sequences 1-2, 21, and 74-86, may bind to one or more cannabinoids and allow it to be solubilized. In this solubilized state, the carrier protein allows for the masking of the cannabinoids natural small and taste. Moreover, in additional embodiments, a FABP-carrier may bind to, and solubilize one or more terpenes, the compounds in *Cannabis* primarily responsible for its distinctive smell. In this manner, the invention may generate cannabinoid-infused commercial products, such as consumables and beverages that eliminate, mask or ameliorate the undesired smell and taste of the cannabinoid and terpene compounds.

Another embodiment of the invention provides for methods of generating solubilized cannabinoids, terpenes and other short-chain fatty-acid phenolic compounds that may have a more rapid metabolic uptake or bioavailability upon ingestion. In this embodiment, a FABP-carrier, such as an engineered FABP-carrier, may bind to one or more cannabinoids and/or terpenes and allow it to be solubilized such that upon ingestion, it may be more readily taken up by the body, for example, through the association with the carrier protein. This embodiment may allow for not only a more rapid uptake of the target compound, but allow for consistent consumer experiences, as well as facilitating safe and effective consumer-controlled dosing of cannabinoids and other compounds. This embodiment may further allow for lower amounts of cannabinoid and terpenes to be used in infused consumables and beverages as a result of this improved bioavailability. For example, absent this enhance bioavailability of the solubilized cannabinoids and terpenes, a large portion of the compounds may not be efficiently taken up by the body and may be eventually eliminated through natural chemical degradation or other strategies to metabolically clear the compounds from the body.

Another embodiment of the invention provides for methods of generating precise doses and/or formulations and/or ratios of cannabinoids, terpenoids, and/or other short-chain fatty-acid phenolic compounds. In a preferred embodiment, a polynucleotide may be generated that is configured to express one or more FABP-carrier proteins configured to have binding affinity motifs that selectively bind an individual or class of cannabinoid, terpenoids, and/or other short-chain fatty-acid phenolic compounds. Again, this selective FABP-carrier-protein may be coupled with a tag for purification or isolation purposes and may be operably linked to a promoter forming an expression vector. This expression vector may be used to transform a microorganism, such as bacteria, yeast, fungi, or algae, which may express the tagged selective FABP-carrier protein which may be further isolated, preferably through affinity purification. The isolated selective FABP-carrier-protein may be placed into a bio-reactor or other suitable environment where they may be introduced to one or more cannabinoid, terpenoids, and/or other short-chain fatty-acid phenolic compounds. The FABP-carrier may selectively solubilize a quantity of cannabinoid, terpenoids, and/or other short-chain fatty-acid phenolic compounds, consistent with its endogenous and/or engineered affinity sites. The solubilized cannabinoid, terpenoids, and/or other short-chain fatty-acid phenolic compounds may be used for commercial, pharmaceutical, and other applications as generally described herein.

Another aspect of the invention provides for methods of generating precise mixed doses, ratios, and/or formulations of cannabinoids, terpenoids, and/or other short-chain fatty acid phenolic compounds. In a preferred embodiment, a first polynucleotide may be generated that is configured to express a FABP-carrier configured to have a selective binding affinity motif(s) that selectively bind an individual or class of cannabinoid, terpenoid, and/or other short-chain fatty-acid phenolic compound. An additional polynucleotide may be generated that is configured to express a FABP-carrier configured to have a cannabinoid binding affinity motif(s) that selectively bind a different individual or class of cannabinoid, terpenoid, and/or other short-chain fatty-acid phenolic compound. Both selective FABP-carrier proteins may be coupled with a tag for purification or isolation purposes and may be incorporated into one or more expression vectors being operably linked to a promotor. Such expression vector(s) may be used to transform a microorganism, such as bacteria, yeast, fungi, or algae, which may express the tagged selective FABP-carrier proteins which may be further isolated, preferably through affinity purification. The isolated selective FABP-carrier proteins may be placed into a bio-reactor or other suitable environment where they may be introduced to one or more cannabinoids, terpenoids, and/or other short-chain fatty-acid phenolic compounds. The first FABP-carrier protein may selectively solubilize a quantity of individual or class of cannabinoid, terpenoid, and/or other short-chain fatty-acid phenolic compound consistent with the number and type of its endogenous and/or engineered affinity sites. The additional FABP-carrier protein may selectively solubilize a quantity of a separate individual or class of cannabinoid, terpenoid, and/or other short-chain fatty-acid phenolic compound consistent with the number and type of its endogenous and/or engineered affinity sites. The solubilized cannabinoid, terpenoids, and/or other short-chain fatty-acid phenolic compounds may be used for commercial, pharmaceutical, and other applications as generally described herein.

Another aspect of the invention may include in vitro systems and methods to solubilize cannabinoids, terpenoids, and/or other short-chain fatty-acid phenolic compounds. In a preferred embodiment, FABP-carrier proteins, for example the proteins identified according to SEQ ID NO. 1-2, 21, and 74-86, may be artificially synthesized in vitro and then placed into a bio-reactor, or other suitable environment, where they may be introduced to one or more cannabinoids, terpenoids, and/or other short-chain fatty-acid phenolic compounds. The FABP-carrier proteins carrier proteins may solubilize the cannabinoids, terpenoids, and/or other short-chain fatty acid phenolic compounds as generally described herein.

Another embodiment of the inventive technology provides for direct systems and methods of high-capacity cannabinoid solubilization. In this preferred embodiment, a polynucleotide configured to express one or more FABP-carriers, for example SEQ ID NO. 1-2, 21, and 74-86, may be coupled with a tag for purification or isolation purposes. This polynucleotide may be operably linked to a promoter forming an expression vector. This expression vector may be used to transform a microorganism which may be grown in an industrial scale fermenter or other like apparatus known in the art for high-level protein production. While in culture, the genetically modified microorganism may express one or more tagged FABP-carrier proteins. Short-chain fatty-acid phenolic compounds, such as cannabinoids, terpenes, and other volatiles may be extracted from cannabinoid-producing plants or artificially biosynthesized and added to the cell culture. The isolated FABP-carrier proteins produced in culture may be introduced to one or more cannabinoids, terpenoids, and/or other short-chain fatty-acid phenolic compounds in the culture. In one embodiment, one or more FABP-carrier proteins produced in culture may be coupled with a secretion signal, for example as identified in SEQ ID NO. 3 or 65, so as to be able to be more easily exported to the cultures media or supernatant, preferably in a yeast culture. The FABP-carrier proteins may bind to, and solubilize one or more cannabinoids, terpenoids, and/or other short-chain fatty-acid phenolic compounds in the culture's supernatant or media. The tagged FABP-carrier proteins, and their bound compounds, may be isolated utilizing affinity chromatography or other purification methods.

Another embodiment of the inventive technology provides for direct systems and methods of high-capacity cannabinoid solubilization. In this preferred embodiment, a polynucleotide configured to express one or more FABP-carrier proteins may be coupled with a tag for purification or isolation purposes. Such polynucleotide may be operably linked to a promoter forming an expression vector. This expression vector may be used to transform a bacterium which may be grown in an industrial scale fermenter or other like apparatus known in the art for high-level protein production. While in culture, the genetically modified bacteria may express one or more tagged FABP-carriers, for example one or more of the amino acid sequences according to SEQ ID NO. 1-2, 74-86, that may also be coupled with a secretion signal. Short-chain fatty-acid phenolic compounds, such as cannabinoids, terpenes, and other volatiles, may be extracted from cannabinoid-producing plants or artificially biosynthesized and added to the cell culture. The isolated FABP-carrier proteins produced in culture may be introduced to one or more cannabinoids, terpenoids, and/or other short-chain fatty-acid phenolic compounds in the culture. The FABP-carrier proteins may bind to and solubilize one or more cannabinoids, terpenoids, and/or other short-chain fatty-acid phenolic compounds. The tagged FABP-carrier proteins carrier proteins, and their bound compounds, may be isolated utilizing affinity chromatography or other purification methods.

Another embodiment of the inventive technology provides for systems and methods of high-capacity cannabinoid solubilization coupled with cannabinoid biosynthesis in microorganisms genetically engineered to produce cannabinoids. Implementing cannabinoid biosynthesis strategies proposed by: Carvalho Â, et al.; US Pat. App. No. US20180371507, by Paulos et al.; and WO2017139496, by Hussain et al.; (all of which are incorporated herein by reference) for the generation of cannabinoids in microorganisms such as yeast, fungi, and bacteria, in one embodiment the inventive technology may include systems and methods for solubilization of cannabinoids produced in non-cannabinoid producing microorganisms or artificial chemically-synthesized cannabinoids.

In one embodiment, one or more metabolic pathways for cannabinoid biosynthesis may be reconstructed in microorganisms, such as bacteria, fungi, algae, or yeast. Such pathways may be reconstructed through the expression of a plurality of heterologous genes necessary for the biosynthesis of precursor and cannabinoid compounds. In one preferred embodiment, a microorganism, such as bacteria, yeast, or fungi, may be genetically engineered to produce one or more cannabinoids, terpenes, or other short-chain fatty acid phenolic compounds. The microorganism may be further genetically modified to express a polynucleotide encoding a cannabinoid-carrier FABPs or a homolog thereof, such as those identified in SEQ ID NO. 1-2, 74-86 or more preferably an engineered FABP-carrier protein, such as those identified in SEQ ID NO. 79-86, or other homolog thereof. In one preferred embodiment, a FABP-carrier protein may bind to and solubilize one or more exogenously biosynthesized cannabinoids. This FABP-carrier protein may be tagged to facilitate isolation and purification as generally described herein and may further be coupled with a secretion signal as discussed below.

In another aspect of the invention, a FABP-carrier protein may be exported out of a cell through the natural action of the cell, gradient movement, or diffusion, as well as the action of the secretion signal, where it may bind to one or more cannabinoid or other compounds located externally to a cell. In one preferred embodiment, a FABP-carrier protein may be generated in a cell culture, preferably a bacterial, yeast, plant or fungi cell culture, and more preferably a plant suspension culture of a cannabinoid-producing plant such as *Cannabis*, where it may be exported out of the cell and bind one or more cannabinoid or other compounds that may be present in the external cellular environment. In additional embodiments, a FABP-carrier protein may bind one or more cannabinoid or other compounds that may be present in the intracellular environment.

In another aspect of the invention, a FABP-carrier protein having a secretion signal may be expressed in a genetically modified yeast culture and exported out of a cell through the action of the secretion signal, or other natural action of the yeast cell. In one preferred embodiment, a heterologous polynucleotide may express one or more exportable FABP-carrier proteins having a secretion signal. In one embodiment, a secretion signal may direct posttranslational protein translocation into the endoplasmic reticulum (ER). In additional embodiments, a secretion signal may direct cotranslational translocation of the carrier protein across the ER membrane. Notably, protein translocation is the process by which peptides are transported across a membrane bilayer. Translocation of proteins across the membrane of the membrane of the ER is known to occur in one of two ways: cotranslationally, in which translocation is concurrent with peptide synthesis by the ribosome, or posttranslationally, in which the protein is first synthesized in the cytosol and later is transported into the ER.

In eukaryotic organisms such as yeast, proteins that are targeted for translocation across the ER membrane have a distinctive amino-terminal signal sequence, such as the amino acid sequence identified in SEQ ID NO. 65, which is recognized by the signal recognition particle (SRP). The SRP in eukaryotes is a large ribonucleoprotein which, when bound to the ribosome and the signal sequence of the nascent peptide, is able to arrest protein translation by blocking tRNA entry. The ribosome is targeted to the ER membrane through a series of interactions, starting with the binding of the SRP by the SRP receptor. The signal sequence of the nascent peptide chain is then transferred to the protein channel, Sec61. The binding of SRP to its receptor causes the SRP to dissociate from the ribosome, and the SRP and SRP receptor also dissociate from each other following GTP hydrolysis. As the SRP and SRP receptor dissociate from the ribosome, the ribosome is able to bind directly Sec61.

The Sec61 translocation channel (known as SecY in prokaryotes) is a highly conserved heterotrimeric complex composed of α-, β- and γ-subunits. The pore of the channel, formed by the α-subunit, is blocked by a short helical segment which may become unstructured during the beginning of protein translocation, allowing the peptide to pass through the channel. The signal sequence of the nascent peptide intercalates into the walls of the channel, through a side opening known as the lateral gate. During translocation, the signal sequence is cleaved by a signal peptide peptidase, freeing the amino terminus of the growing peptide.

During cotranslational translocation in eukaryotes, the ribosome provides the motive power that pushes the growing peptide into the ER lumen. During posttranslational translocation, additional proteins are necessary to ensure that the peptide moves unidirectionally into the ER membrane. In eukaryotes, posttranslational translocation requires the Sec62/Sec63 complex and the chaperone protein BiP. BiP is a member of the Hsp70 family of ATPases, a group which is characterized as having an N-terminal nucleotide-binding domain (NBD), and a C-terminal substrate-binding domain (SBD) which binds to peptides. The nucleotide binding state of the NBD determines whether the SBD can bind to a substrate peptide, in this case a FABP-carrier or engineered FABP-carrier. While the NBD is bound to ATP, the SBD is in an open state, allowing for peptide release, while in the ADP state, the SBD is closed and peptide-bound. The primary role of the membrane protein complex Sec62/Sec63 is to activate the ATPase activity of BiP via a J-domain located on the lumen-facing portion of Sec63. The SBD of BiP binds non-specifically to the peptide as it enters the ER lumen, and keeps the peptide from sliding backwards in a ratchet-type mechanism.

Again, in one preferred embodiment, a FABP-carrier may be modified to include at least one secretion signal that may facilitate vesicle transport of the protein out of the cell, preferably a yeast cell. In one embodiment, a FABP-carrier may be modified to include a secretion signal which directs posttranslational protein translocation into the ER. In one preferred embodiment, a secretion signal which directs posttranslational protein translocation into the ER may be identified in amino acid SEQ ID NO. 3 (see below) which encodes an N-terminal secretion signal from α-factor mating pheromone in *S. cerevisiae*. The secretion signal is made up of a 19 amino acid 'presequence' which directs posttranslational protein translocation into the ER, and a 66-amino acid 'pro region' mediating receptor-dependent packaging into ER-derived COPII transport vesicles.

SEQ ID NO. 3:

MRFPSIFTAVLFAASSALAAPVNTTTEDETAQIPA

EAVIGYSDLEGDFDVAVLPFSNSTNNGLLFINTTI

ASIAAKEEGVSLEKR

In another embodiment, a FABP-carrier may be modified to include a secretion signal which directs cotranslational translocation across the ER membrane. In one preferred embodiment, an enhanced secretion signal which directs cotranslational translocation across the ER membrane may be identified in amino acid sequence of SEQ ID NO. 65, where the 19 amino acid 'presequence' is replaced with the enhance 'presequence' with the Ost1 (OST=oligosaccharyltransferase) signal sequence identified by amino acid SEQ ID NO. 66.

MRQVWFSWIVGLFLCFFNVSSA

In this preferred embodiment, an enhanced secretion signal may be identified as SEQ ID NO. 65:

MRQVWFSWIVGLFLCFFNVSSAAPVNTTTEDETA

QIPAEAVIGYSDLEGDFDVAVLPFSNSTNNGLLF

INTTIASIAAKEEGVSLEKR

Again, in a preferred embodiment, one or more of the FABP-carrier proteins identified herein may be modified and expressed, preferably in a yeast cell, to include a secretion signal which directs posttranslational protein translocation into the ER, such signal preferably being SEQ ID NO. 32 which encode an N-terminal secretion signal from α-factor mating pheromone in *S. cerevisiae*. Such exportable FABP-carrier carrier proteins may include exemplary amino acid sequence identified as SEQ ID NO. 4-5, and amino acid sequences 1-2, 21, and 74-86 coupled with the N-terminal secretion signal according to SEQ ID NO. 3, may bind to, and solubilize one or more cannabinoids located in the cell, or more preferably they may solubilize one or more cannabinoids outside in the cell, such as cannabinoids added to a cell culture supernatant. The exportable FABP-carrier proteins, having solubilized one or more target cannabinoids or other compounds identified herein may be further isolated as generally described herein.

In another embodiment, a FABP-carrier protein may be modified and expressed, preferably in a yeast cell, to include an enhanced secretion signal which directs cotranslational translocation across the ER membrane, such signal preferably being. SEQ ID NO. 65 which include the Ost1 signal sequence identified as amino acid sequence SEQ ID NO. 66 coupled with the 66-amino acid 'pro region' of the N-terminal secretion signal from α-factor mating pheromone in *S. cerevisiae*. Such enhanced exportable FABP-carrier proteins may include exemplary amino acid sequence identified as SEQ ID NO. 67-68, and amino acid sequences 1-2, 21, and 74-86 coupled with the enhanced N-terminal secretion signal according to SEQ ID NO. 65, may bind to, and solubilize one or more cannabinoids located in the cell, or more preferably one or more cannabinoids located outside in the cell, such as cannabinoids added to a cell culture supernatant. The exportable FABP-carrier, having solubilized one or more target cannabinoids or other compound identified herein, may be further isolated as generally described herein.

Additional embodiments also feature a method for producing FABP-carrier polypeptides. The method includes culturing a recombinant bacterium cell in a culture medium under conditions that allow the FABP-carrier polypeptides to be secreted into the culture medium, the recombinant bacterium cell comprising at least one exogenous nucleic acid, the exogenous nucleic acid comprising first and second nucleic acid sequences, wherein the first nucleic acid sequence encodes a signal peptide and the second nucleic acid sequence encodes a FABP-carrier carrier polypeptides, wherein the first and second nucleic acid sequences are operably linked to produce a fusion polypeptide comprising the signal peptide and the FABP-carrier polypeptide, and wherein upon secretion of the fusion polypeptide from the cell into the culture medium, the signal peptide may be removed from the -containing polypeptide. The method further can include isolating the FABP-carrier polypeptides from the culture medium.

In another aspect of the invention, a FABP-carrier protein may be exported out of a bacterial cell through the action of a secretion signal where the FABP-carrier protein may be secreted in an unfolded conformation and bind to one or more cannabinoid or other compounds located externally to a cell. In one preferred embodiment, a FABP-carrier protein may be generated in a cell culture, preferably a bacterial cell culture, where it may be exported out of the cell and bind one or more cannabinoid or other compounds that may be present in the external cellular environment. In this embodiment, a FABP-carrier protein may be coupled with a secretion signal that may direct the carrier protein to be secreted from a bacterium through a SEC-mediated secretion pathway.

Notably, in bacteria, translated peptides may be actively translocated post-translationally through a SecY channel by a protein called SecA. SecA is composed of a nucleotide-binding domain, a polypeptide crosslinking domain, and helical wing and scaffold domains. During translocation, a region of the helical scaffold domain forms a two-finger helix which inserts into the cytoplasmic side of the SecY channel, thereby pushing the translocating carrier peptide through. A tyrosine found on the tip of the two-finger helix plays a critical role in translocation, and is thought to make direct contact with the translocating peptide. The polypeptide crosslinking domain (PPXD) forms a clamp which may open as the translocating peptide is being pushed into the SecY channel by the two-finger helix, and close as the two-finger helix resets to its "up" position. The conformational changes of SecA are powered by its nuclease activity, with one ATP being hydrolyzed during each cycle. This SEC system secretes proteins having a consensus signal peptide that is similar to, but distinct from, that of the Tat system as described below. The Sec signal sequence lacks an N-terminal consecutive-arginine sequence and has a relatively hydrophobic central region and a relatively short signal sequence compared with that of Tat. Exemplary Sec signal sequences may be identified as SEQ ID NO. 69.

Again, in one preferred embodiment, a FABP-carrier may be modified to include at least one Sec-mediated secretion signal that may facilitate translocation of transport of the unfolded carrier protein out of a bacterial cell via a Sec-secretion pathway. In one embodiment, a FABP-carrier may be modified to include a secretion signal which directs posttranslational protein translocation. In one preferred embodiment, a secretion signal which directs posttranslational protein translocation may be identified in amino acid SEQ ID NO. 69 which encodes an exemplary Sec-signal sequence from *E. coli* L-asparaginase II.

Again, in a preferred embodiment, one or more of the FABP-carrier carrier proteins may be selected from SEQ ID NO. 1-2, 21, and 74-86, and may be modified and expressed, preferably in a bacterial cell, to include a secretion signal which directs posttranslational protein translocation of the unfolded protein, such signal preferably being SEQ ID NO. 70, or homologous or similar Tat-secretion signal sequence, which may encode an exemplary Sec-secretion signal sequence. Such exportable FABP-carrier proteins may be translocated from a bacterial cell to the external environment where they may come into contact with, bind to, and solubilize one or more cannabinoids located outside in the cell, such as cannabinoids added to a cell culture supernatant.

In another aspect of the invention, a FABP-carrier protein may be exported out of a bacterial cell through the action of a secretion signal where the FABP-carrier protein may assume its folded three-dimensional configuration prior to secretion. In this embodiment, a FABP-carrier protein may bind to one or more cannabinoid or other compounds located internally or externally to the cell. In one preferred embodiment, a FABP-carrier protein may be generated in a cell culture, preferably a bacterial cell culture, where it may be exported out of the cell and into the external cellular environment. In this embodiment, a FABP-carrier protein may be coupled with a secretion signal that may direct the carrier protein to be secreted from a bacterium through a TAT-mediated secretion pathway.

Unlike the Sec system, the Tat system is involved in the transport of pre-folded protein substrates. Proteins are targeted to the Tat pathway by possession of N-terminal tripartite signal peptides. The signal peptides include a conserved twin-arginine motif in the N-region of Tat signal peptide. The motif has been defined as R-R-x-Φ-Φ, where Φ represents a hydrophobic amino acid. In *E. coli* the Tat pathway comprises the three-membrane protein TatA, TatB and TatC. A fourth protein TatE forms a minor component of the Tat machinery and has a similar function to TatA.

Because of the ability to secrete pre-folded protein substrates, the Tat pathway may be especially suited for secreting a high level of heterologous FABP-carrier proteins. Estimates of Tat substrates in organisms other than *Bacillus subtilis* and *E. coli* have been based predominantly in in silico analysis of genome sequences using programs trained to recognize specific features of tat targeting sequences. An exemplary Tat signal sequences may be identified as SEQ ID NO. 70.

Again, in one preferred embodiment, a FABP-carrier may be modified to include at least one Tat-mediated secretion signal that may facilitate translocation of transport of the folded carrier protein out of a bacterial cell. In one embodiment, a FABP-carrier may be modified to include a secretion signal which directs posttranslational protein translocation via a Tet-secretion pathway. In one preferred embodiment, a secretion signal which directs posttranslational protein translocation may be identified in amino acid SEQ ID NO. 70 or homologous or similar Sec-secretion signal sequence which encodes an exemplary tat signal peptide for *E. coli* strain k12 periplasmic nitrate reductase.

Again, in a preferred embodiment, one or more of the FABP-carrier proteins may be selected from SEQ ID NO. 1-2, 21, and 74-86 and may be modified and expressed, preferably in a bacterial cell, to include a secretion signal which directs posttranslational protein translocation of the folded protein via a Tet-secretion pathway, such signal preferably being SEQ ID NO. 70 or homologous or similar Sec-secretion signal sequence. Such exportable FABP-carrier proteins may be translocated from a bacterial cell already having one or more bound cannabinoids, or other compounds. In alternative embodiments, an exportable FABP-carrier protein may be translocated from a bacterial cell where it may come into contact with, bind to, and solubilize one or more cannabinoids located outside in the cell, such as cannabinoids added to a cell culture supernatant. The exportable FABP-carrier proteins, having solubilized one or more target cannabinoids or other compounds identified herein may be further isolated.

In another embodiment, the invention includes a recombinant plant, or plant cell producing FABP-carrier proteins. The plant or plant cell can include at least one heterologous nucleic acid encoding a FABP-carrier, wherein the plant or plant cell is from a species of *Cannabis*. The plant or plant cell can include at least one heterologous nucleic acid encoding a FABP-carrier, wherein the plant or plant cell is from a species of *Nicotiana*. The plant or plant cell can include at least one heterologous nucleic acid encoding a FABP-carrier, wherein the plant or plant cell is from a species other than *Nicotiana*. The heterologous nucleic acid further can include a regulatory control element such as a promoter (e.g., a tissue-specific promoter such as leaves, roots, stems, or seeds).

A polypeptide can be expressed in monocot plants and/or dicot plants. Techniques for introducing nucleic acids into plants are known in the art, and include, without limitation, *Agrobacterium*-mediated transformation, viral vector-mediated transformation, electroporation, and particle gun transformation (also referred to as biolistic transformation). See, for example, U.S. Pat. Nos. 5,538,880; 5,204,253; 6,329,571; and 6,013,863; Richards et al., Plant Cell. Rep. 20:48-20 54 (2001); Somleva et al., Crop Sci. 42:2080-2087 (2002); Sinagawa-Garcia et al., Plant Mol Biol (2009) 70:487-498; and Lutz et al., Plant Physiol., 2007, Vol. 145, pp. 1201-1210. In some instances, intergenic transformation of plastids can be used as a method of introducing a polynucleotide into a plant cell. In some instances, the method of introduction of a polynucleotide into a plant comprises chloroplast transformation. In some instances, the leaves and/or stems can be the target tissue of the introduced polynucleotide. If a cell or cultured tissue is used as the recipient tissue for transformation, plants can be regenerated from transformed cultures if desired, by techniques known to those skilled in the art.

Other suitable methods for introduce polynucleotides include electroporation of protoplasts, polyethylene glycol-mediated delivery of naked DNA into plant protoplasts, direct gene transformation through imbibition (e.g., introducing a polynucleotide to a dehydrated plant), transformation into protoplasts (which can comprise transferring a polynucleotide through osmotic or electric shocks), chemical transformation (which can comprise the use of a polybrene-spermidine composition), microinjection, pollen-tube pathway transformation (which can comprise delivery of a polynucleotide to the plant ovule), transformation via liposomes, shoot apex method of transformation (which can comprise introduction of a polynucleotide into the shoot and regeneration of the shoot), sonication-assisted *Agrobacterium* transformation (SAAT) method of transformation, infiltration (which can comprise a floral dip, or injection by syringe into a particular part of the plant (e.g., leaf)), silicon-carbide mediated transformation (SCMT) (which can comprise the addition of silicon carbide fibers to plant tissue and the polynucleotide of interest), electroporation, and electrophoresis. Such expression may be from transient or stable transformations.

Additional embodiments also feature a method for producing FABP-carrier polypeptides in plants and preferably a plant cell in culture. The method includes culturing a recombinant plant cell in a culture medium under conditions that allow the FABP-carrier polypeptides to be secreted into the culture medium, the recombinant plant cell comprising at least one heterologous nucleic acid, the heterologous nucleic acid encoding a FABP-carrier polypeptide, wherein the nucleic acid sequence is operably linked to a promoter and optionally may further produce a fusion polypeptide comprising the signal peptide and the FABP-carrier polypeptide, and wherein upon secretion of the polypeptide from the plant cell into the culture medium, the signal peptide may be removed from the FABP-carrier polypeptide. The method further can include isolating the FABP-carrier polypeptides from the culture medium.

In another aspect of the invention, a FABP-carrier protein may be exported out of a plant cell through the action of a secretion signal where the FABP-carrier protein may be secreted via a plant protein secretion pathway. In a preferred embodiment, FABP-carrier may be coupled with an N-terminal signal peptide which may direct their translocation to the extracellular region via the Endoplasmic Reticulum-Golgi apparatus and the subsequent endomembrane system. In one preferred embodiment, a FABP-carrier protein may be generated in a plant, and preferably a plant cell culture, where it may be exported out of the cell and bind one or more cannabinoid or other compounds that may be present in the external cellular environment. In this embodiment, a FABP-carrier protein may be coupled with a secretion signal that may direct the carrier protein to be secreted from a plant cell via the Endoplasmic Reticulum-Golgi apparatus and the subsequent endomembrane system.

Again, in one preferred embodiment, a FABP-carrier may be modified to include at least one plant secretion signal that may facilitate translocation of transport of the protein out of a plant cell. In one embodiment, a FABP-carrier may be modified to include a secretion signal which directs. In one preferred embodiment, a secretion signal which directs protein translocation from a plant cell may be identified in amino acid SEQ ID NO. 71, which encodes an exemplary secretion signal from an extracellular *Arabidopsis* protease Ara12 (At5g67360). Additional examples include the amino acid SEQ ID NO. 72, which encodes an exemplary secretion signal from a barley (*Hordeum vulgare*) alpha amylase. Still further examples include the amino acid SEQ ID NO. 73, which encodes an exemplary secretion signal from a rice a-Amylase.

Again, in a preferred embodiment, one or more of the FABP-carrier carrier proteins may be selected from SEQ ID NO. 1-2, 21, and 74-86, and may be further modified and expressed, preferably in a plant cell, to include a secretion signal which directs protein translocation out of the plant cell, such signal preferably being SEQ ID NO. 71, 72-74. Such exportable FABP-carrier proteins may be translocated from a plant cell already having one or more bound cannabinoids, or other compounds. In alternative embodiments, an exportable FABP-carrier protein may be translocated from a plant cell where it may come into contact with, bind to, and solubilize one or more cannabinoids located outside in the cell, such as cannabinoids added to a cell culture supernatant. The exportable FABP-carrier protein, having solubilized one or more target cannabinoids or other compounds identified herein, may be further isolated.

In another embodiment, one or more of the FABP-carrier proteins may be secreted from a plant cell in culture using the Hydroxyproline-Glycosylation (Hyp-Glyco) technology. In this embodiment, one or more of the FABP-carrier carrier proteins may be selected from SEQ ID NO. 1-2, 21, and 74-86 and may be modified and expressed, preferably in a plant cell and further fused with Hyp-rich repetitive peptide (HypRP) tag that directs extensive Hyp-O-glycosylation in plant cells resulting in arabinogalactan polysaccharides populating this repetitive peptide fusion facilitating the secretion of the expressed protein from cultured plant cells.

In certain embodiments, a catalase enzyme may be co-expressed with cannabinoid biosynthesis genes and FABP-carrier proteins, as well as optionally FABP-transporters or other genes that may reduce cannabinoid biosynthesis toxicity and/or facilitate transport of the solubilized cannabinoids through or out of the cell. In one embodiment a heterologous catalase is selected from the group consisting of: the amino acid sequence SEQ ID NO. 6, the amino acid sequence SEQ ID NO. 7, the amino acid sequence SEQ ID NO. 8, the amino acid sequence SEQ ID NO. 9, the amino acid sequence SEQ ID NO. 10 and a sequence having at least 80% homology to amino acid sequence SEQ ID NO. 6, SEQ ID NO. 7, SEQ ID NO. 8, SEQ ID NO. 9 and SEQ ID NO. 10.

Another embodiment of the inventive technology provides for systems and methods of high-capacity cannabinoid solubilization coupled with cannabinoid biosynthesis in cannabinoid producing plants or plants engineered to produce cannabinoids. In this preferred embodiment, cannabinoid biosynthesis may be redirected from the plant's trichome to be localized in the plant cell's cytosol. In certain embodiments, a cytosolic cannabinoid production system may be established as directed in PCT/US18/24409 and PCT/US18/41710, both by the present inventors Sayre et al. (These applications are both incorporated by reference with respect to their disclosure related to cytosolic cannabinoid production and/or modification in whole, and plant cell systems).

In one embodiment, a cytosolic cannabinoid production and solubilization system may include the in vivo creation of one or more recombinant proteins that may allow cannabinoid biosynthesis to be localized to the cytosol where one or more heterologous FABP-carrier proteins may also be expressed and present in the cytosol. This inventive feature allows not only higher levels of cannabinoid production and accumulation, but efficient production of cannabinoids in suspension cell cultures. Even more importantly, this inventive feature allows cannabinoid production and accumulation without a trichome structure in whole plants, allowing cells that would not traditionally produce cannabinoids, such as cells in *Cannabis* leaves and stalks, to become cannabinoid-producing cells More specifically, in this preferred embodiment, one or more cannabinoid synthases may be modified to remove all or part of an N-terminal extracellular trichome targeting. An exemplary N-terminal trichome targeting sequence for THCA synthase is identified as SEQ ID NO. 11, while an N-terminal trichome targeting sequence for CBDA synthase is identified as SEQ ID NO. 12. Co-expression with this cytosolic-targeted synthase (for example SEQ ID NOs. 13-15) with a heterologous FABP-carrier protein, and preferably an engineered FABP-carrier protein, may allow the localization of cannabinoid synthesis, accumulation and solubilization to the cytosol. The FABP cannabinoid carrier proteins may be later isolated with their bound cannabinoid molecules through a water-based extraction process due to their solubility, as opposed to traditional chemical or supercritical $CO_2$ extractions methods. In this way, a cell culture of a cannabinoid producing plant may form a continuous production platform for solubilized cannabinoids.

As noted below, in certain embodiments cannabinoid biosynthesis may be coupled with cannabinoid glycosylation in a cell cytosol. For example, in one preferred embodiment a cytosol-target glycosyltransferase (for example SEQ ID NOs. 63-64) may be expressed in a cell, preferably a cannabinoid producing cell, and even more preferably a *Cannabis* cell.

Such cytosolic target enzymes may be co-expressed with heterologous catalase and cannabinoid transporters or other genes that may reduce cannabinoid biosynthesis toxicity and/or facilitate transport through or out of the cell. In one embodiment a heterologous catalase is selected from the group consisting of: the amino acid sequence SEQ ID NO. 6, the amino acid sequence SEQ ID NO. 7, the amino acid sequence SEQ ID NO. 8, the amino acid sequence SEQ ID NO. 9, the amino acid sequence SEQ ID NO. 10 and a sequence having at least 80% homology to amino acid sequence SEQ ID NO. 6, SEQ ID NO. 7, SEQ ID NO. 8, SEQ ID NO. 9 and SEQ ID NO. 10.

Such cytosolic target enzymes may also be co-expressed with one or more myb transcriptions factors that may enhance metabolite flux through the cannabinoid biosynthetic pathway which may increase cannabinoid production. In one embodiment a myb transcription factor may be endogenous to *Cannabis*, or an ortholog thereof. Examples of endogenous myb transcription factor may include SEQ ID NO. 16 and 17, or orthologs thereof. In one embodiment a myb transcription factor may be heterologous to *Cannabis*. A heterologous myb transcription factor may be selected from the group consisting of a nucleotide sequence that expresses: amino acid sequence SEQ ID NO. 18, amino acid sequence SEQ ID NO. 19, amino acid sequence SEQ ID NO. 20.

In an alternative embodiment, isolated heterologous FABP-carrier proteins may be added to a cell culture of a cannabinoid-producing plant, preferably a *Cannabis* suspension cell culture, having a cytosolic cannabinoid production system. In this preferred embodiment, one or more cannabinoid may be produced in the cytosol and transported into the surrounding culture media through passive or active transport mechanisms. Once the cannabinoids have been transported to the surrounding culture media, a quantity of FABP-carrier proteins may be added to the media and bind to and solubilize one or more cannabinoids. This media may then be removed and replenished, such that the solubilized cannabinoids bound to FABP-carrier proteins may be further isolated from the media as generally described herein. In one embodiment, the FABP-carrier proteins may be later isolated with their bound cannabinoid molecules through a water-based extraction process due to their solubility, as opposed to traditional chemical or super-critical $CO_2$ extractions methods. In this way, a cell culture of a cannabinoid producing plant may form a continuous production platform for solubilized cannabinoids.

Another embodiment of the invention may include the generation of an expression vector comprising this polynucleotide, namely a cannabinoid synthase lacking an N-terminal extracellular trichome targeting sequence and a heterologous FABP-carrier gene, for example a nucleotide sequence that encodes one or more of the amino acid sequences identified in SEQ ID NOs. 1-2, 21, and 74-86, as well as optionally one or more secretion signals as discussed herein, operably linked to a promoter. This expression vector may be used to create a genetically altered plant or parts thereof and its progeny comprising this polynucleotide operably linked to a promoter, wherein said plant or parts thereof and its progeny produce said proteins. For example, seeds and pollen contain this expression vector, a genetically altered plant cell comprising this expression vector such that said plant cell produces said chimeric protein. Another embodiment comprises a tissue culture comprising a plurality of the genetically altered plant cells having this expression vector.

One preferred embodiment of the invention may include a genetically altered cannabinoid-producing plant or cell expressing a cytosolic-targeted cannabinoid synthase protein having a cannabinoid synthase N-terminal extracellular targeting sequence (SEQ ID NOs. 11-12) inactivated or removed. In one embodiment, a cytosolic targeted THCA synthase (ctTHCAs) may be identified as SEQ ID NO. 13, while in another embodiment, cytosolic targeted CBDA synthase (cytCBDAs) are identified as SEQ ID NO. 14-15, respectively. Such cytosolic-targeted cannabinoid synthase proteins may be operably linked to a promoter. Another embodiment provides a method for constructing a genetically altered plant or part thereof having solubilization of cannabinoids in the plant's cytosol compared to a non-genetically altered plant or part thereof, the method comprising the steps of: introducing a polynucleotide encoding a cannabinoid synthase into a plant or part thereof to provide a genetically altered plant or part thereof, wherein the cannabinoid synthase N-terminal extracellular targeting sequence has been disrupted or removed and further expressing a polynucleotide encoding a cannabinoid-carrier FABPs, such as those identified in SEQ ID NO. 1-2, 21, and 74-86, or a homolog thereof.

Notably, in a preferred embodiment, one or more endogenous cannabinoid synthase genes may be disrupted and/or knocked out and replaced with cytosolic-targeted cannabinoid synthase proteins as described herein. The disrupted endogenous cannabinoid synthase gene(s) may be the same or different than the expressed cytosolic-targeted cannabinoid synthase protein. Methods of disrupting or knocking-out a gene are known in the art and could be accomplished by one of ordinary skill without undue experimentation.

In another embodiment, one or more endogenous cannabinoid synthase genes may be disrupted and/or knocked out in a *Cannabis* plant or suspension cell culture wherein one or more cannabinoid synthase genes has been disrupted and/or knocked out is selected from the group consisting of: a CBG synthase gene; a THCA synthase, a CBDA synthase, and a CBCA synthase. In this embodiment, the *Cannabis* plant or suspension cell culture may express a polynucleotide encoding one or more cannabinoid synthases having its trichome targeting sequence disrupted and/or removed which may be selected from the group consisting of: a CBG synthase gene having its trichome targeting sequence disrupted and/or removed; a THCA synthase having its trichome targeting sequence disrupted and/or removed; a CBDA synthase having its trichome targeting sequence disrupted and/or removed; and a CBCA synthase having its trichome targeting sequence disrupted and/or removed.

The current invention may further include systems, methods and compositions for the solubilization of cannabinoids, terpenoids and other short-chain fatty acid phenolic compounds in cell cultures. Exemplary cell cultures may include bacterial, yeast, plant, algae and fungi cell cultures. FABP-carrier may be coupled with secretion signals to allow such proteins to be exported from the cell culture into the surrounding media. In this embodiment, a FABP-carrier protein may be engineered to include a secretion signal that may allow it to be exported from a cell. In one preferred embodiment, one or more of sequences identified as SEQ ID NO. 1-19, and 74-86, may be coupled with a secretion signal. In one preferred embodiment, one or more of sequences identified as SEQ ID NO. 1-2, 21, and 74-86, may be coupled with the N-terminal secretion signal identified in SEQ ID NO. 3 or SEQ ID NO. 65. One exemplary exportable FABP-carrier protein may include SEQ ID NO. 4 or SEQ ID NO. 5 or a FABP-carrier protein engineered from SEQ ID NO. 4 or SEQ ID NO. 5 or may be coupled with the secretion signal identified as amino acid sequence SEQ ID NO. 66, to form an enhanced exportable a FABP-carrier protein being identified herein as SEQ ID NO. 67 and SEQ ID NO. 68. Naturally, such examples are meant to be illustrative of the type and number of exportable FABP-carrier and FABP-carrier proteins within the scope of the current invention.

Another aspect of the current invention may include systems, methods and compositions for the solubilization of cannabinoids, terpenoids and other short-chain fatty acid phenolic compounds in whole plants and plant cell cultures. In certain embodiments, such plants or cell cultures may be genetically modified to direct cannabinoid synthesis to the cytosol, as opposed to a trichome structure. Further, FABP-carrier proteins may be coupled with a secretion signal, preferable in a plant cell culture, to allow such proteins to be exported from the cell into the surrounding media. Expression of exportable and non-exportable FABP-carrier proteins may be co-expressed with one or more catalase and/or myb transcription factors Another embodiment of the inventive technology may include the generation of a powder containing one or more solubilized cannabinoids. In one preferred embodiment, cannabinoids, terpenes, and other short-chain fatty acid phenolic compounds may be solubilized by association with a FABP-carrier protein. FABP-carrier proteins, having solubilized a quantity of cannabinoids, may undergo lyophilisation, to form a FABP-carrier protein powder containing the solubilized cannabinoids. In a preferred embodiment, a FABP-carrier protein may solubilize a quantity of cannabinoids through one of the methods generally described herein and then may further undergo lyophilisation, to form a FABP-carrier protein powder containing the solubilized cannabinoids. This powder may have enhanced properties, such as enhanced cannabinoid affinity to provide greater retention and shelf-life to the cannabinoids in the powdered composition. Additionally, this cannabinoid infused powder may be reintroduced to a liquid such that the cannabinoids are re-dissolved in the liquid. This powder may be used, for example, by consumers that wish to add a quantity of one or more cannabinoids to a beverage or other consumable product. It may also be used for pharmaceutical preparations and for proper cannabinoid dosing. This type of soluble cannabinoid-infused powder may be used as a food additive, or even coupled with flavoring agents to be used as a beverage additive. The presence of the FABP-carrier proteins, as well as the enhanced cannabinoid affinity and binding capacity, may allow less powder to be used to achieve an equivalent dose, whether in a pharmaceutical or consumer beverage/consumable product.

Other embodiments may allow for the creation of high-concentration solutions of solubilized cannabinoids bound to FABP-carrier proteins. Such solutions may allow a user to generate liquid-based food and beverage additives of varying concentrations. Such solutions may further allow a user to generate liquid-based food and beverage additives of varying types of cannabinoids or combinations of cannabinoids and/or terpenes and the like. Due to the enhanced characteristics of certain FABP-carriers, in particular the enhanced ability to bind and solubilize greater numbers of individual cannabinoid molecules per protein chain, such solutions may achieve higher than normal concentrations of solubilized cannabinoids. Also, due to the enhanced affinity characteristics of certain FABP-carriers, liquid solutions having solubilized cannabinoids may achieve a longer-shelf life.

In another embodiment, the inventive technology may include novel systems, methods and compositions to decrease potential antigenicity for the FABP-carrier proteins. In one preferred embodiment, the recognition sequences of one or more FABP-carrier, or preferably FABP-carrier proteins that correspond to the formation of one or more post-translational glycosylation sites or motifs may be disrupted. In this embodiment, site-directed mutagenesis of recognition sequences that allow for post-translational glycosylation for the sequences identified as SEQ ID NO. 1-2, 21, and 74-86, or a homolog thereof may be accomplished. The removal of such glycosylation sites in a FABP-carrier may result in decreased antigenicity.

The inventive technology may further include novel engineered FABP-carrier proteins that may exhibit enhance cannabinoid affinity and/or novel affinity motifs allowing for a greater of number of individual cannabinoid compounds to be bound and solubilized at one time. In one preferred embodiment, the invention may include a pharmaceutical composition as active ingredient an effective amount or dose of one or more FABP-carrier proteins coupled with one or more cannabinoids, terpenes or other short-chain fatty acid phenolic compounds. In some instances, the active ingredient may be provided together with pharmaceutically tolerable adjuvants and/or excipients in the pharmaceutical composition. Such pharmaceutical composition may optionally be in combination with one or more further active ingredients. In one embodiment, one of the aforementioned FABP-carrier proteins coupled with one or more cannabinoids, terpenes or other short-chain fatty acid phenolic compounds may act as a prodrug. The term "prodrug" is taken to mean FABP-carrier proteins according to the invention which have been modified by, for example, the additional of novel cannabinoid affinity sites, or enhanced cannabinoid affinity sites, and wherein the FABP-carrier proteins are sterically modified in the organism to released the bound cannabinoid or other compound to form the therapeutically effective dose according to the invention. The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, and most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

As noted above, the present invention allows the scaled production of water-soluble or solubilized cannabinoids (the terms being generally used to denote a cannabinoid or other compound, such as a terpene of short-chain fatty acid phenolic compound that is water-soluble or may be dissolved in water). Because of this solubility, the invention allows for the addition of such solubilized cannabinoid to a variety of compositions without requiring oils and/or emulsions that are generally required to maintain the generally hydrophobic cannabinoid compounds in suspension. As a result, the present invention may allow for the production of a variety of compositions for the food and beverage industry, as well as pharmaceutical applications that do not required oils or emulsion suspensions and the like.

In one embodiment, the invention may include aqueous compositions containing one or more solubilized cannabinoids that may be introduced to a food or beverage. In a preferred embodiment, the invention may include an aqueous solution containing one or more solubilized cannabinoids. In this embodiment, one or more cannabinoids, terpenes, or other short-chain fatty acid phenolic compounds may be solubilized through binding to a FABP-carrier protein. Here, the solubilized cannabinoids may be generated in vivo as generally described herein, or in vitro. In additional embodiments, the solubilized cannabinoid may be an isolated non-psychoactive, such as CBD and the like. Such selection of one or more cannabinoids may be due to specific affinity specificities in a FABP-carrier protein for one cannabinoid over another. Moreover, in this embodiment, the aqueous solution may contain one or more of the following: saline, purified water, propylene glycol, deionized water, and/or an alcohol such as ethanol, as well as a pH buffer that may allow the aqueous solution to be maintained at a pH below 7.4. Additional embodiments may include the addition of an acid or base, such as formic acid, or ammonium hydroxide.

In another embodiment, the invention may include a consumable food additive having at least one FABP-carrier solubilized cannabinoid. In this embodiment, one or more cannabinoids, terpenes or other short-chain fatty acid phenolic compounds may be solubilized through binding to a FABP-carrier protein. Here, the solubilized cannabinoids may be generated in vivo as generally described herein, or in vitro. This consumable food additive may further include one or more food additive polysaccharides, such as dextrin and/or maltodextrin, as well as an emulsifier. Example emulsifiers may include, but not be limited to: gum arabic, modified starch, pectin, xanthan gum, gum ghatti, gum tragacanth, fenugreek gum, mesquite gum, mono-glycerides and di-glycerides of long chain fatty acids, sucrose monoesters, sorbitan esters, polyethoxylated glycerols, stearic acid, palmitic acid, mono-glycerides, di-glycerides, propylene glycol esters, lecithin, lactylated mono- and di-glycerides, propylene glycol monoesters, polyglycerol esters, diacetylated tartaric acid esters of mono- and di-glycerides, citric acid esters of monoglycerides, stearoyl-2-lactylates, polysorbates, succinylated monoglycerides, acetylated monoglycerides, ethoxylated monoglycerides, quillaia, whey protein isolate, casein, soy protein, vegetable protein, pullulan, sodium alginate, guar gum, locust bean gum, tragacanth gum, tamarind gum, carrageenan, furcellaran, Gellan gum, psyllium, curdlan, konjac mannan, agar, and cellulose derivatives, or combinations thereof.

The consumable food additive of the invention may be a homogenous composition and may further comprise a flavoring agent. Exemplary flavoring agents may include: sucrose (sugar), glucose, fructose, sorbitol, mannitol, corn syrup, high fructose corn syrup, saccharin, aspartame, sucralose, acesulfame potassium (acesulfame-K), neotame. The consumable food additive of the invention may also contain one or more coloring agents. Exemplary coloring agents may include: FD&C Blue Nos. 1 and 2, FD&C Green No. 3, FD&C Red Nos. 3 and 40, FD&C Yellow Nos. 5 and 6, Orange B, Citrus Red No. 2, annatto extract, beta-carotene, grape skin extract, cochineal extract or carmine, paprika oleoresin, caramel color, fruit and vegetable juices, saffron, Monosodium glutamate (MSG), hydrolyzed soy protein, autolyzed yeast extract, disodium guanylate or inosinate. In one embodiment, this powdered lyophilized FABP-carrier protein, having solubilized a quantity of cannabinoids, may be a food additive. In certain preferred embodiments, one or more flavoring agents may be added to a quantity of powdered or lyophilized FABP-carrier proteins having solubilized a quantity of cannabinoids.

The consumable food additive of the invention may also contain one or more surfactants, such as glycerol monostearate and polysorbate 80. The consumable food additive of the invention may also contain one or more preservatives. Exemplary preservatives may include ascorbic acid, citric acid, sodium benzoate, calcium propionate, sodium erythorbate, sodium nitrite, calcium sorbate, potassium sorbate, BHA, BHT, EDTA, or tocopherols. The consumable food additive of the invention may also contain one or more nutrient supplements, such as: thiamine hydrochloride, riboflavin, niacin, niacinamide, folate or folic acid, beta carotene, potassium iodide, iron or ferrous sulfate, alpha tocopherols, ascorbic acid, Vitamin D, amino acids, multi-vitamin, fish oil, co-enzyme Q-10, and calcium.

In one embodiment, the invention may include a consumable fluid containing at least one FABP-carrier solubilized cannabinoid, terpenoid, or other short chain fatty acid phenolic compound. In one preferred embodiment, this consumable fluid may be added to a drink or beverage to infuse it with the solubilized cannabinoid generated through binding to a FABP-carrier protein, in an in vitro, ex vivo, or in vivo system as generally herein described, or through an in vitro process. The consumable fluid may include a food additive polysaccharide such as maltodextrin and/or dextrin, which may further be in an aqueous form and/or solution. For example, in one embodiment, an aqueous maltodextrin solution may include a quantity of sorbic acid and an acidifying agent to provide a food grade aqueous solution of maltodextrin having a pH of 2-4 and a sorbic acid content of 0.02-0.1% by weight.

In certain embodiments, the consumable fluid may include water, as well as an alcoholic beverage; a non-alcoholic beverage, a noncarbonated beverage, a carbonated beverage, a cola, a root beer, a fruit-flavored beverage, a citrus-flavored beverage, a fruit juice, a fruit-containing beverage, a vegetable juice, a vegetable containing beverage, a tea, a coffee, a dairy beverage, a protein containing beverage, a shake, a sports drink, an energy drink, and a flavored water. The consumable fluid may further include at least one additional ingredient, including but not limited to: xanthan gum, cellulose gum, whey protein hydrolysate, ascorbic acid, citric acid, malic acid, sodium benzoate, sodium citrate, sugar, phosphoric acid, and water. In certain embodiments, the consumable fluid of the invention may be generated by addition of a quantity of solubilized cannabinoid in powder of liquid form as generally described herein to an existing consumable fluid, such as a branded beverage or drink.

In one embodiment, the invention may include a consumable gel having at least one FABP-carrier solubilized cannabinoid and gelatin in an aqueous solution. In a preferred embodiment, the consumable gel may include a one or more cannabinoids, terpenes or other short-chain fatty acid phenolic compounds solubilized through binding to a FABP-carrier protein. Here, the solubilized cannabinoids may be generated in vivo as generally described herein, or in vitro.

Additional embodiments may include a liquid composition having at least one cannabinoid solubilized by a FABP-carrier protein, in a first quantity of water; and at least one of: xanthan gum, cellulose gum, whey protein hydrolysate, ascorbic acid, citric acid, malic acid, sodium benzoate, sodium citrate, sugar, phosphoric acid, and/or a sugar alcohol. In one preferred embodiment, the composition may further include a quantity of ethanol. Here, the amount of solubilized cannabinoids may include: less than 10 mass % water; more than 95 mass % water; about 0.1 mg to about 1000 mg of the solubilized cannabinoid; about 0.1 mg to about 500 mg of the solubilized cannabinoid; about 0.1 mg to about 200 mg of the solubilized cannabinoid; about 0.1 mg to about 100 mg of the solubilized cannabinoid; about 0.1 mg to about 100 mg of the solubilized cannabinoid; about 0.1 mg to about 10 mg of the solubilized cannabinoid; about 0.5 mg to about 5 mg of the solubilized cannabinoid; about 1 mg/kg to 5 mg/kg (body weight) in a human of the solubilized cannabinoid.

In alternative embodiments, the composition may include at least one cannabinoid solubilized by a FABP-carrier protein, in the range of 50 mg/L to 300 mg/L; at least one FABP-carrier solubilized cannabinoid in the range of 50 mg/L to 100 mg/L; at least one FABP-carrier solubilized cannabinoid in the range of 50 mg/L to 500 mg/L; at least one FABP-carrier solubilized cannabinoid over 500 mg/L; at least one FABP-carrier solubilized cannabinoid under 50 mg/L. Additional embodiments may include one or more of the following additional components: a flavoring agent; a coloring agent; and/or caffeine.

In one embodiment, the invention may include a liquid composition having at least one cannabinoid solubilized by a FABP-carrier protein, being solubilized in said first quantity of water and a first quantity of ethanol in a liquid state. In a preferred embodiment, a first quantity of ethanol in a liquid state may be between 1% to 20% weight by volume of the liquid composition. In this embodiment, a solubilized cannabinoid may include a cannabinoid solubilized by a FABP-carrier protein, a terpenoid/terpene solubilized by a FABP-carrier protein, or a mixture of both. Such solubilized cannabinoids may be generated in an in vivo, ex vivo, and/or in vitro system as herein identified. In a preferred embodiment, the ethanol or ethyl alcohol component may be up to about ninety-nine point nine-five percent (99.95%) by weight and the solubilized cannabinoid about zero point zero five percent (0.05%) by weight.

Examples of the preferred embodiment may include liquid ethyl alcohol compositions having at least one cannabinoid solubilized by a FABP-carrier protein, wherein said ethyl alcohol has a proof greater than 100, and/or less than 100. Additional examples of a liquid composition containing ethyl alcohol and at least one cannabinoid solubilized by a FABP-carrier protein, may include, beer, wine and/or distilled spirits.

Additional embodiments of the invention may include a chewing gum composition having a first quantity of at least one cannabinoid solubilized by a FABP-carrier protein. In a preferred embodiment, a chewing gum composition may further include a gum base comprising a buffering agent selected from the group consisting of acetates, glycinates, phosphates, carbonates, glycerophosphates, citrates, borates, and mixtures thereof. Additional components may include at least one sweetening agent and at least one flavoring agent. As noted above, in a preferred embodiment, at least one cannabinoid solubilized by a FABP-carrier protein, may be generated in vitro, or in vivo respectively.

In one embodiment, the chewing gum composition described above may include:
 0.01 to 1% by weight of at least one FABP-carrier solubilized cannabinoid;
 25 to 85% by weight of a gum base;
 10 to 35% by weight of at least one sweetening agent; and
 1 to 10% by weight of a flavoring agent.

Here, such flavoring agents may include: menthol flavor, eucalyptus, mint flavor and/or L-menthol. Sweetening agents may include one or more of the following: xylitol, sorbitol, isomalt, aspartame, sucralose, acesulfame potassium, and saccharin. Additional preferred embodiment may include a chewing gum having a pharmaceutically acceptable excipient selected from the group consisting of: fillers, disintegrants, binders, lubricants, and antioxidants. The chewing gum composition may further be non-disintegrating and also include one or more coloring and/or flavoring agents.

The invention may further include a composition for a cannabinoid infused solution comprising essentially of: water and/or purified water, at least one cannabinoid solubilized by a FABP-carrier protein and at least one flavoring agent. A FABP-carrier solubilized cannabinoid infused solution of the invention may further include a sweetener selected from the group consisting of: glucose, sucrose, invert sugar, corn syrup, stevia extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same. Additional components of the solubilized cannabinoid infused solution may include, but not be limited to: sodium chloride, sodium chloride solution, glycerin, a coloring agent, and a demulcent. As to this last potential component, in certain embodiments, a demulcent may include: pectin, glycerin, honey, methylcellulose, and/or propylene glycol. As noted above, in a preferred embodiment, a FABP-carrier solubilized cannabinoid may include at least one FABP-carrier solubilized cannabinoid wherein such solubilized cannabinoids may be generated in vivo, ex vivo, and/or in vitro respectively.

The invention may further include a composition for a FABP-carrier solubilized cannabinoid infused anesthetic solution having water, or purified water, at least one FABP-carrier solubilized cannabinoid, and at least one oral anesthetic. In a preferred embodiment, an anesthetic may include benzocaine, and/or phenol in a quantity of between 0.1% to 15% volume by weight.

Additional embodiments may include a FABP-carrier solubilized cannabinoid infused anesthetic solution having a sweetener which may be selected from the group consisting of: glucose, sucrose, invert sugar, corn syrup, stevia extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same. Additional components of a FABP-carrier solubilized cannabinoid infused solution may include, but not be limited to: sodium chloride, sodium chloride solution, glycerin, a coloring agent, and a demulcent. In a preferred embodiment, a demulcent may be selected from the group consisting of: pectin, glycerin, honey, methylcellulose, and propylene glycol. As noted above, in a preferred embodiment, a FABP-carrier solubilized cannabinoid may include at least one cannabinoid solubilized by a FABP-carrier protein. In this embodiment, such solubilized cannabinoids may have been generated in vivo, ex vivo, and/or in vitro respectively.

The invention may further include a composition for a hard lozenge for rapid delivery of solubilized cannabinoids through the oral mucosa. In this embodiment, such a hard lozenge composition may include: a crystalized sugar base and at least one FABP-carrier solubilized cannabinoid, wherein the hard lozenge has moisture content between 0.1 to 2%. In this embodiment, the solubilized cannabinoid may be added to the sugar base when it is in a liquefied form and prior to the evaporation of the majority of water content. Such a hard lozenge may further be referred to as a candy.

In a preferred embodiment, a crystalized sugar base may be formed from one or more of the following: sucrose, invert sugar, corn syrup, and isomalt or a combination of the same. Additional components may include at least one acidulant. Examples of acidulants may include, but not be limited to: citric acid, tartaric acid, fumaric acid, and malic acid. Additional components may include at least one pH adjustor. Examples of pH adjustors may include, but not be limited to: calcium carbonate, sodium bicarbonate, and magnesium trisilicate.

In another preferred embodiment, the composition may include at least one anesthetic. Example of such anesthetics may include benzocaine, and phenol. In this embodiment, first quantity of anesthetic may be between 1 mg to 15 mg per lozenge. Additional embodiments may include a quantity of menthol. In this embodiment, such a quantity of menthol may be between 1 mg to 20 mg. The hard lozenge composition may also include a demulcent, for example: pectin, glycerin, honey, methylcellulose, propylene glycol, and glycerin. In this embodiment, a demulcent may be in a quantity between 1 mg to 10 mg. As noted above, in a preferred embodiment, a FABP-carrier solubilized cannabinoid may include at least one cannabinoid solubilized by a FABP-carrier protein. In this embodiment, such solubilized cannabinoid may have been generated in vivo and/or in vitro respectively.

The invention may include a chewable lozenge for rapid delivery of solubilized cannabinoids through the oral mucosa. In a preferred embodiment, the compositions may include: a glycerinated gelatin base, at least one sweetener, and at least one FABP-carrier solubilized cannabinoid dissolved in a first quantity of water. In this embodiment, a sweetener may include a sweetener selected from the group consisting of: glucose, sucrose, invert sugar, corn syrup, stevia extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same.

Additional components may include at least one acidulant. Examples of acidulants may include, but not be limited to: citric acid, tartaric acid, fumaric acid, and malic acid. Additional components may include at least one pH adjustor. Examples of pH adjustors may include, but not be limited to: calcium carbonate, sodium bicarbonate, and magnesium trisilicate.

In another preferred embodiment, the composition may include at least one anesthetic. Example of such anesthetics may include benzocaine and phenol. In this embodiment, first quantity of anesthetic may be between 1 mg to 15 mg per lozenge. Additional embodiments may include a quantity of menthol. In this embodiment, such a quantity of menthol may be between 1 mg to 20 mg. The chewable lozenge composition may also include a demulcent, for example: pectin, glycerin, honey, methylcellulose, propylene glycol, and glycerin. In this embodiment, a demulcent may be in a quantity between 1 mg to 10 mg. As noted above, in a preferred embodiment, a FABP-carrier solubilized cannabinoid may include at least one cannabinoid solubilized by a FABP-carrier protein. In this embodiment, such solubilized cannabinoid may be generated in vivo, ex vivo, or in vitro respectively.

The invention may include a soft lozenge for rapid delivery of solubilized cannabinoids through the oral mucosa. In a preferred embodiment, the compositions may include: a polyethylene glycol base, at least one sweetener, and at least one FABP-carrier solubilized cannabinoid, referring generally to a cannabinoid solubilized by a FABP-carrier, dissolved in a first quantity of water. In this embodiment, a sweetener may include sweetener selected from the group consisting of: glucose, sucrose, invert sugar, corn syrup, stevia extract powder, stevioside, steviol, aspartame, saccharin, saccharin salts, sucralose, potassium acetosulfam, sorbitol, xylitol, mannitol, erythritol, lactitol, alitame, miraculin, monellin, and thaumatin or a combination of the same. Additional components may include at least one acidulant. Examples of acidulants may include, but not be limited to: citric acid, tartaric acid, fumaric acid, and malic acid. Additional components may include at least one pH adjustor. Examples of pH adjustors may include, but not be limited to: calcium carbonate, sodium bicarbonate, and magnesium trisilicate.

In another preferred embodiment, the composition may include at least one anesthetic. Example of such anesthetics may include benzocaine and phenol. In this embodiment, first quantity of anesthetic may be between 1 mg to 15 mg per lozenge. Additional embodiments may include a quantity of menthol. In this embodiment, such a quantity of menthol may be between 1 mg to 20 mg. The soft lozenge composition may also include a demulcent, for example: pectin, glycerin, honey, methylcellulose, propylene glycol, and glycerin. In this embodiment, a demulcent may be in a quantity between 1 mg to 10 mg. As noted above, in a preferred embodiment, a FABP-carrier solubilized cannabinoid may include at least one cannabinoid solubilized by a FABP-carrier protein. In this embodiment, such solubilized cannabinoid may be generated in vivo, ex vivo, or in vitro respectively.

In another embodiment, the invention may include a tablet or capsule consisting essentially of a solubilized cannabinoid and a pharmaceutically acceptable excipient. Examples may include solid, semi-solid, and aqueous excipients such as: maltodextrin, whey protein isolate, xanthan gum, guar gum, diglycerides, monoglycerides, carboxymethyl cellulose, glycerin, gelatin, polyethylene glycol and water-based excipients. In this embodiment, the cannabinoid solubilized by a FABP-carrier protein, may have an improved shelf-life, composition stability, and bioavailability upon injection.

In a preferred embodiment, a solubilized cannabinoid may include at least one cannabinoid solubilized by a FABP-carrier protein. In this embodiment, such solubilized cannabinoids may be generated in vivo, ex vivo, or in vitro respectively. Examples of such in vivo systems being generally described herein, including in plant, as well as cell culture systems including *Cannabis* cell culture, tobacco cell culture, bacterial cell cultures, fungal cell cultures, and yeast cell culture systems. In one embodiment, a tablet or capsule may include an amount of solubilized cannabinoid of 5 milligrams or less. Alternative embodiments may include an amount of solubilized cannabinoid between 5 milligrams and 200 milligrams. Still other embodiments may include a tablet or capsule having an amount of solubilized cannabinoid that is more than 200 milligrams. Still other embodiments may include a tablet or capsule having an amount of solubilized cannabinoid that is more than 500 milligrams.

The invention may further include a method of manufacturing and packaging a solubilized cannabinoid dosage, consisting of the following steps: 1) preparing a fill solution with a desired concentration of one or more FABP-carrier solubilized cannabinoid in a liquid carrier wherein said cannabinoid is dissolved in said liquid carrier; 2) encapsulating said fill solution in capsules; 3) packaging said capsules in a closed packaging system; and 4) removing atmospheric air from the capsules. In one embodiment, the step of removing atmospheric air consists of purging the packaging system with an inert gas, such as, for example, nitrogen gas, such that said packaging system provides a room temperature stable product. In one preferred embodiment, the packaging system may include a plaster package, which may be constructed of material that minimizes exposure to moisture and air.

In one embodiment, a preferred liquid carrier may include a water-based carrier, such as for example an aqueous sodium chloride solution. In a preferred embodiment, a solubilized cannabinoid may include at least one cannabinoid solubilized by a FABP-carrier protein. In this embodiment, such solubilized cannabinoids may be generated in vivo, ex vivo, or in vitro respectively. In one embodiment, a desired solubilized cannabinoid concentration may be about 1-10% w/w, while in other embodiments it may be about 1.5-6.5% w/w. Alternative embodiments may include an amount of solubilized cannabinoid between 5 milligrams and 200 milligrams. Still, other embodiments may include a tablet or capsule having amount of solubilized cannabinoid that is more than 200 milligrams. Other embodiments may include a tablet or capsule having an amount of solubilized cannabinoid that is more than 500 milligrams.

The invention may include an oral pharmaceutical solution, such as a sub-lingual spray having solubilized cannabinoids and a liquid carrier. One embodiment may include a solubilized cannabinoid, 30-33% w/w water, about 50% w/w alcohol, 0.01% w/w butylated hydroxylanisole (BHA) or 0.1% w/w ethylenediaminetetraacetic acid (EDTA) and 5-21% w/w co-solvent, having a combined total of 100%, wherein said co-solvent is selected from the group consisting of propylene glycol, polyethylene glycol, and combinations thereof, and wherein said solubilized cannabinoid is at least one cannabinoid solubilized by a FABP-carrier protein. In an alternative embodiment, such a oral pharmaceutical solution may consist essentially of 0.1 to 5% w/w of said solubilized cannabinoid, about 50% w/w alcohol, 5.5% w/w propylene glycol, 12% w/w polyethylene glycol and 30-33% w/w water. In a preferred composition, the alcohol component may be ethanol.

The invention may include an oral pharmaceutical solution, such as a sublingual spray, consisting essentially of about 0.1% to 1% w/w solubilized cannabinoids, about 50% w/w alcohol, 5.5% w/w propylene glycol, 12% w/w polyethylene glycol, 30-33% w/w water, 0.01% w/w butylated hydroxyanisole, having a combined total of 100%, and wherein said solubilized cannabinoid is at least one cannabinoid solubilized by a FABP-carrier protein, that may be further generated in vivo, ex vivo, or in vitro respectively. In an alternative embodiment, such a oral pharmaceutical solution may consist essentially of 0.54% w/w solubilized cannabinoid, 31.9% w/w water, 12% w/w polyethylene glycol 400, 5.5% w/w propylene glycol, 0.01% w/w butylated hydroxyanisole, 0.05% w/w sucralose, and 50% w/w alcohol, wherein the a the alcohol components may be ethanol.

The invention may include a solution for nasal and/or sublingual administration of a solubilized cannabinoid including: 1) an excipient of propylene glycol, ethanol anhydrous, or a mixture of both; and 2) a solubilized cannabinoid which may include at least one cannabinoid solubilized by a FABP-carrier protein, that may be further generated in vivo, ex vivo, or in vitro respectively. In a preferred embodiment, the composition may further include a topical decongestant, which may include phenylephrine hydrochloride, Oxymetazoline hydrochloride, and Xylometazoline in certain preferred embodiments. The composition may further include an antihistamine, and/or a steroid. Preferably, the steroid component is a corticosteroid selected from the group consisting of: neclomethasone dipropionate, budesonide, ciclesonide, flunisolide, fluticasone furoate, fluticasone propionate, mometasone, and triamcinolone acetonide. In alternative embodiments, the solution for nasal and/or sublingual administration of a solubilized cannabinoid may further comprise at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, and propylene glycol.

The invention may further include an aqueous solution for nasal and/or sublingual administration of a solubilized cannabinoid comprising: a water and/or saline solution; and a solubilized cannabinoid which may include at least one cannabinoid solubilized by a FABP-carrier protein that may be further generated in vivo, ex vivo, or in vitro, respectively. In a preferred embodiment, the composition may further include a topical decongestant, which may include phenylephrine hydrochloride, Oxymetazoline hydrochloride, and Xylometazoline in certain preferred embodiments. The composition may further include an antihistamine and/or a steroid. Preferably, the steroid component is a corticosteroid selected from the group consisting of: neclomethasone dipropionate, budesonide, ciclesonide, flunisolide, fluticasone furoate, fluticasone propionate, mometasone, and triamcinolone acetonide. In alternative embodiments, the aqueous solution may further comprise at least one of the following: benzalkonium chloride solution, benzyl alcohol, boric acid, purified water, sodium borate, polysorbate 80, phenylethyl alcohol, microcrystalline cellulose, carboxymethylcellulose sodium, dextrose, dipasic, sodium phosphate, edetate disodium, monobasic sodium phosphate, or propylene glycol.

The invention may include a topical formulation for the transdermal delivery of solubilized cannabinoids. In a preferred embodiment, a topical formulation for the transdermal delivery of solubilized cannabinoids which may include at least one cannabinoid solubilized by a FABP-carrier protein, and a pharmaceutically acceptable excipient. The solubilized cannabinoids may be generated in vivo, ex vivo, or in vitro respectively. Preferably a pharmaceutically acceptable excipient may include one or more: gels, ointments, cataplasms, poultices, pastes, creams, lotions, plasters and jellies or even polyethylene glycol. Additional embodiments may further include one or more of the following components: a quantity of capsaicin; a quantity of benzocaine; a quantity of lidocaine; a quantity of camphor; a quantity of benzoin resin; a quantity of methylsalicilate; a quantity of triethanolamine salicylate; a quantity of hydrocortisone; or a quantity of salicylic acid.

The invention may include a gel for transdermal administration of a solubilized cannabinoid which may include at least one cannabinoid solubilized by a FABP-carrier protein, and which may be generated in vivo, ex vivo, or in vitro. In this embodiment, the mixture preferably contains from 15% to about 90% ethanol, about 10% to about 60% buffered aqueous solution or water, about 0.1 to about 25% propylene glycol, from about 0.1 to about 20% of a gelling agent, from about 0.1 to about 20% of a base, from about 0.1 to about 20% of an absorption enhancer and from about 1% to about 25% polyethylene glycol, and a solubilized cannabinoid as generally described herein.

In another embodiment, the invention may further include a transdermal composition having a pharmaceutically effective amount of a solubilized cannabinoid for delivery of the cannabinoid to the bloodstream of a user. This transdermal composition may include a pharmaceutically acceptable excipient and at least one FABP-carrier solubilized cannabinoid, which may include at least one cannabinoid solubilized by a FABP-carrier protein, and which may be generated in vivo, ex vivo, or in vitro, wherein the solubilized cannabinoid is capable of diffusing from the composition into the bloodstream of the user. In a preferred embodiment, a pharmaceutically acceptable excipient to create a transdermal dosage form selected from the group consisting of: gels, ointments, cataplasms, poultices, pastes, creams, lotions, plasters and jellies. The transdermal composition may further include one or more surfactants. In one preferred embodiment, the surfactant may include a surfactant-lecithin organogel, which may further be present in an amount of between about 95% and about 98% w/w. In an alternative embodiment, a surfactant-lecithin organogel comprises lecithin and PPG-2 myristyl ether propionate and/or high molecular weight polyacrylic acid polymers. The transdermal composition may further include a quantity of isopropyl myristate.

The invention may further include transdermal composition having one or more permeation enhancers to facilitate transfer of the solubilized cannabinoid across a dermal layer. In a preferred embodiment, a permeation enhancer may include one or more of the following: propylene glycol monolaurate, diethylene glycol monoethyl ether, an oleoyl macrogolglyceride, a caprylocaproyl macrogolglyceride, and an oleyl alcohol.

The invention may also include a liquid cannabinoid liniment composition consisting of water, isopropyl alcohol solution, and a solubilized cannabinoid, which may include at least one cannabinoid solubilized by a FABP-carrier protein, and which may be generated in vivo, ex vivo, or in vitro. This liquid cannabinoid liniment composition may further include approximately 97.5% to about 99.5% by weight of 70% isopropyl alcohol solution and from about 0.5% to about 2.5% by weight of a solubilized cannabinoid mixture.

Based on the improved solubility and other physical properties, as well as cost advantages, improved cannabinoid affinity and capacity, extended shelf-life, and scalability of the inventions in vivo, ex vivo, or in vitro solubilized cannabinoid production platform, the invention may include one or more commercial infusions. For example, commercially available products, such a lip balm, soap, shampoos, lotions, creams, and cosmetics may be infused with one or more solubilized cannabinoids.

The invention may further include a novel composition that may be used to supplement a cigarette or other tobacco-based product. In this embodiment, the composition may include at least one FABP-carrier solubilized cannabinoid in a powder as already described, or dissolved in an aqueous solution. This aqueous solution may be introduced to a tobacco product, such as a cigarette and/or a tobacco leaf such that the aqueous solution may evaporate generating a cigarette and/or a tobacco leaf that contains the aforementioned solubilized cannabinoid(s), which may further have been generated in vivo as generally described herein.

In one embodiment, the invention may include one or more methods of treating a medical condition in a mammal. In this embodiment, the novel method may include of administering a therapeutically effective amount of a solubilized cannabinoid, such as an in vivo, ex vivo, or in vitro cannabinoid solubilized by a FABP-carrier protein, wherein the medical condition is selected from the group consisting of: obesity, post-traumatic stress syndrome, anorexia, nausea, emesis, pain, wasting syndrome, HIV-wasting, chemotherapy induced nausea and vomiting, alcohol use disorders, anti-tumor, amyotrophic lateral sclerosis, glioblastoma multiforme, glioma, increased intraocular pressure, glaucoma, Cannabis use disorders, Tourette's syndrome, dystonia, multiple sclerosis, inflammatory bowel disorders, arthritis, dermatitis, Rheumatoid arthritis, systemic lupus erythematosus, anti-inflammatory, anti-convulsant, anti-psychotic, anti-oxidant, neuroprotective, anti-cancer, immunomodulatory effects, peripheral neuropathic pain, neuropathic pain associated with post-herpetic neuralgia, diabetic neuropathy, shingles, burns, actinic keratosis, oral cavity sores and ulcers, post-episiotomy pain, psoriasis, pruritis, contact dermatitis, eczema, bullous dermatitis herpetiformis, exfoliative dermatitis, mycosis fungoides, pemphigus, severe erythema multiforme (e.g., Stevens-Johnson syndrome), seborrheic dermatitis, ankylosing spondylitis, psoriatic arthritis, Reiter's syndrome, gout, chondrocalcinosis, joint pain secondary to dysmenorrhea, fibromyalgia, musculoskeletal pain, neuropathic-postoperative complications, polymyositis, acute nonspecific tenosynovitis, bursitis, epicondylitis, post-traumatic osteoarthritis, synovitis, and juvenile rheumatoid arthritis. In a preferred embodiment, the pharmaceutical composition may be administered by a route selected from the group consisting of: transdermal, topical, oral, buccal, sublingual, intra-venous, intra-muscular, vaginal, rectal, ocular, nasal and follicular. The amount of solubilized cannabinoids may be a therapeutically effective amount, which may be determined by the patient's age, weight, medical condition cannabinoid-delivered, route of delivery, and the like. In one embodiment, a therapeutically effective amount may be 50 mg or less of a solubilized cannabinoid. In another embodiment, a therapeutically effective amount may be 50 mg or more of a solubilized cannabinoid.

It should be noted that for any of the above composition, unless otherwise stated, an effective amount of solubilized cannabinoids may include amounts between: 0.01 mg to 0.1 mg; 0.01 mg to 0.5 mg; 0.01 mg to 1 mg; 0.01 mg to 5 mg; 0.01 mg to 10 mg; 0.01 mg to 25 mg; 0.01 mg to 50 mg; 0.01 mg to 75 mg; 0.01 mg to 100 mg; 0.01 mg to 125 mg; 0.01 mg to 150 mg; 0.01 mg to 175 mg; 0.01 mg to 200 mg; 0.01 mg to 225 mg; 0.01 mg to 250 mg; 0.01 mg to 275 mg; 0.01 mg to 300 mg; 0.01 mg to 225 mg; 0.01 mg to 350 mg; 0.01 mg to 375 mg; 0.01 mg to 400 mg; 0.01 mg to 425 mg; 0.01 mg to 450 mg; 0.01 mg to 475 mg; 0.01 mg to 500 mg; 0.01 mg to 525 mg; 0.01 mg to 550 mg; 0.01 mg to 575 mg; 0.01 mg to 600 mg; 0.01 mg to 625 mg; 0.01 mg to 650 mg; 0.01 mg to 675 mg; 0.01 mg to 700 mg; 0.01 mg to 725 mg; 0.01 mg to 750 mg; 0.01 mg to 775 mg; 0.01 mg to 800 mg; 0.01 mg to 825 mg; 0.01 mg to 950 mg; 0.01 mg to 875 mg; 0.01 mg to 900 mg; 0.01 mg to 925 mg; 0.01 mg to 950 mg; 0.01 mg to 975 mg; 0.01 mg to 1000 mg; 0.01 mg to 2000 mg; 0.01 mg to 3000 mg; 0.01 mg to 4000 mg; 01 mg to 5000 mg; 0.01 mg to 0.1 mg/kg; 0.01 mg to 0.5 mg/kg; 01 mg to 1 mg/kg; 0.01 mg to 5 mg/kg; 0.01 mg to 10 mg/kg; 0.01 mg to 25 mg/kg; 0.01 mg to 50 mg/kg; 0.01 mg to 75 mg/kg; and 0.01 mg to 100 mg/kg.

The FABP solubilized cannabinoid compounds of the present invention are useful for a variety of therapeutic applications. For example, the compounds are useful for treating or alleviating symptoms of diseases and disorders involving CB1 and CB2 receptors, including appetite loss, nausea and vomiting, pain, multiple sclerosis and epilepsy. For example, they may be used to treat pain (i.e. as analgesics) in a variety of applications including but not limited to pain management. In additional embodiments, such solubilized cannabinoids may be used as an appetite suppressant. Additional embodiments may include administering the FABP solubilized cannabinoid compounds of the invention.

By "treating," the present inventors mean that the compound is administered in order to alleviate symptoms of the disease or disorder being treated. Those of skill in the art will recognize that the symptoms of the disease or disorder that is treated may be completely eliminated or may simply be lessened. Further, the compounds may be administered in combination with other drugs or treatment modalities, such as with chemotherapy or other cancer-fighting drugs.

Implementation may generally involve identifying patients suffering from the indicated disorders and administering the compounds of the present invention in an acceptable form by an appropriate route. The exact dosage to be administered may vary depending on the age, gender, weight, and overall health status of the individual patient, as well as the precise etiology of the disease. However, in general, for administration in mammals (e.g. humans), dosages in the range of from about 0.01 to about 300 mg of compound per kg of body weight per 24 hr., and more preferably about 0.01 to about 100 mg of compound per kg of body weight per 24 hr., may be effective.

Administration may be oral or parenteral, including intravenously, intramuscularly, subcutaneously, intradermal injection, intraperitoneal injection, etc., or by other routes (e.g. transdermal, sublingual, oral, rectal and buccal delivery, inhalation of an aerosol, etc.). In a preferred embodiment of the invention, the solubilized cannabinoid are provided orally or intravenously.

The compounds, for example a cannabinoid solubilized by a FABP-carrier, may be administered in the pure form or in a pharmaceutically acceptable formulation including suitable elixirs, binders, and the like (generally referred to as a "secondary carrier") or as pharmaceutically acceptable salts (e.g. alkali metal salts such as sodium, potassium, calcium or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the compounds may be formulated with aqueous or oil based vehicles. Water may be used as the carrier for the preparation of compositions (e.g. injectable compositions), which may also include conventional buffers and agents to render the composition isotonic. Other potential additives and other materials (preferably those which are generally regarded as safe [GRAS]) include: colorants; flavorings; surfactants (TWEEN, oleic acid, etc.); solvents, stabilizers, elixirs, and binders or encapsulants (lactose, liposomes, etc). Solid diluents and excipients include lactose, starch, conventional disintegrating agents, coatings and the like. Preservatives such as methyl paraben or benzalkium chloride may also be used. Depending on the formulation, it is expected that the active composition will consist of about 1% to about 99% of the composition and the secondary carrier will constitute about 1% to about 99% of the composition. The pharmaceutical compositions of the present invention may include any suitable pharmaceutically acceptable additives or adjuncts to the extent that they do not hinder or interfere with the therapeutic effect of the active compound.

The administration of the solubilized compounds of the present invention may be intermittent, bolus dose, or at a gradual or continuous, constant, or controlled rate to a patient. In addition, the time of day and the number of times per day that the pharmaceutical formulation is administered may vary and are best determined by a skilled practitioner such as a physician. Further, the effective dose can vary depending upon factors such as the mode of delivery, gender, age, and other conditions of the patient, as well as the extent or progression of the disease. The compounds may be provided alone, in a mixture containing two or more of the compounds, or in combination with other medications or treatment modalities.

Notably, as used herein, "FABP," or "FABP-carrier" or "FABP-carrier protein" explicitly includes any FABPs that have affinity for a cannabinoid, terpene or other short-chain fatty acid phenolic compounds. Additionally, "FABP-carrier" may be generically used to explicitly describe FABP-like proteins, regardless of family or classification, that exhibit an affinity for a cannabinoid, terpene or other short-chain fatty acid phenolic compounds. The term "FABP-carrier" explicitly encompasses FABP-like proteins, FABP homologs, and FABP orthologs having affinity for a cannabinoid, terpene or other short-chain fatty acid phenolic compounds. As used herein a "FABP," or "FABP-carrier" or "FABP-carrier protein" specifically encompasses wilt-type, as well as "engineered" or "engineered FABP-carrier" or "engineered FABP-carrier proteins." As used herein, a "engineered" or "engineered FABP-carrier" or "engineered FABP-carrier protein" may be a FABP-carrier protein that may bind or, to have some affinity for a target compound, such as a cannabinoid, that may be further modified to have enhanced affinity, or additional affinity sites for the target compound, such as a mutation that may modulate a characteristic of that protein, such as cannabinoid binding characteristic, or antigenicity characteristic, or for example may be modified to form a chimera or fusions protein through the addition of a secretion signal. In one embodiment, as "engineered" may be established through bioinformatics approaches such as computational docking, binding affinity estimation, and molecular dynamics simulations. Additional embodiments may include the site-directed mutations of an "engineered," "engineered FABP-carrier," or "engineered carrier protein" may also be determined by through bioinformatics approaches such as computational docking, binding affinity estimation, and molecular dynamics simulations as well as in high-throughput binding assays and the like. According to some embodiments of the present invention, a suitable computational platform for executing the method presented herein, in one embodiment may include the generation of an engineered FABP-carrier, may include the Rosetta™ software suite platform, publically available from the "Rosetta@home" at the Baker laboratory, University of Washington, U.S.A. Briefly, Rosetta™ is a molecular modeling software package for understanding protein structures, protein design, protein docking, protein-DNA and protein-protein interactions. The Rosetta software contains multiple functional modules, including RosettaAbinitio, RosettaDesign, RosettaDock, RosettaAntibody, RosettaFragments, RosettaNMR, RosettaDNA, RosettaRNA, RosettaLigand, RosettaSymmetry, and more. According to some embodiments of the present invention, a suitable computational platform for executing the method presented herein, is the SMINA software suite platform, which generally encompasses a version of AutoDock Vina specially optimized to support high-throughput scoring and user-specified custom scoring functions. Additional embodiment may further include software suites for AutoDock Vina, and idock.

As used herein, the term "enhanced" as used to described the binding of a cannabinoid to a FABP-carrier, or engineered FABP-carrier means having a binding affinity greater then wild-type binding affinity.

As used herein, a "cannabinoid" is a chemical compound (such as cannabinol, THC or cannabidiol) that is found in the plant species *Cannabis* among others like: *Echinacea; Acmella Oleracea; Helichrysum umbraculigerum; Radula marginata* (Liverwort) and *Theobroma cacao*, and metabolites and synthetic analogues thereof that may or may not have psychoactive properties. Cannabinoids therefore include (without limitation) compounds (such as THC) that have high affinity for the cannabinoid receptor (for example Ki<250 nM), and compounds that do not have significant affinity for the cannabinoid receptor (such as cannabidiol, CBD). Cannabinoids also include compounds that have a characteristic dibenzopyran ring structure (of the type seen in THC) and cannabinoids which do not possess a pyran ring (such as cannabidiol). Hence a partial list of cannabinoids includes THC, CBD, dimethyl heptylpentyl cannabidiol (DMHP-CBD), 6,12-dihydro-6-hydroxy-cannabidiol (described in U.S. Pat. No. 5,227,537, incorporated by reference); (3S,4R)-7-hydroxy-Δ6-tetrahydrocannabinol homologs and derivatives described in U.S. Pat. No. 4,876,276, incorporated by reference; (+)-4-[4-DMH-2,6-diacetoxy-phenyl]-2-carboxy-6,6-dimethylbicyclo[3.1.1]hept-2-en, and other 4-phenylpinene derivatives disclosed in U.S. Pat. No. 5,434,295, which is incorporated by reference; and cannabidiol (−)(CBD) analogs such as (−)CBD-monomethylether, (−)CBD dimethyl ether; (−)CBD diacetate; (−)3'-acetyl-CBD monoacetate; and ±AF11, all of which are disclosed in Consroe et al., J. Clin. Pharmacol. 21:428S-436S, 1981, which is also incorporated by reference. Many other cannabinoids are similarly disclosed in Agurell et al., Pharmacol. Rev. 38:31-43, 1986, which is also incorporated by reference.

As claimed herein, the term "cannabinoid" may also be generically applied to describe all cannabinoids, short-chain fatty acid phenolic compounds, endocannabinoids, phytocannabinoids, as well as terpenes that have affinity for one or more FABP-carrier proteins, or their homologs as generally described herein. Moreover, as used herein, the term "solubilized cannabinoid" describes a "cannabinoid," that binds to or interacts with one or more FABP-carrier proteins, or their homologs as generally described herein.

Examples of cannabinoids are tetrahydrocannabinol, cannabidiol, cannabigerol, cannabichromene, cannabicyclol, cannabivarin, cannabielsoin, cannabicitran, cannabigerolic acid, cannabigerolic acid monomethylether, cannabigerol monomethylether, cannabigerovarinic acid, cannabigerovarin, cannabichromenic acid, cannabichromevarinic acid, cannabichromevarin, cannabidolic acid, cannabidiol monomethylether, cannabidiol-C4, cannabidivarinic acid, cannabidiorcol, delta-9-tetrahydrocannabinolic acid A, delta-9-tetrahydrocannabinolic acid B, delta-9-tetrahydrocannabinolic acid-C4, delta-9-tetrahydrocannabivarinic acid, delta-9-tetrahydrocannabivarin, delta-9-tetrahydrocannabiorcolic acid, delta-9-tetrahydrocannabiorcol, delta-7-cis-iso-tetrahydrocannabivarin, delta-8-tetrahydrocannabiniolic acid, delta-8-tetrahydrocannabinol, cannabicyclolic acid, cannabicylovarin, cannabielsoic acid A, cannabielsoic acid B, cannabinolic acid, cannabinol methylether, cannabinol-C4, cannabinol-C2, cannabiorcol, 10-ethoxy-9-hydroxy-delta-6a-tetrahydrocannabinol, 8,9-dihydroxy-delta-6a-tetrahydrocannabinol, cannabitriolvarin, ethoxycannabitriolvarin, dehydrocannabifuran, cannabifuran, cannabichromanon, cannabicitran, 10-oxo-delta-6a-tetrahydrocannabinol, delta-9-cis-tetrahydrocannabinol, 3,4,5,6-tetrahydro-7-hydroxy-alpha-alpha-2-trimethyl-9-n-propyl-2,6-methano-2H-1-benzoxocin-5-methanol-cannabiripsol, trihydroxy-delta-9-tetrahydrocannabinol, and cannabinol. Examples of cannabinoids within the context of this disclosure include tetrahydrocannabinol and cannabidiol.

The term "endocannabinoid" refers to compounds including arachidonoyl ethanolamide (anandamide, AEA), 2-arachidonoyl ethanolamide (2-AG), 1-arachidonoyl ethanolamide (1-AG), and docosahexaenoyl ethanolamide (DHEA, synaptamide), oleoyl ethanolamide (OEA), eicsapentaenoyl ethanolamide, prostaglandin ethanolamide, docosahexaenoyl ethanolamide, linolenoyl ethanolamide, 5(Z),8(Z),11(Z)-eicosatrienoic acid ethanolamide (mead acid ethanolamide), heptadecanoul ethanolamide, stearoyl ethanolamide, docosaenoyl ethanolamide, nervonoyl ethanolamide, tricosanoyl ethanolamide, lignoceroyl ethanolamide, myristoyl ethanolamide, pentadecanoyl ethanolamide, palmitoleoyl ethanolamide, docosahexaenoic acid (DHA). Particularly preferred endocannabinoids are AEA, 2-AG, 1-AG, and DHEA.

Terpenoids a.k.a. isoprenoids, are a large and diverse class of naturally occurring organic chemicals similar to terpenes, derived from five-carbon isoprene units assembled and modified in a number of varying configurations. Most are multi-cyclic structures that differ from one another not only in functional groups but also in their basic carbon skeletons. Terpenoids are essential for plant metabolism, influencing general development, herbivory defense, pollination and stress response. These compounds have been extensively used as flavoring and scenting agents in cosmetics, detergents, food and pharmaceutical products. They also display multiple biological activities in humans, such as anti-inflammatory, anti-microbial, antifungal and antiviral.

*Cannabis* terpenoid profiles define the aroma of each plant and share the same precursor (geranyl pyrophosphate) and the same synthesis location (glandular trichomes) as phytocannabinoids. The terpenoids most commonly found in *Cannabis* extracts include: limonine, myrcene, alpha-pinene, linalool, beta-caryophyllene, caryophyllene oxide, nerolidol, and phytol. Terpenoids are mainly synthesized in two metabolic pathways: mevalonic acid pathway (a.k.a. HMG-CoA reductase pathway, which takes place in the cytosol) and MEP/DOXP pathway (a.k.a. The 2-C-methyl-D-erythritol 4-phosphate/1-deoxy-D-xylulose 5-phosphate pathway, non-mevalonate pathway, or mevalonic acid-independent pathway, which takes place in plastids). Geranyl pyrophosphate (GPP), which is used by *Cannabis* plants to produce cannabinoids, is formed by condensation of dimethylallyl pyrophosphate (DMAPP) and isopentenyl pyrophosphate (IPP) via the catalysis of GPP synthase. Alternatively, DMAPP and IPP are ligated by FPP synthase to produce farnesyl pyrophosphate (FPP), which can be used to produce sesquiterpenoids. Geranyl pyrophospliate (GPP) can also be converted into monoterpenoids by limonene synthase.

Some examples of terpenes, and their classification, are as follows. Hemiterpenes: Examples of hemiterpenes, which do not necessarily have an odor, are 2-methyl-1,3-butadiene, hemialboside, and hymenoside. Monoterpenes: pinene, α-pinene, β-pinene, cis-pinane, trans-pinane, cis-pinanol, trans-pinanol (Erman and Kane (2008) Chem. Biodivers. 5:910-919), limonene; linalool; myrcene; eucalyptol; α-phellandrene; β-phellandrene; a-ocimene; β-ocimene, cis-ocimene, ocimene, Δ-3-carene; fenchol; sabinene, borneol, isoborneol, camphene, camphor, phellandrene, a-phellandrene, a-terpinene, geraniol, linalool, nerol, menthol, myrcene, terpinolene, a-terpinolene, β-terpinolene, γ-terpinolene, Δ-terpinolene, α-terpineol, and trans-2-pinanol. Sesquiterpenes: caryophyllene, caryophyllene oxide, humulene, a-humulene, a-bisabolene; β-bisabolene; santalol; selinene; nerolidol, bisabolol; a-cedrene, β-cedrene, β-eudesmol, eudesm-7(ll)-en-4-ol, selina-3,7(ll)-diene, guaiol, valencene, a-guaiene, β-guaiene, Δ-guaiene, guaiene, farnesene, a-farnesene, β-farnesene, elemene, a-elemene, β-elemene, γ-elemene, Δ-elemene, germacrene, germacrene A, germacrene B, germacrene C, germacrene D, and germacrene E. Diterpenes: oridonin, phytol, and isophytol. Triterpenes: ursolic acid, oleanolic acid. Terpenoids, also known as isoprenoids, are a large and diverse class of naturally occurring organic chemicals similar to terpenes, derived from five-carbon isoprene units assembled and modified in a number of ways. Most are multicyclic structures that differ from one another not only in functional groups but also in their basic carbon skeletons. Plant terpenoids are used extensively for their aromatic qualities.

The term "prodrug" refers to a precursor of a biologically active pharmaceutical agent (drug). Prodrugs must undergo a chemical or a metabolic conversion to become a biologically active pharmaceutical agent. A prodrug can be converted ex vivo to the biologically active pharmaceutical agent by chemical transformative processes. In vivo, a prodrug is converted to the biologically active pharmaceutical agent by the action of a metabolic process, an enzymatic process, or a degradative process that removes the prodrug moiety to form the biologically active pharmaceutical agent.

As used herein, the term "transformation" refers to the transfer of one or more nucleic acid molecule(s) into a cell. A plant is "transformed" or "genetically modified" by a nucleic acid molecule transduced into the plant when the nucleic acid molecule becomes stably replicated by the plant. As used herein, the term "transformation" or "genetically modified" encompasses all techniques by which a nucleic acid molecule can be introduced into an organism or cell. A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. (Thus, the term "homologous proteins" is defined to mean that the two proteins have similar amino acid sequences). More specifically, in certain embodiments, the term "homologous" with regard to a contiguous nucleic acid sequence, refers to contiguous nucleotide sequences that hybridize under appropriate conditions to the reference nucleic acid sequence. For example, homologous sequences may have from about 75%-100, or more generally 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions. For example, in one embodiment, SEQ ID NO. 1 is 84% homologous to *Homo sapiens* FABP1 identified as SEQ ID NO. 21), and would fall within the range of a homolog. In another embodiment, expression optimization, for example for a mammalian FABP, to be expressed in yeast may be considered homologous and having a variable sequence identity due to the variable codon positions. Additional embodiments may also include homology to include redundant nucleotide codons.

The term "homolog", used with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

The term "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. An "inducible" promoter may be a promoter which may be under environmental control. Tissue-specific, tissue-preferred, cell type specific, and inducible promoters constitute the class of "non-constitutive" promoters. A "constitutive" promoter is a promoter which may be active under most environmental conditions or in most cell or tissue types.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; or can be regulatory in nature, etc. There are various types of vectors including virus, plasmid, bacteriophages, cosmids, and bacteria.

As is known in the art, different organisms preferentially utilize different codons for generating polypeptides. Such "codon usage" preferences may be used in the design of nucleic acid molecules encoding the proteins of the invention in order to optimize expression in a particular host cell system.

An "expression vector" is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette." In contrast, as described in the examples herein, a "cassette" is a polynucleotide containing a section of an expression vector of this invention. The use of a cassette assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is operably linked to an expression control sequence(s) (e.g., a promoter and, optionally, an enhancer) when the expression control sequence controls and regulates the transcription and/or translation of that polynucleotide sequence.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Because of the degeneracy of nucleic acid codons, one can use various different polynucleotides to encode identical polypeptides. The Table below, contains information about which nucleic acid codons encode which amino acids.
Amino Acid Nucleic Acid Codons

| Amino Acid | Nucleic Acid Codons |
| --- | --- |
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

Moreover, because the proteins are described herein, one can chemically synthesize a polynucleotide which encodes these polypeptides described herein. Oligonucleotides and polynucleotides that are not commercially available can be chemically synthesized e.g., according to the solid phase phosphoramidite triester method first described by Beaucage and Caruthers, Tetrahedron Letts. 22:1859-1862 (1981), or using an automated synthesizer, as described in Van Devanter et al., Nucleic Acids Res. 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, J. Chrom. 255:137-149 (1983).

The term "plant" or "plant system" includes whole plants, plant organs, progeny of whole plants or plant organs, embryos, somatic embryos, embryo-like structures, protocorms, protocorm-like bodies (PLBs), and culture and/or suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The invention may also include Cannabaceae and other *Cannabis* strains, such as *C. sativa* generally.

The term "expression," as used herein, or "expression of a coding sequence" (for example, a gene or a transgene) refer to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

The term "nucleic acid" or "nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNA), whether charged or discharged with a corresponding acetylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment," or more generally "segment," will be understood by those in the art as a functional term that includes both genomic sequences, ribosomal RNA sequences, transfer RNA sequences, messenger RNA sequences, operon sequences, and smaller engineered nucleotide sequences that encoded or may be adapted to encode, peptides, polypeptides, or proteins.

The term "gene" or "sequence" refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (down-stream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide. It should be noted that any reference to a SEQ ID or sequence specifically encompasses that sequence, as well as all corresponding sequences that correspond to that first sequence. For example, for any amino acid sequence identified, the specific specifically includes all compatible nucleotide (DNA and RNA) sequences that give rise to that amino acid sequence or protein, and vice versa.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivative nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hair-pinned, circular, and padlocked conformations.

As used herein with respect to DNA, the term "coding sequence," "structural nucleotide sequence," or "structural nucleic acid molecule" refers to a nucleotide sequence that is ultimately translated into a polypeptide, via transcription and mRNA, when placed under the control of appropriate regulatory sequences. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; EST; and recombinant nucleotide sequences.

The term "sequence identity" or "identity," as used herein in the context of two nucleic acid or polypeptide sequences, refers to the residues in the two sequences that are the same when aligned for maximum correspondence over a specified comparison window.

The term "recombinant" when used with reference, e.g., to a cell, or nucleic acid, protein, or vector, indicates that the cell, organism, nucleic acid, protein, or vector has been modified by the introduction of a heterologous nucleic acid or protein, or the alteration of a native nucleic acid or protein, or that the cell is derived from a cell so modified. Thus, for example, recombinant cells may express genes that are not found within the native (nonrecombinant or wild-type) form of the cell or express native genes that are otherwise abnormally expressed—over-expressed, under expressed, or not expressed at all.

The terms "approximately" and "about" refer to a quantity, level, value, or amount that varies by as much as 30%, or in another embodiment by as much as 20%, and in a third embodiment by as much as 10% to a reference quantity, level, value or amount. As used herein, the singular form "a," "an," and "the" include plural references unless the context clearly dictates otherwise.

As used herein, "heterologous" or "exogenous" in reference to a nucleic acid is a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention. By "host cell" is meant a cell which contains an introduced nucleic acid construct and supports the replication and/or expression of the construct.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: Genetic Modification of FABP and Predictive Binding Affinity Determination Utilizing in Silico Directed Evolution In one embodiment the present invention demonstrated an increase water solubility, transport, and storage stability of cannabinoids, terpenoids, and volatiles through the use of genetically modified, or engineered fatty acid-binding proteins (FABPs). The present inventors selected FABP isoforms 1, 3, 5, and 7 as an initial set of exemplary targets as these have been experimentally shown to bind the cannabinoids THC and CBD. The present inventors generated crystal structures for the human versions of these four FABP isoforms, while corresponding homology models were built for various mammalian versions (cow, pig, sheep, horse, rabbit, and chicken) as well as for a plant-based FABP identified from a rainforest tree named *Rhodamnia argentea*. Computational docking of CBD was then combined with in silico directed evolution (via random mutagenesis) to identify FABP variants with enhanced binding affinity to CBD as an exemplary cannabinoids. FABP variants were screened using two separate scoring schemes. Variants selected for experimental testing comprised those with the best predicted binding affinities based on wither score. As generally shown in Table 1, exemplary top predicted CBD-binding variants were identified for chicken FABP7 (SEQ ID NOs. 74, and 79-80), pig FABP1 (SEQ ID NOs. 75, and 81-82), horse FABP1 (SEQ ID NOs. 76, and 83-84) and plant FABP (SEQ ID NOs. 77, and 85-86). The top scoring variants using either scoring scheme were selected, leading to 8 engineered FABP sequences provided for experimental testing.

Example 2: FABP Binding to Cannabinoids by ANS Displacement

Figure 5A:
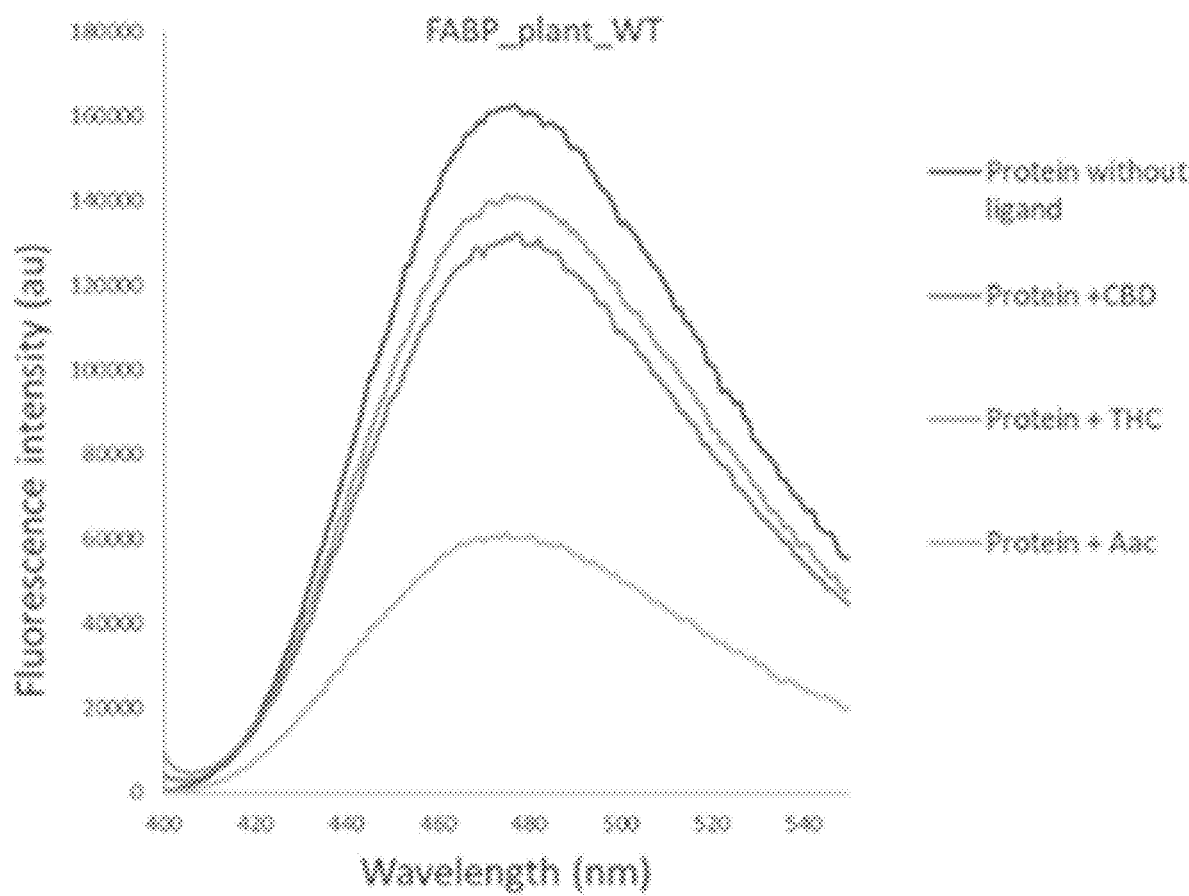
FIG. 5. Binding of the plant wild type (A) and engineered (B and C) FABP to cannabinoids by ANS displacement. Both wild-type and engineered proteins bind to CBD and THC.
Figure 5B:
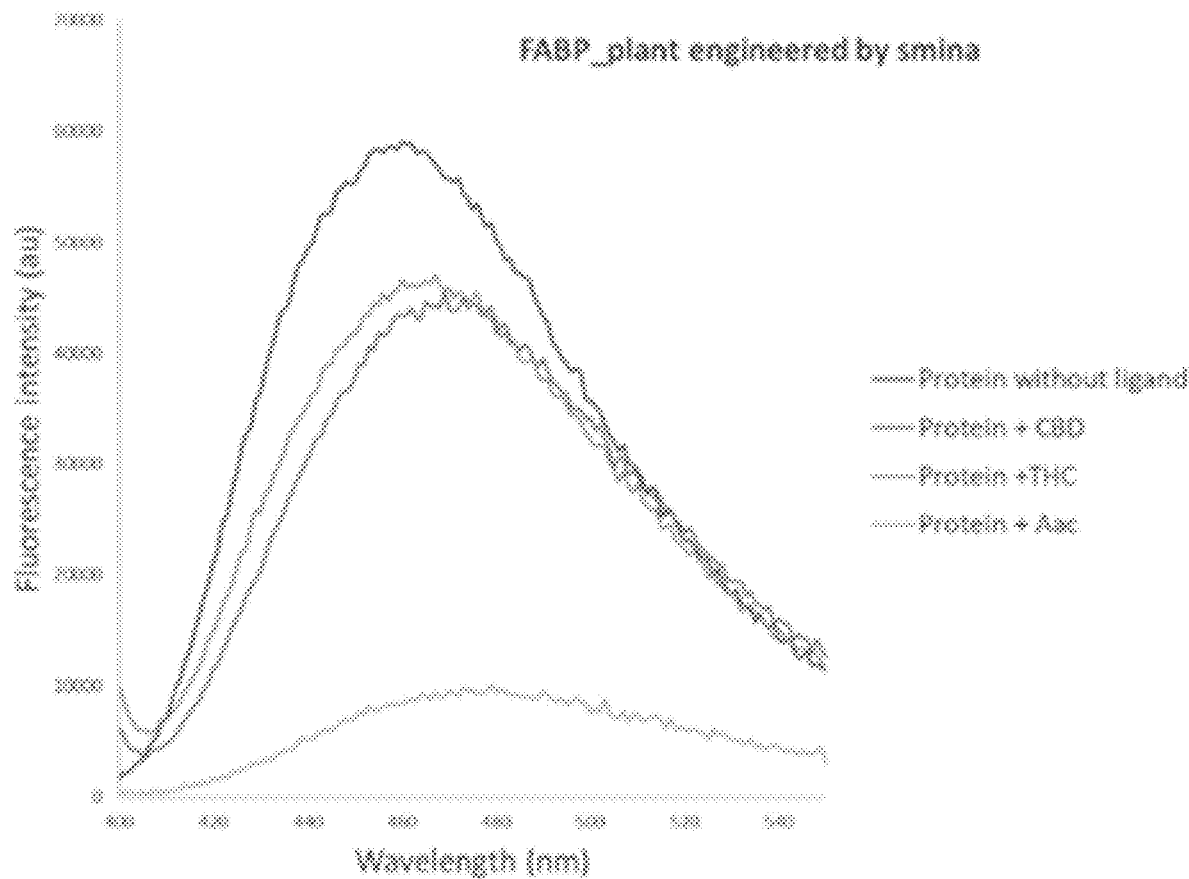
Figure 5C:
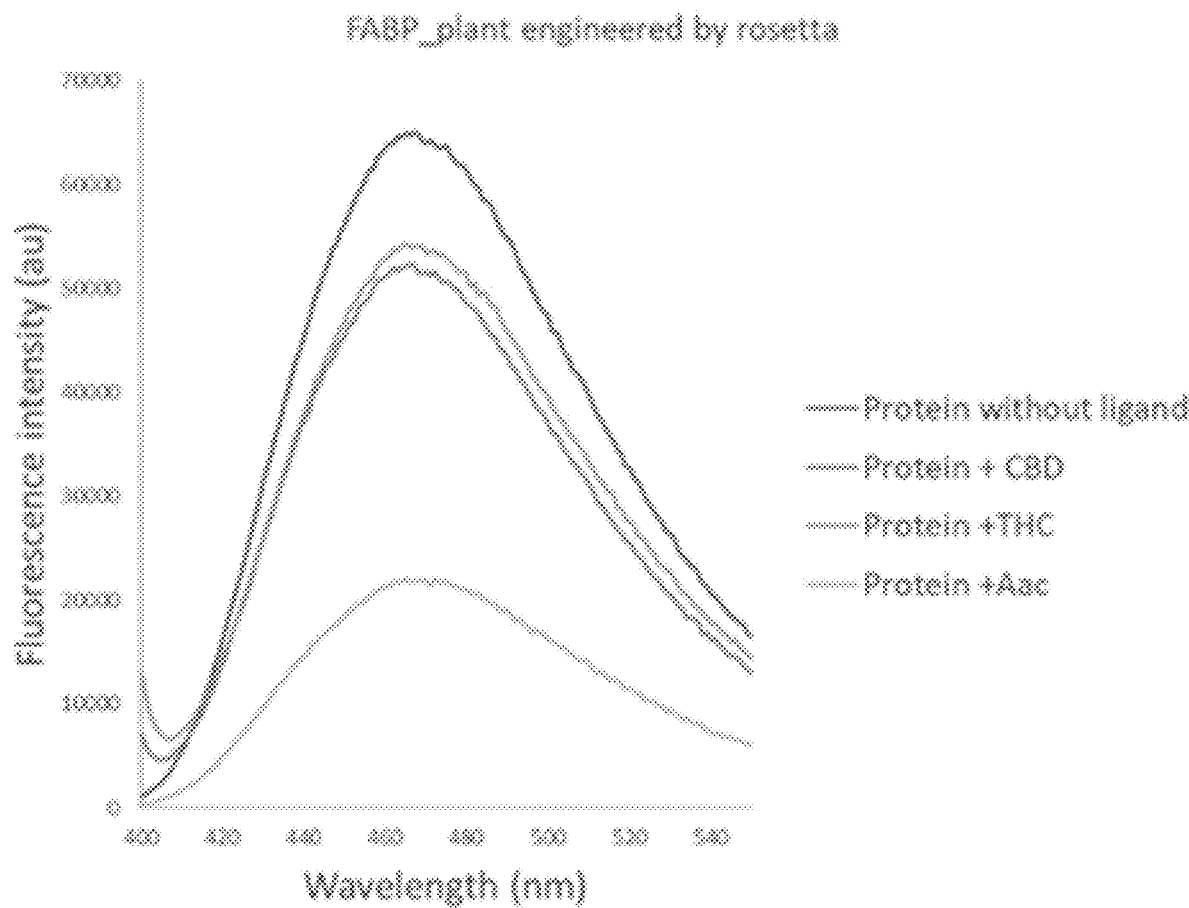
Figure 6A:
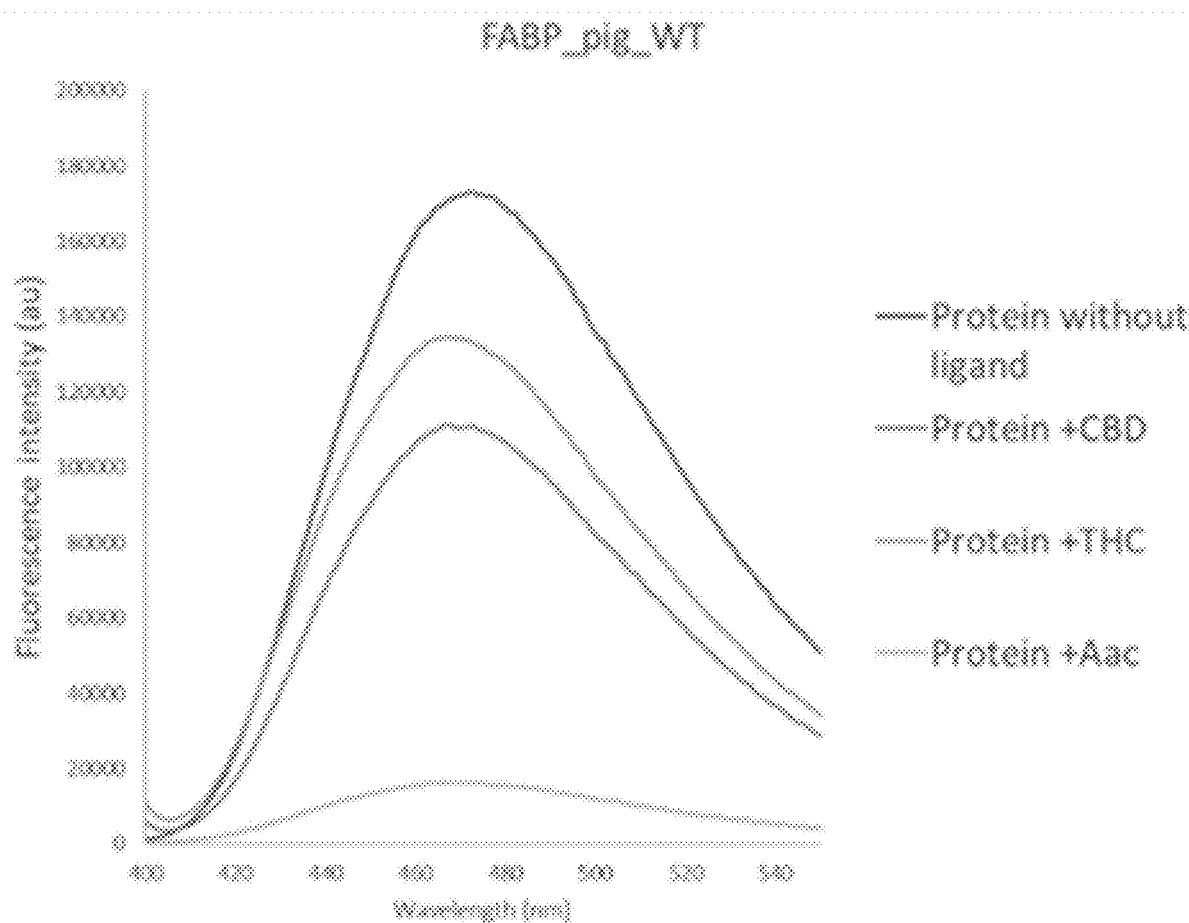
FIG. 6. Binding of pig wild type (A) and engineered (B and C) FABP to CBD and THC by ANS displacement.
Figure 6B:
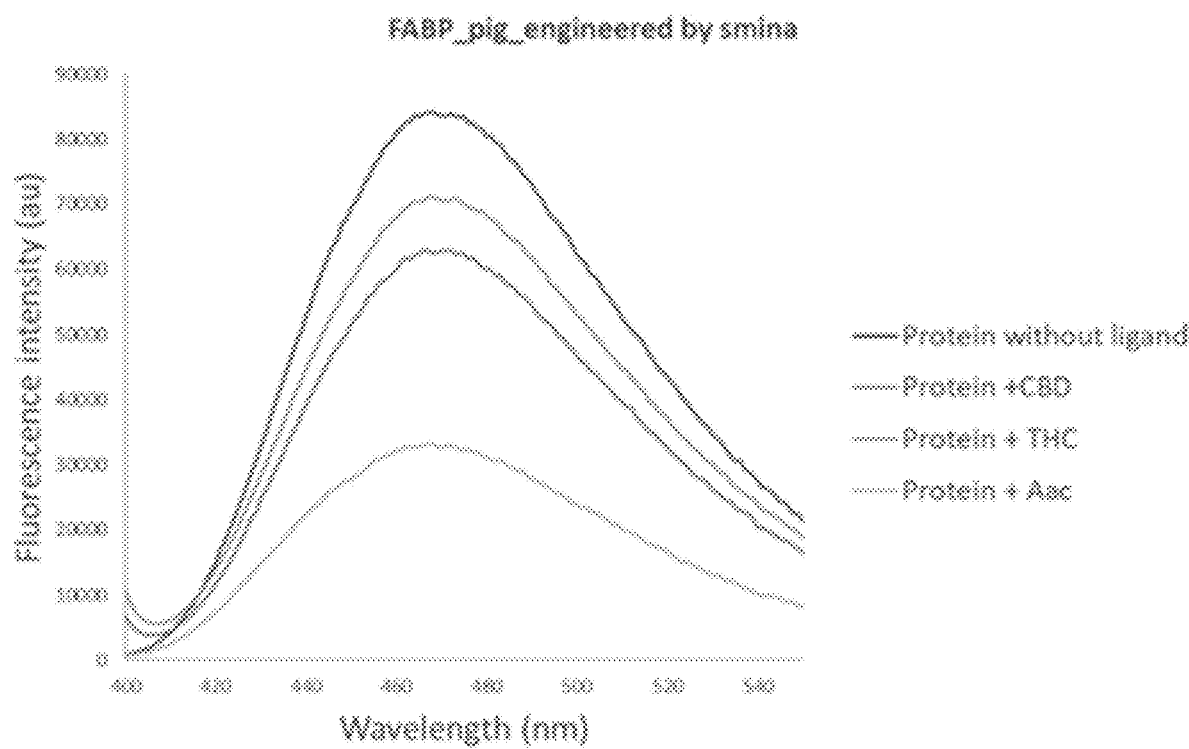
Figure 6C:
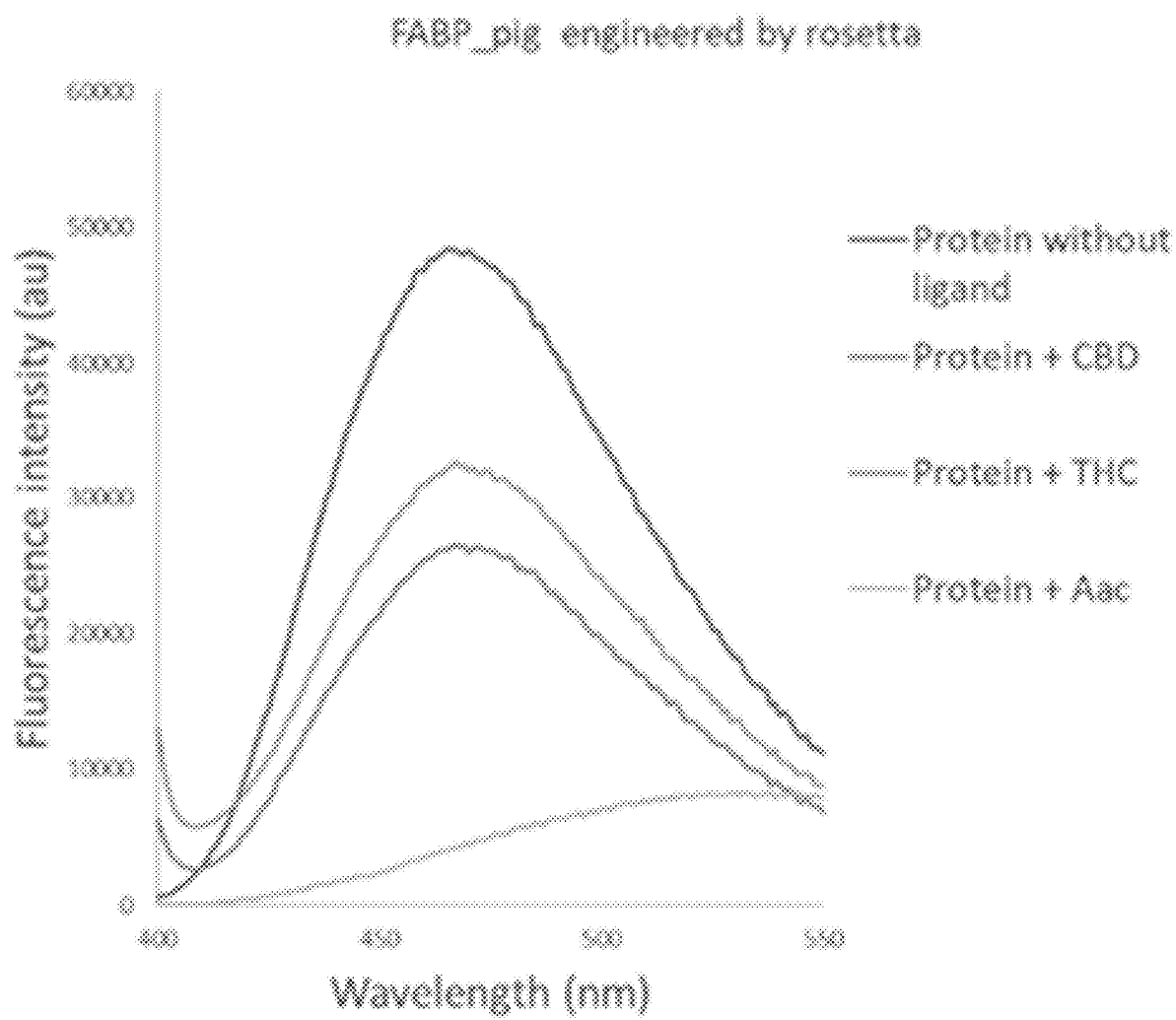
Figure 7:
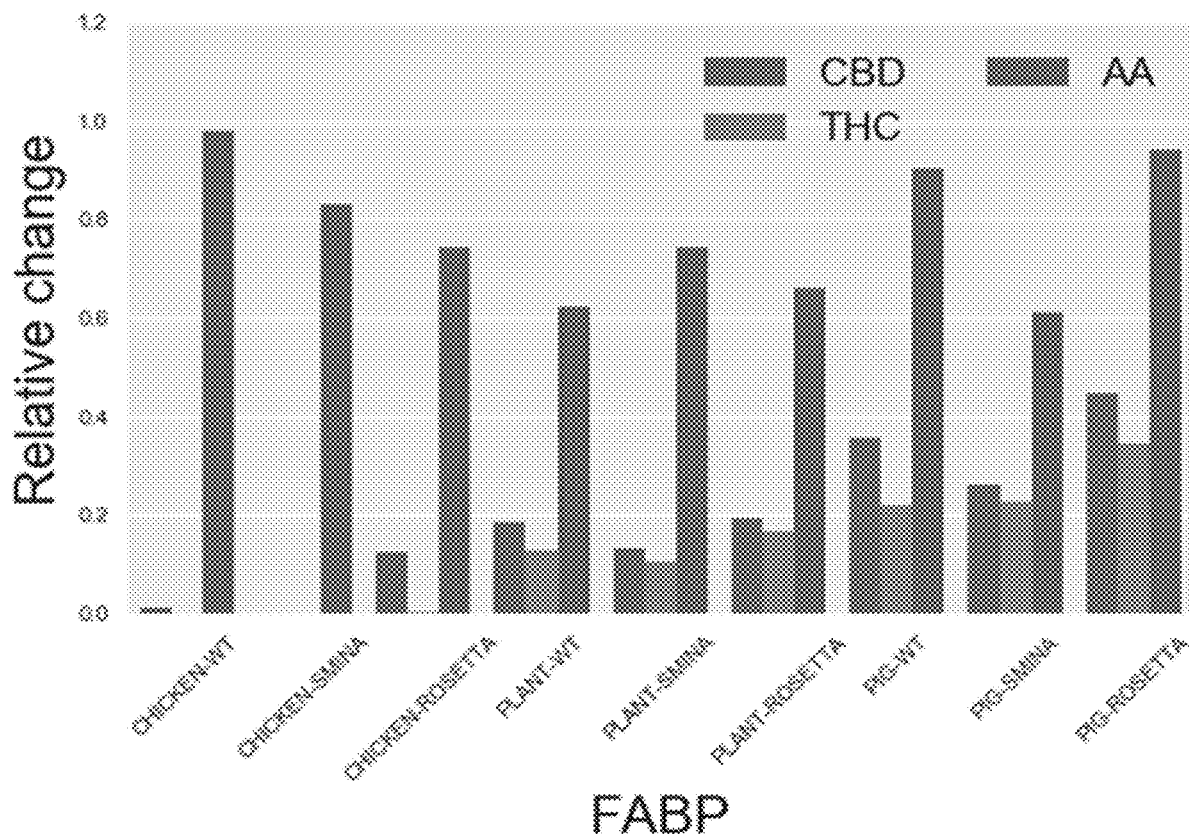
FIG. 7. Summary of ANS-displacement by ligand, showing the relative change in fluorescence. 2 uM of protein in 50 mM Tris-HCl buffer was labelled with 20 uM ANS. 33 uM of CBD, THC and Arachidonic acid (AAc) was used as ligand diluted in 10% of MeOH.

As noted above, FABPs with higher predicted binding affinity to cannabinoids were selected for overexpression, purification and binding assays. In addition, select FABPs were modified to enhance binding affinity to cannabinoids. Binding of cannabinoids to FABPs was measured by ANS displacement. Arachidonic acid was used as a positive control. The decrease in fluorescence compared to protein without ligand provides a measure of binding of the ligand, for example one or more cannabinoid such as CBD or THC to the target protein. As shown generally in FIGS. 4-6, representative spectral images for binding experiments conducted by the present inventors with the selected FABPs are demonstrated. As specifically noted in FIG. 7, the present inventors demonstrated the quantified binding results as changes in fluorescence from protein without ligand.

Figure 4A:
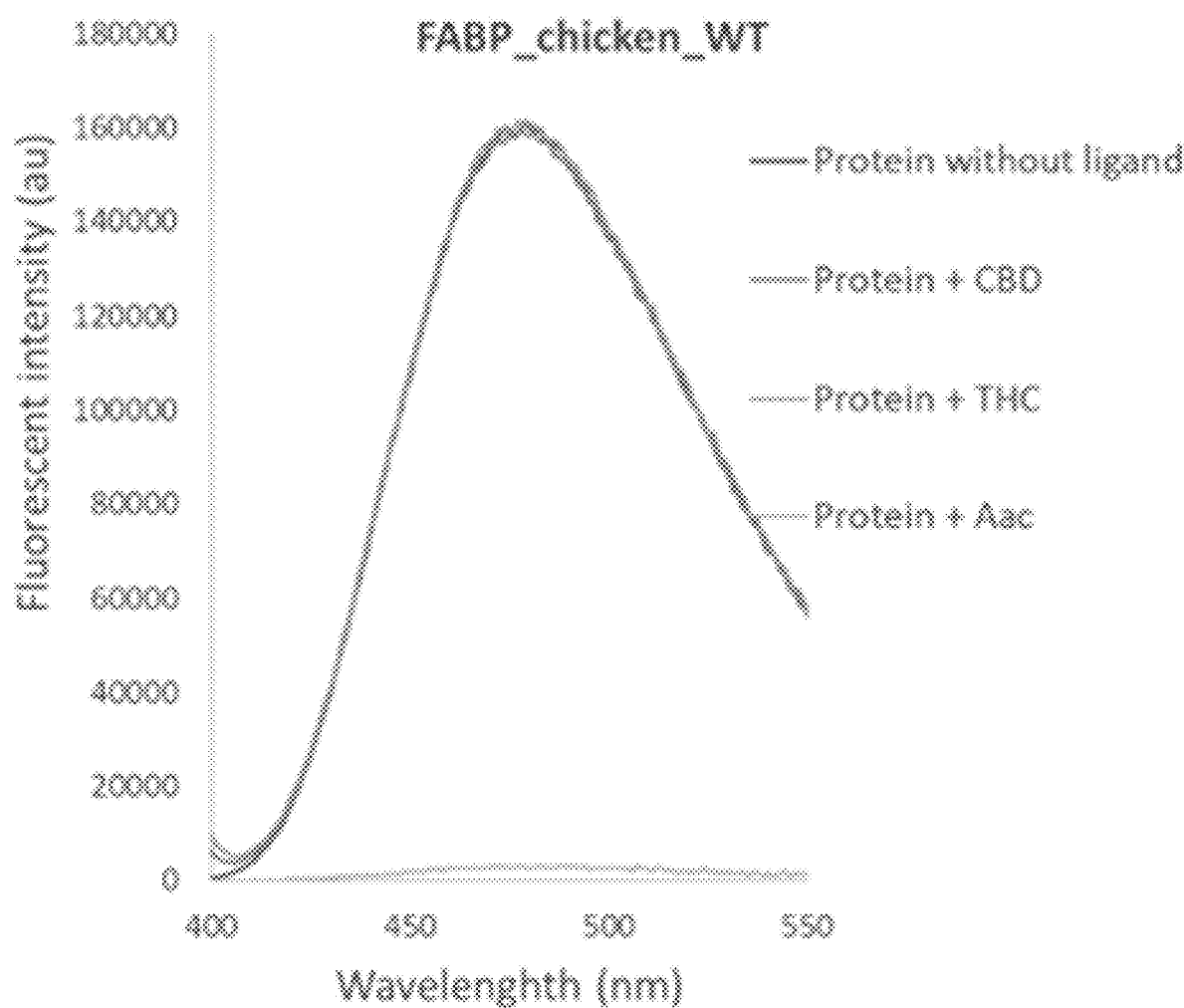
FIG. 4. FABP binding to cannabinoids by ANS displacement by ligands. (A) Wild type FABP from chicken indicating no binding to either CBD or THC. (B) Chicken FABP engineered by smima showing no binding to THC or CBD. (C) Chicken FABP engineered by rosetta showing binding to CBD but not THC.
Figure 4B:
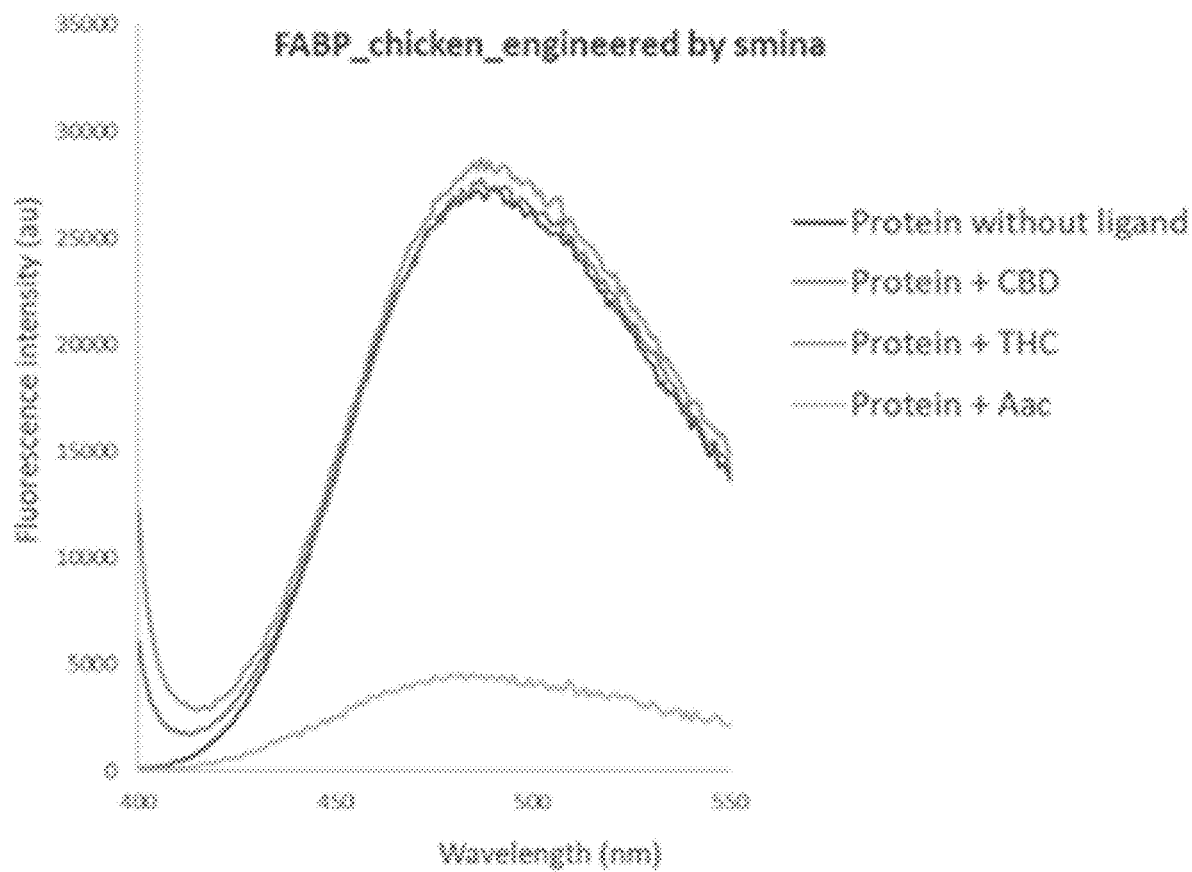
Figure 4C:
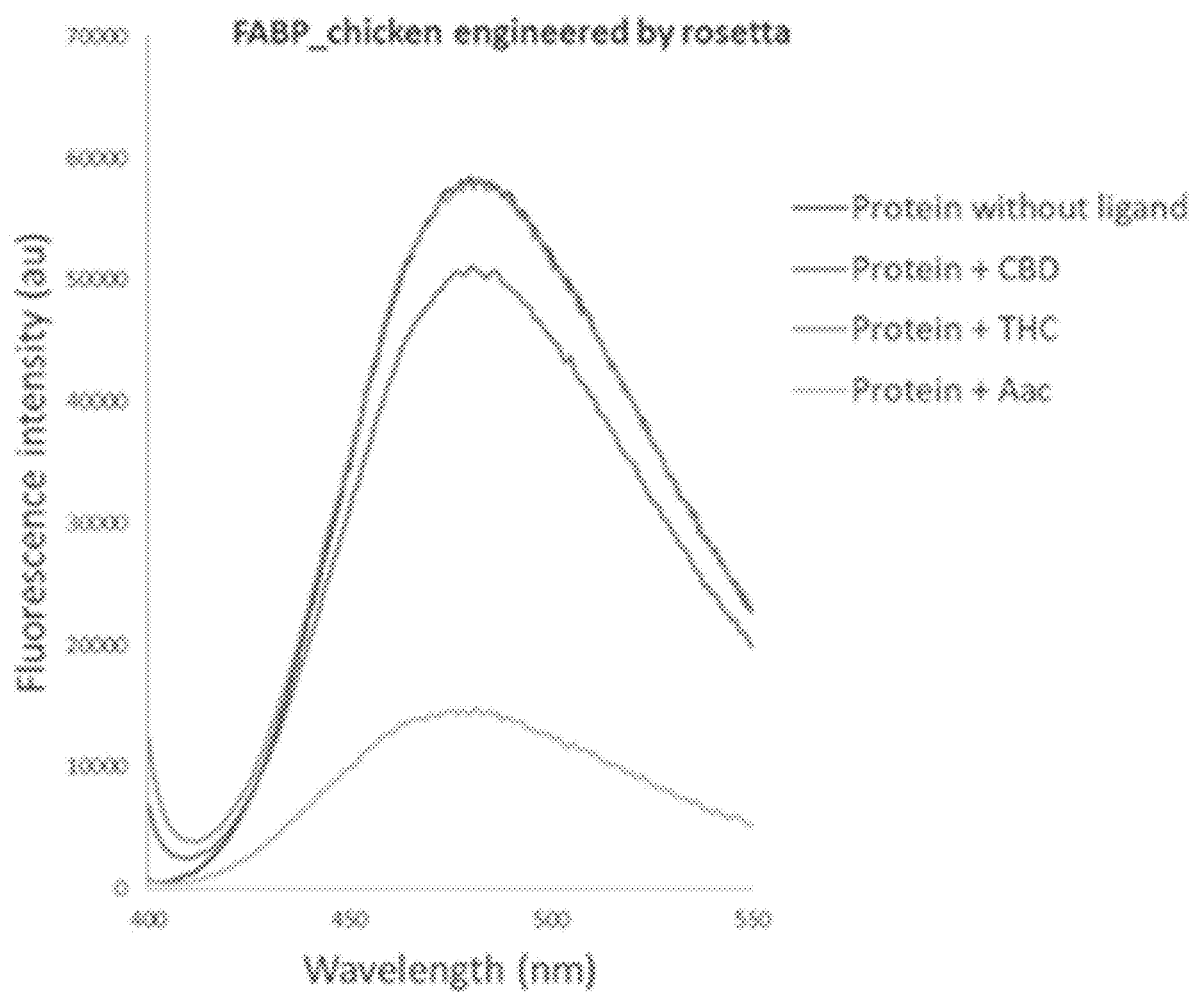

As shown in FIG. 4A, no, or negligible binding to cannabinoids, which in this exemplary embodiment included CBD and THC, was observed with the wild type target FABP identified from chicken (SEQ ID NO. 74). Notably, the present inventor demonstrated that the genetically modified target FABP identified from chicken (SEQ ID NO. 79) demonstrated cannabinoid binding, and particularly binding to CBD (FIG. 4C). As further shown in FIG. 7, an exemplary rosetta-engineered FABP from pig (SEQ ID NO. 81) also demonstrated improved binding to both CBD and THC relative to the wild type based on relative change in fluorescence.

Example 3: Materials and Methods

Figure 2:
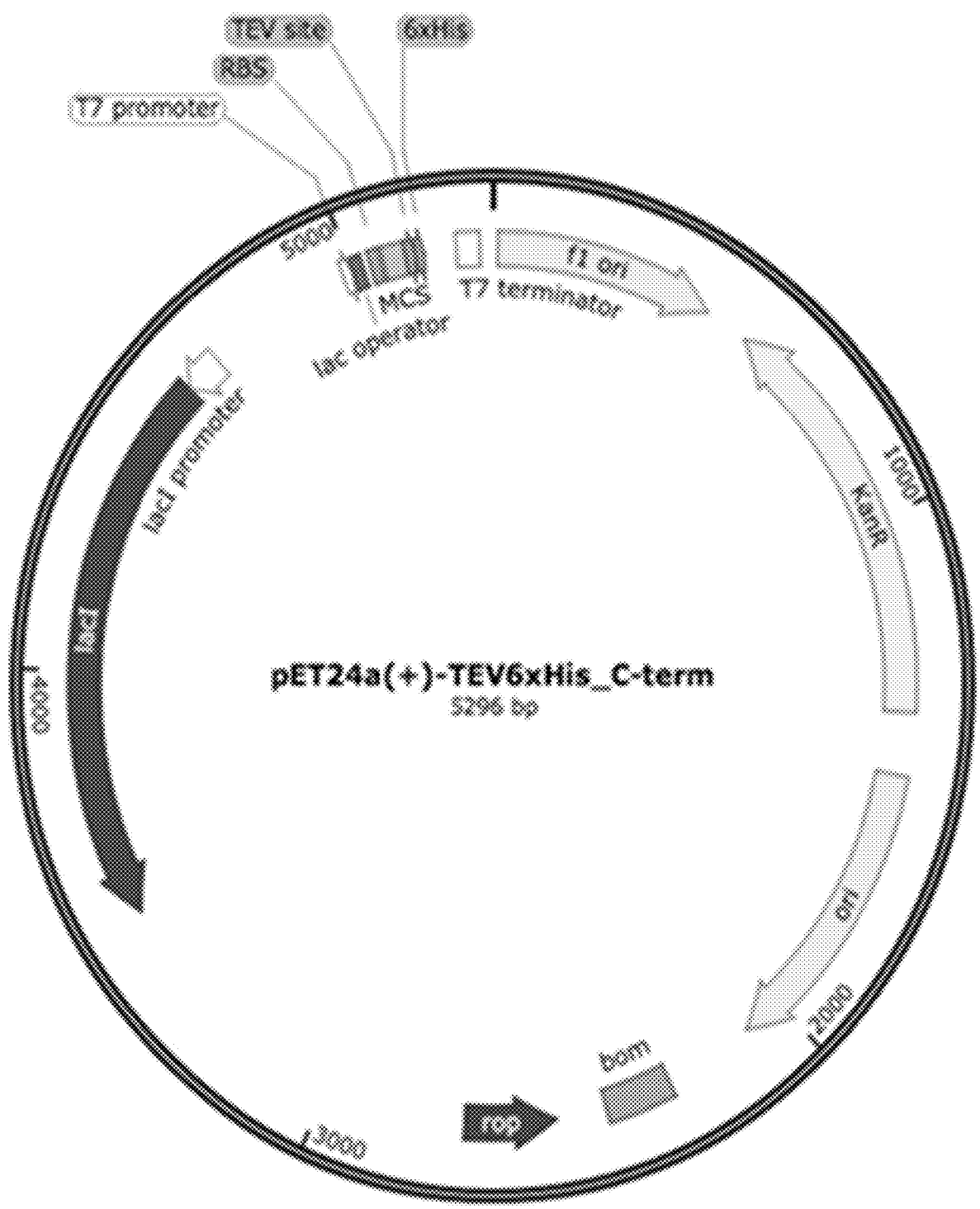
FIG. 2. Vector map of modified pET24a(+).
Figure 3A:
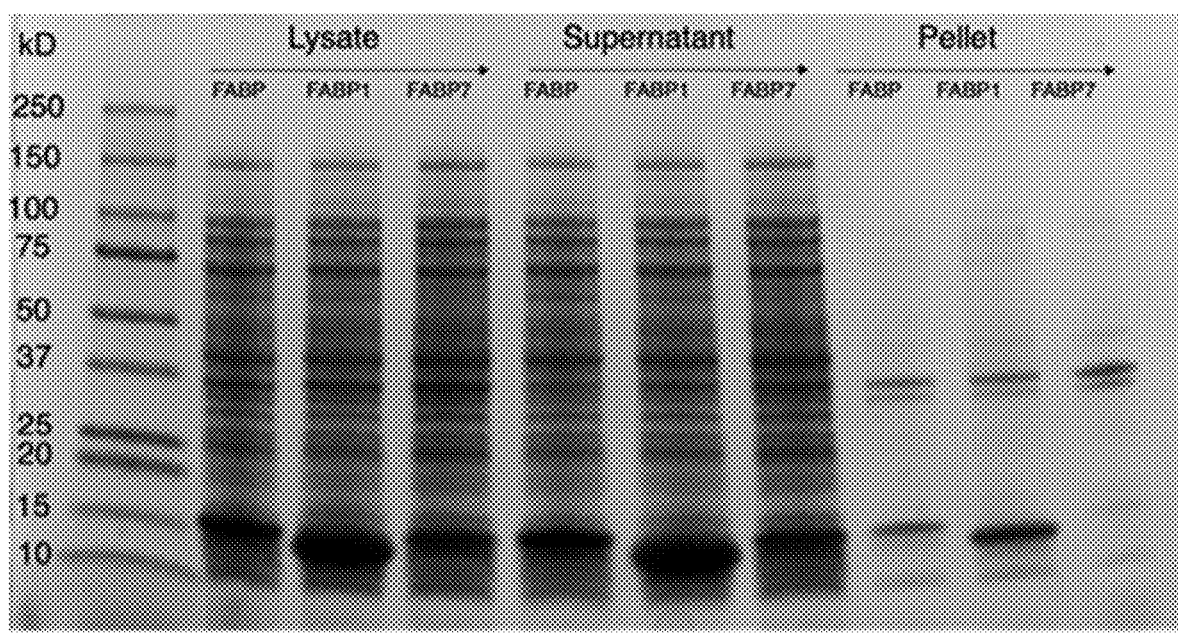
FIG. 3 Small-scale of protein expression from 10 ml of culture for WT and engineered FABPs. (A) FABP (from the plant Rhodamnia argentea), FABP1 (from pig) and FABP7 (from chicken) Wild type (no modification, natural protein). (B) Engineered FABP from the same organism described above with mutations in binding sites using smina (sm) method of binding prediction of affinity binding. (C) Engineered FABP using rosetta (ro) method for prediction of affinity binding. All wild type FABPs expressed as soluble protein, the protein is found in supernatant (soluble).
Figure 3B:
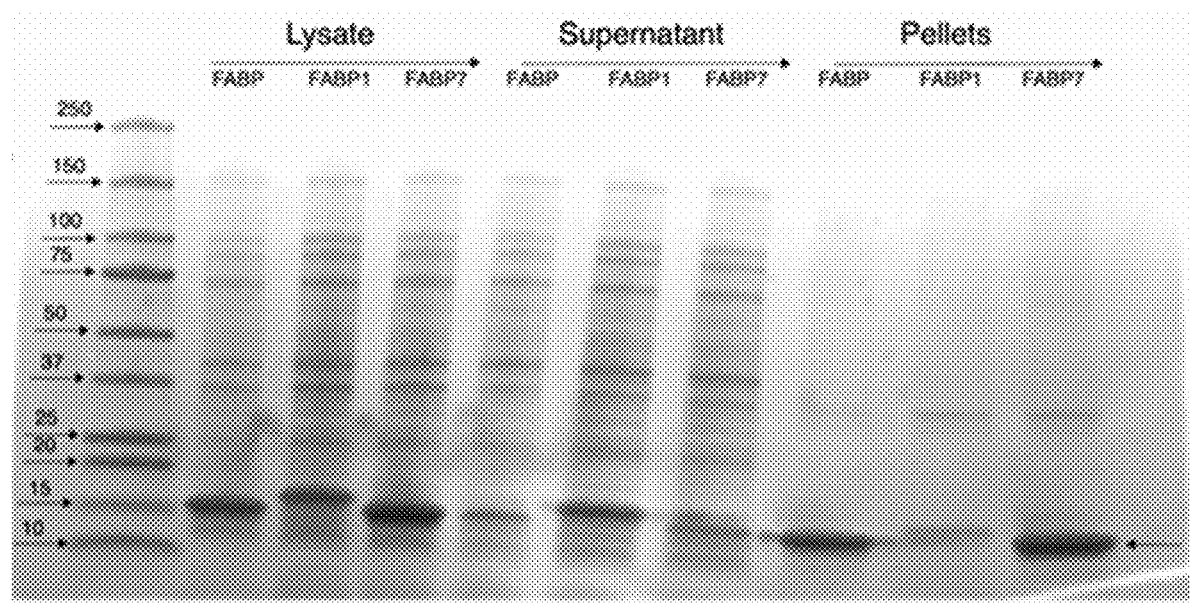
Figure 3C:
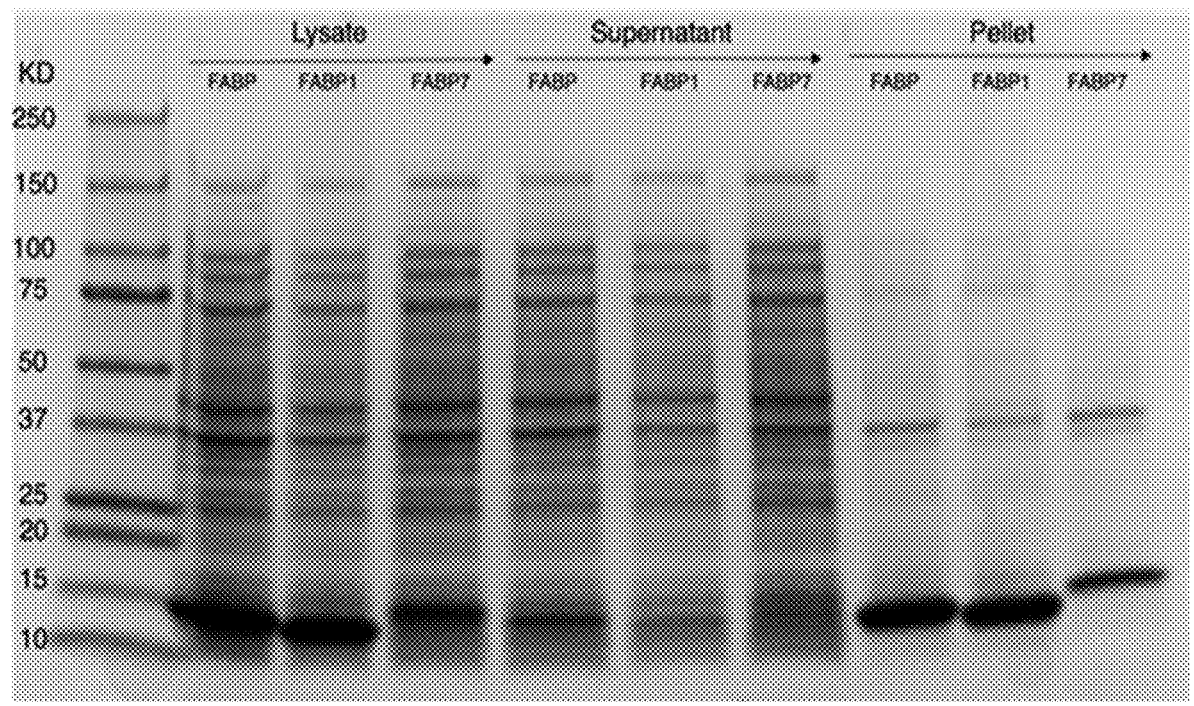

Cloning, transformation and protein expression in *E. coli*: and FABPs were cloned in a bacteria expression system using a modified pET 24a(+) vector (from GenScript, FIG. 2) and transformed in BL21 (DE3) competent cells. This vector is under the control of the strong T7 promoter, and has 6×His tag at the C-terminal of the protein sequence for purification. One colony was inoculated in 10 ml of LB and grown overnight for small scale protein expression. Next day, the culture was diluted 1:100 in LB medium and grown until OD reached 0.5. Protein expression was induced with 400 µM of isopropyl-β-d-thio-galactoside (IPTG) for 3 hours at 30 C and with shaking at 250 rpm. After 3 hours of growth, the cells were harvested and washed with 50 mM Tris-HCl and cell pellets were stored at −80° C. for further protein purification.

Protein purification: Cell pellets of 500 ml cell culture were thawed and resuspended in 15 ml of cell lysis containing 50 mM of Tris-HCl and protease inhibitors. Cells were lysed using Ultrasonic-Homogenizer, Biologics Inc Model 3000. After sonication lysed cells were spun down at 14,000 rpm for 10 min. For soluble proteins, supernatants were used for affinity chromatography purification using TALON resin. For insoluble proteins, pellets were dissolved in the detergent-based buffer SoluLyse (Genlantis, San Diego, CA) with multiple washing steps to extract protein from inclusion bodies according to SoluLyse manufacturers. Proteins from inclusion bodies were unfolded in 9M Urea and 5 mM DTT and refolded by dilution with 50 mM Tris-HCl and 150 mM NaCl pH 8.

Ligand binding assays-ANS binding studies: Binding assays of cannabinoids to proteins were assessed by 8-anilino-1-naphthalenesulfonic acid (ANS, Thermofisher scientific, Waltham, MA) displacement. ANS is a fluorescent probe commonly used to measure conformational changes due to ligand binding. ANS binds mostly to hydrophobic sites in the protein (Yu and Strobel, 1996; Huang et al., 2016). 2 µM of protein was labelled with 20 µM of ANS. 100 µM stocks of cannabidiol (CBD), delta 9 tetrahydrocannabinol (THC) and Arachidonic acid were prepared in 10% of MeOH. Protein-ANS complex were excited at 390 nm and emission scan were recorded from 400 to 550 nm. All the experiments were done at 20 C on a FluroMax Spectrofluorometer.

TABLE 1

Predicted CBD binding affinities for the WT and engineered FABPs.

| Species and isoform | Variant | CBD binding affinity using Rosetta (REU) | CBD binding affinity using Smina (kcal/mol) |
|---|---|---|---|
| Chicken FABP7 | mdl_r5_0225_ro | −31.444 | −8.074 |
|  | mdl_r3_1403_sm | −29.481 | −10.116 |
|  | WT | −20.864 | −7.606 |
| Pig FABP1 | mdl_r5_1652_ro | −33.233 | −7.516 |
|  | mdl_r4_0372_sm | −31.764 | −10.065 |
|  | WT | −24.231 | −7.265 |
| Horse FABP1 | mdl_r5_0954_ro | −33.131 | −9.451 |
|  | mdl_r5_1179_sm | −31.288 | −10.995 |
|  | WT | −27.447 | −8.759 |
| Plant FABP | mdl_r3_0887_ro_sm | −35.135 | −10.536 |
|  | mdl_r4_1489_ro | −31.257 | −9.026 |
|  | WT | −23.775 | −9.022 |

```
SEQUENCE LISTINGS
Amino Acid
Hepatic Fatty acid-binding protein 1
Mus musculus
                                                       SEQ ID NO. 1
MNFSGKYQLQSQENFEPFMKAIGLPEDLIQKGKDIKGVSEIVHEGKKIKLTITYGPKVVRNEFT

LGEECELETMTGEKVKAVVKLEGDNKMVTTFKGIKSVTELNGDTITNTMTLGDIVYKRVSKRI

Amino Acid
Hepatic Fatty acid-binding protein 1
Bos taurus
                                                       SEQ ID NO. 2
MNFSGKYQVQTQENYEAFMKAVGMPDDIIQKGKDIKGVSEIVQNGKHFKFIITAGSKVIQNEFT

LGEECEMEFMTGEKIKAVVQQEGDNKLVTTFKGIKSVTEFNGDTVTSTMTKGDVVFKRVSKRI

N-terminal secretion signal
S. cerevisiae
                                                       SEQ ID NO. 3
MRFPSIFTAVLFAASSALAAPVNTTTEDETAQIPAEAVIGYSDLEGDFDVAVLPFSNSTNNGLL

FINTTIASIAAKEEGVSLEKR
```

-continued

Amino Acid
Exportable Hepatic Fatty acid-binding protein 1
*Mus musculus*
SEQ ID NO. 4
MRFPSIFTAVLFAASSALAAPVNTTTEDETAQIPAEAVIGYSDLEGDFDVAVLPFSNSTNNGLL

FINTTIASIAAKEEGVSLEKRMNFSGKYQLQSQENFEPFMKAIGLPEDLIQKGKDIKGVSEIVH

EGKKIKLTITYGPKVVRNEFTLGEECELETMTGEKVKAVVKLEGDNKMVTTFKGIKSVTELNGD

TITNTMTLGDIVYKRVSKRI

Amino Acid
Exportable Hepatic Fatty acid-binding protein 1
*Bos taurus*
SEQ ID NO. 5
MRFPSIFTAVLFAASSALAAPVNTTTEDETAQIPAEAVIGYSDLEGDFDVAVLPFSNSTNNGLL

FINTTIASIAAKEEGVSLEKRMNFSGKYQVQTQENYEAFMKAVGMPDDIIQKGKDIKGVSEIVQ

NGKHFKFIITAGSKVIQNEFTLGEECEMEFMTGEKIKAVVQQEGDNKLVTTFKGIKSVTEFNGD

TVTSTMTKGDVVFKRVSKRI

Amino Acid
Catalase
*Arabidopsis thaliana*
SEQ ID NO. 6
MDPYKYRPASSYNSPFFTTNSGAPVWNNNSSMTVGPRGLILLEDYHLVEKLANFDRERIPERVV

HARGASAKGFFEVTHDISNLTCADFLRAPGVQTPVIVRFSTVIHARGSPETLRDPRGFAVKFYT

REGNFDLVGNNFPVFFIRDGMKFPDIVHALKPNPKSHIQENWRILDFFSHHPESLNMFTFLFDD

IGIPQDYRHMDGSGVNTYMLINKAGKAHYVKFHWKPTCGVKSLLEEDAIRLGGTNHSHATQDLY

DSIAAGNYPEWKLFIQIIDPADEDKFDFDPLDVTKTWPEDILPLQPVGRMVLNKNIDNFFAENE

QLAFCPAIIVPGIHYSDDKLLQTRVFSYADTQRHRLGPNYLQLPVNAPKCAHHNNHHEGFMNFM

HRDEEVNYFPSRYDQVRHAEKYPTPPAVCSGKRERCIIEKENNFKEPGERYRTFTPERQERFIQ

RWIDALSDPRITHEIRSIWISYWSQADKSLGQKLASRLNVRPSI

Amino Acid
Catalase HPII (KatE)
*Escherichia coli*
SEQ ID NO. 7
MSQHNEKNPHQHQSPLHDSSEAKPGMDSLAPEDGSHRPAAEPTPPGAQPTAPGSLKAPDTRNEK

LNSLEDVRKGSENYALTTNQGVRIADDQNSLRAGSRGPTLLEDFILREKITHFDHERIPERIVH

ARGSAAHGYFQPYKSLSDITKADFLSDPNKITPVFVRFSTVQGGAGSADTVRDIRGFATKFYTE

EGIFDLVGNNTPIFFIQDAHKFPDFVHAVKPEPHWAIPQGQSAHDTFWDYVSLQPETLHNVMWA

MSDRGIPRSYRTMEGFGIHTFRLINAEGKATFVRFHWKPLAGKASLVWDEAQKLTGRDPDFHRR

ELWEAIEAGDFPEYELGFQLIPEEDEFKFDFDLLDPTKLIPEELVPVQRVGKMVLNRNPDNFFA

ENEQAAFHPGHIVPGLDFTNDPLLQGRLFSYTDTQISRLGGPNFHEIPINRPTCPYHNFQRDGM

HRMGIDTNPANYEPNSINDNWPRETPPGPKRGGFESYQERVEGNKVRERSPSFGEYYSHPRLFW

LSQTPFEQRHIVDGFSFELSKVVRPYIRERVVDQLAHIDLTLAQAVAKNLGIELTDDQLNITPP

PDVNGLKKDPSLSLYAIPDGDVKGRVVAILLNDEVRSADLLAILKALKAKGVHAKLLYSRMGEV

TADDGTVLPIAATFAGAPSLTVDAVIVPCGNIADIADNGDANYYLMEAYKHLKPIALAGDARKF

KATIKIADQGEEGIVEADSADGSFMDELLTLMAAHRVWSRIPKIDKIPA

Amino Acid
Catalase 1
*Arabidopsis thaliana*
SEQ ID NO. 8
MDPYRVRPSSAHDSPFFTTNSGAPVWNNNSSLTVGTRGPILLEDYHLLEKLANFDRERIPERVV

HARGASAKGFFEVTHDITQLTSADFLRGPGVQTPVIVRFSTVIHERGSPETLRDPRGFAVKFYT

REGNFDLVGNNFPVFFVRDGMKFPDMVHALKPNPKSHIQENWRILDFFSHHPESLHMFSFLFDD

```
LGIPQDYRHMEGAGVNTYMLINKAGKAHYVKFHWKPTCGIKCLSDEEAIRVGGANHSHATKDLY

DSIAAGNYPQWNLFVQVMDPAHEDKFDFDPLDVTKIWPEDILPLQPVGRLVLNKNIDNFFNENE

QIAFCPALVVPGIHYSDDKLLQTRIFSYADSQRHRLGPNYLQLPVNAPKCAHHNNHHDGFMNFM

HRDEEVNYFPSRLDPVRHAEKYPTTPIVCSGNREKCFIGKENNFKQPGERYRSWDSDRQERFVK

RFVEALSEPRVTHEIRSIWISYWSQADKSLGQKLATRLNVRPNF

Amino Acid
Catalase 2
Arabidopsis thaliana
                                                   SEQ ID NO. 9
MDPYKYRPASSYNSPFFTTNSGAPVWNNNSSMTVGPRGPILLEDYHLVEKLANFDRERIPERVV

HARGASAKGFFEVTHDISNLTCADFLRAPGVQTPVIVRFSTVIHERGSPETLRDPRGFAVKFYT

REGNFDLVGNNFPVFFIRDGMKFPDMVHALKPNPKSHIQENWRILDFFSHHPESLNMFTFLFDD

IGIPQDYRHMDGSGVNTYMLINKAGKAHYVKFHWKPTCGVKSLLEEDAIRVGGTNHSHATQDLY

DSIAAGNYPEWKLFIQIIDPADEDKFDFDPLDVTKTWPEDILPLQPVGRMVLNKNIDNFFAENE

QLAFCPAIIVPGIHYSDDKLLQTRVFSYADTQRHRLGPNYLQLPVNAPKCAHHNNHHEGFMNFM

HRDEEVNYFPSRYDQVRHAEKYPTPPAVCSGKRERCIIEKENNFKEPGERYRTFTPERQERFIQ

RWIDALSDPRITHEIRSIWISYWSQADKSLGQKLASRLNVRPSI

Amino Acid
Catalase 3
Arabidopsis thaliana
                                                   SEQ ID NO. 10
MDPYKYRPSSAYNAPFYTTNGGAPVSNNISSLTIGERGPVLLEDYHLIEKVANFTRERIPERVV

HARGISAKGFFEVTHDISNLTCADFLRAPGVQTPVIVRFSTVVHERASPETMRDIRGFAVKFYT

REGNFDLVGNNTPVFFIRDGIQFPDVVHALKPNPKTNIQEYWRILDYMSHLPESLLTWCWMFDD

VGIPQDYRHMEGFGVHTYTLIAKSGKVLFVKFHWKPTCGIKNLTDEEAKVVGGANHSHATKDLH

DAIASGNYPEWKLFIQTMDPADEDKFDFDPLDVTKIWPEDILPLQPVGRLVLNRTIDNFFNETE

QLAFNPGLVVPGIYYSDDKLLQCRIFAYGDTQRHRLGPNYLQLPVNAPKCAHHNNHHEGFMNFM

HRDEEINYYPSKFDPVRCAEKVPTPTNSYTGIRTKCVIKKENNFKQAGDRYRSWAPDRQDRFVK

RWVEILSEPRLTHEIRGIWISYWSQADRSLGQKLASRLNVRPSI

Amino Acid
THCA Synthase Trichome targeting domain
Cannabis
                                                   SEQ ID NO. 11
MNCSAFSFWFVCKIIFFFLSFHIQISIA Amino Acid
CBDA Synthase Trichome targeting domain
Cannabis
                                                   SEQ ID NO. 12
MKCSTFSFWFVCKIIFFFFSFNIQTSIA Amino Acid
Cytosolic targeted THCA Synthase (ctTHCAs)
Cannabis
                                                   SEQ ID NO. 13
NPRENFLKCFSKHIPNNVANPKLVYTQHDQLYMSILNSTIQNLRFISDTTPKPLVIVTPSNNSH

IQATILCSKKVGLQIRTRSGGHDAEGMSYISQVPFVVVDLRNMHSIKIDVHSQTAWVEAGATLG

EVYYWINEKNENLSFPGGYCPTVGVGGHFSGGGYGALMRNYGLAADNIIDAHLVNVDGKVLDRK

SMGEDLFWAIRGGGGENFGIIAAWKIKLVDVPSKSTIFSVKKNMEIHGLVKLFNKWQNIAYKYD

KDLVLMTHFITKNITDNHGKNKTTVHGYFSSIFHGGVDSLVDLMNKSFPELGIKKTDCKEFSWI
```

-continued

```
DTTIFYSGVVNFNTANFKKEILLDRSAGKKTAFSIKLDYVKKPIPETAMVKILEKLYEEDVGAG

MYVLYPYGGIMEEISESAIPFPHRAGIMYELWYTASWEKQEDNEKHINWVRSVYNFTTPYVSQN

PRLAYLNYRDLDLGKTNHASPNNYTQARIWGEKYFGKNFNRLVKVKTKVDPNNFFRNEQSIPPL

PPHHH

DNA
Cytosolic CBDA synthase (cytCBDAs)
Cannabis sativa
                                                      SEQ ID NO. 14
ATGAATCCTCGAGAAAACTTCCTTAAATGCTTCTCGCAATATATTCCCAATAATGCAACAAATC

TAAAACTCGTATACACTCAAAACAACCCATTGTATATGTCTGTCCTAAATTCGACAATACACAA

TCTTAGATTCACCTCTGACACAACCCCAAAACCACTTGTTATCGTCACTCCTTCACATGTCTCT

CATATCCAAGGCACTATTCTATGCTCCAAGAAAGTTGGCTTGCAGATTCGAACTCGAAGTGGTG

GTCATGATTCTGAGGGCATGTCCTACATATCTCAAGTCCCATTTGTTATAGTAGACTTGAGAAA

CATGCGTTCAATCAAAATAGATGTTCATAGCCAAACTGCATGGGTTGAAGCCGGAGCTACCCTT

GGAGAAGTTTATTATTGGGTTAATGAGAAAAATGAGAATCTTAGTTTGGCGGCTGGGTATTGCC

CTACTGTTTGCGCAGGTGGACACTTTGGTGGAGGAGGCTATGGACCATTGATGAGAAACTATGG

CCTCGCGGCTGATAATATCATTGATGCACACTTAGTCAACGTTCATGGAAAAGTGCTAGATCGA

AAATCTATGGGGGAAGATCTCTTTTGGGCTTTACGTGGTGGTGGAGCAGAAAGCTTCGGAATCA

TTGTAGCATGGAAAATTAGACTGGTTGCTGTCCCAAAGTCTACTATGTTTAGTGTTAAAAAGAT

CATGGAGATACATGAGCTTGTCAAGTTAGTTAACAAATGGCAAAATATTGCTTACAAGTATGAC

AAAGATTTATTACTCATGACTCACTTCATAACTAGGAACATTACAGATAATCAAGGGAAGAATA

AGACAGCAATACACACTTACTTCTCTTCAGTTTTCCTTGGTGGAGTGGATAGTCTAGTCGACTT

GATGAACAAGAGTTTTCCTGAGTTGGGTATTAAAAAAACGGATTGCAGACAATTGAGCTGGATT

GATACTATCATCTTCTATAGTGGTGTTGTAAATTACGACACTGATAATTTTAACAAGGAAATTT

TGCTTGATAGATCCGCTGGGCAGAACGGTGCTTTCAAGATTAAGTTAGACTACGTTAAGAAACC

AATTCCAGAATCTGTATTTGTCCAAATTTTGGAAAAATTATATGAAGAAGATATAGGAGCTGGG

ATGTATGCGTTGTACCCTTACGGTGGTATAATGGATGAGATTTCAGAATCAGCAATTCCATTCC

CTCATCGAGCTGGAATCTTGTATGAGTTATGGTACATATGTAGTTGGGAAGCAAGAAGATAA

CGAAAAGCATCTAAACTGGATTAGAAATATTTATAACTTCATGACTCCTTATGTGTCCAAAAAT

CCAAGATTGGCATATCTCAATTATAGAGACCTTGATATAGGAATAAATGATCCCAAGAATCCAA

ATAATTACACACAAGCACGTATTTGGGGTGAGAAGTATTTTGGTAAAAATTTTGACAGGCTAGT

AAAAGTGAAAACCCTGGTTGATCCCAATAACTTTTTTAGAAACGAACAAAGCATCCCACCTCTA

CCACGGCATCGTCATTAA

Amino Acid
Cytosolic CBDA synthase (cytCBDAs)
Cannabis sativa
                                                      SEQ ID NO. 15
MNPRENFLKCFSQYIPNNATNLKLVYTQNNPLYMSVLNSTIHNLRFTSDTTPKPLVIVTPSHVS

HIQGTILCSKKVGLQIRTRSGGHDSEGMSYISQVPFVIVDLRNMRSIKIDVHSQTAWVEAGATL

GEVYYWVNEKNENLSLAAGYCPTVCAGGHFGGGGYGPLMRNYGLAADNIIDAHLVNVHGKVLDR

KSMGEDLFWALRGGGAESFGIIVAWKIRLVAVPKSTMFSVKKIMEIHELVKLVNKWQNIAYKYD

KDLLLMTHFITRNITDNQGKNKTAIHTYFSSVFLGGVDSLVDLMNKSFPELGIKKTDCRQLSWI
```

-continued

DTIIFYSGVVNYDTDNFNKEILLDRSAGQNGAFKIKLDYVKKPIPESVFVQILEKLYEEDIGAG

MYALYPYGGIMDEISESAIPFPHRAGILYELWYICSWEKQEDNEKHLNWIRNIYNFMTPYVSKN

PRLAYLNYRDLDIGINDPKNPNNYTQARIWGEKYFGKNFDRLVKVKTLVDPNNFFRNEQSIPPL

PRHRH

DNA
MYB12-like
*Cannabis*

SEQ ID NO. 16

ATGAAGAAGAACAAATCAACTAGTAATAATAAGAACAACAACAGTAATAATATCATCAAAAACG

ACATCGTATCATCATCATCATCAACAACAACAACATCATCAACAACTACAGCAACATCATCATT

TCATAATGAGAAAGTTACTGTCAGTACTGATCATATTATTAATCTTGATGATAAGCAGAAACGA

CAATTATGTCGTTGTCGTTTAGAAAAAGAAGAAGAAGAAGAAGGAAGTGGTGGTTGTGGTGAGA

CAGTAGTAATGATGCTAGGGTCAGTATCTCCTGCTGCTGCTACTGCTGCTGCAGCTGGGGGCTC

ATCAAGTTGTGATGAAGACATGTTGGGTGGTCATGATCAACTGTTGTTGTTGTGTTGTTCTGAG

AAAAAAACGACAGAAATTTCATCAGTGGTGAACTTTAATAATAATAATAATAATAATAAGGAAA

ATGGTGACGAAGTTTCAGGACCGTACGATTATCATCATCATAAAGAAGAGGAAGAAGAAGAAGA

AGAAGATGAAGCATCTGCATCAGTAGCAGCTGTTGATGAAGGGATGTTGTTGTGCTTTGATGAC

ATAATAGATAGCCACTTGCTAAATCCAAATGAGGTTTTGACTTTAAGAGAAGATAGCCATAATG

AAGGTGGGGCAGCTGATCAGATTGACAAGACTACTTGTAATAATACTACTATTACTACTAATGA

TGATTATAACAATAACTTGATGATGTTGAGCTGCAATAATAACGGAGATTATGTTATTAGTGAT

GATCATGATGATCAGTACTGGATAGACGACGTCGTTGGAGTTGACTTTTGGAGTTGGGAGAGTT

CGACTACTACTGTTATTACCCAAGAACAAGAACAAGAACAAGATCAAGTTCAAGAACAGAAGAA

TATGTGGGATAATGAGAAAGAGAAACTGTTGTCTTTGCTATGGGATAATAGTGATAACAGCAGC

AGTTGGGAGTTACAAGATAAAAGCAATAATAATAATAATAATAATGTTCCTAACAAATGTCAAG

AGATTACCTCTGATAAAGAAAATGCTATGGTTGCATGGCTTCTCTCCTGA

Amino Acid
MYB12
*Cannabis*

SEQ ID NO. 17

MKKNKSTSNNKNNNSNNIIKNDIVSSSSSTTTTSSTTTATSSFHNEKVTVSTDHIINLDDKQKR

QLCRCRLEKEEEEGSGGCGETVVMMLGSVSPAAATAAAAGGSSSCDEDMLGGHDQLLLLCCSE

KKTTEISSVVNFNNNNNNNKENGDEVSGPYDYHHHKEEEEEEEEDEASASVAAVDEGMLLCFDD

IIDSHLLNPNEVLTLREDSHNEGGAADQIDKTTCNNTTITTNDDYNNNLMMLSCNNNGDYVISD

DHDDQYWIDDVVGVDFWSWESSTTTVITQEQEQEQDVQEQKNMWDNEKEKLLSLLWDNSDNSS

SWELQDKSNNNNNNNNVPNKCQEITSDKENAMVAWLLS

Amino Acid
MYB8 - orthologue for CAN738
*Humulus lupulus*

SEQ ID NO. 18

MGRAPCCEKVGLKKGRWTSEEDEILTKYIQSNGEGCWRSLPKNAGLLRCGKSCRLRWINYLRAD

LKRGNISSEEEDIIIKLHSTLGNRWSLIASHLPGRTDNEIKNYWNSHLSRKIHTFRRCNNTTTH

HHHLPNLVTVTKVNLPIPKRKGGRTSRLAMKKNKSSTSNQNSSVIKNDVGSSSSTTTTSVHQRT

TTTTPTMDDQQKRQLSRCRLEEKEDQDGASTGTVVMMLGQAAAVGSSCDEDMLGHDQLSFLCCS

EEKTTENSMTNLKENGDHEVSGPYDYDHRYEKETSVDEGMLLCFNDIIDSNLLNPNEVLTLSEE

SLNLGGALMDTTTSTTTNNNNYSLSYNNNGDCVISDDHDQYWLDDVVGVDFWSWESSTTVTQEQ

EQEQEQEQEQEQEQEQEHHHQQDQKKNTWDNEKEKMLALLWDSDNSNWELQDNNNYHKCQEI

TSDKENAMVAWLLS

Amino Acid
atMYB12 - orthologue for CAN739
*Arabidopsis thaliana*
SEQ ID NO. 19
MGRAPCCEKVGIKRGRWTAEEDQILSNYIQSNGEGSWRSLPKNAGLKRCGKSCRLRWINYLRSD

LKRGNITPEEEELVVKLHSTLGNRWSLIAGHLPGRTDNEIKNYWNSHLSRKLHNFIRKPSISQD

VSAVIMTNASSAPPPPQAKRRLGRTSRSAMKPKIHRTKTRKTKKTSAPPEPNADVAGADKEALM

VESSGAEAELGRPCDYYGDDCNKNLMSINGDNGVLTFDDDIIDLLLDESDPGHLYTNTTCGGDG

ELHNIRDSEGARGFSDTWNQGNLDCLLQSCPSVESFLNYDHQVNDASTDEFIDWDCVWQEGSDN

NLWHEKENPDSMVSWLLDGDDEATIGNSNCENFGEPLDHDDESALVAWLLS

Amino Acid
MYB112 - orthologue for CAN833
*Arabidopsis thaliana*
SEQ ID NO. 20
MNISRTEFANCKTLINHKEEVEEVEKKMEIEIRRGPWTVEEDMKLVSYISLHGEGRWNSLSRSA

GLNRTGKSCRLRWLNYLRPDIRRGDISLQEQFIILELHSRWGNRWSKIAQHLPGRTDNEIKNYW

RTRVQKHAKLLKCDVNSKQFKDTIKHLWMPRLIERIAATQSVQFTSNHYSPENSSVATATSSTS

SSEAVRSSFYGGDQVEFGTLDHMTNGGYWFNGGDTFETLCSFDELNKWLIQ

Amino Acid
Hepatic Fatty acid-binding protein 1
*Homo Sapiens*
SEQ ID NO. 21
MSFSGKYQLQSQENFEAFMKAIGLPEELIQKGKDIKGVSEIVQNGKHFKFTITAGSKVIQNEFT

VGEECELETMTGEKVKTVVQLEGDNKLVTTFKNIKSVTELNGDIITNTMTLGDIVFKRISKRI

DNA
Cytochrome P450 (CYP3A4)
*Mus musculus*
SEQ ID NO. 22
ATGAACTTGTTTTCTGCTTTGTCTTTGGATACTTTGGTTTTGTTGGCTATTATTTTGGTTTTGT

TGTACAGATACGGTACTAGAACTCATGGTTTGTTTAAGAAGCAAGGTATTCCAGGTCCAAAGCC

ATTGCCATTTTTGGGTACTGTTTTGAACTACTACACTGGTATTTGGAAGTTTGATATGGAATGT

TACGAAAAGTACGGTAAGACTTGGGGTTTGTTTGATGGTCAAACTCCATTGTTGGTTATTACTG

ATCCAGAAACTATTAAGAACGTTTTGGTTAAGGATTGTTTGTCTGTTTTTACTAACAGAAGAGA

ATTTGGTCCAGTTGGTATTATGTCTAAGGCTATTTCTATTTCTAAGGATGAAGAATGGAAGAGA

TACAGAGCTTTGTTGTCTCCAACTTTTACTTCTGGTAGATTGAAGGAAATGTTTCCAGTTATTG

AACAATACGGTGATATTTTGGTTAAGTACTTGAGACAAGAAGCTGAAAAGGGTATGCCAGTTGC

TATGAAGGATGTTTTGGGTGCTTACTCTATGGATGTTATTACTTCTACTTCTTTTGGTGTTAAC

GTTGATTCTTTGAACAACCCAGAAGATCCATTTGTTGAAGAAGCTAAGAAGTTTTTGAGAGTTG

ATTTTTTTGATCCATTGTTGTTTTCTGTTGTTTTGTTTCCATTGTTGACTCCAGTTTACGAAAT

GTTGAACATTTGTATGTTTCCAAACGATTCTATTGAATTTTTTAAGAAGTTTGTTGATAGAATG

CAAGAATCTAGATTGGATTCTAACCAAAAGCATAGAGTTGATTTTTTGCAATTGATGATGAACT

CTCATAACAACTCTAAGGATAAGGATTCTCATAAGGCTTTTTCTAACATGGAAATTACTGTTCA

ATCTATTATTTTTATTTCTGCTGGTTACGAAACTACTTCTTCTACTTTGTCTTTTACTTTGTAC

TGTTTGGCTACTCATCCAGATATTCAAAAGAAGTTGCAAGCTGAAATTGATAAGGCTTTGCCAA

ACAAGGCTACTCCAACTTGTGATACTGTTATGGAAATGGAATACTTGGATATGGTTTTGAACGA

AACTTTGAGATTGTACCCAATTGTTACTAGATTGGAAAGAGTTTGTAAGAAGGATGTTGAATTG

AACGGTGTTTACATTCCAAAGGGTTCTATGGTTATGATTCCATCTTACGCTTTGCATCATGATC

CACAACATTGGCCAGATCCAGAAGAATTTCAACCAGAAAGATTTTCTAAGGAAAACAAGGGTTC

-continued

```
TATTGATCCATACGTTTACTTGCCATTTGGTATTGGTCCAAGAAACTGTATTGGTATGAGATTT

GCTTTGATGAACATGAAGTTGGCTGTTACTAAGGTTTTGCAAAACTTTTCTTTTCAACCATGTC

AAGAAACTCAAATTCCATTGAAGTTGTCTAGACAAGGTATTTTGCAACCAGAAAAGCCAATTGT

TTTGAAGGTTGTTCCAAGAGATGCTGTTATTACTGGTGCTTAA
```

Amino Acid
Cytochrome P450 (CYP3A4)
*Mus musculus*

SEQ ID NO. 23

```
MNLFSALSLDTLVLLAIILVLLYRYGTRTHGLFKKQGIPGPKPLPFLGTVLNYYTGIWKFDMEC

YEKYGKTWGLFDGQTPLLVITDPETIKNVLVKDCLSVFTNRREFGPVGIMSKAISISKDEEWKR

YRALLSPTFTSGRLKEMFPVIEQYGDILVKYLRQEAEKGMPVAMKDVLGAYSMDVITSTSFGVN

VDSLNNPEDPFVEEAKKFLRVDFFDPLLFSVVLFPLLTPVYEMLNICMFPNDSIEFFKKFVDRM

QESRLDSNQKHRVDFLQLMMNSHNNSKDKDSHKAFSNMEITVQSIIFISAGYETTSSTLSFTLY

CLATHPDIQKKLQAEIDKALPNKATPTCDTVMEMEYLDMVLNETLRLYPIVTRLERVCKKDVEL

NGVYIPKGSMVMIPSYALHHDPQHWPDPEEFQPERFSKENKGSIDPYVYLPFGIGPRNCIGMRF

ALMNMKLAVTKVLQNFSFQPCQETQIPLKLSRQGILQPEKPIVLKVVPRDAVITGA
```

DNA
P450 oxidoreductase gene (CYP oxidoreductase)
*Mus musculus*

SEQ ID NO. 24

```
ATGGGTGATTCTCATGAAGATACTTCTGCTACTGTTCCAGAAGCTGTTGCTGAAGAAGTTTCTT

TGTTTTCTACTACTGATATTGTTTTGTTTTCTTTGATTGTTGGTGTTTTGACTTACTGGTTTAT

TTTTAAGAAGAAGAAGGAAGAAATTCCAGAATTTTCTAAGATTCAAACTACTGCTCCACCAGTT

AAGGAATCTTCTTTTGTTGAAAAGATGAAGAAGACTGGTAGAAACATTATTGTTTTTTACGGTT

CTCAAACTGGTACTGCTGAAGAATTTGCTAACAGATTGTCTAAGGATGCTCATAGATACGGTAT

GAGAGGTATGTCTGCTGATCCAGAAGAATACGATTTGGCTGATTTGTCTTCTTTGCCAGAAATT

GATAAGTCTTTGGTTGTTTTTTGTATGGCTACTTACGGTGAAGGTGATCCAACTGATAACGCTC

AAGATTTTTACGATTGGTTGCAAGAAACTGATGTTGATTTGACTGGTGTTAAGTTTGCTGTTTT

TGGTTTGGGTAACAAGACTTACGAACATTTTAACGCTATGGGTAAGTACGTTGATCAAAGATTG

GAACAATTGGGTGCTCAAAGAATTTTTGAATTGGGTTTGGGTGATGATGATGGTAACTTGGAAG

AAGATTTTATTACTTGGAGAGAACAATTTTGGCCAGCTGTTTGTGAATTTTTTGGTGTTGAAGC

TACTGGTGAAGAATCTTCTATTAGACAATACGAATTGGTTGTTCATGAAGATATGGATACTGCT

AAGGTTTACACTGGTGAAATGGGTAGATTGAAGTCTTACGAAAACCAAAAGCCACCATTTGATG

CTAAGAACCCATTTTTGGCTGCTGTTACTACTAACAGAAAGTTGAACCAAGGTACTGAAAGACA

TTTGATGCATTTGGAATTGGATATTTCTGATTCTAAGATTAGATACGAATCTGGTGATCATGTT

GCTGTTTACCCAGCTAACGATTCTACTTTGGTTAACCAAATTGGTGAAATTTTGGGTGCTGATT

TGGATGTTATTATGTCTTTGAACAACTTGGATGAAGAATCTAACAAGAAGCATCCATTTCCATG

TCCAACTACTTACAGAACTGCTTTGACTTACTACTTGGATATTACTAACCCACCAAGAACTAAC

GTTTTGTACGAATTGGCTCAATACGCTTCTGAACCATCTGAACAAGAACATTTGCATAAGATGG

CTTCTTCTTCTGGTGAAGGTAAGGAATTGTACTTGTCTTGGGTTGTTGAAGCTAGAAGACATAT

TTTGGCTATTTTGCAAGATTACCCATCTTTGAGACCACCAATTGATCATTTGTGTGAATTGTTG

CCAAGATTGCAAGCTAGATACTACTCTATTGCTTCTTCTTCTAAGGTTCATCCAAACTCTGTTC

ATATTTGTGCTGTTGCTGTTGAATACGAAGCTAAGTCTGGTAGAGTTAACAAGGGTGTTGCTAC

TTCTTGGTTGAGAACTAAGGAACCAGCTGGTGAAAACGGTAGAAGAGCTTTGGTTCCAATGTTT

GTTAGAAAGTCTCAATTTAGATTGCCATTTAAGCCAACTACTCCAGTTATTATGGTTGGTCCAG
```

```
GTACTGGTGTTGCTCCATTTATGGGTTTTATTCAAGAAAGAGCTTGGTTGAGAGAACAAGGTAA

GGAAGTTGGTGAAACTTTGTTGTACTACGGTTGTAGAAGATCTGATGAAGATTACTTGTACAGA

GAAGAATTGGCTAGATTTCATAAGGATGGTGCTTTGACTCAATTGAACGTTGCTTTTTCTAGAG

AACAAGCTCATAAGGTTTACGTTCAACATTTGTTGAAGAGAGATAAGGAACATTTGTGGAAGTT

GATTCATGAAGGTGGTGCTCATATTTACGTTTGTGGTGATGCTAGAAACATGGCTAAGGATGTT

CAAAACACTTTTTACGATATTGTTGCTGAATTTGGTCCAATGGAACATACTCAAGCTGTTGATT

ACGTTAAGAAGTTGATGACTAAGGGTAGATACTCTTTGGATGTTTGGTCTTAA
```

Amino Acid
P450 oxidoreductase (CYP oxidoreductase)
*Mus musculus*

SEQ ID NO. 25

```
MGDSHEDTSATVPEAVAEEVSLFSTTDIVLFSLIVGVLTYWFIFKKKKEEIPEFSKIQTTAPPV

KESSFVEKMKKTGRNIIVFYGSQTGTAEEFANRLSKDAHRYGMRGMSADPEEYDLADLSSLPEI

DKSLVVFCMATYGEGDPTDNAQDFYDWLQETDVDLTGVKFAVFGLGNKTYEHFNAMGKYVDQRL

EQLGAQRIFELGLGDDDGNLEEDFITWREQFWPAVCEFFGVEATGEESSIRQYELVVHEDMDTA

KVYTGEMGRLKSYENQKPPFDAKNPFLAAVTTNRKLNQGTERHLMHLELDISDSKIRYESGDHV

AVYPANDSTLVNQIGEILGADLDVIMSLNNLDEESNKKHPFPCPTTYRTALTYYLDITNPPRTN

VLYELAQYASEPSEQEHLHKMASSSGEGKELYLSWVVEARRHILAILQDYPSLRPPIDHLCELL

PRLQARYYSIASSSKVHPNSVHICAVAVEYEAKSGRVNKGVATSWLRTKEPAGENGRRALVPMF

VRKSQFRLPFKPTTPVIMVGPGTGVAPFMGFIQERAWLREQGKEVGETLLYYGCRRSDEDYLYR

EELARFHKDGALTQLNVAFSREQAHKVYVQHLLKRDKEHLWKLIHEGGAHIYVCGDARNMAKDV

QNTFYDIVAEFGPMEHTQAVDYVKKLMTKGRYSLDVWS
```

DNA
Cytochrome P450 (CYP3A4)
Human

SEQ ID NO. 26

```
ATGGCTTTGATTCCTGATTTGGCTATGGAAACTAGATTGTTGTTGGCTGTTTCATTGGTTTTGT

TGTATTTGTATGGAACTCATTCACATGGATTGTTTAAAAAATTGGGAATTCCTGGACCTACTCC

TTTGCCTTTTTTGGGAAATATTTTGTCATATCATAAAGGATTTTGCATGTTTGATATGGAATGC

CATAAAAAATATGGAAAAGTTTGGGGATTTTATGATGGACAACAACCTGTTTTGGCTATTACTG

ATCCTGATATGATTAAAACTGTTTTGGTTAAAGAATGCTATTCAGTTTTTACTAATAGAAGACC

TTTTGGACCTGTTGGATTTATGAAATCAGCTATTTCAATTGCTGAAGATGAAGAATGGAAAAGA

TTGAGATCATTGTTGTCACCTACTTTTACTTCAGGAAAATTGAAAGAAATGGTTCCTATTATTG

CTCAATATGGAGATGTTTTGGTTAGAAATTTGAGAAGAGAAGCTGAAACTGGAAAACCTGTTAC

TTTGAAAGATGTTTTTGGAGCTTATTCAATGGATGTTATTACTTCAACTTCATTTGGAGTTAAT

ATTGATTCATTGAATAATCCTCAAGATCCTTTTGTTGAAAATACTAAAAAATTGTTGAGATTTG

ATTTTTTGGATCCTTTTTTTTGTCAATTACTGTTTTCCTTTTTTGATTCCTATTTTGGAAGT

TTTGAATATTTGCGTTTTTCCTAGAGAAGTTACTAATTTTTTGAGAAAATCAGTTAAAAGAATG

AAAGAATCAAGATTGGAAGATACTCAAAAACATAGAGTTGATTTTTTGCAATTGATGATTGATT

CACAAAAATTCAAAAGAAACTGAATCACATAAAGCTTTGTCAGATTTGGAATTGGTTGCTCAATC

AATTATTTTATTTTTGCTGGATGCGAAACTACTTCATCAGTTTTGTCATTTATTATGTATGAA

TTGGCTACTCATCCTGATGTTCAACAAAAATTGCAAGAAGAAATTGATGCTGTTTTGCCTAATA

AAGCTCCTCCTACTTATGATACTGTTTTGCAAATGGAATATTTGGATATGGTTGTTAATGAAAC

TTTGAGATTGTTTCCTATTGCTATGAGATTGGAAAGAGTTTGCAAAAAAGATGTTGAAATTAAT
```

-continued

```
GGAATGTTTATTCCTAAAGGAGTTGTTGTTATGATTCCTTCATATGCTTTGCATAGAGATCCTA

AATATTGGACTGAACCTGAAAAATTTTTGCCTGAAAGATTTTCAAAAAAAATAAAGATAATAT

TGATCCTTATATTTATACTCCTTTTGGATCAGGACCTAGAAATTGCATTGGAATGAGATTTGCT

TTGATGAATATGAAATTGGCTTTGATTAGAGTTTTGCAAAATTTTTCATTTAAACCTTGCAAAG

AAACTCAAATTCCTTTGAAATTGTCATTGGGAGGATTGTTGCAACCTGAAAAACCTGTTGTTTT

GAAAGTTGAATCAAGAGATGGAACTGTTTCAGGAGCT
```

Amino Acid
Cytochrome P450 (CYP3A4)
Human

SEQ ID NO. 27

```
MALIPDLAMETRLLLAVSLVLLYLYGTHSHGLFKKLGIPGPTPLPFLGNILSYHKGFCMFDMEC

HKKYGKVWGFYDGQQPVLAITDPDMIKTVLVKECYSVFTNRRPFGPVGFMKSAISIAEDEEWKR

LRSLLSPTFTSGKLKEMVPIIAQYGDVLVRNLRREAETGKPVTLKDVFGAYSMDVITSTSFGVN

IDSLNNPQDPFVENTKKLLRFDFLDPFFLSITVFPFLIPILEVLNICVFPREVTNFLRKSVKRM

KESRLEDTQKHRVDFLQLMIDSQNSKETESHKALSDLELVAQSIIFIFAGCETTSSVLSFIMYE

LATHPDVQQKLQEEIDAVLPNKAPPTYDTVLQMEYLDMVVNETLRLFPIAMRLERVCKKDVEIN

GMFIPKGVVVMIPSYALHRDPKYWTEPEKFLPERFSKKNKDNIDPYIYTPFGSGPRNCIGMRFA

LMNMKLALIRVLQNFSFKPCKETQIPLKLSLGGLLQPEKPVVLKVESRDGTVSGA
```

DNA
P450 oxidoreductase gene (oxred)
Human

SEQ ID NO. 28

```
ATGATTAATATGGGAGATTCACATGTTGATACTTCATCAACTGTTTCAGAAGCTGTTGCTGAAG

AAGTTTCATTGTTTTCAATGACTGATATGATTTTGTTTTCATTGATTGTTGGATTGTTGACTTA

TTGGTTTTTGTTTAGGAAAAAAAAAAGAAGAATTCCTGAATTTACTAAAATTCAAACTTTGACT

TCATCAGTTAGAGAATCATCATTTGTTGAAAAAATGAAAAAAACTGGAAGAAATATTATTGTTT

TTTATGGATCACAAACTGGAACTGCTGAAGAATTTGCTAATAGATTGTCAAAAGATGCTCATAG

ATATGGAATGAGAGGAATGTCAGCTGATCCTGAAGAATATGATTTGGCTGATTTGTCATCATTG

CCTGAAATTGATAATGCTTTGGTTGTTTTTTGCATGGCTACTTATGGAGAAGGAGATCCTACTG

ATAATGCTCAAGATTTTTATGATTGGTTGCAAGAAACTGATGTTGATTTGTCAGGAGTTAAATT

TGCTGTTTTTGGATTGGGAAATAAAACTTATGAACATTTTAATGCTATGGGAAAATATGTTGAT

AAAAGATTGGAACAATTGGGAGCTCAAAGAATTTTTGAATTGGGATTGGGAGATGATGATGGAA

ATTTGGAAGAAGATTTTATTACTTGGAGAGAACAATTTTGGTTGGCTGTTTGCGAACATTTTGG

AGTTGAAGCTACTGGAGAAGAATCATCAATTAGACAATATGAATTGGTTGTTCATACTGATATT

GATGCTGCTAAAGTTTATATGGGAGAAATGGAAGATTGAAATCATATGAAAATCAAAAACCTC

CTTTTGATGCTAAAAATCCTTTTTTGGCTGCTGTTACTACTAATAGAAAATTGAATCAAGGAAC

TGAAAGACATTTGATGCATTTGGAATTGGATATTTCAGATTCAAAAATTAGATATGAATCAGGA

GATCATGTTGCTGTTTATCCTGCTAATGATTCAGCTTTGGTTAATCAATTGGGAAAAATTTTGG

GAGCTGATTTGGATGTTGTTATGTCATTGAATAATTTGGATGAAGAATCAAATAAAAACATCC

TTTTCCTTGCCCTACTTCATATAGAACTGCTTTGACTTATTATTTGGATATTACTAATCCTCCT

AGAACTAATGTTTTGTATGAATTGGCTCAATATGCTTCAGAACCTTCAGAACAAGAATTGTTGA

GAAAAATGGCTTCATCATCAGGAGAAGGAAAAGAATTGTATTTGTCATGGGTTGTTGAAGCTAG

AAGACATATTTTGGCTATTTTGCAAGATTGCCCTTCATTGAGACCTCCTATTGATCATTTGTGC

GAATTGTTGCCTAGATTGCAAGCTAGATATTATTCAATTGCTTCATCATCAAAAGTTCATCCTA

ATTCAGTTCATATTTGCGCTGTTGTTGTTGAATATGAAACTAAAGCTGGAAGAATTAATAAAGG
```

-continued

```
AGTTGCTACTAATTGGTTGAGAGCTAAAGAACCTGTTGGAGAAAATGGAGGAAGAGCTTTGGTT

CCTATGTTTGTTAGAAAATCACAATTTAGATTGCCTTTTAAAGCTACTACTCCTGTTATTATGG

TTGGACCTGGAACTGGAGTTGCTCCTTTTATTGGATTTATTCAAGAAAGAGCTTGGTTGAGACA

ACAAGGAAAAGAAGTTGGAGAAACTTTGTTGTATTATGGATGCAGAAGATCAGATGAAGATTAT

TTGTATAGAGAAGAATTGGCTCAATTTCATAGAGATGGAGCTTTGACTCAATTGAATGTTGCTT

TTTCAAGAGAACAATCACATAAAGTTTATGTTCAACATTTGTTGAAACAAGATAGAGAACATTT

GTGGAAATTGATTGAAGGAGGAGCTCATATTTATGTTTGCGGAGATGCTAGAAATATGGCTAGA

GATGTTCAAAATACTTTTTATGATATTGTTGCTGAATTGGGAGCTATGGAACATGCTCAAGCTG

TTGATTATATTAAAAAATTGATGACTAAAGGAAGATATTCATTGGATGTTTGGTCA
```

Amino Acid
P450 oxidoreductase
Human

SEQ ID NO. 29

```
MINMGDSHVDTSSTVSEAVAEEVSLFSMTDMILFSLIVGLLTYWFLFRKKKEEVPEFTKIQTLT

SSVRESSFVEKMKKTGRNIIVFYGSQTGTAEEFANRLSKDAHRYGMRGMSADPEEYDLADLSSL

PEIDNALVVFCMATYGEGDPTDNAQDFYDWLQETDVDLSGVKFAVFGLGNKTYEHFNAMGKYVD

KRLEQLGAQRIFELGLGDDDGNLEEDFITWREQFWLAVCEHFGVEATGEESSIRQYELVVHTDI

DAAKVYMGEMGRLKSYENQKPPFDAKNPFLAAVTTNRKLNQGTERHLMHLELDISDSKIRYESG

DHVAVYPANDSALVNQLGKILGADLDVVMSLNNLDEESNKKHPFPCPTSYRTALTYYLDITNPP

RTNVLYELAQYASEPSEQELLRKMASSSGEGKELYLSWVVEARRHILAILQDCPSLRPPIDHLC

ELLPRLQARYYSIASSSKVHPNSVHICAVVVEYETKAGRINKGVATNWLRAKEPVGENGGRALV

PMFVRKSQFRLPFKATTPVIMVGPGTGVAPFIGFIQERAWLRQQGKEVGETLLYYGCRRSDEDY

LYREELAQFHRDGALTQLNVAFSREQSHKVYVQHLLKQDREHLWKLIEGGAHIYVCGDARNMAR

DVQNTFYDIVAELGAMEHAQAVDYIKKLMTKGRYSLDVWS
```

DNA
cannabidiolic acid (CBDA) synthase
Cannabis sativa

SEQ ID NO. 43

```
ATGAATCCTCGAGAAAACTTCCTTAAATGCTTCTCGCAATATATTCCCAATAATGCAACAAATC

TAAAACTCGTATACACTCAAAACAACCCATTGTATATGTCTGTCCTAAATTCGACAATACACAA

TCTTAGATTCACCTCTGACACAACCCCAAAACCACTTGTTATCGTCACTCCTTCACATGTCTCT

CATATCCAAGGCACTATTCTATGCTCCAAGAAAGTTGGCTTGCAGATTCGAACTCGAAGTGGTG

GTCATGATTCTGAGGGCATGTCCTACATATCTCAAGTCCCATTTGTTATAGTAGACTTGAGAAA

CATGCGTTCAATCAAAATAGATGTTCATAGCCAAACTGCATGGGTTGAAGCCGGAGCTACCCTT

GGAGAAGTTTATTATTGGGTTAATGAGAAAAATGAGAATCTTAGTTTGGCGGCTGGGTATTGCC

CTACTGTTTGCGCAGGTGGACACTTTGGTGGAGGAGGCTATGGACCATTGATGAGAAACTATGG

CCTCGCGGCTGATAATATCATTGATGCACACTTAGTCAACGTTCATGGAAAAGTGCTAGATCGA

AAATCTATGGGGGAAGATCTCTTTTGGGCTTTACGTGGTGGTGGAGCAGAAAGCTTCGGAATCA

TTGTAGCATGGAAAATTAGACTGGTTGCTGTCCCAAAGTCTACTATGTTTAGTGTTAAAAAGAT

CATGGAGATACATGAGCTTGTCAAGTTAGTTAACAAATGGCAAAATATTGCTTACAAGTATGAC

AAAGATTATTACTCATGACTCACTTCATAACTAGGAACATTACAGATAATCAAGGGAAGAATA

AGACAGCAATACACACTTACTTCTCTTCAGTTTTCCTTGGTGGAGTGGATAGTCTAGTCGACTT

GATGAACAAGAGTTTTCCTGAGTTGGGTATTAAAAAAACGGATTGCAGACAATTGAGCTGGATT

GATACTATCATCTTCTATAGTGGTGTTGTAAATTACGACACTGATAATTTTAACAAGGAAATTT
```

-continued

```
TGCTTGATAGATCCGCTGGGCAGAACGGTGCTTTCAAGATTAAGTTAGACTACGTTAAGAAACC

AATTCCAGAATCTGTATTTGTCCAAATTTTGGAAAAATTATATGAAGAAGATATAGGAGCTGGG

ATGTATGCGTTGTACCCTTACGGTGGTATAATGGATGAGATTTCAGAATCAGCAATTCCATTCC

CTCATCGAGCTGGAATCTTGTATGAGTTATGGTACATATGTAGTTGGGAGAAGCAAGAAGATAA

CGAAAAGCATCTAAACTGGATTAGAAATATTTATAACTTCATGACTCCTTATGTGTCCAAAAAT

TCAAGATTGGCATATCTCAATTATAGAGACCTTGATATAGGAATAAATGATCCCAAGAATCCAA

ATAATTACACACAAGCACGTATTTGGGGTGAGAAGTATTTTGGTAAAAATTTTGACAGGCTAGT

AAAAGTGAAAACCCTGGTTGATCCCAATAACTTTTTTAGAAACGAACAAAGCATCCCACCTCAA

CCACGGCATCGTCATTAA
```

Amino Acid
Cannabidiolic acid (CBDA) synthase
*Cannabis sativa*
SEQ ID NO. 31

```
MNPRENFLKCFSQYIPNNATNLKLVYTQNNPLYMSVLNSTIHNLRFTSDTTPKPLVIVTPSHVS

HIQGTILCSKKVGLQIRTRSGGHDSEGMSYISQVPFVIVDLRNMRSIKIDVHSQTAWVEAGATL

GEVYYWVNEKNENLSLAAGYCPTVCAGGHFGGGGYGPLMRNYGLAADNIIDAHLVNVHGKVLDR

KSMGEDLFWALRGGGAESFGIIVAWKIRLVAVPKSTMFSVKKIMEIHELVKLVNKWQNIAYKYD

KDLLLMTHFITRNITDNQGKNKTAIHTYFSSVFLGGVDSLVDLMNKSFPELGIKKTDCRQLSWI

DTIIFYSGVVNYDTDNFNKEILLDRSAGQNGAFKIKLDYVKKPIPESVFVQILEKLYEEDIGAG

MYALYPYGGIMDEISESAIPFPHRAGILYELWYICSWEKQEDNEKHLNWIRNIYNFMTPYVSKN

SRLAYLNYRDLDIGINDPKNPNNYTQARIWGEKYFGKNFDRLVKVKTLVDPNNFFRNEQSIPPQ

PRHRH
```

DNA
UDP glycosyltransferase 76G1
*Stevia rebaudiana*
SEQ ID NO. 32

```
ATGGAAAATAAAACTGAAACTACTGTTAGAAGAAGAAGAAGAATTATTTTGTTTCCTGTTCCTT

TTCAAGGACATATTAATCCTATTTTGCAATTGGCTAATGTTTTGTATTCAAAAGGATTTTCAAT

TACTATTTTTCATACTAATTTTAATAAACCTAAAACTTCAAATTATCCTCATTTTACTTTTAGA

TTTATTTTGGATAATGATCCTCAAGATGAAAGAATTTCAAATTTGCCTACTCATGGACCTTTGG

CTGGAATGAGAATTCCTATTATTAATGAACATGGAGCTGATGAATTGAGAAGAGAATTGGAATT

GTTGATGTTGGCTTCAGAAGAAGATGAAGAAGTTTCATGCTTGATTACTGATGCTTTGTGGTAT

TTTGCTCAATCAGTTGCTGATTCATTGAATTTGAGAAGATTGGTTTTGATGACTTCATCATTGT

TTAATTTTCATGCTCATGTTTCATTGCCTCAATTTGATGAATTGGGATATTTGGATCCTGATGA

TAAAACTAGATTGGAAGAACAAGCTTCAGGATTTCCTATGTTGAAAGTTAAAGATATTAAATCA

GCTTATTCAAATTGGCAAATTTTGAAAGAAATTTTGGGAAAAATGATTAAACAAACTAGAGCTT

CATCAGGAGTTATTTGGAATTCATTTAAAGAATTGGAAGAATCAGAATTGGAAACTGTTATTAG

AGAAATTCCTGCTCCTTCATTTTTGATTCCTTTGCCTAAACATTTGACTGCTTCATCATCATCA

TTGTTGGATCATGATAGAACTGTTTTTCAATGGTTGGATCAACAACCTCCTTCATCAGTTTTGT

ATGTTTCATTTGGATCAACTTCAGAAGTTGATGAAAAAGATTTTTTGGAAATTGCTAGAGGATT

GGTTGATTCAAAACAATCATTTTTGTGGGTTGTTAGACCTGGATTTGTTAAAGGATCAACTTGG

GTTGAACCTTTGCCTGATGGATTTTTGGGAGAAAGAGGAAGAATTGTTAAATGGGTTCCTCAAC

AAGAAGTTTTGGCTCATGGAGCTATTGGAGCTTTTTGGACTCATTCAGGATGGAATTCAACTTT

GGAATCAGTTTGCGAAGGAGTTCCTATGATTTTTTCAGATTTTGGATTGGATCAACCTTTGAAT

GCTAGATATATGTCAGATGTTTTGAAAGTTGGAGTTTATTTGGAAAATGGATGGGAAAGAGGAG
```

-continued

```
AAATTGCTAATGCTATTAGAAGAGTTATGGTTGATGAAGAAGGAGAATATATTAGACAAAATGC

TAGAGTTTTGAAACAAAAAGCTGATGTTTCATTGATGAAAGGAGGATCATCATATGAATCATTG

GAATCATTGGTTTCATATATTTCATCATTG
```

```
Amino Acid
UPD gycosyltransferase 76G1
Stevia rebaudiana
                                                         SEQ ID NO. 33
MENKTETTVRRRRRIILFPVPFQGHINPILQLANVLYSKGFSITIFHTNFNKPKTSNYPHFTFR

FILDNDPQDERISNLPTHGPLAGMRIPIINEHGADELRRELELLMLASEEDEEVSCLITDALWY

FAQSVADSLNLRRLVLMTSSLFNFHAHVSLPQFDELGYLDPDDKTRLEEQASGFPMLKVKDIKS

AYSNWQILKEILGKMIKQTRASSGVIWNSFKELEESELETVIREIPAPSFLIPLPKHLTASSSS

LLDHDRTVFQWLDQQPPSSVLYVSFGSTSEVDEKDFLEIARGLVDSKQSFLWVVRPGFVKGSTW

VEPLPDGFLGERGRIVKWVPQQEVLAHGAIGAFWTHSGWNSTLESVCEGVPMIFSDFGLDQPLN

ARYMSDVLKVGVYLENGWERGEIANAIRRVMVDEEGEYIRQNARVLKQKADVSLMKGGSSYESL

ESLVSYISSL
```

```
Amino Acid
Glycosyltransferase (NtGT5a)
Nicotiana tabacum
                                                         SEQ ID NO. 34
MGSIGAELTKPHAVCIPYPAQGHINPMLKLAKILHHKGFHITFVNTEFNHRRLLKSRGPDSLKG

LSSFRFETIPDGLPPCEADATQDIPSLCESTTNTCLAPFRDLLAKLNDTNTSNVPPVSCIVSDG

VMSFTLAAAQELGVPEVLFWTTSACGFLGYMHYCKVIEKGYAPLKDASDLTNGYLETTLDFIPG

MKDVRLRDLPSFLRTTNPDEFMIKFVLQETERARKASAIILNTFETLEAEVLESLRNLLPPVYP

IGPLHFLVKHVDDENLKGLRSSLWKEEPECIQWLDTKEPNSVVYVNFGSITVMTPNQLIEFAWG

LANSQQTFLWIIRPDIVSGDASILPPEFVEETKNRGMLASWCSQEEVLSHPAIVGFLTHSGWNS

TLESISSGVPMICWPFFAEQQTNCWFSVTKWDVGMEIDSDVKRDEVESLVRELMVGGKGKKMKK

KAMEWKELAEASAKEHSGSSYVNIEKLVNDILLSSKH
```

```
DNA
Glycosyltransferase (NtGT5a)
Nicotiana tabacum
                                                         SEQ ID NO. 35
ATGGGTTCCATTGGTGCTGAATTAACAAAGCCACATGCAGTTTGCATACCATATCCCGCCCAAG

GCCATATTAACCCCATGTTAAAGCTAGCCAAAATCCTTCATCACAAAGGCTTTCACATCACTTT

TGTCAATACTGAATTTAACCACCGACGTCTCCTTAAATCTCGTGGCCCTGATTCTCTCAAGGGT

CTTTCTTCTTTCCGTTTTGAGACCATTCCTGATGGACTTCCGCCATGTGAGGCAGATGCCACAC

AAGATATACCTTCTTTGTGTGAATCTACAACCAATACTTGCTTGGCTCCTTTTAGGGATCTTCT

TGCGAAACTCAATGATACTAACACATCTAACGTGCCACCCGTTTCGTGCATCGTCTCGGATGGT

GTCATGAGCTTCACCTTAGCCGCTGCACAAGAATTGGGAGTCCCTGAAGTTCTGTTTTGGACCA

CTAGTGCTTGTGGTTTCTTAGGTTACATGCATTACTGCAAGGTTATTGAAAAAGGATATGCTCC

ACTTAAAGATGCGAGTGACTTGACAAATGGATACCTAGAGACAACATTGGATTTTATACCAGGC

ATGAAAGACGTACGTTTAAGGGATCTTCCAAGTTTCTTGAGAACTACAAATCCAGATGAATTCA

TGATCAAATTTGTCCTCCAAGAAACAGAGAGAGCAAGAAAGGCTTCTGCAATTATCCTCAACAC

ATTTGAAACACTAGAGGCTGAAGTTCTTGATCGCTCCGAAATCTTCTTCCTCCAGTCTACCCC

ATAGGGCCCTTGCATTTTCTAGTGAAACATGTTGATGATGAGAATTTGAAGGGACTTAGATCCA

GCCTTTGGAAAGAGGAACCAGAGTGTATACAATGGCTTGATACCAAAGAACCAAATTCTGTTGT

TTATGTTAACTTTGGAAGCATTACTGTTATGACTCCTAATCAGCTTATTGAGTTTGCTTGGGGA
```

-continued

```
CTTGCAAACAGCCAGCAAACATTCTTATGGATCATAAGACCTGATATTGTTTCAGGTGATGCAT

CGATTCTTCCACCCGAATTCGTGGAAGAAACGAAGAACAGAGGTATGCTTGCTAGTTGGTGTTC

ACAAGAAGAAGTACTTAGTCACCCTGCAATAGTAGGATTCTTGACTCACAGTGGATGGAATTCG

ACACTCGAAAGTATAAGCAGTGGGGTGCCTATGATTTGCTGGCCATTTTTCGCTGAACAGCAAA

CAAATTGTTGGTTTTCCGTCACTAAATGGGATGTTGGAATGGAGATTGACAGTGATGTGAAGAG

AGATGAAGTGGAAAGCCTTGTAAGGGAATTGATGGTTGGGGGAAAAGGCAAAAAGATGAAGAAA

AAGGCAATGGAATGGAAGGAATTGGCTGAAGCATCTGCTAAAGAACATTCAGGGTCATCTTATG

TGAACATTGAAAAGTTGGTCAATGATATTCTTCTTTCATCCAAACATTAA
```

Amino Acid
Glycosyltransferase (NtGT5b)
*Nicotiana tabacum*
SEQ ID NO. 36

```
MGSIGAEFTKPHAVCIPYPAQGHINPMLKLAKILHHKGFHITFVNTEFNHRRLLKSRGPDSLKG

LSSFRFETIPDGLPPCDADATQDIPSLCESTTNTCLGPFRDLLAKLNDTNTSNVPPVSCIISDG

VMSFTLAAAQELGVPEVLFWTTSACGFLGYMHYYKVIEKGYAPLKDASDLTNGYLETTLDFIPC

MKDVRLRDLPSFLRTTNPDEFMIKFVLQETERARKASAIILNTYETLEAEVLESLRNLLPPVYP

IGPLHFLVKHVDDENLKGLRSSLWKEEPECIQWLDTKEPNSVVYVNFGSITVMTPNQLIEFAWG

LANSQQSFLWIIRPDIVSGDASILPPEFVEETKKRGMLASWCSQEEVLSHPAIGGFLTHSGWNS

TLESISSGVPMICWPFFAEQQTNCWFSVTKWDVGMEIDCDVKRDEVESLVRELMVGGKGKKMKK

KAMEWKELAEASAKEHSGSSYVNIEKVVNDILLSSKH
```

DNA
Glycosyltransferase (NtGT5b)
*Nicotiana tabacum*
SEQ ID NO. 37

```
ATGGGTTCCATTGGTGCTGAATTTACAAAGCCACATGCAGTTTGCATACCATATCCCGCCCAAG

GCCATATTAACCCCATGTTAAAGCTAGCCAAAATCCTTCATCACAAAGGCTTTCACATCACTTT

TGTCAATACTGAATTTAACCACAGACGTCTGCTTAAATCTCGTGGCCCTGATTCTCTCAAGGGT

CTTTCTTCTTTCCGTTTTGAGACAATTCCTGATGGACTTCCGCCATGTGATGCAGATGCCACAC

AAGATATACCTTCTTTGTGTGAATCTACAACCAATACTTGCTTGGGTCCTTTTAGGGATCTTCT

TGCGAAACTCAATGATACTAACACATCTAACGTGCCACCCGTTTCGTGCATCATCTCAGATGGT

GTCATGAGCTTCACCTTAGCCGCTGCACAAGAATTGGGAGTCCCTGAAGTTCTGTTTTGGACCA

CTAGTGCTTGTGGTTTCTTAGGTTACATGCATTATTACAAGGTTATTGAAAAGGATACGCTCC

ACTTAAAGATGCGAGTGACTTGACAAATGGATACCTAGAGACAACATTGGATTTTATACCATGC

ATGAAAGACGTACGTTTAAGGGATCTTCCAAGTTTCTTGAGAACTACAAATCCAGATGAATTCA

TGATCAAATTTGTCCTCCAAGAAACAGAGAGAGCAAGAAAGGCTTCTGCAATTATCCTCAACAC

ATATGAAACACTAGAGGCTGAAGTTCTTGAATCGCTCCGAAATCTTCTTCCTCCAGTCTACCCC

ATTGGGCCCTTGCATTTTCTAGTGAAACATGTTGATGATGAGAATTTGAAGGGACTTAGATCCA

GCCTTTGGAAAGAGGAACCAGAGTGTATACAATGGCTTGATACCAAAGAACCAAATTCTGTTGT

TTATGTTAACTTTGGAAGCATTACTGTTATGACTCCTAATCAACTTATTGAATTTGCTTGGGGA

CTTGCAAACAGCCAACAATCATTCTTATGGATCATAAGACCTGATATTGTTTCAGGTGATGCAT

CGATTCTTCCCCCCGAATTCGTGGAAGAAACGAAGAAGAGAGGTATGCTTGCTAGTTGGTGTTC

ACAAGAAGAAGTACTTAGTCACCCTGCAATAGGAGGATTCTTGACTCACAGTGGATGGAATTCG

ACACTCGAAAGTATAAGCAGTGGGGTGCCTATGATTTGCTGGCCATTTTTCGCTGAACAGCAAA

CAAATTGTTGGTTTTCCGTCACTAAATGGGATGTTGGAATGGAGATTGACTGTGATGTGAAGAG

GGATGAAGTGGAAAGCCTTGTAAGGGAATTGATGGTTGGGGGAAAAGGCAAAAAGATGAAGAAA
```

-continued

AAGGCAATGGAATGGAAGGAATTGGCTGAAGCATCTGCTAAAGAACATTCAGGGTCATCTTATG

TGAACATTGAGAAGGTGGTCAATGATATTCTTCTTTCGTCCAAACATTAA

Amino Acid
UDP-glycosyltransferase 73C3 (NtGT4)
*Nicotiana tabacum*
SEQ ID NO. 38
MATQVHKLHFILFPLMAPGHMIPMIDIAKLLANRGVITTIITTPVNANRFSSTITRAIKSGLRI

QILTLKFPSVEVGLPEGCENIDMLPSLDLASKFFAAISMLKQQVENLLEGINPSPSCVISDMGF

PWTTQIAQNFNIPRIVFHGTCCFSLLCSYKILSSNILENITSDSEYFVVPDLPDRVELTKAQVS

GSTKNTTSVSSSVLKEVTEQIRLAEESSYGVIVNSFEELEQVYEKEYRKARGKKVWCVGPVSLC

NKEIEDLVTRGNKTAIDNQDCLKWLDNFETESVVYASLGSLSRLTLLQMVELGLGLEESNRPFV

WVLGGGDKLNDLEKWILENGFEQRIKERGVLIRGWAPQVLILSHPAIGGVLTHCGWNSTLEGIS

AGLPMVTWPLFAEQFCNEKLVVQVLKIGVSLGVKVPVKWGDEENVGVLVKKDDVKKALDKLMDE

GEEGQVRRTKAKELGELAKKAFGEGGSSYVNLTSLIEDIIEQQNHKEK

DNA
UDP-glycosyltransferase 73C3 (NtGT4)
*Nicotiana tabacum*
SEQ ID NO. 39
ATGGCAACTCAAGTGCACAAACTTCATTTCATACTATTCCCTTTAATGGCTCCAGGCCACATGA

TTCCTATGATAGACATAGCTAAACTTCTAGCAAATCGCGGTGTCATTACCACTATCATCACCAC

TCCAGTAAACGCCAATCGTTTCAGTTCAACAATTACTCGTGCCATAAAATCCGGTCTAAGAATC

CAAATTCTTACACTCAAATTTCCAAGTGTAGAAGTAGGATTACCAGAAGGTTGCGAAATATTG

ACATGCTTCCTTCTCTTGACTTGGCTTCAAAGTTTTTTGCTGCAATTAGTATGCTGAAACAACA

AGTTGAAAATCTCTTAGAAGGAATAAATCCAAGTCCAAGTTGTGTTATTTCAGATATGGGATTT

CCTTGGACTACTCAAATTGCACAAAATTTTAATATCCCAAGAATTGTTTTTCATGGTACTTGTT

GTTTCTCACTTTTATGTTCCTATAAAATACTTTCCTCCAACATTCTTGAAAATATAACCTCAGA

TTCAGAGTATTTTGTTGTTCCTGATTTACCCGATAGAGTTGAACTAACGAAAGCTCAGGTTTCA

GGATCGACGAAAAATACTACTTCTGTTAGTTCTTCTGTATTGAAAGAAGTTACTGAGCAAATCA

GATTAGCCGAGGAATCATCATATGGTGTAATTGTTAATAGTTTTGAGGAGTTGGAGCAAGTGTA

TGAGAAAGAATATAGGAAAGCTAGAGGGAAAAAAGTTTGGTGTGTTGGTCCTGTTTCTTTGTGT

AATAAGGAAATTGAAGATTTGGTTACAAGGGGTAATAAAACTGCAATTGATAATCAAGATTGCT

TGAAATGGTTAGATAATTTTGAAACAGAATCTGTGGTTTATGCAAGTCTTGGAAGTTTATCTCG

TTTGACATTATTGCAAATGGTGGAACTTGGTCTTGGTTTAGAAGAGTCAAATAGGCCTTTTGTA

TGGGTATTAGGAGGAGGTGATAAATTAAATGATTTAGAGAAATGGATTCTTGAGAATGGATTTG

AGCAAAGAATTAAAGAAAGAGGAGTTTTGATTAGAGGATGGGCTCCTCAAGTGCTTATACTTTC

ACACCCTGCAATTGGTGGAGTATTGACTCATTGCGGATGGAATTCTACATTGGAAGGTATTTCA

GCAGGATTACCAATGGTAACATGGCCACTATTTGCTGAGCAATTTTGCAATGAGAAGTTAGTAG

TCCAAGTGCTAAAAATTGGAGTGAGCCTAGGTGTGAAGGTGCCTGTCAAATGGGGAGATGAGGA

AAATGTTGGAGTTTTGGTAAAAAAGGATGATGTTAAGAAAGCATTAGACAAACTAATGGATGAA

-continued

```
GGAGAAGAAGGACAAGTAAGAAGAACAAAAGCAAAAGAGTTAGGAGAATTGGCTAAAAAGGCAT

TTGGAGAAGGTGGTTCTTCTTATGTTAACTTAACATCTCTGATTGAAGACATCATTGAGCAACA

AAATCACAAGGAAAAATAG
```

Amino Acid
Glycosyltransferase (NtGT1b)
*Nicotiana tabacum*
SEQ ID NO. 40

```
MKTAELVFIPAPGMGHLVPTVEVAKQLVDRHEQLSITVLIMTIPLETNIPSYTKSLSSDYSSRI

TLLPLSQPETSVTMSSFNAINFFEYISSYKGRVKDAVSETSFSSSNSVKLAGFVIDMFCTAMID

VANEFGIPSYVFYTSSAAMLGLQLHFQSLSIECSPKVHNYVEPESEVLISTYMNPVPVKCLPGI

ILVNDESSTMFVNHARRFRETKGIMVNTFTELESHALKALSDDEKIPPIYPVGPILNLENGNED

HNQEYDAIMKWLDEKPNSSVVFLCFGSKGSFEEDQVKEIANALESSGYHFLWSLRRPPPKDKLQ

FPSEFENPEEVLPEGFFQRTKGRGKVIGWAPQLAILSHPSVGGFVSHCGWNSTLESVRSGVPIA

TWPLYAEQQSNAFQLVKDLGMAVEIKMDYREDFNTRNPPLVKAEEIEDGIRKLMDSENKIRAKV

TEMKDKSRAALLEGGSSYVALGHFVETVMKN
```

DNA
Glycosyltransferase (NtGT1b)
*Nicotiana tabacum*
SEQ ID NO. 41

```
ATGAAGACAGCAGAGTTAGTATTCATTCCTGCTCCTGGGATGGGTCACCTTGTACCAACTGTGG

AGGTGGCAAAGCAACTAGTCGACAGACACGAGCAGCTTTCGATCACAGTTCTAATCATGACAAT

TCCTTTGGAAACAAATATTCCATCATATACTAAATCACTGTCCTCAGACTACAGTTCTCGTATA

ACGCTGCTTCCACTCTCTCAACCTGAGACCTCTGTTACTATGAGCAGTTTTAATGCCATCAATT

TTTTTGAGTACATCTCCAGCTACAAGGGTCGTGTCAAAGATGCTGTTAGTGAAACCTCCTTTAG

TTCGTCAAATTCTGTGAAACTTGCAGGATTTGTAATAGACATGTTCTGCACTGCGATGATTGAT

GTAGCGAACGAGTTTGGAATCCCAAGTTATGTGTTCTACACTTCTAGTGCAGCTATGCTTGGAC

TACAACTGCATTTTCAAAGTCTTAGCATTGAATGCAGTCCGAAAGTTCATAACTACGTTGAACC

TGAATCAGAAGTTCTGATCTCAACTTACATGAATCCGGTTCCAGTCAAATGTTTGCCCGGAATT

ATACTAGTAAATGATGAAAGTAGCACCATGTTTGTCAATCATGCACGAAGATTCAGGGAGACGA

AAGGAATTATGGTGAACACGTTCACTGAGCTTGAATCACACGCTTTGAAAGCCCTTTCCGATGA

TGAAAAAATCCCACCAATCTACCCAGTTGGACCTATACTTAACCTTGAAAATGGGAATGAAGAT

CACAATCAAGAATATGATGCGATTATGAAGTGGCTTGACGAGAAGCCTAATTCATCAGTGGTGT

TCTTATGCTTTGGAAGCAAGGGGTCTTTCGAAGAAGATCAGGTGAAGGAAATAGCAAATGCTCT

AGAGAGCAGTGGCTACCACTTCTTGTGGTCGCTAAGGCGACCGCCACCAAAAGACAAGCTACAA

TTCCCAAGCGAATTCGAGAATCCAGAGGAAGTCTTACCAGAGGGATTCTTTCAAAGGACTAAAG

GAAGAGGAAAGGTGATAGGATGGGCACCCCAGTTGGCTATTTTGTCTCATCCTTCAGTAGGAGG

ATTCGTGTCGCATTGTGGGTGGAATTCAACTCTGGAGAGCGTTCGAAGTGGAGTGCCGATAGCA

ACATGGCCATTGTATGCAGAGCAACAGAGCAATGCATTTCAACTGGTGAAGGATTTGGGTATGG

CAGTAGAGATTAAGATGGATTACAGGGAAGATTTTAATACGAGAAATCCACCACTGGTTAAAGC
```

-continued

```
TGAGGAGATAGAAGATGGAATTAGGAAGCTGATGGATTCAGAGAATAAAATCAGGGCTAAGGTG

ACGGAGATGAAGGACAAAAGTAGAGCAGCACTGCTGGAGGGCGGATCATCATATGTAGCTCTTG

GGCATTTTGTTGAGACTGTCATGAAAAACTAG
```

```
Amino Acid
Glycosyltransferase (NtGT1a)
Nicotiana tabacum
                                              SEQ ID NO. 42
MKTTELVFIPAPGMGHLVPTVEVAKQLVDRDEQLSITVLIMTLPLETNIPSYTKSLSSDYSSRI

TLLQLSQPETSVSMSSFNAINFFEYISSYKDRVKDAVNETFSSSSSVKLKGFVIDMFCTAMIDV

ANEFGIPSYVFYTSNAAMLGLQLHFQSLSIEYSPKVHNYLDPESEVAISTYINPIPVKCLPGII

LDNDKSGTMFVNHARRFRETKGIMVNTFAELESHALKALSDDEKIPPIYPVGPILNLGDGNEDH

NQEYDMIMKWLDEQPHSSVVFLCFGSKGSFEEDQVKEIANALERSGNRFLWSLRRPPPKDTLQF

PSEFENPEEVLPVGFFQRTKGRGKVIGWAPQLAILSHPAVGGFVSHCGWNSTLESVRSGVPIAT

WPLYAEQQSNAFQLVKDLGMAVEIKMDYREDFNKTNPPLVKAEEIEDGIRKLMDSENKIRAKVM

EMKDKSRAALLEGGSSYVALGHFVETVMKN
```

```
DNA
Glycosyltransferase (NtGT1a)
Nicotiana tabacum
                                              SEQ ID NO. 43
ATGAAGACAACAGAGTTAGTATTCATTCCTGCTCCTGGCATGGGTCACCTTGTACCCACTGTGG

AGGTGGCAAAGCAACTAGTCGACAGAGACGAACAGCTTTCAATCACAGTTCTCATCATGACGCT

TCCTTTGGAAACAAATATTCCATCATATACTAAATCACTGTCCTCAGACTACAGTTCTCGTATA

ACGCTGCTTCAACTTTCTCAACCTGAGACCTCTGTTAGTATGAGCAGTTTTAATGCCATCAATT

TTTTTGAGTACATCTCCAGCTACAAGGATCGTGTCAAAGATGCTGTTAATGAAACCTTTAGTTC

GTCAAGTTCTGTGAAACTCAAAGGATTTGTAATAGACATGTTCTGCACTGCGATGATTGATGTG

GCGAACGAGTTTGGAATCCCAAGTTATGTCTTCTACACTTCTAATGCAGCTATGCTTGGACTCC

AACTCCATTTTCAAAGTCTTAGTATTGAATACAGTCCGAAAGTTCATAATTACCTAGACCCTGA

ATCAGAAGTAGCGATCTCAACTTACATTAATCCGATTCCAGTCAAATGTTTGCCCGGGATTATA

CTAGACAATGATAAAAGTGGCACCATGTTCGTCAATCATGCACGAAGATTCAGGGAGACGAAAG

GAATTATGGTGAACACATTCGCTGAGCTTGAATCACACGCTTTGAAAGCCCTTTCCGATGATGA

GAAAATCCCACCAATCTACCCAGTTGGGCCTATACTTAACCTTGGAGATGGGAATGAAGATCAC

AATCAAGAATATGATATGATTATGAAGTGGCTCGACGAGCAGCCTCATTCATCAGTGGTGTTCC

TATGCTTTGGAAGCAAGGGATCTTTCGAAGAAGATCAAGTGAAGGAAATAGCAAATGCTCTAGA

GAGAAGTGGTAACCGGTTCTTGTGGTCGCTAAGACGACCGCCACCAAAAGACACGCTACAATTC

CCAAGCGAATTCGAGAATCCAGAGGAAGTCTTGCCGGTGGGATTCTTTCAAAGGACTAAAGGAA

GAGGAAAGGTGATAGGATGGGCACCCCAGTTGGCTATTTTGTCTCATCCTGCAGTAGGAGGATT

CGTGTCGCATTGTGGGTGGAATTCAACTTTGGAGAGTGTTCGTAGTGGAGTACCGATAGCAACA

TGGCCATTGTAATGCAGAGCAACAGAGCAATGCATTTCACTGGTGAAGGATTTGGGGATGGCAG

TGGAGATTAAGATGGATTACAGGGAAGATTTTAATAAGACAAATCCACCACTGGTTAAAGCTGA
```

-continued

```
GGAGATAGAAGATGGAATTAGGAAGCTGATGGATTCAGAGAATAAAATCAGGGCTAAGGTGATG

GAGATGAAGGACAAAAGTAGAGCAGCGTTATTAGAAGGCGGATCATCATATGTAGCTCTCGGGC

ATTTTGTTGAGACTGTCATGAAAAACTAA
```

```
Amino Acid
Glycosyltransferase (NtGT3)
Nicotiana tabacum
                                                     SEQ ID NO. 44
MKETKKIELVFIPSPGIGHLVSTVEMAKLLIAREEQLSITVLIIQWPNDKKLDSYIQSVANFSS

RLKFIRLPQDDSIMQLLKSNIFTTFIASHKPAVRDAVADILKSESNNTLAGIVIDLFCTSMIDV

ANEFELPTYVFYTSGAATLGLHYHIQNLRDEFNKDITKYKDEPEEKLSIATYLNPFPAKCLPSV

ALDKEGGSTMFLDLAKRFRETKGIMINTFLELESYALNSLSRDKNLPPIYPVGPVLNLNNVEGD

NLGSSDQNTMKWLDDQPASSVVFLCFGSGGSFEKHQVKEIAYALESSGCRFLWSLRRPPTEDAR

FPSNYENLEEILPEGFLERTKGIGKVIGWAPQLAILSHKSTGGFVSHCGWNSTLESTYFGVPIA

TWPMYAEQQANAFQLVKDLRMGVEIKMDYRKDMKVMGKEVIVKAEEIEKAIREIMDSESEIRVK

VKEMKEKSRAAQMEGGSSYTSIGGFIQIIMENSQ
```

```
DNA
Glycosyltransferase (NtGT3)
Nicotiana tabacum
                                                     SEQ ID NO. 45
ATGAAAGAAACCAAGAAAATAGAGTTAGTCTTCATTCCTTCACCAGGAATTGGCCATTTAGTAT

CCACAGTTGAAATGGCAAAGCTTCTTATAGCTAGAGAAGAGCAGCTATCTATCACAGTCCTCAT

CATCCAATGGCCTAACGACAAGAAGCTCGATTCTTATATCCAATCAGTCGCCAATTTCAGCTCG

CGTTTGAAATTCATTCGACTCCCTCAGGATGATTCCATTATGCAGCTACTCAAAAGCAACATTT

TCACCACGTTTATTGCCAGTCATAAGCCTGCAGTTAGAGATGCTGTTGCTGATATTCTCAAGTC

AGAATCAAATAATACGCTAGCAGGTATTGTTATCGACTTGTTCTGCACCTCAATGATAGACGTG

GCCAATGAGTTCGAGCTACCAACCTATGTTTTCTACACGTCTGGTGCAGCAACCCTTGGTCTTC

ATTATCATATACAGAATCTCAGGGATGAATTTAACAAAGATATTACCAAGTACAAAGACGAACC

TGAAGAAAAACTCTCTATAGCAACATATCTCAATCCATTTCCAGCAAAATGTTTGCCGTCTGTA

GCCTTAGACAAAGAAGGTGGTTCAACAATGTTTCTTGATCTCGCAAAAAGGTTTCGAGAAACCA

AAGGTATTATGATAAACACATTTCTAGAGCTCGAATCCTATGCATTAAACTCGCTCTCACGAGA

CAAGAATCTTCCACCTATATACCCTGTCGGACCAGTATTGAACCTTAACAATGTTGAAGGTGAC

AACTTAGGTTCATCTGACCAGAATACTATGAAATGGTTAGATGATCAGCCCGCTTCATCTGTAG

TGTTCCTTTGTTTTGGTAGTGGTGGAAGCTTTGAAAAACATCAAGTTAAGGAAATAGCCTATGC

TCTGGAGAGCAGTGGGTGTCGGTTTTTGTGGTCGTTAAGGCGACCACCAACCGAAGATGCAAGA

TTTCCAAGCAACTATGAAAATCTTGAAGAAATTTTGCCAGAAGGATTCTTGGAAAGAACAAAAG

GGATTGGAAAAGTGATAGGATGGGCACCTCAGTTGGCGATTTTGTCACATAAATCGACGGGGGG

ATTTGTGTCGCACTGTGGATGGAATTCGACTTTGGAAAGTACATATTTTGGAGTGCCAATAGCA

ACCTGGCCAATGTACGCGGAGCAACAAGCGAATGCATTTCAATTGGTTAAGGATTTGAGAATGG

GAGTTGAGATTAAGATGGATTATAGGAAGGATATGAAAGTGATGGGCAAAGAAGTTATAGTGAA

AGCTGAGGAGATTGAGAAAGCAATAAGAGAAATTATGGATTCCGAGAGTGAAATTCGGGTGAAG
```

```
GTGAAAGAGATGAAGGAGAAGAGCAGAGCAGCACAAATGGAAGGTGGCTCTTCTTACACTTCTA

TTGGAGGTTTCATCCAAATTATCATGGAGAATTCTCAATAA
```

Amino Acid
Glycosyltransferase (NtGT2)
*Nicotiana tabacum*
SEQ ID NO. 46

```
MVQPHVLLVTFPAQGHINPCLQFAKRLIRMGIEVTFATSVFAHRRMAKTTTSTLSKGLNFAAFS

DGYDDGFKADEHDSQHYMSEIKSRGSKTLKDIILKSSDEGRPVTSLVYSLLLPWAAKVAREFHI

PCALLWIQPATVLDIYYYYFNGYEDAIKGSTNDPNWCIQLPRLPLLKSQDLPSFLLSSSNEEKY

SFALPTFKEQLDTLDVEENPKVLVNTFDALEPKELKAIEKYNLIGIGPLIPSTFLDGKDPLDSS

FGGDLFQKSNDYIEWLNSKANSSVVYISFGSLLNLSKNQKEEIAKGLIEIKKPFLWVIRDQENG

KGDEKEEKLSCMMELEKQGKIVPWCSQLEVLTHPSIGCFVSHCGWNSTLESLSSGVSVVAFPHW

TDQGTNAKLIEDVWKTGVRLKKNEDGVVESEEIKRCIEMVMDGGEKGEEMRRNAQKWKELAREA

VKEGGSSEMNLKAFVQEVGKGC
```

DNA
Glycosyltransferase (NtGT2)
*Nicotiana tabacum*
SEQ ID NO. 47

```
ATGGTGCAACCCCATGTCCTCTTGGTGACTTTTCCAGCACAAGGCCATATTAATCCATGTCTCC

AATTTGCCAAGAGGCTAATTAGAATGGGCATTGAGGTAACTTTTGCCACGAGCGTTTTCGCCCA

TCGTCGTATGGCAAAAACTACGACTTCCACTCTATCCAAGGGCTTAAATTTTGCGGCATTCTCT

GATGGGTACGACGATGGTTTCAAGGCCGATGAGCATGATTCTCAACATTACATGTCGGAGATAA

AAAGTCGCGGTTCTAAAACCCTAAAAGATATCATTTTGAAGAGCTCAGACGAGGGACGTCCTGT

GACATCCCTCGTCTATTCTCTTTTGCTTCCATGGGCTGCAAAGGTAGCGCGTGAATTTCACATA

CCGTGCGCGTTACTATGGATTCAACCAGCAACTGTGCTAGACATATATTATTATTACTTCAATG

GCTATGAGGATGCCATAAAAGGTAGCACCAATGATCCAAATTGGTGTATTCAATTGCCTAGGCT

TCCACTACTAAAAAGCCAAGATCTTCCTTCTTTTTTACTTTCTTCTAGTAATGAAGAAAAATAT

AGCTTTGCTCTACCAACATTTAAAGAGCAACTTGACACATTAGATGTTGAAGAAAATCCTAAAG

TACTTGTGAACACATTTGATGCATTAGAGCCAAAGGAACTCAAAGCTATTGAAAAGTACAATTT

AATTGGGATTGGACCATTGATTCCTTCAACATTTTTGGACGGAAAAGACCCTTTGGATTCTTCC

TTTGGTGGTGATCTTTTTCAAAAGTCTAATGACTATATTGAATGGTTGAACTCAAAGGCTAACT

CATCTGTGGTTTATATCTCATTTGGGAGTCTCTTGAATTTGTCAAAAAATCAAAAGGAGGAGAT

TGCAAAAGGGTTGATAGAGATTAAAAAGCCATTCTTGTGGGTAATAAGAGATCAAGAAAATGGT

AAGGGAGATGAAAAAGAAGAGAAATTAAGTTGTATGATGGAGTTGGAAAAGCAAGGGAAAATAG

TACCATGGTGTTCACAACTTGAAGTCTTAACACATCCATCTATAGGATGTTTCGTGTCACATTG

TGGATGGAATTCGACTCTGGAAAGTTTATCGTCAGGCGTGTCAGTAGTGGCATTTCCTCATTGG

ACGGATCAAGGGACAAATGCTAAACTAATTGAAGATGTTTGGAAGACAGGTGTAAGGTTGAAAA

AGAATGAAGATGGTGTGGTTGAGAGTGAAGAGATAAAAAGGTGCATAGAAATGGTAATGGATGG

TGGAGAGAAAGGAGAAGAAATGAGAAGAAATGCTCAAAAATGGAAAGAATTGGCAAGGGAAGCT

GTAAAAGAAGGCGGATCTTCGGAAATGAATCTAAAAGCTTTTGTTCAAGAAGTTGGCAAAGGTT

GCTGA
```

Amino Acid
THCA Synthase
*Cannabis*
SEQ ID NO. 48

```
MNCSAFSFWFVCKIIFFFLSFHIQISIANPRENFLKCFSKHIPNNVANPKLVYTQHDQLYMSIL

NSTIQNLRFISDTTPKPLVIVTPSNNSHIQATILCSKKVGLQIRTRSGGHDAEGMSYISQVPFV
```

-continued

VVDLRNMHSIKIDVHSQTAWVEAGATLGEVYYWINEKNENLSFPGGYCPTVGVGGHFSGGGYGA

LMRNYGLAADNIIDAHLVNVDGKVLDRKSMGEDLFWAIRGGGGENFGIIAAWKIKLVDVPSKST

IFSVKKNMEIHGLVKLFNKWQNIAYKYDKDLVLMTHFITKNITDNHGKNKTTVHGYFSSIFHGG

VDSLVDLMNKSFPELGIKKTDCKEFSWIDTTIFYSGVVNFNTANFKKEILLDRSAGKKTAFSIK

LDYVKKPIPETAMVKILEKLYEEDVGAGMYVLYPYGGIMEEISESAIPFPHRAGIMYELWYTAS

WEKQEDNEKHINWVRSVYNFTTPYVSQNPRLAYLNYRDLDLGKTNHASPNNYTQARIWGEKYFG

KNFNRLVKVKTKVDPNNFFRNEQSIPPLPPHHH

DNA
Glycosyltransferase (NtGT1b - codon optimized for yeast expression)
Nicotiana tabacum
SEQ ID NO. 49

ATGAAAACAACAGAACTTGTCTTCATACCCGCCCCCGGTATGGGTCACCTTGTACCCACAGTCG

AAGTCGCCAAACAACTAGTTGATAGAGACGAACAGTTGTCTATTACCGTCTTGATAATGACGTT

ACCCCTGGAGACTAATATCCCAAGTTACACCAAGAGTTTGTCCTCTGACTATTCATCCCGTATC

ACGTTGTTACAACTAAGTCAACCTGAGACGAGTGTCTCAATGAGTAGTTTTAACGCCATAAACT

TCTTCGAATACATTAGTTCCTATAAGGATCGTGTTAAAGATGCCGTAAACGAGACATTCTCCTC

TTCATCCTCCGTCAAACTTAAAGGATTTGTAATCGACATGTTTTGCACGGCAATGATAGACGTG

GCCAACGAGTTCGGTATTCCATCTTATGTATTCTACACGTCCAACGCTGCCATGCTAGGCCTAC

AACTTCACTTCCAATCCTTGTCCATCGAATATTCACCTAAGGTTCATAATTATTTAGACCCTGA

ATCTGAGGTAGCTATATCAACGTACATTAACCCAATACCAGTAAAATGCTTACCCGGTATAATT

CTTGACAATGATAAGAGTGGCACTATGTTCGTAAACCATGCCAGGAGATTCCGTGAAACAAAGG

GTATAATGGTAAATACTTTTGCAGAATTAGAAAGTCACGCCCTAAAGGCACTTAGTGACGATGA

GAAAATTCCTCCAATCTATCCCGTCGGACCCATTCTAAACTTGGGTGATGGTAATGAGGATCAT

AACCAAGAGTACGACATGATAATGAAATGGCTGGATGAACAACCACACAGTTCAGTGGTTTTCC

TGTGCTTCGGTTCCAAAGGTTCATTTGAAGAAGACCAGGTTAAAGAGATAGCAAATGCTTTAGA

GAGATCAGGCAATAGGTTCCTGTGGAGTTTAAGACGTCCCCCTCCCAAGGATACTCTTCAATTC

CCTTCCGAATTTGAAAACCCCGAGGAAGTGCTACCTGTAGGATTTTTTCAAAGAACCAAAGGCA

GAGGAAAAGTCATCGGATGGGCACCACAGCTTGCAATTCTATCTCACCCTGCCGTCGGTGGATT

CGTTTCCCACTGCGGCTGGAATAGTACTTTGGAATCAGTTAGATCAGGTGTACCCATAGCAACA

TGGCCTCTTTATGCAGAGCAGCAGTCCAATGCATTTCAATTGGTCAAGGATCTAGGTATGGCCG

TCGAAATTAAAATGGATTACCGTGAGGACTTTAACAAGACTAATCCTCCATTGGTAAAGGCAGA

GGAAATAGAAGACGGCATTAGGAAGTTGATGGACTCCGAGAATAAGATTAGGGCAAAGGTGATG

GAAATGAAAGATAAGTCCAGAGCTGCATTACTGGAAGGAGGATCCTCCTATGTTGCACTGGGTC

ACTTCGTGGAGACCGTAATGAAGAACTAA

Amino Acid
Glycosyltransferase (NtGT1b - generated from codon optimized sequence
for yeast expression)
Nicotiana tabacum
SEQ ID NO. 50

MKTTELVFIPAPGMGHLVPTVEVAKQLVDRDEQLSITVLIMTLPLETNIPSYTKSLSSDYSSRI

TLLQLSQPETSVSMSSFNAINFFEYISSYKDRVKDAVNETFSSSSSVKLKGFVIDMFCTAMIDV

ANEFGIPSYVFYTSNAAMLGLQLHFQSLSIEYSPKVHNYLDPESEVAISTYINPIPVKCLPGII

LDNDKSGTMFVNHARRFRETKGIMVNTFAELESHALKALSDDEKIPPIYPVGPILNLGDGNEDH

NQEYDMIMKWLDEQPHSSVVFLCFGSKGSFEEDQVKEIANALERSGNRFLWSLRRPPPKDTLQF

PSEFENPEEVLPVGFFQRTKGRGKVIGWAPQLAILSHPAVGGFVSHCGWNSTLESVRSGVPIAT

WPLYAEQQSNAFQLVKDLGMAVEIKMDYREDFNKTNPPLVKAEEIEDGIRKLMDSENKIRAKVM

EMKDKSRAALLEGGSSYVALGHFVETVMKN

DNA
Glycosyltransferase (NtGT2 - codon optimized for yeast expression)
*Nicotiana tabacum*
SEQ ID NO. 51

ATGGTTCAACCACACGTCTTACTGGTTACTTTTCCAGCACAAGGCCATATCAACCCTTGCCTAC

AATTCGCCAAAAGACTAATAAGGATGGGCATCGAAGTAACTTTTGCCACGAGTGTATTCGCACA

TAGGCGTATGGCTAAAACTACGACATCAACTTTGTCCAAAGGACTAAACTTCGCCGCCTTCAGT

GATGGCTATGACGATGGATTCAAAGCCGACGAACATGACAGTCAACACTACATGAGTGAAATAA

AGTCCCGTGGATCTAAAACACTTAAGGATATTATACTTAAATCCTCCGATGAGGGAAGACCCGT

TACCTCTTTAGTTTATTCACTGTTACTGCCCTGGGCTGCAAAAGTCGCCAGAGAGTTTCATATT

CCTTGCGCTTTATTGTGGATCCAACCAGCTACGGTATTAGACATCTACTATTACTACTTCAATG

GATACGAGGATGCAATAAAGGGATCAACAAACGACCCCAACTGGTGTATTCAACTGCCTAGACT

TCCTCTATTAAAAAGTCAGGACTTACCTAGTTTTTTACTGTCATCCAGTAACGAAGAAAAATAT

TCATTCGCTTTACCCACCTTCAAAGAGCAGCTTGACACTTTGGATGTTGAAGAGAACCCCAAGG

TTTTGGTCAATACTTTTGACGCTTTGGAGCCAAAAGAGCTAAAGGCTATTGAAAAATATAACCT

TATCGGCATAGGACCTTTAATCCCCTCTACTTTCTTAGATGGCAAAGACCCTCTAGATTCAAGT

TTCGGAGGTGATTTGTTTCAAAAGAGTAACGATTATATCGAGTGGCTAAATAGTAAAGCCAACT

CCAGTGTGGTCTACATTTCTTTCGGAAGTCTTCTGAATTTATCAAAAAACCAAAAGGAAGAGAT

CGCAAAAGGACTGATAGAGATAAAAAAACCTTTCTTATGGGTGATCAGAGACCAGGAAAACGGT

AAAGGCGATGAGAAGGAGGAAAAACTGTCCTGTATGATGGAGCTAGAGAAACAAGGAAAAATCG

TTCCCTGGTGTTCACAGTTAGAAGTGTTAACCCATCCATCCATAGGTTGCTTCGTATCACATTG

TGGTTGGAATAGTACACTTGAAAGTCTTTCATCAGGCGTCTCTGTCGTCGCATTCCCCCACTGG

ACGGACCAGGGCACAAACGCCAAACTGATCGAAGATGTATGGAAGACGGGCGTCAGGCTAAAAA

AAAATGAGGATGGCGTGGTAGAGAGTGAAGAGATAAAGCGTTGCATAGAAATGGTCATGGATGG

CGGTGAAAAGGGAGAGGAAATGAGGCGTAACGCACAAAGTGGAAGGAACTAGCCCGTGAAGCA

GTGAAAGAAGGAGGTTCTAGTGAGATGAATTTAAAAGCTTTCGTGCAGGAAGTTGGAAAAGGCT

GCTGA

Amino Acid
Glycosyltransferase (NtGT2 - generated from codon optimized sequence
for yeast expression)
*Nicotiana tabacum*
SEQ ID NO. 52

MVQPHVLLVTFPAQGHINPCLQFAKRLIRMGIEVTFATSVFAHRRMAKTTTSTLSKGLNFAAFS

DGYDDGFKADEHDSQHYMSEIKSRGSKTLKDIILKSSDEGRPVTSLVYSLLLPWAAKVAREFHI

PCALLWIQPATVLDIYYYYFNGYEDAIKGSTNDPNWCIQLPRLPLLKSQDLPSFLLSSSNEEKY

SFALPTFKEQLDTLDVEENPKVLVNTFDALEPKELKAIEKYNLIGIGPLIPSTFLDGKDPLDSS

FGGDLFQKSNDYIEWLNSKANSSVVYISFGSLLNLSKNQKEEIAKGLIEIKKPFLWVIRDQENG

KGDEKEEKLSCMMELEKQGKIVPWCSQLEVLTHPSIGCFVSHCGWNSTLESLSSGVSVVAFPHW

-continued

TDQGTNAKLIEDVWKTGVRLKKNEDGVVESEEIKRCIEMVMDGGEKGEEMRRNAQKWKELAREA

VKEGGSSEMNLKAFVQEVGKGC

DNA
Glycosyltransferase (NtGT3 - codon optimized for yeast expression)
Nicotiana tabacum
SEQ ID NO. 53

ATGAAAGAGACTAAAAAAATTGAGTTAGTTTTTATCCCCAGTCCTGGTATAGGACACTTAGTCT

CAACTGTGGAGATGGCCAAACTGTTGATAGCCCGTGAAGAGCAACTTTCTATTACTGTCCTGAT

TATACAATGGCCTAATGATAAAAAGCTAGACAGTTATATCCAGTCCGTCGCAAACTTTAGTTCT

AGACTGAAGTTTATACGTCTGCCCCAAGATGACTCAATCATGCAACTTTTGAAATCAAACATTT

TCACGACATTCATCGCCTCTCACAAGCCAGCTGTAAGAGACGCCGTTGCTGACATACTAAAGAG

TGAAAGTAATAACACATTGGCAGGCATTGTAATCGATCTTTTCTGCACATCCATGATCGATGTA

GCCAATGAGTTTGAGCTGCCTACTTATGTGTTTTACACTAGTGGCGCAGCCACGTTGGGTCTGC

ACTACCATATTCAAAATCTGCGTGATGAGTTTAATAAAGACATTACCAAATATAAGGATGAGCC

AGAAGAAAAATTAAGTATAGCCACGTACCTTAACCCATTCCCTGCTAAGTGTCTACCCTCCGTG

GCATTGGATAAGGAAGGAGGATCAACGATGTTCCTAGACTTAGCTAAGAGGTTCAGGGAGACCA

AAGGCATAATGATTAACACTTTTCTTGAGCTGGAATCATACGCTCTAAACTCATTGTCTAGAGA

TAAAAACTTGCCCCCTATATACCCTGTAGGCCCTGTTTTGAACTTGAACAACGTTGAGGGTGAT

AACTTGGGCTCTAGTGATCAAAATACCATGAAATGGCTGGACGACCAGCCAGCTTCTTCCGTTG

TGTTCCTATGTTTTGGCTCAGGAGGAAGTTTCGAAAAACACCAAGTCAAAGAAATAGCTTATGC

CTTAGAATCTTCCGGATGCAGGTTCTTGTGGAGTTTGCGTAGACCCCCCACGGAAGATGCTAGG

TTCCCTTCTAATTACGAAAACTTAGAGGAAATTTTACCAGAGGGATTTCTGGAAAGAACGAAAG

GCATTGGTAAGGTCATTGGATGGGCCCCACAGTTAGCAATCTTGTCTCACAAGTCCACAGGAGG

ATTCGTGTCTCATTGCGGATGGAACTCTACCCTTGAAAGTACCTATTTCGGCGTTCCTATTGCT

ACTTGGCCAATGTATGCTGAACAACAGGCCAACGCTTTTCAACTTGTTAAAGATTTGAGGATGG

GTGTTGAGATCAAAATGGATTATAGGAAGGATATGAAGGTAATGGGCAAGGAGGTTATCGTTAA

GGCAGAAGAAATTGAAAAGGCCATAAGGGAAATCATGGACTCAGAATCAGAAATCAGGGTCAAG

GTCAAAGAGATGAAGGAGAAAAGTCGTGCAGCCCAAATGGAAGGAGGATCATCATATACCTCTA

TCGGCGGCTTCATTCAAATAATCATGGAGAACTCACAGTAA

Amino Acid
Glycosyltransferase (NtGT3 - generated from codon optimized sequence
for yeast expression)
Nicotiana tabacum
SEQ ID NO. 54

MKETKKIELVFIPSPGIGHLVSTVEMAKLLIAREEQLSITVLIIQWPNDKKLDSYIQSVANFSS

RLKFIRLPQDDSIMQLLKSNIFTTFIASHKPAVRDAVADILKSESNNTLAGIVIDLFCTSMIDV

ANEFELPTYVFYTSGAATLGLHYHIQNLRDEFNKDITKYKDEPEEKLSIATYLNPFPAKCLPSV

ALDKEGGSTMFLDLAKRFRETKGIMINTFLELESYALNSLSRDKNLPPIYPVGPVLNLNNVEGD

NLGSSDQNTMKWLDDQPASSVVFLCFGSGGSFEKHQVKEIAYALESSGCRFLWSLRRPPTEDAR

FPSNYENLEEILPEGFLERTKGIGKVIGWAPQLAILSHKSTGGFVSHCGWNSTLESTYFGVPIA

-continued

TWPMYAEQQANAFQLVKDLRMGVEIKMDYRKDMKVMGKEVIVKAEEIEKAIREIMDSESEIRVK

VKEMKEKSRAAQMEGGSSYTSIGGFIQIIMENSQ

DNA
UDP-glycosyltransferase 73C3 (NtGT4 - codon optimized for yeast expression)
*Nicotiana tabacum*

SEQ ID NO. 55

ATGGCTACTCAGGTGCATAAATTGCATTTCATTCTGTTCCCACTGATGGCTCCCGGTCACATGA

TCCCTATGATAGACATCGCAAAACTATTGGCTAACCGTGGCGTGATAACTACCATAATAACTAC

GCCCGTTAACGCCAATCGTTTTTCCTCTACGATCACTAGGGCCATTAAATCAGGCCTAAGAATC

CAGATTTTAACCTTAAAATTCCCATCAGTTGAGGTAGGCCTGCCTGAAGGATGTGAAAACATCG

ACATGTTGCCATCTTTGGACTTAGCCTCTAAATTCTTTGCTGCTATTTCTATGCTTAAACAACA

AGTGGAGAACTTGCTAGAGGGTATTAACCCTAGTCCCTCATGCGTTATTTCTGACATGGGCTTC

CCATGGACGACACAGATCGCTCAAAATTTCAATATTCCTCGTATCGTATTTCATGGCACGTGTT

GCTTTTCTCTTCTTTGTTCTTACAAAATCCTGTCATCCAATATCTTAGAGAACATTACTAGTGA

CTCAGAGTATTTTGTCGTGCCAGATCTGCCAGACCGTGTCGAGCTAACTAAGGCCCAAGTCTCT

GGATCTACAAAGAATACTACATCAGTAAGTAGTTCAGTACTGAAGGAGGTTACAGAGCAGATCA

GGCTTGCAGAGGAATCATCCTACGGTGTGATAGTTAATTCCTTCGAAGAACTGGAACAGGTGTA

TGAAAAAGAGTACAGAAAAGCCAGGGGCAAAAAGGTCTGGTGCGTGGGTCCTGTCTCTTTGTGC

AACAAGGAGATTGAAGATCTTGTTACTAGAGGAAACAAAACCGCTATAGACAATCAGGATTGTC

TTAAGTGGTTAGACAACTTCGAGACTGAATCCGTCGTCTATGCAAGTTTAGGCTCACTAAGTAG

GCTTACGTTACTGCAAATGGTTGAGCTGGGATTGGGACTGGAGGAGAGTAATAGGCCATTTGTA

TGGGTTCTGGGAGGAGGAGACAAACTAAATGATCTTGAGAAATGGATATTGGAGAATGGCTTTG

AACAGCGTATAAAGGAGAGAGGTGTCCTGATACGTGGCTGGGCACCTCAAGTATTGATTTTAAG

TCACCCCGCAATTGGAGGAGTTTTAACGCATTGTGGATGGAACTCTACATTAGAGGGCATTTCA

GCCGGACTACCCATGGTCACCTGGCCACTATTTGCCGAACAGTTCTGTAACGAAAAATTAGTAG

TGCAGGTTCTTAAAATCGGTGTCTCACTTGGAGTGAAGGTCCCTGTTAAGTGGGGTGACGAAGA

GAACGTAGGTGTCTTAGTGAAAAAGGATGACGTTAAAAAAGCACTGGATAAGCTAATGGATGAG

GGTGAGGAGGGCCAGGTTAGGAGGACCAAAGCCAAAGAGCTTGGTGAGTTAGCTAAAAAAGCCT

TTGGAGAGGGCGGATCATCCTACGTGAACCTAACGTCCCTAATTGAAGATATAATCGAGCAGCA

GACCATAAGGAGAAGTAG

Amino Acid
UDP-glycosyltransferase 73C3 (NtGT4 - generated from codon optimized sequence for yeast expression)
*Nicotiana tabacum*

SEQ ID NO. 56

MATQVHKLHFILFPLMAPGHMIPMIDIAKLLANRGVITTIITTPVNANRFSSTITRAIKSGLRI

QILTLKFPSVEVGLPEGCENIDMLPSLDLASKFFAAISMLKQQVENLLEGINPSPSCVISDMGF

PWTTQIAQNFNIPRIVFHGTCCFSLLCSYKILSSNILENITSDSEYFVVPDLPDRVELTKAQVS

GSTKNTTSVSSSVLKEVTEQIRLAEESSYGVIVNSFEELEQVYEKEYRKARGKKVWCVGPVSLC

NKEIEDLVTRGNKTAIDNQDCLKWLDNFETESVVYASLGSLSRLTLLQMVELGLGLEESNRPFV

WVLGGGDKLNDLEKWILENGFEQRIKERGVLIRGWAPQVLILSHPAIGGVLTHCGWNSTLEGIS

-continued

AGLPMVTWPLFAEQFCNEKLVVQVLKIGVSLGVKVPVKWGDEENVGVLVKKDDVKKALDKLMDE

GEEGQVRRTKAKELGELAKKAFGEGGSSYVNLTSLIEDIIEQQNHKEK

DNA
Glycosyltransferase (NtGT5 - codon optimized for yeast expression)
*Nicotiana tabacum*
SEQ ID NO. 57

ATGGGCTCTATCGGTGCAGAACTAACCAAGCCACACGCCGTATGCATTCCCTATCCCGCCCAGG

GACACATAAATCCTATGCTGAAGTTAGCTAAGATACTGCATCACAAGGGCTTCCATATAACCTT

CGTAAATACGGAATTTAATCACAGGCGTCTGCTGAAGTCCAGAGGTCCTGACTCCCTGAAAGGT

CTTTCAAGTTTCAGGTTCGAGACGATACCTGACGGACTGCCCCCATGCGAAGCTGACGCTACAC

AGGACATTCCTTCACTGTGTGAATCCACGACTAATACATGTCTAGCTCCTTTTAGAGACCTACT

TGCTAAGCTAAATGATACGAATACTTCTAACGTCCCTCCCGTAAGTTGTATTGTCAGTGACGGA

GTGATGTCATTTACCCTTGCAGCTGCACAGGAACTGGGTGTCCCAGAGGTTTTATTTTGGACTA

CATCTGCTTGTGGATTCTTAGGITACATGCACTATTGCAAAGTCATTGAAAAAGGATATGCTCC

ATTAAAAGACGCATCAGACCTGACGAATGGCTATCTTGAGACAACCTTGGACTTCATCCCCGGC

ATGAAGGACGTCAGGCTGAGAGACTTACCTTCCTTTCTTAGGACCACCAATCCAGACGAATTTA

TGATTAAGTTTGTACTACAGGAAACTGAGCGTGCTCGTAAGGCCAGTGCCATAATACTTAATAC

CTTTGAAACCTTAGAGGCAGAGGTATTAGAATCATTAAGGAACCTTCTACCCCCCGTCTATCCA

ATCGGCCCCTTGCATTTCCTTGTCAAACACGTAGACGATGAGAACCTAAAAGGTCTACGTTCCT

CACTTTGGAAGGAGGAACCTGAATGTATTCAATGGTTAGACACCAAAGAACCTAACTCTGTCGT

GTACGTGAATTTCGGATCCATTACTGTGATGACTCCCAATCAATTAATAGAGTTCGCTTGGGGA

CTGGCAAACTCTCAACAGACCTTCCTTTGGATCATAAGGCCTGACATCGTAAGTGGTGATGCTT

CCATATTACCTCCCGAGTTTGTTGAGGAGACTAAGAACAGAGGCATGCTTGCCTCCTGGTGCTC

TCAGGAGGAGGTACTATCCCATCCCGCAATAGTGGGATTTTTGACGCACTCTGGTTGGAACTCA

ACTTTAGAATCAATTTCTAGTGGCGTCCCCATGATCTGTTGGCCTTTCTTTGCTGAGCAGCAAA

CGAACTGCTGGTTTTCAGTGACGAAGTGGGACGTTGGAATGGAAATTGATTCAGATGTGAAGAG

AGATGAAGTAGAGAGTTTAGTAAGAGAGTTAATGGTGGGTGGTAAAGGCAAGAAGATGAAGAAG

AAGGCAATGGAGTGGAAGGAACTGGCCGAGGCTCAGCAAAAGAACACTCTGGCTCCTCTTACG

TCAATATCGAGAAGTTGGTTAACGATATATTACTATCTAGTAAGCACTAA

Amino Acid
Glycosyltransferase (NtGT5 - generated from codon optimized
sequence for yeast expression)
*Nicotiana tabacum*
SEQ ID NO. 58

MGSIGAELTKPHAVCIPYPAQGHINPMLKLAKILHHKGFHITFVNTEFNHRRLLKSRGPDSLKG

LSSFRFETIPDGLPPCEADATQDIPSLCESTTNTCLAPFRDLLAKLNDTNTSNVPPVSCIVSDG

VMSFTLAAAQELGVPEVLFWTTSACGFLGYMHYCKVIEKGYAPLKDASDLTNGYLETTLDFIPG

MKDVRLRDLPSFLRTTNPDEFMIKFVLQETERARKASAIILNTFETLEAEVLESLRNLLPPVYP

IGPLHFLVKHVDDENLKGLRSSLWKEEPECIQWLDTKEPNSVVYVNFGSITVMTPNQLIEFAWG

LANSQQTFLWIIRPDIVSGDASILPPEFVEETKNRGMLASWCSQEEVLSHPAIVGFLTHSGWNS

-continued

TLESISSGVPMICWPFFAEQQTNCWFSVTKWDVGMEIDSDVKRDEVESLVRELMVGGKGKKMKK

KAMEWKELAEASAKEHSGSSYVNIEKLVNDILLSSKH

DNA
UDP glycosyltransferase 76G1 (UGT76G1 - codon optimized for yeast
expression)
*Stevia rebaudiana*
SEQ ID NO. 59

ATGGAGAACAAAACCGAGACAACCGTTAGGCGTAGACGTAGGATAATATTGTTTCCCGTGCCCT

TTCAAGGCCATATAAACCCAATCCTGCAGCTAGCCAACGTATTGTACTCAAAGGGCTTCAGTAT

AACGATCTTCCACACCAACTTTAATAAGCCAAAAACGTCTAATTATCCACACTTCACATTTAGA

TTTATACTTGATAACGACCCACAGGATGAAAGAATATCAAACTTGCCCACGCACGGCCCACTAG

CCGGAATGAGAATACCAATAATCAATGAGCATGGCGCCGACGAGTTGCGTAGAGAGCTGGAATT

GTTGATGCTAGCCAGTGAGGAAGACGAAGAGGTGTCCTGCTTAATAACGGATGCACTTTGGTAT

TTTGCTCAATCTGTGGCCGACTCCCTTAACCTGAGGCGTCTTGTCCTTATGACCTCCAGTCTAT

TCAACTTTCATGCCCATGTCTCATTGCCCCAATTTGATGAGCTTGGCTATTTGGATCCTGATGA

CAAAACTAGGCTGGAGGAACAGGCTTCCGGTTTTCCCATGCTAAAGGTTAAGGACATCAAATCC

GCCTACTCAAACTGGCAGATCCTTAAGGAAATTCTTGGCAAAATGATCAAACAGACGAGGGCAT

CCAGTGGCGTCATCTGGAACTCCTTTAAGGAACTTGAAGAATCAGAACTTGAAACAGTAATCAG

AGAAATACCTGCCCCAAGTTTCTTGATCCCTCTACCTAAGCACCTTACGGCTTCTAGTTCTTCT

TTGTTGGACCACGATCGTACTGTCTTTCAATGGTTAGATCAGCAACCCCCCTCATCAGTGCTAT

ATGTGTCATTCGGTAGTACATCAGAAGTGGACGAAAAGGATTTCCTTGAGATAGCCCGTGGATT

GGTGGACTCTAAACAGTCCTTTTTATGGGTTGTGAGACCTGGATTTGTAAAGGGATCCACGTGG

GTCGAACCCTTGCCCGATGGTTTCCTGGGTGAAAGAGGAAGGATAGTGAAGTGGGTCCCTCAGC

AAGAGGTACTGGCCCATGGTGCTATAGGTGCTTTCTGGACCCACTCCGGCTGGAATAGTACACT

AGAATCCGTTTGCGAGGGTGTCCCTATGATTTTTTCTGATTTTGGTTTAGATCAACCCCTGAAT

GCTAGGTACATGTCAGACGTCCTTAAAGTCGGCGTCTACCTAGAAAATGGCTGGGAGAGGGGTG

AGATAGCAAACGCTATCAGACGTGTTATGGTAGACGAAGAGGGAGAGTACATAAGGCAAAACGC

CAGGGTCCTGAAACAAAAGCCGATGTGTCCTTGATGAAGGGCGGCTCTTCATACGAAAGTCTA

GAAAGTCTTGTTTCTTATATTTCCTCACTATAA

Amino Acid
UDP glycosyltransferase 76G1 (UGT76G1 - generated from codon
optimized sequence for yeast expression)
*Stevia rebaudiana*
SEQ ID NO. 60

MENKTETTVRRRRRIILFPVPFQGHINPILQLANVLYSKGFSITIFHTNFNKPKTSNYPHFTFR

FILDNDPQDERISNLPTHGPLAGMRIPIINEHGADELRRELELLMLASEEDEEVSCLITDALWY

FAQSVADSLNLRRLVLMTSSLFNFHAHVSLPQFDELGYLDPDDKTRLEEQASGFPMLKVKDIKS

AYSNWQILKEILGKMIKQTRASSGVIWNSFKELEESELETVIREIPAPSFLIPLPKHLTASSSS

LLDHDRTVFQWLDQQPPSSVLYVSFGSTSEVDEKDFLEIARGLVDSKQSFLWVVRPGFVKGSTW

VEPLPDGFLGERGRIVKWVPQQEVLAHGAIGAFWTHSGWNSTLESVCEGVPMIFSDFGLDQPLN

ARYMSDVLKVGVYLENGWERGEIANAIRRVMVDEEGEYIRQNARVLKQKADVSLMKGGSSYESL

ESLVSYISSL

DNA
glycosyltransferase (UGT73A10)
*Lycium barbarum*
SEQ ID NO. 61

ATGGGTCAATTGCATTTTTTTTGTTTCCAATGATGGCTCAAGGTCATATGATTCCAACTTTGG

ATATGGCTAAGTTGATTGCTTCTAGAGGTGTTAAGGCTACTATTATTACTACTCCATTGAACGA

-continued

```
ATCTGTTTTTTCTAAGGCTATTCAAAGAAACAAGCAATTGGGTATTGAAATTGAAATTGAAATT

AGATTGATTAAGTTTCCAGCTTTGGAAAACGATTTGCCAGAAGATTGTGAAAGATTGGATTTGA

TTCCAACTGAAGCTCATTTGCCAAACTTTTTTAAGGCTGCTGCTATGATGCAAGAACCATTGGA

ACAATTGATTCAAGAATGTAGACCAGATTGTTTGGTTTCTGATATGTTTTTGCCATGGACTACT

GATACTGCTGCTAAGTTTAACATTCCAAGAATTGTTTTTCATGGTACTAACTACTTTGCTTTGT

GTGTTGGTGATTCTATGAGAAGAAACAAGCCATTTAAGAACGTTTCTTCTGATTCTGAAACTTT

TGTTGTTCCAAACTTGCCACATGAAATTAAGTTGACTAGAACTCAAGTTTCTCCATTTGAACAA

TCTGATGAAGAATCTGTTATGTCTAGAGTTTTGAAGGAAGTTAGAGAATCTGATTTGAAGTCTT

ACGGTGTTATTTTTAACTCTTTTTACGAATTGGAACCAGATTACGTTGAACATTACACTAAGGT

TATGGGTAGAAAGTCTTGGGCTATTGGTCCATTGTCTTTGTGTAACAGAGATGTTGAAGATAAG

GCTGAAAGAGGTAAGAAGTCTTCTATTGATAAGCATGAATGTTTGGAATGGTTGGATTCTAAGA

AGCCATCTTCTATTGTTTACGTTTGTTTTGGTTCTGTTGCTAACTTTACTGTTACTCAAATGAG

AGAATTGGCTTTGGGTTTGGAAGCTTCTGGTTTGGATTTTATTTGGGCTGTTAGAGCTGATAAC

GAAGATTGGTTGCCAGAAGGTTTTGAAGAAAGAACTAAGGAAAAGGGTTTGATTATTAGAGGTT

GGGCTCCACAAGTTTTGATTTTGGATCATGAATCTGTTGGTGCTTTTGTTACTCATTGTGGTTG

GAACTCTACTTTGGAAGGTATTTCTGCTGGTGTTCCAATGGTTACTTGGCCAGTTTTTGCTGAA

CAATTTTTTAACGAAAAGTTGGTTACTCAAGTTATGAGAACTGGTGCTGGTGTTGGTTCTGTTC

AATGGAAGAGATCTGCTTCTGAAGGTGTTGAAAAGGAAGCTATTGCTAAGGCTATTAAGAGAGT

TATGGTTTCTGAAGAAGCTGAAGGTTTTAGAAACAGAGCTAGAGCTTACAAGGAAATGGCTAGA

CAAGCTATTGAAGAAGGTGGTTCTTCTTACACTGGTTTGACTACTTTGTTGGAAGATATTTCTT

CTTACGAATCTTTGTCTTCTGATTAA
```

Amino Acid
Glycosyltransferase (UGT73A10)
*Lycium barbarum*

SEQ ID NO. 62

```
MGQLHFFLFPMMAQGHMIPTLDMAKLIASRGVKATIITTPLNESVFSKAIQRNKQLGIEIEIEI

RLIKFPALENDLPEDCERLDLIPTEAHLPNFFKAAAMMQEPLEQLIQECRPDCLVSDMFLPWTT

DTAAKFNIPRIVFHGTNYFALCVGDSMRRNKPFKNVSSDSETFVVPNLPHEIKLTRTQVSPFEQ

SDEESVMSRVLKEVRESDLKSYGVIFNSFYELEPDYVEHYTKVMGRKSWAIGPLSLCNRDVEDK

AERGKKSSIDKHECLEWLDSKKPSSIVYVCFGSVANFTVTQMRELALGLEASGLDFIWAVRADN

EDWLPEGFEERTKEKGLIIRGWAPQVLILDHESVGAFVTHCGWNSTLEGISAGVPMVTWPVFAE

QFFNEKLVTQVMRTGAGVGSVQWKRSASEGVEKEAIAKAIKRVMVSEEAEGFRNRARAYKEMAR

QAIEEGGSSYTGLTTLLEDISSYESLSSD
```

DNA
Cytosolic-targeted UDP glycosyltransferase 76G1 (cytUTG)
*Stevia rebaudiana*

SEQ ID NO. 63

```
ATGGAAAATAAAACCGAAACCACCGTCCGCCGTCGTCGCCGTATCATTCTGTTCCCGGTCCGT

TCCAGGGCCACATCAACCCGATTCTGCAACTGGCGAACGTGCTGTATTCGAAAGGTTTCAGCAT

CACCATCTTCCATACGAACTTCAACAAGCCGAAGACCAGCAATTACCCGCACTTTACGTTCCGT

TTTATTCTGGATAACGACCCGCAGGATGAACGCATCTCTAATCTGCCGACCCACGGCCCGCTGG

CGGGTATGCGTATTCCGATTATCAACGAACACGGCGCAGATGAACTGCGTCGCGAACTGGAACT

GCTGATGCTGGCCAGCGAAGAAGATGAAGAAGTTTCTTGCCTGATCACCGACGCACTGTGGTAT

TTTGCCCAGTCTGTTGCAGATAGTCTGAACCTGCGTCGCCTGGTCCTGATGACCAGCAGCCTGT
```

-continued

```
TCAATTTTCATGCCCACGTTAGTCTGCCGCAGTTCGATGAACTGGGTTATCTGGACCCGGATGA

CAAAACCCGCCTGGAAGAACAGGCGAGCGGCTTTCCGATGCTGAAAGTCAAGGATATTAAGTCA

GCGTACTCGAACTGGCAGATTCTGAAAGAAATCCTGGGTAAAATGATTAAGCAAACCAAAGCAA

GTTCCGGCGTCATCTGGAATAGTTTCAAAGAACTGGAAGAATCCGAACTGGAAACGGTGATTCG

TGAAATCCCGGCTCCGAGTTTTCTGATTCCGCTGCCGAAGCATCTGACCGCGAGCAGCAGCAGC

CTGCTGGATCACGACCGCACGGTGTTTCAGTGGCTGGATCAGCAACCGCCGAGTTCCGTGCTGT

ATGTTAGCTTCGGTAGTACCTCGGAAGTGGATGAAAAGGACTTTCTGGAAATCGCTCGTGGCCT

GGTTGATAGCAAACAATCTTTCCTGTGGGTGGTTCGCCCGGGTTTTGTGAAGGGCTCTACGTGG

GTTGAACCGCTGCCGGACGGCTTCCTGGGTGAACGTGGCCGCATTGTCAAATGGGTGCCGCAGC

AAGAAGTGCTGGCGCATGGCGCGATTGGCGCGTTTTGGACCCACTCCGGTTGGAACTCAACGCT

GGAATCGGTTTGTGAAGGTGTCCCGATGATTTTCTCAGATTTTGGCCTGGACCAGCCGCTGAAT

GCACGTTATATGTCGGATGTTCTGAAAGTCGGTGTGTACCTGGAAAACGGTTGGGAACGCGGCG

AAATTGCGAATGCCATCCGTCGCGTTATGGTCGATGAAGAAGGCGAATACATTCGTCAGAATGC

TCGCGTCCTGAAACAAAGGCGGACGTGAGCCTGATGAAAGGCGGTTCATCGTATGAAAGTCTG

GAATCCCTGGTTTCATACATCAGCTCTCTGTAA

Amino Acid
Cytosolic-targeted UDP glycosyltransferase 76G1 (cytUTG)
Stevia rebaudiana
                                                       SEQ ID NO. 64
MENKTETTVRRRRRIILFPVPFQGHINPILQLANVLYSKGFSITIFHTNFNKPKTSNYPHFTFR

FILDNDPQDERISNLPTHGPLAGMRIPIINEHGADELRRELELLMLASEEDEEVSCLITDALWY

FAQSVADSLNLRRLVLMTSSLFNFHAHVSLPQFDELGYLDPDDKTRLEEQASGFPMLKVKDIKS

AYSNWQILKEILGKMIKQTKASSGVIWNSFKELEESELETVIREIPAPSFLIPLPKHLTASSSS

LLDHDRTVFQWLDQQPPSSVLYVSFGSTSEVDEKDFLEIARGLVDSKQSFLWVVRPGFVKGSTW

VEPLPDGFLGERGRIVKWVPQQEVLAHGAIGAFWTHSGWNSTLESVCEGVPMIFSDFGLDQPLN

ARYMSDVLKVGVYLENGWEREIANAIRRVMVDEEGEYIRQNARVLKQKADVSLMKGGSSYESL

ESLVSYISSL

Enhanced N-terminal chimera secretion signal with Ost1 signal sequence
S. cerevisiae
                                                       SEQ ID NO. 65
MRQVWFSWIVGLFLCFFNVSSAAPVNTTTEDETAQIPAEAVIGYSDLEGDFDVAVLPFNSTNNG

LLFINTTIASIAAKEEGVSLEKR

Enhanced Ost1 secretion signal presequence
S. cerevisiae
                                                       SEQ ID NO. 66
MRQVWFSWIVGLFLCFFNVSSA Amino Acid
Enhanced Exportable Hepatic Fatty acid-binding protein 1
Mus musculus
                                                       SEQ ID NO. 67
MRQVWFSWIVGLFLCFFNVSSAAPVNTTTEDETAQIPAEAVIGYSDLEGDFDVAVLPFSNTNN

GLLFINTTIASIAAKEEGVSLEKRMNFSGKYQLQSQENFEPFMKAIGLPEDLIQKGKDIKGVSE

IVHEGKKIKLTITYGPKVVRNEFTLGEECELETMTGEKVKAVVKLEGDNKMVTTFKGIKSVTEL

NGDTITNTMTLGDIVYKRVSKRI
```

-continued

Amino Acid
Enhanced Exportable Hepatic Fatty acid-binding protein 1
*Bos taurus*
SEQ ID NO. 68

MRQVWFSWIVGLFLCFFNVSSAAPVNTTTEDETAQIPAEAVIGYSDLEGDFDVAVLPFSNSTNN

GLLFINTTIASIAAKEEGVSLEKRMNFSGKYQVQTQENYEAFMKAVGMPDDIIQKGKDIKGVSE

IVQNGKHFKFIITAGSKVIQNEFTLGEECEMEFMTGEKIKAVVQQEGDNKLVTTFKGIKSVTEF

NGDTVTSTMTKGDVVFKRVSKRI

Amino Acid
Sec signal peptide for *E coli* L-asparaginase II
*E. Coli*
SEQ ID NO. 69

MEFFKKTALAALVMGFSGAALA

Amino Acid
Tat signal pepride for *E coli* strain k12 periplasmic nitrate reductase
*E. Coli*
SEQ ID NO. 70

MKLSRRSFMKANAVAAAAAAGLSVPGVARAVVGQQ

Amino Acid
secretion signal from an extracellular protease Ara12 (At5g67360)
*Arabidopsis thalinia*
SEQ ID NO. 71

MSSSFLSSTAFFLLLCLGFCHVSSS

Amino Acid
secretion signal from a alpha amylase
barley (*Hordeum vulgare*)
SEQ ID NO. 72

MGKKSHICCFSLLLLLFAGLASG

Amino Acid
secretion signal from a a-Amylase
rice
SEQ ID NO. 73

MKNTSSLCLLLLVVLCSLTCNSGQAAQV

Amino Acid
Chicken FABP7 WT
*Gallus gallus*
SEQ ID NO. 74

MVEAFCATWKLADSHNFDEYMKALGVGFAMRQVGNVTKPTVIISSEGDKVVIRTQSTFKNTEIS

FKLGEEFDETTPDDRNCKSVVTLDGDKLVHVQKWDGKETNFVREIKDGRMVMTLTFGDVVAVRH

YEKA

Amino Acid
Pig FABP1 WT
*Sus scrofa*
SEQ ID NO. 75

MNFSGKYQVQSQENFEAFMKAVGLPDELIQKGKDIKGTSEIVQNGKHFKLTITTGSKVVQNEFT

LGEECEMETLTGEKVKTVVQLEGDNKLVTTFKGIKSVTELNGDIITSTMTLGDIVFKRISKRI

Amino Acid
Horse FABP1 WT
*Equus caballus*
SEQ ID NO. 76

MNFSGKYQLQSQENFEPFMKAVGMSDDLIQKGKDLKETSEIVHNGNHFKITITTGPKVVHHEFT

LGEEFELESFTGEKVKAITHMEGDKLVSTIKGIKSVTELKGDIITNQLSVWHTPVVCATSALVP

ACRPGPVLDLGTMTLGDIVFKRVSKRI

Amino Acid
Plant FABP WT
*Rhodamnia argentea*
SEQ ID NO. 77

MTEFAGVYEFVKDDGKFEEILKAMDVNFLIRKVAGKMNPNTAIDVLDDGKMAFKTITPLKTVEI

HFELGKEYENKRLDGTVVKGIVTRDGNKLIQEQMSEPKFKVIRELDGPEKLIVTWMCKDIVCVR

EYKRIQT

-continued

Amino Acid
Mouse FABP1 WT
*Mus musculus*
SEQ ID NO. 78

MNFSGKYQLQSQENFEPFMKAIGLPEDLIQKGKDIKGVSEIVHEGKKIKLTITYGPKVVRNEFT

LGEECELETMTGEKVKAVVKLEGDNKMVTTFKGIKSVTELNGDTITNTMTLGDIVYKRVSKRI

Amino Acid
Modified Chicken FABP7 mdl_r5_0225_ro
*Gallus gallus*
SEQ ID NO. 79

MVEAFCATWKLADSHNMDEALKAWGVGFAIRQVANVTKPTVIISSEGDKVVIRMQSTFKNTEIS

FKLGEEFDETTADDRNCKSVVTLDGDKLVHVQKWDGKETNVVREIKDGRMVMTVTFGDVVAVRH

YEKA

Amino Acid
Modified Chicken FABP7 mdl_r3_1403_sm
*Gallus gallus*
SEQ ID NO. 80

MVEAFCATWKLADSHNQDEGLKALGVGFAMRQLFNDKPTVIISSEGDKVVIRIEGTVKNTEIS

FKLGEEFDETTADDRNCKSVVTLDGDKLVHVQKWDGKETNVVREIKDGRMVATFTFGDVVAVAH

YEKA

Amino Acid
Modified Pig FABP1 mdl_r5_1652_ro
*Sus scrofa*
SEQ ID NO. 81

MNFSGKYQVQSQENFEAFMKAVGQPDELIQKGKDIKGTSEIVQNGKHFKVTITTGSKVVQAEFT

LGEECEAETDTGEKVKVVVQLEGDNKAVVTAKGIKAVFELNGDIITATATLGDIVFKRISKRI

Amino Acid
Modified Pig FABP1 mdl_r4_0372_sm
*Sus scrofa*
SEQ ID NO. 82

MNFSGKYQVQSQENFEAAAKAAGVPDEEIQKGKDIKGTLEIVQNGKHFKLTLTTGSKVVQNEFT

LGEECEMETLGGEKAKTVVQLEGDNKAVWTFKGIKAVIELNGDIITLTVTLGDIVFKRISKRI

Amino Acid
Modified Horse FABP1 mdl_r5_0954_ro
*Equus caballus*
SEQ ID NO. 83

MNFSGKYQLQSQENAEPFFKAVGMSDDLIQLAKDLKVTGEIVHNGNHFKITHTSGAAVVHHEFT

LGEEFELESLTGEKVKAITHMEGDKLVSTIKGIKSVTELKGDIITNQLSVWHTPVVCATSALVP

ACRPGPVLDLGTMTLGDIVMKFVSKRI

Amino Acid
Modified Horse FABP1 mdl_r5_1179_sm
*Equus caballus*
SEQ ID NO. 84

MNFSGKYQLQSSENVEPFNKAVGMSDDLIQKAKDLKFTGEIVHNGNHFKITITTGPKVVHHEFT

LGEEFELEHFTGEKVKAITHMEGDKLVMTVKGIKSVMVWKGDIITNQLSVWHTPVVCATSALVP

ACRPGPVLDLGTGVLGDIVMKHVSKRI

Amino Acid
Modified Plant FABP mdl_r3_0887_ro_sm
*Rhodamnia argentea*
SEQ ID NO. 85

MTEFAGVYEFVKDDGKFEEILKAMDVNFLIRKVGMKMNANVAIDVLDDGKMAIKVITPLKTVEI

HFELGKEYENKRFDGTVVKGIVTRDGNKLIIEQMSEPKFKVAELDGPEKLIFTEMCKDIVCVA

EYKRIQT

-continued

Amino Acid
Modified Plant FABP mdl_r4_1489_ro
Rhodamnia argentea

SEQ ID NO. 86

MTEFAGVYEFVKDDGKFEEILKAMDVNFLIRKVAGKMNPN<u>IAI</u>DVLDDGKMA<u>IKMI</u>TPLKTVE<u>V</u>

HFELGKEYE<u>AKA</u>LDGTVVK<u>AI</u>VTRDGNKLI<u>IEN</u>MSEPKF<u>T</u>VIRELDGPEKLIVTWMCKDIVCV<u>A</u>

EYKRIQT

REFERENCES

[1] Elmes M W, et al. Fatty acid binding proteins (FABPs) are intracellular carriers for Δ⁹-tetrahydrocannabinol (THC) and cannabidiol (CBD). J Biol Chem. 290: 8711-8721 (2015).

[2] Huang H, et al. FABP1: a novel hepatic endocannabinoid and cannabinoid binding protein. Biochemistry. 55: 5243-5255.

[3] Huestis M A. Pharmacokinetics and metabolism of the plant cannabinoids, Δ⁹-tetrahydrocannabinol, cannabidiol and cannabinol. Handb Exp Pharmacol. 168: 657-690 (2005).

[4] Smathers R K and Petersen D R. The human fatty acid-binding protein family: evolutionary divergences and functions. Hum Genomics. 5: 170-191 (2011).

[5] van der Vusse G J. Albumin as fatty acid transporter. Drug Metab Pharmacokinet. 24: 300-307 (2009).

[6] Mullenbach, G. T., Urdea, M. S., Valenzuela, P., & Barr, P. J. (1984). a-Factor-directed synthesis and secretion of mature foreign proteins in *Saccharomyces cerevisiae*, 81 (August), 4642-4646.

[7] Fitzgerald, I., & Glick, B. S. (2014). Secretion of a foreign protein from budding yeasts is enhanced by cotranslational translocation and by suppression of vacuolar targeting, 1-12.

[8] Barrero, J. J., Casler, J. C., Valero, F., Ferrer, P., & Glick, B. S. (2018). An improved secretion signal enhances the secretion of model proteins from *Pichia pastoris*. *Microbial Cell Factories*, 1-13.

[9] Chen M H, Huang L F, Li H M, Chen Y R, Yu S M. Signal peptide-dependent targeting of a rice alpha-amylase and cargo proteins to plastids and extracellular compartments of plant cells. Plant Physiol. 2004; 135(3): 1367-77

[10] Castilho, A., Windwarder, M., Gattinger, P., Mach, L., Strasser, R., Altmann, F., & Steinkellner, H. (2014). Proteolytic and N-Glycan Processing of Human 1-Antitrypsin Expressed in *Nicotiana benthamiana*. *Plant Physiology*, 166(4), 1839-1851

[11] Huang, L. F., Tan, C. C., Yeh, J. F., Liu, H. Y., Liu, Y. K., Ho, S. L., & Lu, C. A. (2015). Efficient secretion of recombinant proteins from rice suspension-cultured cells modulated by the choice of signal peptide. *PLoS ONE*, 10(10), 1-16

[12] Yu, X. C. & Strobel, H. W. Interactions of 8-anilino-1-napthalenesulfonic acid (ANS) and cytochrome P450 2B1: Role of ANS as an effector as well as a reporter group. Mol. Cell. Biochem. 162, 89-95 (1996).

[13] Chen M H, Huang L F, Li H M, Chen Y R, Yu S M. Signal peptide-dependent targeting of a rice alpha-amylase and cargo proteins to plastids and extracellular compartments of plant cells. Plant Physiol. 2004; 135(3): 1367-77

What is claimed is:

1. A method of solubilizing a cannabinoid comprising the steps of:
   modifying a Fatty-Acid Binding Protein (FABP)-carrier protein having affinity towards a cannabinoid to produce a recombinant FABP-carrier protein having enhanced affinity towards said cannabinoid;
   introducing said recombinant FABP-carrier protein to said cannabinoid, wherein said recombinant FABP-carrier protein binds said cannabinoid forming a water-soluble protein-cannabinoid complex; and
   wherein the recombinant FABP-carrier protein comprises a recombinant FABP-carrier protein having the amino acid sequence selected from the group consisting of: SEQ ID NOs. 79-86, and wherein said cannabinoid is cannabidiol (CBD), or $D^9$-tetrahydrocannabinol (THC).

2. The method of claim 1, wherein said step of genetically modifying the FABP-carrier protein comprises at least one of the following:
   replacing one or more amino acid residues of the FABP-carrier protein cannabinoid binding pocket with side chains orientated toward the binding cavity;
   replacing one or more amino acid residues of the FABP-carrier protein cannabinoid binding pocket having a hydrophilic side chain with amino acid residues having a hydrophobic side chain; and
   replacing one or more small hydrophobic amino acid residues of the FABP-carrier protein cannabinoid binding pocket with larger hydrophobic amino acid residues.

3. The method of claim 1, wherein the recombinant FABP-carrier protein is expressed in a protein production system selected from the group consisting of:
   a bacterial cell culture;
   a yeast cell culture;
   a plant cell culture;
   a fungi cell culture;
   an algae cell culture;
   a bioreactor production system; and
   a plant.

4. The method of claim 1, wherein the recombinant FABP-carrier protein is coupled with a secretion signal.

5. The method of claim 4, wherein said secretion signal is selected from the group consisting of: SEQ ID NO. 3, SEQ ID NO. 65, and SEQ ID NOs. 69-73.

6. The method of claim 1, wherein said recombinant FABP-carrier protein is further genetically modified to decrease aggregation propensity and potential antigenicity.

7. The method of claim 6, wherein said recombinant FABP-carrier protein comprises a recombinant FABP-carrier protein having one or both of the following mutations: V58E, and V42R.

8. A method of solubilizing a cannabinoid comprising the steps of:

expressing in a protein production system a heterologous nucleotide sequence, operably linked to a promoter, encoding generating a Fatty-Acid Binding Protein (FABP)-carrier protein having affinity towards a cannabinoid; and introducing said FABP-carrier protein to said cannabinoid, wherein said FABP-carrier protein binds said cannabinoid to form a water-soluble protein-cannabinoid complex, wherein the FABP-carrier protein comprises a FABP-carrier protein having the amino acid sequence selected from the group of consisting of: SEQ ID NOs. 79-86, or a sequence having at least 95% or more sequence identity with any of the SEQ ID NOs. 79-86, and wherein said cannabinoid is cannabidiol (CBD), or $\Delta^9$-tetrahydrocannabinol (THC).

9. The method of claim 8, wherein the recombinant FABP-carrier protein is expressed in a protein production system selected from the group consisting of:

a bacterial cell culture;

a yeast cell culture;

a plant cell culture;

a fungi cell culture;

an algae cell culture;

a bioreactor production system; and a plant.

10. The method of claim 8, wherein said recombinant FABP-carrier protein comprises a recombinant FABP-carrier protein having one or both of the following mutations: V58E, and V42R.

* * * * *

SEQUENCE LISTING

```
<160> NUMBER OF SEQ ID NOS: 86

<210> SEQ ID NO 1
<211> LENGTH: 127
<212> TYPE: PRT
<213> ORGANISM: Mus musculus

<400> SEQUENCE: 1

Met Asn Phe Ser Gly Lys Tyr Gln Leu Gln Ser Gln Glu Asn Phe Glu
1               5                   10                  15

Pro Phe Met Lys Ala Ile Gly Leu Pro Glu Asp Leu Ile Gln Lys Gly
            20                  25                  30

Lys Asp Ile Lys Gly Val Ser Glu Ile Val His Glu Gly Lys Lys Ile
        35                  40                  45

Lys Leu Thr Ile Thr Tyr Gly Pro Lys Val Val Arg Asn Glu Phe Thr
    50                  55                  60

Leu Gly Glu Glu Cys Glu Leu Glu Thr Met Thr Gly Glu Lys Val Lys
65                  70                  75                  80

Ala Val Val Lys Leu Glu Gly Asp Asn Lys Met Val Thr Thr Phe Lys
                85                  90                  95

Gly Ile Lys Ser Val Thr Glu Leu Asn Gly Asp Thr Ile Thr Asn Thr
            100                 105                 110

Met Thr Leu Gly Asp Ile Val Tyr Lys Arg Val Ser Lys Arg Ile
```

```
            115                 120                 125

<210> SEQ ID NO 2
<211> LENGTH: 127
<212> TYPE: PRT
<213> ORGANISM: Bos taurus

<400> SEQUENCE: 2

Met Asn Phe Ser Gly Lys Tyr Gln Val Gln Thr Gln Glu Asn Tyr Glu
1               5                   10                  15

Ala Phe Met Lys Ala Val Gly Met Pro Asp Asp Ile Ile Gln Lys Gly
            20                  25                  30

Lys Asp Ile Lys Gly Val Ser Glu Ile Val Gln Asn Gly Lys His Phe
        35                  40                  45

Lys Phe Ile Ile Thr Ala Gly Ser Lys Val Ile Gln Asn Glu Phe Thr
    50                  55                  60

Leu Gly Glu Glu Cys Glu Met Glu Phe Met Thr Gly Glu Lys Ile Lys
65                  70                  75                  80

Ala Val Val Gln Gln Glu Gly Asp Asn Lys Leu Val Thr Thr Phe Lys
                85                  90                  95

Gly Ile Lys Ser Val Thr Glu Phe Asn Gly Asp Thr Val Thr Ser Thr
            100                 105                 110

Met Thr Lys Gly Asp Val Val Phe Lys Arg Val Ser Lys Arg Ile
        115                 120                 125

<210> SEQ ID NO 3
<211> LENGTH: 85
<212> TYPE: PRT
<213> ORGANISM: S. cerevisiae

<400> SEQUENCE: 3

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg
                85

<210> SEQ ID NO 4
<211> LENGTH: 212
<212> TYPE: PRT
<213> ORGANISM: Mus musculus

<400> SEQUENCE: 4

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60
```

```
Phe Ile Asn Thr Thr Ile Ala Ser Ile Ala Ala Lys Glu Glu Gly Val
 65                  70                  75                  80

Ser Leu Glu Lys Arg Met Asn Phe Ser Gly Lys Tyr Gln Leu Gln Ser
                 85                  90                  95

Gln Glu Asn Phe Glu Pro Phe Met Lys Ala Ile Gly Leu Pro Glu Asp
            100                 105                 110

Leu Ile Gln Lys Gly Lys Asp Ile Lys Gly Val Ser Glu Ile Val His
            115                 120                 125

Glu Gly Lys Lys Ile Lys Leu Thr Ile Thr Tyr Gly Pro Lys Val Val
130                 135                 140

Arg Asn Glu Phe Thr Leu Gly Glu Glu Cys Glu Leu Glu Thr Met Thr
145                 150                 155                 160

Gly Glu Lys Val Lys Ala Val Val Lys Leu Glu Gly Asp Asn Lys Met
                165                 170                 175

Val Thr Thr Phe Lys Gly Ile Lys Ser Val Thr Glu Leu Asn Gly Asp
            180                 185                 190

Thr Ile Thr Asn Thr Met Thr Leu Gly Asp Ile Val Tyr Lys Arg Val
            195                 200                 205

Ser Lys Arg Ile
        210

<210> SEQ ID NO 5
<211> LENGTH: 212
<212> TYPE: PRT
<213> ORGANISM: Bos taurus

<400> SEQUENCE: 5

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
 50                 55                  60

Phe Ile Asn Thr Thr Ile Ala Ser Ile Ala Ala Lys Glu Glu Gly Val
 65                  70                  75                  80

Ser Leu Glu Lys Arg Met Asn Phe Ser Gly Lys Tyr Gln Val Gln Thr
                 85                  90                  95

Gln Glu Asn Tyr Glu Ala Phe Met Lys Ala Val Gly Met Pro Asp Asp
            100                 105                 110

Ile Ile Gln Lys Gly Lys Asp Ile Lys Gly Val Ser Glu Ile Val Gln
            115                 120                 125

Asn Gly Lys His Phe Lys Phe Ile Ile Thr Ala Gly Ser Lys Val Ile
130                 135                 140

Gln Asn Glu Phe Thr Leu Gly Glu Glu Cys Glu Met Glu Phe Met Thr
145                 150                 155                 160

Gly Glu Lys Ile Lys Ala Val Val Gln Gln Glu Gly Asp Asn Lys Leu
                165                 170                 175

Val Thr Thr Phe Lys Gly Ile Lys Ser Val Thr Glu Phe Asn Gly Asp
            180                 185                 190

Thr Val Thr Ser Thr Met Thr Lys Gly Asp Val Val Phe Lys Arg Val
            195                 200                 205

Ser Lys Arg Ile
```

<210> SEQ ID NO 6
<211> LENGTH: 492
<212> TYPE: PRT
<213> ORGANISM: Arabidopsis thaliana

<400> SEQUENCE: 6

Met Asp Pro Tyr Lys Tyr Arg Pro Ala Ser Ser Tyr Asn Ser Pro Phe
1               5                   10                  15

Phe Thr Thr Asn Ser Gly Ala Pro Val Trp Asn Asn Ser Ser Met
            20                  25                  30

Thr Val Gly Pro Arg Gly Leu Ile Leu Leu Glu Asp Tyr His Leu Val
        35                  40                  45

Glu Lys Leu Ala Asn Phe Asp Arg Glu Arg Ile Pro Glu Arg Val Val
    50                  55                  60

His Ala Arg Gly Ala Ser Ala Lys Gly Phe Phe Glu Val Thr His Asp
65                  70                  75                  80

Ile Ser Asn Leu Thr Cys Ala Asp Phe Leu Arg Ala Pro Gly Val Gln
                85                  90                  95

Thr Pro Val Ile Val Arg Phe Ser Thr Val Ile His Ala Arg Gly Ser
            100                 105                 110

Pro Glu Thr Leu Arg Asp Pro Arg Gly Phe Ala Val Lys Phe Tyr Thr
        115                 120                 125

Arg Glu Gly Asn Phe Asp Leu Val Gly Asn Asn Phe Pro Val Phe Phe
130                 135                 140

Ile Arg Asp Gly Met Lys Phe Pro Asp Ile Val His Ala Leu Lys Pro
145                 150                 155                 160

Asn Pro Lys Ser His Ile Gln Glu Asn Trp Arg Ile Leu Asp Phe Phe
                165                 170                 175

Ser His His Pro Glu Ser Leu Asn Met Phe Thr Phe Leu Phe Asp Asp
            180                 185                 190

Ile Gly Ile Pro Gln Asp Tyr Arg His Met Asp Gly Ser Gly Val Asn
        195                 200                 205

Thr Tyr Met Leu Ile Asn Lys Ala Gly Lys Ala His Tyr Val Lys Phe
210                 215                 220

His Trp Lys Pro Thr Cys Gly Val Lys Ser Leu Leu Glu Glu Asp Ala
225                 230                 235                 240

Ile Arg Leu Gly Gly Thr Asn His Ser His Ala Thr Gln Asp Leu Tyr
                245                 250                 255

Asp Ser Ile Ala Ala Gly Asn Tyr Pro Glu Trp Lys Leu Phe Ile Gln
            260                 265                 270

Ile Ile Asp Pro Ala Asp Glu Asp Lys Phe Asp Phe Asp Pro Leu Asp
        275                 280                 285

Val Thr Lys Thr Trp Pro Glu Asp Ile Leu Pro Leu Gln Pro Val Gly
    290                 295                 300

Arg Met Val Leu Asn Lys Asn Ile Asp Asn Phe Ala Glu Asn Glu
305                 310                 315                 320

Gln Leu Ala Phe Cys Pro Ala Ile Ile Val Pro Gly Ile His Tyr Ser
                325                 330                 335

Asp Asp Lys Leu Leu Gln Thr Arg Val Phe Ser Tyr Ala Asp Thr Gln
            340                 345                 350

Arg His Arg Leu Gly Pro Asn Tyr Leu Gln Leu Pro Val Asn Ala Pro
        355                 360                 365

-continued

```
Lys Cys Ala His His Asn Asn His His Glu Gly Phe Met Asn Phe Met
370                 375                 380

His Arg Asp Glu Glu Val Asn Tyr Phe Pro Ser Arg Tyr Asp Gln Val
385                 390                 395                 400

Arg His Ala Glu Lys Tyr Pro Thr Pro Pro Ala Val Cys Ser Gly Lys
            405                 410                 415

Arg Glu Arg Cys Ile Ile Glu Lys Glu Asn Asn Phe Lys Glu Pro Gly
        420                 425                 430

Glu Arg Tyr Arg Thr Phe Thr Pro Glu Arg Gln Glu Arg Phe Ile Gln
    435                 440                 445

Arg Trp Ile Asp Ala Leu Ser Asp Pro Arg Ile Thr His Glu Ile Arg
450                 455                 460

Ser Ile Trp Ile Ser Tyr Trp Ser Gln Ala Asp Lys Ser Leu Gly Gln
465                 470                 475                 480

Lys Leu Ala Ser Arg Leu Asn Val Arg Pro Ser Ile
                485                 490

<210> SEQ ID NO 7
<211> LENGTH: 753
<212> TYPE: PRT
<213> ORGANISM: Escherichia coli

<400> SEQUENCE: 7

Met Ser Gln His Asn Glu Lys Asn Pro His Gln His Gln Ser Pro Leu
1               5                   10                  15

His Asp Ser Ser Glu Ala Lys Pro Gly Met Asp Ser Leu Ala Pro Glu
            20                  25                  30

Asp Gly Ser His Arg Pro Ala Ala Glu Pro Thr Pro Pro Gly Ala Gln
        35                  40                  45

Pro Thr Ala Pro Gly Ser Leu Lys Ala Pro Asp Thr Arg Asn Glu Lys
    50                  55                  60

Leu Asn Ser Leu Glu Asp Val Arg Lys Gly Ser Glu Asn Tyr Ala Leu
65                  70                  75                  80

Thr Thr Asn Gln Gly Val Arg Ile Ala Asp Asp Gln Asn Ser Leu Arg
                85                  90                  95

Ala Gly Ser Arg Gly Pro Thr Leu Leu Glu Asp Phe Ile Leu Arg Glu
            100                 105                 110

Lys Ile Thr His Phe Asp His Glu Arg Ile Pro Glu Arg Ile Val His
        115                 120                 125

Ala Arg Gly Ser Ala Ala His Gly Tyr Phe Gln Pro Tyr Lys Ser Leu
    130                 135                 140

Ser Asp Ile Thr Lys Ala Asp Phe Leu Ser Asp Pro Asn Lys Ile Thr
145                 150                 155                 160

Pro Val Phe Val Arg Phe Ser Thr Val Gln Gly Gly Ala Gly Ser Ala
                165                 170                 175

Asp Thr Val Arg Asp Ile Arg Gly Phe Ala Thr Lys Phe Tyr Thr Glu
            180                 185                 190

Glu Gly Ile Phe Asp Leu Val Gly Asn Asn Thr Pro Ile Phe Phe Ile
        195                 200                 205

Gln Asp Ala His Lys Phe Pro Asp Phe Val His Ala Val Lys Pro Glu
    210                 215                 220

Pro His Trp Ala Ile Pro Gln Gly Gln Ser Ala His Asp Thr Phe Trp
225                 230                 235                 240

Asp Tyr Val Ser Leu Gln Pro Glu Thr Leu His Asn Val Met Trp Ala
                245                 250                 255
```

Met Ser Asp Arg Gly Ile Pro Arg Ser Tyr Arg Thr Met Glu Gly Phe
                260                 265                 270

Gly Ile His Thr Phe Arg Leu Ile Asn Ala Glu Gly Lys Ala Thr Phe
            275                 280                 285

Val Arg Phe His Trp Lys Pro Leu Ala Gly Lys Ala Ser Leu Val Trp
290                 295                 300

Asp Glu Ala Gln Lys Leu Thr Gly Arg Asp Pro Asp Phe His Arg Arg
305                 310                 315                 320

Glu Leu Trp Glu Ala Ile Glu Ala Gly Asp Phe Pro Glu Tyr Glu Leu
                325                 330                 335

Gly Phe Gln Leu Ile Pro Glu Glu Asp Glu Phe Lys Asp Phe Asp
                340                 345                 350

Leu Leu Asp Pro Thr Lys Leu Ile Pro Glu Glu Leu Val Pro Val Gln
                355                 360                 365

Arg Val Gly Lys Met Val Leu Asn Arg Asn Pro Asp Asn Phe Phe Ala
            370                 375                 380

Glu Asn Glu Gln Ala Ala Phe His Pro Gly His Ile Val Pro Gly Leu
385                 390                 395                 400

Asp Phe Thr Asn Asp Pro Leu Leu Gln Gly Arg Leu Phe Ser Tyr Thr
                405                 410                 415

Asp Thr Gln Ile Ser Arg Leu Gly Gly Pro Asn Phe His Glu Ile Pro
            420                 425                 430

Ile Asn Arg Pro Thr Cys Pro Tyr His Asn Phe Gln Arg Asp Gly Met
            435                 440                 445

His Arg Met Gly Ile Asp Thr Asn Pro Ala Asn Tyr Glu Pro Asn Ser
450                 455                 460

Ile Asn Asp Asn Trp Pro Arg Glu Thr Pro Pro Gly Pro Lys Arg Gly
465                 470                 475                 480

Gly Phe Glu Ser Tyr Gln Glu Arg Val Glu Gly Asn Lys Val Arg Glu
                485                 490                 495

Arg Ser Pro Ser Phe Gly Glu Tyr Tyr Ser His Pro Arg Leu Phe Trp
                500                 505                 510

Leu Ser Gln Thr Pro Phe Glu Gln Arg His Ile Val Asp Gly Phe Ser
            515                 520                 525

Phe Glu Leu Ser Lys Val Val Arg Pro Tyr Ile Arg Glu Arg Val Val
            530                 535                 540

Asp Gln Leu Ala His Ile Asp Leu Thr Leu Ala Gln Ala Val Ala Lys
545                 550                 555                 560

Asn Leu Gly Ile Glu Leu Thr Asp Asp Gln Leu Asn Ile Thr Pro Pro
                565                 570                 575

Pro Asp Val Asn Gly Leu Lys Lys Asp Pro Ser Leu Ser Leu Tyr Ala
            580                 585                 590

Ile Pro Asp Gly Asp Val Lys Gly Arg Val Val Ala Ile Leu Leu Asn
            595                 600                 605

Asp Glu Val Arg Ser Ala Asp Leu Leu Ala Ile Leu Lys Ala Leu Lys
                610                 615                 620

Ala Lys Gly Val His Ala Lys Leu Leu Tyr Ser Arg Met Gly Glu Val
625                 630                 635                 640

Thr Ala Asp Asp Gly Thr Val Leu Pro Ile Ala Ala Thr Phe Ala Gly
                645                 650                 655

Ala Pro Ser Leu Thr Val Asp Ala Val Ile Val Pro Cys Gly Asn Ile
            660                 665                 670

```
Ala Asp Ile Ala Asp Asn Gly Asp Ala Asn Tyr Tyr Leu Met Glu Ala
            675                 680                 685

Tyr Lys His Leu Lys Pro Ile Ala Leu Ala Gly Asp Ala Arg Lys Phe
    690                 695                 700

Lys Ala Thr Ile Lys Ile Ala Asp Gln Gly Glu Glu Gly Ile Val Glu
705                 710                 715                 720

Ala Asp Ser Ala Asp Gly Ser Phe Met Asp Glu Leu Leu Thr Leu Met
                725                 730                 735

Ala Ala His Arg Val Trp Ser Arg Ile Pro Lys Ile Asp Lys Ile Pro
            740                 745                 750

Ala

<210> SEQ ID NO 8
<211> LENGTH: 492
<212> TYPE: PRT
<213> ORGANISM: Arabidopsis thaliana

<400> SEQUENCE: 8

Met Asp Pro Tyr Arg Val Arg Pro Ser Ser Ala His Asp Ser Pro Phe
1               5                   10                  15

Phe Thr Thr Asn Ser Gly Ala Pro Val Trp Asn Asn Ser Ser Leu
                20                  25                  30

Thr Val Gly Thr Arg Gly Pro Ile Leu Leu Glu Asp Tyr His Leu Leu
            35                  40                  45

Glu Lys Leu Ala Asn Phe Asp Arg Glu Arg Ile Pro Glu Arg Val Val
    50                  55                  60

His Ala Arg Gly Ala Ser Ala Lys Gly Phe Phe Glu Val Thr His Asp
65                  70                  75                  80

Ile Thr Gln Leu Thr Ser Ala Asp Phe Leu Arg Gly Pro Gly Val Gln
                85                  90                  95

Thr Pro Val Ile Val Arg Phe Ser Thr Val Ile His Glu Arg Gly Ser
            100                 105                 110

Pro Glu Thr Leu Arg Asp Pro Arg Gly Phe Ala Val Lys Phe Tyr Thr
        115                 120                 125

Arg Glu Gly Asn Phe Asp Leu Val Gly Asn Asn Phe Pro Val Phe Phe
    130                 135                 140

Val Arg Asp Gly Met Lys Phe Pro Asp Met Val His Ala Leu Lys Pro
145                 150                 155                 160

Asn Pro Lys Ser His Ile Gln Glu Asn Trp Arg Ile Leu Asp Phe Phe
                165                 170                 175

Ser His His Pro Glu Ser Leu His Met Phe Ser Phe Leu Phe Asp Asp
            180                 185                 190

Leu Gly Ile Pro Gln Asp Tyr Arg His Met Glu Gly Ala Gly Val Asn
        195                 200                 205

Thr Tyr Met Leu Ile Asn Lys Ala Gly Lys Ala His Tyr Val Lys Phe
    210                 215                 220

His Trp Lys Pro Thr Cys Gly Ile Lys Cys Leu Ser Asp Glu Glu Ala
225                 230                 235                 240

Ile Arg Val Gly Gly Ala Asn His Ser His Ala Thr Lys Asp Leu Tyr
                245                 250                 255

Asp Ser Ile Ala Ala Gly Asn Tyr Pro Gln Trp Asn Leu Phe Val Gln
            260                 265                 270

Val Met Asp Pro Ala His Glu Asp Lys Phe Asp Phe Asp Pro Leu Asp
        275                 280                 285
```

```
Val Thr Lys Ile Trp Pro Glu Asp Ile Leu Pro Leu Gln Pro Val Gly
    290                 295                 300

Arg Leu Val Leu Asn Lys Asn Ile Asp Asn Phe Phe Asn Glu Asn Glu
305                 310                 315                 320

Gln Ile Ala Phe Cys Pro Ala Leu Val Val Pro Gly Ile His Tyr Ser
                325                 330                 335

Asp Asp Lys Leu Leu Gln Thr Arg Ile Phe Ser Tyr Ala Asp Ser Gln
            340                 345                 350

Arg His Arg Leu Gly Pro Asn Tyr Leu Gln Leu Pro Val Asn Ala Pro
        355                 360                 365

Lys Cys Ala His His Asn Asn His His Asp Gly Phe Met Asn Phe Met
370                 375                 380

His Arg Asp Glu Glu Val Asn Tyr Phe Pro Ser Arg Leu Asp Pro Val
385                 390                 395                 400

Arg His Ala Glu Lys Tyr Pro Thr Thr Pro Ile Val Cys Ser Gly Asn
                405                 410                 415

Arg Glu Lys Cys Phe Ile Gly Lys Glu Asn Asn Phe Lys Gln Pro Gly
            420                 425                 430

Glu Arg Tyr Arg Ser Trp Asp Ser Asp Arg Gln Glu Arg Phe Val Lys
        435                 440                 445

Arg Phe Val Glu Ala Leu Ser Glu Pro Arg Val Thr His Glu Ile Arg
450                 455                 460

Ser Ile Trp Ile Ser Tyr Trp Ser Gln Ala Asp Lys Ser Leu Gly Gln
465                 470                 475                 480

Lys Leu Ala Thr Arg Leu Asn Val Arg Pro Asn Phe
                485                 490

<210> SEQ ID NO 9
<211> LENGTH: 492
<212> TYPE: PRT
<213> ORGANISM: Arabidopsis thaliana

<400> SEQUENCE: 9

Met Asp Pro Tyr Lys Tyr Arg Pro Ala Ser Ser Tyr Asn Ser Pro Phe
1               5                   10                  15

Phe Thr Thr Asn Ser Gly Ala Pro Val Trp Asn Asn Asn Ser Ser Met
                20                  25                  30

Thr Val Gly Pro Arg Gly Pro Ile Leu Leu Glu Asp Tyr His Leu Val
            35                  40                  45

Glu Lys Leu Ala Asn Phe Asp Arg Glu Arg Ile Pro Glu Arg Val Val
50                  55                  60

His Ala Arg Gly Ala Ser Ala Lys Gly Phe Phe Glu Val Thr His Asp
65                  70                  75                  80

Ile Ser Asn Leu Thr Cys Ala Asp Phe Leu Arg Ala Pro Gly Val Gln
                85                  90                  95

Thr Pro Val Ile Val Arg Phe Ser Thr Val Ile His Glu Arg Gly Ser
                100                 105                 110

Pro Glu Thr Leu Arg Asp Pro Arg Gly Phe Ala Val Lys Phe Tyr Thr
            115                 120                 125

Arg Glu Gly Asn Phe Asp Leu Val Gly Asn Asn Phe Pro Val Phe Phe
        130                 135                 140

Ile Arg Asp Gly Met Lys Phe Pro Asp Met Val His Ala Leu Lys Pro
145                 150                 155                 160

Asn Pro Lys Ser His Ile Gln Glu Asn Trp Arg Ile Leu Asp Phe Phe
                165                 170                 175
```

Ser His His Pro Glu Ser Leu Asn Met Phe Thr Phe Leu Phe Asp Asp
                180                 185                 190

Ile Gly Ile Pro Gln Asp Tyr Arg His Met Asp Gly Ser Gly Val Asn
            195                 200                 205

Thr Tyr Met Leu Ile Asn Lys Ala Gly Lys Ala His Tyr Val Lys Phe
        210                 215                 220

His Trp Lys Pro Thr Cys Gly Val Lys Ser Leu Leu Glu Glu Asp Ala
225                 230                 235                 240

Ile Arg Val Gly Gly Thr Asn His Ser His Ala Thr Gln Asp Leu Tyr
                245                 250                 255

Asp Ser Ile Ala Ala Gly Asn Tyr Pro Glu Trp Lys Leu Phe Ile Gln
            260                 265                 270

Ile Ile Asp Pro Ala Asp Glu Asp Lys Phe Asp Phe Asp Pro Leu Asp
        275                 280                 285

Val Thr Lys Thr Trp Pro Glu Asp Ile Leu Pro Leu Gln Pro Val Gly
290                 295                 300

Arg Met Val Leu Asn Lys Asn Ile Asp Asn Phe Ala Glu Asn Glu
305                 310                 315                 320

Gln Leu Ala Phe Cys Pro Ala Ile Ile Val Pro Gly Ile His Tyr Ser
                325                 330                 335

Asp Asp Lys Leu Leu Gln Thr Arg Val Phe Ser Tyr Ala Asp Thr Gln
            340                 345                 350

Arg His Arg Leu Gly Pro Asn Tyr Leu Gln Leu Pro Val Asn Ala Pro
        355                 360                 365

Lys Cys Ala His His Asn Asn His His Glu Gly Phe Met Asn Phe Met
370                 375                 380

His Arg Asp Glu Glu Val Asn Tyr Phe Pro Ser Arg Tyr Asp Gln Val
385                 390                 395                 400

Arg His Ala Glu Lys Tyr Pro Thr Pro Ala Val Cys Ser Gly Lys
                405                 410                 415

Arg Glu Arg Cys Ile Ile Glu Lys Glu Asn Asn Phe Lys Glu Pro Gly
            420                 425                 430

Glu Arg Tyr Arg Thr Phe Thr Pro Glu Arg Gln Glu Arg Phe Ile Gln
        435                 440                 445

Arg Trp Ile Asp Ala Leu Ser Asp Pro Arg Ile Thr His Glu Ile Arg
450                 455                 460

Ser Ile Trp Ile Ser Tyr Trp Ser Gln Ala Asp Lys Ser Leu Gly Gln
465                 470                 475                 480

Lys Leu Ala Ser Arg Leu Asn Val Arg Pro Ser Ile
                485                 490

<210> SEQ ID NO 10
<211> LENGTH: 492
<212> TYPE: PRT
<213> ORGANISM: Arabidopsis thaliana

<400> SEQUENCE: 10

Met Asp Pro Tyr Lys Tyr Arg Pro Ser Ala Tyr Asn Ala Pro Phe
1               5                   10                  15

Tyr Thr Thr Asn Gly Gly Ala Pro Val Ser Asn Ile Ser Ser Leu
            20                  25                  30

Thr Ile Gly Glu Arg Gly Pro Val Leu Leu Glu Asp Tyr His Leu Ile
        35                  40                  45

Glu Lys Val Ala Asn Phe Thr Arg Glu Arg Ile Pro Glu Arg Val Val

```
                 50                  55                  60
His Ala Arg Gly Ile Ser Ala Lys Gly Phe Phe Glu Val Thr His Asp
 65                  70                  75                  80

Ile Ser Asn Leu Thr Cys Ala Asp Phe Leu Arg Ala Pro Gly Val Gln
                 85                  90                  95

Thr Pro Val Ile Val Arg Phe Ser Thr Val Val His Glu Arg Ala Ser
            100                 105                 110

Pro Glu Thr Met Arg Asp Ile Arg Gly Phe Ala Val Lys Phe Tyr Thr
            115                 120                 125

Arg Glu Gly Asn Phe Asp Leu Val Gly Asn Asn Thr Pro Val Phe Phe
            130                 135                 140

Ile Arg Asp Gly Ile Gln Phe Pro Asp Val Val His Ala Leu Lys Pro
145                 150                 155                 160

Asn Pro Lys Thr Asn Ile Gln Glu Tyr Trp Arg Ile Leu Asp Tyr Met
                165                 170                 175

Ser His Leu Pro Glu Ser Leu Leu Thr Trp Cys Trp Met Phe Asp Asp
                180                 185                 190

Val Gly Ile Pro Gln Asp Tyr Arg His Met Glu Gly Phe Gly Val His
                195                 200                 205

Thr Tyr Thr Leu Ile Ala Lys Ser Gly Lys Val Leu Phe Val Lys Phe
            210                 215                 220

His Trp Lys Pro Thr Cys Gly Ile Lys Asn Leu Thr Asp Glu Glu Ala
225                 230                 235                 240

Lys Val Val Gly Gly Ala Asn His Ser His Ala Thr Lys Asp Leu His
                245                 250                 255

Asp Ala Ile Ala Ser Gly Asn Tyr Pro Glu Trp Lys Leu Phe Ile Gln
                260                 265                 270

Thr Met Asp Pro Ala Asp Glu Asp Lys Phe Asp Phe Asp Pro Leu Asp
            275                 280                 285

Val Thr Lys Ile Trp Pro Glu Asp Ile Leu Pro Leu Gln Pro Val Gly
            290                 295                 300

Arg Leu Val Leu Asn Arg Thr Ile Asp Asn Phe Phe Asn Glu Thr Glu
305                 310                 315                 320

Gln Leu Ala Phe Asn Pro Gly Leu Val Val Pro Gly Ile Tyr Tyr Ser
                325                 330                 335

Asp Asp Lys Leu Leu Gln Cys Arg Ile Phe Ala Tyr Gly Asp Thr Gln
                340                 345                 350

Arg His Arg Leu Gly Pro Asn Tyr Leu Gln Leu Pro Val Asn Ala Pro
            355                 360                 365

Lys Cys Ala His His Asn Asn His Glu Gly Phe Met Asn Phe Met
            370                 375                 380

His Arg Asp Glu Glu Ile Asn Tyr Tyr Pro Ser Lys Phe Asp Pro Val
385                 390                 395                 400

Arg Cys Ala Glu Lys Val Pro Thr Pro Thr Asn Ser Tyr Thr Gly Ile
                405                 410                 415

Arg Thr Lys Cys Val Ile Lys Lys Glu Asn Asn Phe Lys Gln Ala Gly
                420                 425                 430

Asp Arg Tyr Arg Ser Trp Ala Pro Asp Arg Gln Asp Arg Phe Val Lys
            435                 440                 445

Arg Trp Val Glu Ile Leu Ser Glu Pro Arg Leu Thr His Glu Ile Arg
            450                 455                 460

Gly Ile Trp Ile Ser Tyr Trp Ser Gln Ala Asp Arg Ser Leu Gly Gln
465                 470                 475                 480
```

Lys Leu Ala Ser Arg Leu Asn Val Arg Pro Ser Ile
            485                 490

<210> SEQ ID NO 11
<211> LENGTH: 28
<212> TYPE: PRT
<213> ORGANISM: Cannabis

<400> SEQUENCE: 11

Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala
            20                  25

<210> SEQ ID NO 12
<211> LENGTH: 28
<212> TYPE: PRT
<213> ORGANISM: Cannabis

<400> SEQUENCE: 12

Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala
            20                  25

<210> SEQ ID NO 13
<211> LENGTH: 517
<212> TYPE: PRT
<213> ORGANISM: Cannabis

<400> SEQUENCE: 13

Asn Pro Arg Glu Asn Phe Leu Lys Cys Phe Ser Lys His Ile Pro Asn
1               5                   10                  15

Asn Val Ala Asn Pro Lys Leu Val Tyr Thr Gln His Asp Gln Leu Tyr
            20                  25                  30

Met Ser Ile Leu Asn Ser Thr Ile Gln Asn Leu Arg Phe Ile Ser Asp
            35                  40                  45

Thr Thr Pro Lys Pro Leu Val Ile Val Thr Pro Ser Asn Asn Ser His
        50                  55                  60

Ile Gln Ala Thr Ile Leu Cys Ser Lys Val Gly Leu Gln Ile Arg
65                  70                  75                  80

Thr Arg Ser Gly Gly His Asp Ala Glu Gly Met Ser Tyr Ile Ser Gln
                85                  90                  95

Val Pro Phe Val Val Asp Leu Arg Asn Met His Ser Ile Lys Ile
            100                 105                 110

Asp Val His Ser Gln Thr Ala Trp Val Glu Ala Gly Ala Thr Leu Gly
        115                 120                 125

Glu Val Tyr Tyr Trp Ile Asn Glu Lys Asn Glu Asn Leu Ser Phe Pro
    130                 135                 140

Gly Gly Tyr Cys Pro Thr Val Gly Val Gly His Phe Ser Gly Gly
145                 150                 155                 160

Gly Tyr Gly Ala Leu Met Arg Asn Tyr Gly Leu Ala Ala Asp Asn Ile
                165                 170                 175

Ile Asp Ala His Leu Val Asn Val Asp Gly Lys Val Leu Asp Arg Lys
            180                 185                 190

Ser Met Gly Glu Asp Leu Phe Trp Ala Ile Arg Gly Gly Gly Gly Glu
        195                 200                 205

-continued

Asn Phe Gly Ile Ile Ala Ala Trp Lys Ile Lys Leu Val Asp Val Pro
            210                 215                 220

Ser Lys Ser Thr Ile Phe Ser Val Lys Asn Met Glu Ile His Gly
225                 230                 235                 240

Leu Val Lys Leu Phe Asn Lys Trp Gln Asn Ile Ala Tyr Lys Tyr Asp
                    245                 250                 255

Lys Asp Leu Val Leu Met Thr His Phe Ile Thr Lys Asn Ile Thr Asp
                260                 265                 270

Asn His Gly Lys Asn Lys Thr Thr Val His Gly Tyr Phe Ser Ser Ile
            275                 280                 285

Phe His Gly Gly Val Asp Ser Leu Val Asp Leu Met Asn Lys Ser Phe
290                 295                 300

Pro Glu Leu Gly Ile Lys Lys Thr Asp Cys Lys Glu Phe Ser Trp Ile
305                 310                 315                 320

Asp Thr Thr Ile Phe Tyr Ser Gly Val Asn Phe Asn Thr Ala Asn
                    325                 330                 335

Phe Lys Lys Glu Ile Leu Leu Asp Arg Ser Ala Gly Lys Lys Thr Ala
                340                 345                 350

Phe Ser Ile Lys Leu Asp Tyr Val Lys Lys Pro Ile Pro Glu Thr Ala
            355                 360                 365

Met Val Lys Ile Leu Glu Lys Leu Tyr Glu Glu Asp Val Gly Ala Gly
370                 375                 380

Met Tyr Val Leu Tyr Pro Tyr Gly Gly Ile Met Glu Glu Ile Ser Glu
385                 390                 395                 400

Ser Ala Ile Pro Phe Pro His Arg Ala Gly Ile Met Tyr Glu Leu Trp
                    405                 410                 415

Tyr Thr Ala Ser Trp Glu Lys Gln Glu Asp Asn Glu Lys His Ile Asn
                420                 425                 430

Trp Val Arg Ser Val Tyr Asn Phe Thr Thr Pro Tyr Val Ser Gln Asn
            435                 440                 445

Pro Arg Leu Ala Tyr Leu Asn Tyr Arg Asp Leu Asp Leu Gly Lys Thr
450                 455                 460

Asn His Ala Ser Pro Asn Asn Tyr Thr Gln Ala Arg Ile Trp Gly Glu
465                 470                 475                 480

Lys Tyr Phe Gly Lys Asn Phe Asn Arg Leu Val Lys Val Lys Thr Lys
                    485                 490                 495

Val Asp Pro Asn Asn Phe Phe Arg Asn Glu Gln Ser Ile Pro Pro Leu
                500                 505                 510

Pro Pro His His His
            515

<210> SEQ ID NO 14
<211> LENGTH: 1554
<212> TYPE: DNA
<213> ORGANISM: Cannabis sativa

<400> SEQUENCE: 14
atgaatcctc gagaaaactt ccttaaatgc ttctcgcaat atattcccaa taatgcaaca      60
aatctaaaac tcgtatacac tcaaaacaac ccattgtata tgtctgtcct aaattcgaca     120
atacacaatc ttagattcac ctctgacaca accccaaaac cacttgttat cgtcactcct     180
tcacatgtct ctcatatcca aggcactatt ctatgctcca agaaagttgg cttgcagatt     240
cgaactcgaa gtggtggtca tgattctgag ggcatgtcct acatatctca agtcccattt     300
gttatagtag acttgagaaa catgcgttca atcaaaatag atgttcatag ccaaactgca     360

-continued

```
tgggttgaag ccggagctac ccttggagaa gtttattatt gggttaatga gaaaaatgag    420
aatcttagtt tggcggctgg gtattgccct actgtttgcg caggtggaca ctttggtgga    480
ggaggctatg gaccattgat gagaaactat ggcctcgcgg ctgataatat cattgatgca    540
cacttagtca acgttcatgg aaaagtgcta gatcgaaaat ctatggggga agatctcttt    600
tgggctttac gtggtggtgg agcagaaagc ttcggaatca ttgtagcatg gaaaattaga    660
ctggttgctg tcccaaagtc tactatgttt agtgttaaaa agatcatgga gatacatgag    720
cttgtcaagt tagttaacaa atggcaaaat attgcttaca agtatgacaa agatttatta    780
ctcatgactc acttcataac taggaacatt acagataatc aagggaagaa taagacagca    840
atacacactt acttctcttc agttttcctt ggtggagtgg atagtctagt cgacttgatg    900
aacaagagtt ttcctgagtt gggtattaaa aaaacggatt gcagacaatt gagctggatt    960
gatactatca tcttctatag tggtgttgta aattacgaca ctgataattt taacaaggaa   1020
attttgcttg atagatccgc tgggcagaac ggtgctttca agattaagtt agactacgtt   1080
aagaaaccaa ttccagaatc tgtatttgtc caaattttgg aaaaattata tgaagaagat   1140
ataggagctg ggatgtatgc gttgtaccct tacggtggta taatggatga gatttcagaa   1200
tcagcaattc cattccctca tcgagctgga atcttgtatg agttatggta catatgtagt   1260
tgggagaagc aagaagataa cgaaaagcat ctaaactgga ttagaaatat ttataacttc   1320
atgactcctt atgtgtccaa aaatccaaga ttggcatatc tcaattatag agaccttgat   1380
ataggaataa atgatcccaa gaatccaaat aattacacac aagcacgtat ttggggtgag   1440
aagtattttg gtaaaaattt tgacaggcta gtaaaagtga aaccctggt tgatcccaat    1500 aacttttta gaaacgaaca aagcatccca cctctaccac ggcatcgtca ttaa           1554
```

<210> SEQ ID NO 15
<211> LENGTH: 517
<212> TYPE: PRT
<213> ORGANISM: Cannabis sativa

<400> SEQUENCE: 15

```
Met Asn Pro Arg Glu Asn Phe Leu Lys Cys Phe Ser Gln Tyr Ile Pro
1               5                   10                  15

Asn Asn Ala Thr Asn Leu Lys Leu Val Tyr Thr Gln Asn Asn Pro Leu
            20                  25                  30

Tyr Met Ser Val Leu Asn Ser Thr Ile His Asn Leu Arg Phe Thr Ser
        35                  40                  45

Asp Thr Thr Pro Lys Pro Leu Val Ile Val Thr Pro Ser His Val Ser
    50                  55                  60

His Ile Gln Gly Thr Ile Leu Cys Ser Lys Lys Val Gly Leu Gln Ile
65                  70                  75                  80

Arg Thr Arg Ser Gly Gly His Asp Ser Glu Gly Met Ser Tyr Ile Ser
                85                  90                  95

Gln Val Pro Phe Val Ile Val Asp Leu Arg Asn Met Arg Ser Ile Lys
            100                 105                 110

Ile Asp Val His Ser Gln Thr Ala Trp Val Glu Ala Gly Ala Thr Leu
        115                 120                 125

Gly Glu Val Tyr Tyr Trp Val Asn Glu Lys Asn Glu Asn Leu Ser Leu
    130                 135                 140

Ala Ala Gly Tyr Cys Pro Thr Val Cys Ala Gly Gly His Phe Gly Gly
145                 150                 155                 160
```

```
Gly Gly Tyr Gly Pro Leu Met Arg Asn Tyr Gly Leu Ala Ala Asp Asn
                165                 170                 175

Ile Ile Asp Ala His Leu Val Asn Val His Gly Lys Val Leu Asp Arg
            180                 185                 190

Lys Ser Met Gly Glu Asp Leu Phe Trp Ala Leu Arg Gly Gly Gly Ala
        195                 200                 205

Glu Ser Phe Gly Ile Ile Val Ala Trp Lys Ile Arg Leu Val Ala Val
    210                 215                 220

Pro Lys Ser Thr Met Phe Ser Val Lys Lys Ile Met Glu Ile His Glu
225                 230                 235                 240

Leu Val Lys Leu Val Asn Lys Trp Gln Asn Ile Ala Tyr Lys Tyr Asp
                245                 250                 255

Lys Asp Leu Leu Leu Met Thr His Phe Ile Thr Arg Asn Ile Thr Asp
            260                 265                 270

Asn Gln Gly Lys Asn Lys Thr Ala Ile His Thr Tyr Phe Ser Ser Val
        275                 280                 285

Phe Leu Gly Gly Val Asp Ser Leu Val Asp Leu Met Asn Lys Ser Phe
    290                 295                 300

Pro Glu Leu Gly Ile Lys Lys Thr Asp Cys Arg Gln Leu Ser Trp Ile
305                 310                 315                 320

Asp Thr Ile Ile Phe Tyr Ser Gly Val Val Asn Tyr Asp Thr Asp Asn
                325                 330                 335

Phe Asn Lys Glu Ile Leu Leu Asp Arg Ser Ala Gly Gln Asn Gly Ala
            340                 345                 350

Phe Lys Ile Lys Leu Asp Tyr Val Lys Lys Pro Ile Pro Glu Ser Val
        355                 360                 365

Phe Val Gln Ile Leu Glu Lys Leu Tyr Glu Glu Asp Ile Gly Ala Gly
    370                 375                 380

Met Tyr Ala Leu Tyr Pro Tyr Gly Gly Ile Met Asp Glu Ile Ser Glu
385                 390                 395                 400

Ser Ala Ile Pro Phe Pro His Arg Ala Gly Ile Leu Tyr Glu Leu Trp
                405                 410                 415

Tyr Ile Cys Ser Trp Glu Lys Gln Glu Asp Asn Glu Lys His Leu Asn
            420                 425                 430

Trp Ile Arg Asn Ile Tyr Asn Phe Met Thr Pro Tyr Val Ser Lys Asn
        435                 440                 445

Pro Arg Leu Ala Tyr Leu Asn Tyr Arg Asp Leu Asp Ile Gly Ile Asn
    450                 455                 460

Asp Pro Lys Asn Pro Asn Asn Tyr Thr Gln Ala Arg Ile Trp Gly Glu
465                 470                 475                 480

Lys Tyr Phe Gly Lys Asn Phe Asp Arg Leu Val Lys Val Lys Thr Leu
                485                 490                 495

Val Asp Pro Asn Asn Phe Phe Arg Asn Glu Gln Ser Ile Pro Pro Leu
            500                 505                 510

Pro Arg His Arg His
        515

<210> SEQ ID NO 16
<211> LENGTH: 1074
<212> TYPE: DNA
<213> ORGANISM: Cannabis

<400> SEQUENCE: 16
atgaagaaga acaaatcaac tagtaataat aagaacaaca acagtaataa tatcatcaaa      60
```

```
aacgacatcg tatcatcatc atcatcaaca acaacaacat catcaacaac tacagcaaca    120
tcatcatttc ataatgagaa agttactgtc agtactgatc atattattaa tcttgatgat    180
aagcagaaac gacaattatg tcgttgtcgt ttagaaaaag aagaagaaga agaaggaagt    240
ggtggttgtg gtgagacagt agtaatgatg ctagggtcag tatctcctgc tgctgctact    300
gctgctgcag ctgggggctc atcaagttgt gatgaagaca tgttgggtgg tcatgatcaa    360
ctgttgttgt gtgttgttc tgagaaaaaa acgacagaaa tttcatcagt ggtgaacttt    420
aataataata ataataataa taaggaaaat ggtgacgaag tttcaggacc gtacgattat    480
catcatcata agaagagga agaagaagaa gaagaagatg aagcatctgc atcagtagca    540
gctgttgatg aagggatgtt gttgtgcttt gatgacataa tagatagcca cttgctaaat    600
ccaaatgagg ttttgacttt aagagaagat agccataatg aaggtggggc agctgatcag    660
attgacaaga ctacttgtaa taatactact attactacta atgatgatta taacaataac    720
ttgatgatgt tgagctgcaa taataacgga gattatgtta ttagtgatga tcatgatgat    780
cagtactgga tagacgacgt cgttggagtt gacttttgga gttgggagag ttcgactact    840
actgttatta cccaagaaca agaacaagaa caagatcaag ttcaagaaca gaagaatatg    900
tgggataatg agaaagagaa actgttgtct ttgctatggg ataatagtga taacagcagc    960
agttgggagt tacaagataa aagcaataat aataataata ataatgttcc taacaaatgt    1020
caagagatta cctctgataa agaaaatgct atggttgcat ggcttctctc ctga           1074
```

<210> SEQ ID NO 17
<211> LENGTH: 357
<212> TYPE: PRT
<213> ORGANISM: Cannabis

<400> SEQUENCE: 17

```
Met Lys Lys Asn Lys Ser Thr Ser Asn Asn Lys Asn Asn Ser Asn
1               5                   10                  15

Asn Ile Ile Lys Asn Asp Ile Val Ser Ser Ser Ser Thr Thr Thr
            20                  25                  30

Thr Ser Ser Thr Thr Thr Ala Thr Ser Ser Phe His Asn Glu Lys Val
        35                  40                  45

Thr Val Ser Thr Asp His Ile Ile Asn Leu Asp Asp Lys Gln Lys Arg
    50                  55                  60

Gln Leu Cys Arg Cys Arg Leu Glu Lys Glu Glu Glu Glu Gly Ser
65              70                  75                  80

Gly Gly Cys Gly Glu Thr Val Val Met Met Leu Gly Ser Val Ser Pro
                85                  90                  95

Ala Ala Ala Thr Ala Ala Ala Ala Gly Gly Ser Ser Ser Cys Asp Glu
            100                 105                 110

Asp Met Leu Gly Gly His Asp Gln Leu Leu Leu Cys Cys Ser Glu
        115                 120                 125

Lys Lys Thr Thr Glu Ile Ser Ser Val Val Asn Phe Asn Asn Asn
    130                 135                 140

Asn Asn Asn Lys Glu Asn Gly Asp Glu Val Ser Gly Pro Tyr Asp Tyr
145                 150                 155                 160

His His His Lys Glu Glu Glu Glu Glu Glu Asp Glu Ala Ser
                165                 170                 175

Ala Ser Val Ala Ala Val Asp Glu Gly Met Leu Leu Cys Phe Asp Asp
            180                 185                 190

Ile Ile Asp Ser His Leu Leu Asn Pro Asn Glu Val Leu Thr Leu Arg
```

```
            195                 200                 205
Glu Asp Ser His Asn Glu Gly Gly Ala Ala Asp Gln Ile Asp Lys Thr
    210                 215                 220

Thr Cys Asn Asn Thr Thr Ile Thr Thr Asn Asp Asp Tyr Asn Asn Asn
225                 230                 235                 240

Leu Met Met Leu Ser Cys Asn Asn Asn Gly Asp Tyr Val Ile Ser Asp
                245                 250                 255

Asp His Asp Asp Gln Tyr Trp Ile Asp Asp Val Val Gly Val Asp Phe
            260                 265                 270

Trp Ser Trp Glu Ser Ser Thr Thr Val Ile Thr Gln Glu Gln Glu
                275                 280                 285

Gln Glu Gln Asp Gln Val Gln Glu Gln Lys Asn Met Trp Asp Asn Glu
    290                 295                 300

Lys Glu Lys Leu Leu Ser Leu Leu Trp Asp Asn Ser Asp Asn Ser Ser
305                 310                 315                 320

Ser Trp Glu Leu Gln Asp Lys Ser Asn Asn Asn Asn Asn Asn Asn Val
                325                 330                 335

Pro Asn Lys Cys Gln Glu Ile Thr Ser Asp Lys Glu Asn Ala Met Val
            340                 345                 350

Ala Trp Leu Leu Ser
            355

<210> SEQ ID NO 18
<211> LENGTH: 462
<212> TYPE: PRT
<213> ORGANISM: Humulus lupulus

<400> SEQUENCE: 18

Met Gly Arg Ala Pro Cys Cys Glu Lys Val Gly Leu Lys Lys Gly Arg
1               5                   10                  15

Trp Thr Ser Glu Glu Asp Glu Ile Leu Thr Lys Tyr Ile Gln Ser Asn
                20                  25                  30

Gly Glu Gly Cys Trp Arg Ser Leu Pro Lys Asn Ala Gly Leu Leu Arg
            35                  40                  45

Cys Gly Lys Ser Cys Arg Leu Arg Trp Ile Asn Tyr Leu Arg Ala Asp
    50                  55                  60

Leu Lys Arg Gly Asn Ile Ser Ser Glu Glu Asp Ile Ile Ile Lys
65                  70                  75                  80

Leu His Ser Thr Leu Gly Asn Arg Trp Ser Leu Ile Ala Ser His Leu
                85                  90                  95

Pro Gly Arg Thr Asp Asn Glu Ile Lys Asn Tyr Trp Asn Ser His Leu
            100                 105                 110

Ser Arg Lys Ile His Thr Phe Arg Arg Cys Asn Asn Thr Thr Thr His
    115                 120                 125

His His His Leu Pro Asn Leu Val Thr Val Thr Lys Val Asn Leu Pro
130                 135                 140

Ile Pro Lys Arg Lys Gly Gly Arg Thr Ser Arg Leu Ala Met Lys Lys
145                 150                 155                 160

Asn Lys Ser Ser Thr Ser Asn Gln Asn Ser Ser Val Ile Lys Asn Asp
                165                 170                 175

Val Gly Ser Ser Ser Ser Thr Thr Thr Thr Ser Val His Gln Arg Thr
            180                 185                 190

Thr Thr Thr Thr Pro Thr Met Asp Asp Gln Gln Lys Arg Gln Leu Ser
    195                 200                 205
```

```
Arg Cys Arg Leu Glu Glu Lys Glu Asp Gln Asp Gly Ala Ser Thr Gly
    210                 215                 220

Thr Val Val Met Met Leu Gly Gln Ala Ala Val Gly Ser Ser Cys
225                 230                 235                 240

Asp Glu Asp Met Leu Gly His Asp Gln Leu Ser Phe Leu Cys Cys Ser
                245                 250                 255

Glu Glu Lys Thr Thr Glu Asn Ser Met Thr Asn Leu Lys Glu Asn Gly
                260                 265                 270

Asp His Glu Val Ser Gly Pro Tyr Asp Tyr Asp His Arg Tyr Glu Lys
                275                 280                 285

Glu Thr Ser Val Asp Glu Gly Met Leu Leu Cys Phe Asn Asp Ile Ile
    290                 295                 300

Asp Ser Asn Leu Leu Asn Pro Asn Glu Val Leu Thr Leu Ser Glu Glu
305                 310                 315                 320

Ser Leu Asn Leu Gly Gly Ala Leu Met Asp Thr Thr Thr Ser Thr Thr
                325                 330                 335

Thr Asn Asn Asn Asn Tyr Ser Leu Ser Tyr Asn Asn Gly Asp Cys
                340                 345                 350

Val Ile Ser Asp Asp His Asp Gln Tyr Trp Leu Asp Asp Val Val Gly
            355                 360                 365

Val Asp Phe Trp Ser Trp Glu Ser Ser Thr Thr Val Thr Gln Glu Gln
370                 375                 380

Glu Gln Glu Gln Glu Gln Glu Gln Glu Gln Glu Gln Glu Gln Glu Gln
385                 390                 395                 400

Glu Gln Glu His His His Gln Gln Asp Gln Lys Lys Asn Thr Trp Asp
                405                 410                 415

Asn Glu Lys Glu Lys Met Leu Ala Leu Leu Trp Asp Ser Asp Asn Ser
                420                 425                 430

Asn Trp Glu Leu Gln Asp Asn Asn Tyr His Lys Cys Gln Glu Ile
            435                 440                 445

Thr Ser Asp Lys Glu Asn Ala Met Val Ala Trp Leu Leu Ser
    450                 455                 460

<210> SEQ ID NO 19
<211> LENGTH: 371
<212> TYPE: PRT
<213> ORGANISM: Arabidopsis thaliana

<400> SEQUENCE: 19

Met Gly Arg Ala Pro Cys Cys Glu Lys Val Gly Ile Lys Arg Gly Arg
1               5                   10                  15

Trp Thr Ala Glu Glu Asp Gln Ile Leu Ser Asn Tyr Ile Gln Ser Asn
                20                  25                  30

Gly Glu Gly Ser Trp Arg Ser Leu Pro Lys Asn Ala Gly Leu Lys Arg
            35                  40                  45

Cys Gly Lys Ser Cys Arg Leu Arg Trp Ile Asn Tyr Leu Arg Ser Asp
        50                  55                  60

Leu Lys Arg Gly Asn Ile Thr Pro Glu Glu Glu Glu Leu Val Val Lys
65                  70                  75                  80

Leu His Ser Thr Leu Gly Asn Arg Trp Ser Leu Ile Ala Gly His Leu
                85                  90                  95

Pro Gly Arg Thr Asp Asn Glu Ile Lys Asn Tyr Trp Asn Ser His Leu
                100                 105                 110

Ser Arg Lys Leu His Asn Phe Ile Arg Lys Pro Ser Ile Ser Gln Asp
            115                 120                 125
```

```
Val Ser Ala Val Ile Met Thr Asn Ala Ser Ala Pro Pro Pro
    130                 135                 140

Gln Ala Lys Arg Arg Leu Gly Arg Thr Ser Arg Ser Ala Met Lys Pro
145                 150                 155                 160

Lys Ile His Arg Thr Lys Thr Arg Lys Thr Lys Lys Thr Ser Ala Pro
                    165                 170                 175

Pro Glu Pro Asn Ala Asp Val Ala Gly Ala Asp Lys Glu Ala Leu Met
                180                 185                 190

Val Glu Ser Ser Gly Ala Glu Ala Glu Leu Gly Arg Pro Cys Asp Tyr
            195                 200                 205

Tyr Gly Asp Asp Cys Asn Lys Asn Leu Met Ser Ile Asn Gly Asp Asn
        210                 215                 220

Gly Val Leu Thr Phe Asp Asp Ile Ile Asp Leu Leu Asp Glu
225                 230                 235                 240

Ser Asp Pro Gly His Leu Tyr Thr Asn Thr Thr Cys Gly Gly Asp Gly
                245                 250                 255

Glu Leu His Asn Ile Arg Asp Ser Glu Gly Ala Arg Gly Phe Ser Asp
                260                 265                 270

Thr Trp Asn Gln Gly Asn Leu Asp Cys Leu Leu Gln Ser Cys Pro Ser
            275                 280                 285

Val Glu Ser Phe Leu Asn Tyr Asp His Gln Val Asn Asp Ala Ser Thr
290                 295                 300

Asp Glu Phe Ile Asp Trp Asp Cys Val Trp Gln Gly Ser Asp Asn
305                 310                 315                 320

Asn Leu Trp His Glu Lys Glu Asn Pro Asp Ser Met Val Ser Trp Leu
                325                 330                 335

Leu Asp Gly Asp Asp Glu Ala Thr Ile Gly Asn Ser Asn Cys Glu Asn
                340                 345                 350

Phe Gly Glu Pro Leu Asp His Asp Asp Glu Ser Ala Leu Val Ala Trp
                355                 360                 365

Leu Leu Ser
    370

<210> SEQ ID NO 20
<211> LENGTH: 243
<212> TYPE: PRT
<213> ORGANISM: Arabidopsis thaliana

<400> SEQUENCE: 20

Met Asn Ile Ser Arg Thr Glu Phe Ala Asn Cys Lys Thr Leu Ile Asn
1               5                   10                  15

His Lys Glu Glu Val Glu Glu Val Glu Lys Lys Met Glu Ile Glu Ile
                20                  25                  30

Arg Arg Gly Pro Trp Thr Val Glu Glu Asp Met Lys Leu Val Ser Tyr
            35                  40                  45

Ile Ser Leu His Gly Glu Gly Arg Trp Asn Ser Leu Ser Arg Ser Ala
        50                  55                  60

Gly Leu Asn Arg Thr Gly Lys Ser Cys Arg Leu Arg Trp Leu Asn Tyr
65                  70                  75                  80

Leu Arg Pro Asp Ile Arg Arg Gly Asp Ile Ser Leu Gln Glu Gln Phe
                85                  90                  95

Ile Ile Leu Glu Leu His Ser Arg Trp Gly Asn Arg Trp Ser Lys Ile
                100                 105                 110

Ala Gln His Leu Pro Gly Arg Thr Asp Asn Glu Ile Lys Asn Tyr Trp
```

```
            115                 120                 125
Arg Thr Arg Val Gln Lys His Ala Lys Leu Leu Lys Cys Asp Val Asn
        130                 135                 140

Ser Lys Gln Phe Lys Asp Thr Ile Lys His Leu Trp Met Pro Arg Leu
145                 150                 155                 160

Ile Glu Arg Ile Ala Ala Thr Gln Ser Val Gln Phe Thr Ser Asn His
                165                 170                 175

Tyr Ser Pro Glu Asn Ser Ser Val Ala Thr Ala Thr Ser Ser Thr Ser
            180                 185                 190

Ser Ser Glu Ala Val Arg Ser Ser Phe Tyr Gly Gly Asp Gln Val Glu
        195                 200                 205

Phe Gly Thr Leu Asp His Met Thr Asn Gly Gly Tyr Trp Phe Asn Gly
    210                 215                 220

Gly Asp Thr Phe Glu Thr Leu Cys Ser Phe Asp Glu Leu Asn Lys Trp
225                 230                 235                 240

Leu Ile Gln

<210> SEQ ID NO 21
<211> LENGTH: 127
<212> TYPE: PRT
<213> ORGANISM: Homo Sapiens

<400> SEQUENCE: 21

Met Ser Phe Ser Gly Lys Tyr Gln Leu Gln Ser Gln Glu Asn Phe Glu
1               5                   10                  15

Ala Phe Met Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
        35                  40                  45

Lys Phe Thr Ile Thr Ala Gly Ser Lys Val Ile Gln Asn Glu Phe Thr
    50                  55                  60

Val Gly Glu Glu Cys Glu Leu Glu Thr Met Thr Gly Glu Lys Val Lys
65                  70                  75                  80

Thr Val Val Gln Leu Glu Gly Asp Asn Lys Leu Val Thr Thr Phe Lys
                85                  90                  95

Asn Ile Lys Ser Val Thr Glu Leu Asn Gly Asp Ile Ile Thr Asn Thr
            100                 105                 110

Met Thr Leu Gly Asp Ile Val Phe Lys Arg Ile Ser Lys Arg Ile
        115                 120                 125

<210> SEQ ID NO 22
<211> LENGTH: 1515
<212> TYPE: DNA
<213> ORGANISM: Mus musculus

<400> SEQUENCE: 22
atgaacttgt tttctgcttt gtctttggat actttggttt tgttggctat tattttggtt     60
ttgttgtaca gatacggtac tagaactcat ggtttgttta agaagcaagg tattccaggt    120
ccaaagccat tgccattttt gggtactgtt ttgaactact acactggtat ttggaagttt    180
gatatggaat gttacgaaaa gtacggtaag acttgggggt tgtttgatgg tcaaactcca    240 tgttggtta ttactgatcc agaaactatt aagaacgttt ggttaaggat tgtttgtct    300 gtttttacta acagaagaga atttggtcca gttggtatta tgtctaaggc tatttctatt    360
tctaaggatg aagaatggaa gagatacaga gctttgttgt ctccaacttt tacttctggt    420
```

| | | |
|---|---|---|
| agattgaagg aaatgtttcc agttattgaa caatacggtg atattttggt taagtacttg | 480 | |
| agacaagaag ctgaaaaggg tatgccagtt gctatgaagg atgttttggg tgcttactct | 540 | |
| atggatgtta ttacttctac ttcttttggt gttaacgttg attctttgaa caacccagaa | 600 | |
| gatccatttg ttgaagaagc taagaagttt ttgagagttg attttttttga tccattgttg | 660 | |
| ttttctgttg ttttgtttcc attgttgact ccagtttacg aaatgttgaa catttgtatg | 720 | |
| tttccaaacg attctattga atttttttaag aagtttgttg atagaatgca agaatctaga | 780 | |
| ttggattcta accaaaagca tagagttgat ttttttgcaat tgatgatgaa ctctcataac | 840 | |
| aactctaagg ataaggattc tcataaggct ttttctaaca tggaaattac tgttcaatct | 900 | |
| attatttta tttctgctgg ttacgaaact acttcttcta ctttgtcttt tactttgtac | 960 | |
| tgtttggcta ctcatccaga tattcaaaag aagttgcaag ctgaaattga taaggctttg | 1020 | |
| ccaaacaagg ctactccaac ttgtgatact gttatggaaa tggaatactt ggatatggtt | 1080 | |
| ttgaacgaaa ctttgagatt gtacccaatt gttactagat tggaaagagt ttgtaagaag | 1140 | |
| gatgttgaat tgaacggtgt ttacattcca aagggttcta tggttatgat tccatcttac | 1200 | |
| gctttgcatc atgatccaca acattggcca gatccagaag aatttcaacc agaaagatt t| 1260 | |
| tctaaggaaa caagggttc tattgatcca tacgttact tgccatttgg tattggtcca | 1320 | |
| agaaactgta ttggtatgag atttgctttg atgaacatga agttggctgt tactaaggtt | 1380 | |
| ttgcaaaact tttcttttca accatgtcaa gaaactcaaa ttccattgaa gttgtctaga | 1440 | |
| caaggtattt tgcaaccaga aaagccaatt gttttgaagg ttgttccaag agatgctgtt | 1500 | |
| attactggtg cttaa | 1515 | |

<210> SEQ ID NO 23
<211> LENGTH: 504
<212> TYPE: PRT
<213> ORGANISM: Mus musculus

<400> SEQUENCE: 23

Met Asn Leu Phe Ser Ala Leu Ser Leu Asp Thr Leu Val Leu Leu Ala
1               5                   10                  15

Ile Ile Leu Val Leu Leu Tyr Arg Tyr Gly Thr Arg Thr His Gly Leu
            20                  25                  30

Phe Lys Lys Gln Gly Ile Pro Gly Pro Lys Pro Leu Pro Phe Leu Gly
        35                  40                  45

Thr Val Leu Asn Tyr Tyr Thr Gly Ile Trp Lys Phe Asp Met Glu Cys
    50                  55                  60

Tyr Glu Lys Tyr Gly Lys Thr Trp Gly Leu Phe Asp Gly Gln Thr Pro
65                  70                  75                  80

Leu Leu Val Ile Thr Asp Pro Glu Thr Ile Lys Asn Val Leu Val Lys
                85                  90                  95

Asp Cys Leu Ser Val Phe Thr Asn Arg Arg Glu Phe Gly Pro Val Gly
            100                 105                 110

Ile Met Ser Lys Ala Ile Ser Ile Ser Lys Asp Glu Trp Lys Arg
        115                 120                 125

Tyr Arg Ala Leu Leu Ser Pro Thr Phe Thr Ser Gly Arg Leu Lys Glu
    130                 135                 140

Met Phe Pro Val Ile Glu Gln Tyr Gly Asp Ile Leu Val Lys Tyr Leu
145                 150                 155                 160

Arg Gln Glu Ala Glu Lys Gly Met Pro Val Ala Met Lys Asp Val Leu
                165                 170                 175

Gly Ala Tyr Ser Met Asp Val Ile Thr Ser Thr Ser Phe Gly Val Asn
                180                 185                 190

Val Asp Ser Leu Asn Asn Pro Glu Asp Pro Phe Val Glu Ala Lys
            195                 200                 205

Lys Phe Leu Arg Val Asp Phe Phe Asp Pro Leu Leu Phe Ser Val Val
210                 215                 220

Leu Phe Pro Leu Leu Thr Pro Val Tyr Glu Met Leu Asn Ile Cys Met
225                 230                 235                 240

Phe Pro Asn Asp Ser Ile Glu Phe Phe Lys Lys Phe Val Asp Arg Met
                245                 250                 255

Gln Glu Ser Arg Leu Asp Ser Asn Gln Lys His Arg Val Asp Phe Leu
            260                 265                 270

Gln Leu Met Met Asn Ser His Asn Asn Ser Lys Asp Lys Asp Ser His
        275                 280                 285

Lys Ala Phe Ser Asn Met Glu Ile Thr Val Gln Ser Ile Ile Phe Ile
    290                 295                 300

Ser Ala Gly Tyr Glu Thr Thr Ser Ser Thr Leu Ser Phe Thr Leu Tyr
305                 310                 315                 320

Cys Leu Ala Thr His Pro Asp Ile Gln Lys Lys Leu Gln Ala Glu Ile
                325                 330                 335

Asp Lys Ala Leu Pro Asn Lys Ala Thr Pro Thr Cys Asp Thr Val Met
            340                 345                 350

Glu Met Glu Tyr Leu Asp Met Val Leu Asn Glu Thr Leu Arg Leu Tyr
        355                 360                 365

Pro Ile Val Thr Arg Leu Glu Arg Val Cys Lys Lys Asp Val Glu Leu
    370                 375                 380

Asn Gly Val Tyr Ile Pro Lys Gly Ser Met Val Met Ile Pro Ser Tyr
385                 390                 395                 400

Ala Leu His His Asp Pro Gln His Trp Pro Asp Pro Glu Glu Phe Gln
                405                 410                 415

Pro Glu Arg Phe Ser Lys Glu Asn Lys Gly Ser Ile Asp Pro Tyr Val
            420                 425                 430

Tyr Leu Pro Phe Gly Ile Gly Pro Arg Asn Cys Ile Gly Met Arg Phe
        435                 440                 445

Ala Leu Met Asn Met Lys Leu Ala Val Thr Lys Val Leu Gln Asn Phe
    450                 455                 460

Ser Phe Gln Pro Cys Gln Glu Thr Gln Ile Pro Leu Lys Leu Ser Arg
465                 470                 475                 480

Gln Gly Ile Leu Gln Pro Glu Lys Pro Ile Val Leu Lys Val Val Pro
                485                 490                 495

Arg Asp Ala Val Ile Thr Gly Ala
            500

<210> SEQ ID NO 24
<211> LENGTH: 2037
<212> TYPE: DNA
<213> ORGANISM: Mus musculus

<400> SEQUENCE: 24
atgggtgatt ctcatgaaga tacttctgct actgttccag aagctgttgc tgaagaagtt      60
tctttgtttt ctactactga tattgttttg ttttctttga ttgttggtgt tttgacttac     120
tggtttattt ttaagaagaa gaaggaagaa attccagaat ttctaagat  tcaaactact     180 gctccaccag ttaaggaatc ttcttttgtt gaaaagatga agaagactgg tagaaacatt     240

```
attgttttt   acggttctca   aactggtact   gctgaagaat   ttgctaacag   attgtctaag      300
gatgctcata   gatacggtat   gagaggtatg   tctgctgatc   cagaagaata   cgatttggct      360
gatttgtctt   ctttgccaga   aattgataag   tctttggttg   ttttttgtat   ggctacttac      420
ggtgaaggtg   atccaactga   taacgctcaa   gattttacg    attggttgca   agaaactgat      480
gttgatttga   ctggtgttaa   gtttgctgtt   tttggtttgg   gtaacaagac   ttacgaacat      540
tttaacgcta   tgggtaagta   cgttgatcaa   agattggaac   aattgggtgc   tcaaagaatt      600
tttgaattgg   gtttgggtga   tgatgatggt   aacttggaag   aagatttat    acttggaga       660
gaacaatttt   ggccagctgt   tgtgaatt     tttggtgttg   aagctactgg   tgaagaatct      720
tctattagac   aatacgaatt   ggttgttcat   gaagatatgg   atactgctaa   ggtttacact      780
ggtgaaatgg   gtagattgaa   gtcttacgaa   aaccaaaagc   caccatttga   tgctaagaac      840
ccatttttgg   ctgctgttac   tactaacaga   aagttgaacc   aaggtactga   aagacatttg      900
atgcatttgg   aattggatat   ttctgattct   aagattagat   acgaatctgg   tgatcatgtt      960
gctgtttacc   cagctaacga   ttctactttg   gttaaccaaa   ttggtgaaat   tttgggtgct    1020
gatttggatg   ttattatgtc   tttgaacaac   ttggatgaag   aatctaacaa   gaagcatcca    1080
tttccatgtc   caactactta   cagaactgct   ttgacttact   acttggatat   tactaaccca    1140
ccaagaacta   acgttttgta   cgaattggct   caatacgctt   ctgaaccatc   tgaacaagaa    1200
catttgcata   agatggcttc   ttcttctggt   gaaggtaagg   aattgtactt   gtcttgggtt    1260
gttgaagcta   gaagacatat   tttggctatt   ttgcaagatt   acccatcttt   gagaccacca    1320
attgatcatt   tgtgtgaatt   gttgccaaga   ttgcaagcta   gatactactc   tattgcttct    1380
tcttctaagg   ttcatccaaa   ctctgttcat   atttgtgctg   ttgctgttga   atacgaagct    1440
aagtctggta   gagttaacaa   gggtgttgct   acttcttggt   tgagaactaa   ggaaccagct    1500
ggtgaaaacg   gtagaagagc   tttggttcca   atgtttgtta   gaaagtctca   atttagattg    1560
ccatttaagc   caactactcc   agttattatg   gttggtccag   gtactggtgt   tgctccatt     1620
atgggtttta   ttcaagaaag   agcttggttg   agagaacaag   gtaaggaagt   tggtgaaact    1680
ttgttgtact   acggttgtag   aagatctgat   gaagattact   tgtacagaga   agaattggct    1740
agatttcata   aggatggtgc   tttgactcaa   ttgaacgttg   cttttttctag  agaacaagct    1800
cataaggttt   acgttcaaca   tttgttgaag   agagataagg   aacatttgtg   aagttgatt     1860
catgaaggtg   gtgctcatat   ttacgtttgt   ggtgatgcta   gaaacatggc   taaggatgtt    1920
caaaacactt   tttacgatat   tgttgctgaa   tttggtccaa   tgaacatac    tcaagctgtt    1980
gattacgtta   agaagttgat   gactaagggt   agatactctt   tggatgtttg   gtcttaa       2037
```

<210> SEQ ID NO 25
<211> LENGTH: 678
<212> TYPE: PRT
<213> ORGANISM: Mus musculus

<400> SEQUENCE: 25

Met Gly Asp Ser His Glu Asp Thr Ser Ala Thr Val Pro Glu Ala Val
1               5                   10                  15

Ala Glu Glu Val Ser Leu Phe Ser Thr Thr Asp Ile Val Leu Phe Ser
            20                  25                  30

Leu Ile Val Gly Val Leu Thr Tyr Trp Phe Ile Phe Lys Lys Lys Lys
        35                  40                  45

Glu Glu Ile Pro Glu Phe Ser Lys Ile Gln Thr Thr Ala Pro Pro Val
    50                  55                  60

```
Lys Glu Ser Ser Phe Val Glu Lys Met Lys Lys Thr Gly Arg Asn Ile
 65                  70                  75                  80

Ile Val Phe Tyr Gly Ser Gln Thr Gly Thr Ala Glu Glu Phe Ala Asn
                 85                  90                  95

Arg Leu Ser Lys Asp Ala His Arg Tyr Gly Met Arg Gly Met Ser Ala
            100                 105                 110

Asp Pro Glu Glu Tyr Asp Leu Ala Asp Leu Ser Ser Leu Pro Glu Ile
            115                 120                 125

Asp Lys Ser Leu Val Val Phe Cys Met Ala Thr Tyr Gly Glu Gly Asp
            130                 135                 140

Pro Thr Asp Asn Ala Gln Asp Phe Tyr Asp Trp Leu Gln Glu Thr Asp
145                 150                 155                 160

Val Asp Leu Thr Gly Val Lys Phe Ala Val Phe Gly Leu Gly Asn Lys
                165                 170                 175

Thr Tyr Glu His Phe Asn Ala Met Gly Lys Tyr Val Asp Gln Arg Leu
            180                 185                 190

Glu Gln Leu Gly Ala Gln Arg Ile Phe Glu Leu Gly Leu Gly Asp Asp
            195                 200                 205

Asp Gly Asn Leu Glu Glu Asp Phe Ile Thr Trp Arg Glu Gln Phe Trp
210                 215                 220

Pro Ala Val Cys Glu Phe Phe Gly Val Glu Ala Thr Gly Glu Glu Ser
225                 230                 235                 240

Ser Ile Arg Gln Tyr Glu Leu Val Val His Glu Asp Met Asp Thr Ala
                245                 250                 255

Lys Val Tyr Thr Gly Glu Met Gly Arg Leu Lys Ser Tyr Glu Asn Gln
                260                 265                 270

Lys Pro Pro Phe Asp Ala Lys Asn Pro Phe Leu Ala Ala Val Thr Thr
            275                 280                 285

Asn Arg Lys Leu Asn Gln Gly Thr Glu Arg His Leu Met His Leu Glu
            290                 295                 300

Leu Asp Ile Ser Asp Ser Lys Ile Arg Tyr Glu Ser Gly Asp His Val
305                 310                 315                 320

Ala Val Tyr Pro Ala Asn Asp Ser Thr Leu Val Asn Gln Ile Gly Glu
                325                 330                 335

Ile Leu Gly Ala Asp Leu Asp Val Ile Met Ser Leu Asn Asn Leu Asp
            340                 345                 350

Glu Glu Ser Asn Lys Lys His Pro Phe Pro Cys Pro Thr Thr Tyr Arg
            355                 360                 365

Thr Ala Leu Thr Tyr Tyr Leu Asp Ile Thr Asn Pro Pro Arg Thr Asn
370                 375                 380

Val Leu Tyr Glu Leu Ala Gln Tyr Ala Ser Glu Pro Ser Glu Gln Glu
385                 390                 395                 400

His Leu His Lys Met Ala Ser Ser Ser Gly Glu Gly Lys Glu Leu Tyr
                405                 410                 415

Leu Ser Trp Val Val Glu Ala Arg Arg His Ile Leu Ala Ile Leu Gln
                420                 425                 430

Asp Tyr Pro Ser Leu Arg Pro Pro Ile Asp His Leu Cys Glu Leu Leu
            435                 440                 445

Pro Arg Leu Gln Ala Arg Tyr Tyr Ser Ile Ala Ser Ser Ser Lys Val
            450                 455                 460

His Pro Asn Ser Val His Ile Cys Ala Val Ala Val Glu Tyr Glu Ala
465                 470                 475                 480
```

```
Lys Ser Gly Arg Val Asn Lys Gly Val Ala Thr Ser Trp Leu Arg Thr
                485                 490                 495

Lys Glu Pro Ala Gly Glu Asn Gly Arg Arg Ala Leu Val Pro Met Phe
            500                 505                 510

Val Arg Lys Ser Gln Phe Arg Leu Pro Phe Lys Pro Thr Thr Pro Val
        515                 520                 525

Ile Met Val Gly Pro Gly Thr Gly Val Ala Pro Phe Met Gly Phe Ile
    530                 535                 540

Gln Glu Arg Ala Trp Leu Arg Glu Gln Gly Lys Glu Val Gly Glu Thr
545                 550                 555                 560

Leu Leu Tyr Tyr Gly Cys Arg Arg Ser Asp Glu Asp Tyr Leu Tyr Arg
                565                 570                 575

Glu Glu Leu Ala Arg Phe His Lys Asp Gly Ala Leu Thr Gln Leu Asn
            580                 585                 590

Val Ala Phe Ser Arg Glu Gln Ala His Lys Val Tyr Val Gln His Leu
        595                 600                 605

Leu Lys Arg Asp Lys Glu His Leu Trp Lys Leu Ile His Glu Gly Gly
    610                 615                 620

Ala His Ile Tyr Val Cys Gly Asp Ala Arg Asn Met Ala Lys Asp Val
625                 630                 635                 640

Gln Asn Thr Phe Tyr Asp Ile Val Ala Glu Phe Gly Pro Met Glu His
                645                 650                 655

Thr Gln Ala Val Asp Tyr Val Lys Lys Leu Met Thr Lys Gly Arg Tyr
            660                 665                 670

Ser Leu Asp Val Trp Ser
            675

<210> SEQ ID NO 26
<211> LENGTH: 1509
<212> TYPE: DNA
<213> ORGANISM: Human

<400> SEQUENCE: 26
atggctttga ttcctgattt ggctatggaa actagattgt tgttggctgt ttcattggtt      60
ttgttgtatt tgtatggaac tcattcacat ggattgttta aaaaattggg aattcctgga     120
cctactcctt tgcctttttt gggaaatatt ttgtcatatc ataaaggatt ttgcatgttt     180
gatatggaat gccataaaaa atatggaaaa gtttggggat tttatgatgg acaacaacct     240
gttttggcta ttactgatcc tgatatgatt aaaactgttt tggttaaaga atgctattca     300 gttttttacta atagaagacc ttttggacct gttggattta tgaaatcagc tatttcaatt     360
gctgaagatg aagaatggaa aagattgaga tcattgttgt cacctacttt tacttcagga     420
aaattgaaag aaatggttcc tattattgct caatatggag atgttttggt tagaaatttg     480
agaagagaag ctgaaactgg aaaacctgtt actttgaaag atgttttggg agcttattca     540
atggatgtta ttacttcaac ttcatttgga gttaatattg attcattgaa taatcctcaa     600 gatcctttg ttgaaaatac taaaaaattg ttgagatttg attttttgga tcctttttt     660 ttgtcaatta ctgttttttcc tttttttgatt cctatttttgg aagttttgaa tatttgcgtt     720
tttcctagag aagttactaa ttttttgaga aaatcagtta aaagaatgaa agaatcaaga     780
ttggaagata ctcaaaaaca tagagttgat tttttgcaat tgatgattga ttcacaaaat     840
tcaaaagaaa ctgaatcaca taaagctttg tcagatttgg aattggttgc tcaatcaatt     900 attttattt ttgctggatg cgaaactact tcatcagttt tgtcatttat tatgtatgaa     960
```

-continued

```
ttggctactc atcctgatgt tcaacaaaaa ttgcaagaag aaattgatgc tgttttgcct    1020
aataaagctc ctcctactta tgatactgtt ttgcaaatgg aatatttgga tatggttgtt    1080
aatgaaactt tgagattgtt tcctattgct atgagattgg aaagagtttg caaaaaagat    1140
gttgaaatta atggaatgtt tattcctaaa ggagttgttg ttatgattcc ttcatatgct    1200
ttgcatagag atcctaaata ttggactgaa cctgaaaaat ttttgcctga agattttca    1260 aaaaaaaata aagataatat tgatccttat atttatactc cttttggatc aggacctaga    1320
aattgcattg gaatgagatt tgctttgatg aatatgaaat tggctttgat tagagttttg    1380 caaattttt catttaaacc ttgcaaagaa actcaaattc ctttgaaatt gtcattggga    1440
ggattgttgc aacctgaaaa acctgttgtt ttgaaagttg aatcaagaga tggaactgtt    1500
tcaggagct                                                            1509
```

<210> SEQ ID NO 27
<211> LENGTH: 503
<212> TYPE: PRT
<213> ORGANISM: Human

<400> SEQUENCE: 27

```
Met Ala Leu Ile Pro Asp Leu Ala Met Glu Thr Arg Leu Leu Leu Ala
1               5                   10                  15

Val Ser Leu Val Leu Leu Tyr Leu Tyr Gly Thr His Ser His Gly Leu
            20                  25                  30

Phe Lys Lys Leu Gly Ile Pro Gly Pro Thr Pro Leu Pro Phe Leu Gly
        35                  40                  45

Asn Ile Leu Ser Tyr His Lys Gly Phe Cys Met Phe Asp Met Glu Cys
    50                  55                  60

His Lys Lys Tyr Gly Lys Val Trp Gly Phe Tyr Asp Gly Gln Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Ser Ala Ile Ser Ile Ala Glu Asp Glu Glu Trp Lys Arg
        115                 120                 125

Leu Arg Ser Leu Leu Ser Pro Thr Phe Thr Ser Gly Lys Leu Lys Glu
    130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175

Gly Ala Tyr Ser Met Asp Val Ile Thr Ser Thr Ser Phe Gly Val Asn
            180                 185                 190

Ile Asp Ser Leu Asn Asn Pro Gln Asp Pro Phe Val Glu Asn Thr Lys
        195                 200                 205

Lys Leu Leu Arg Phe Asp Phe Leu Asp Pro Phe Phe Leu Ser Ile Thr
    210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ser Val Lys Arg Met
                245                 250                 255

Lys Glu Ser Arg Leu Glu Asp Thr Gln Lys His Arg Val Asp Phe Leu
            260                 265                 270
```

```
Gln Leu Met Ile Asp Ser Gln Asn Ser Lys Glu Thr Glu Ser His Lys
            275                 280                 285

Ala Leu Ser Asp Leu Glu Leu Val Ala Gln Ser Ile Ile Phe Ile Phe
        290                 295                 300

Ala Gly Cys Glu Thr Thr Ser Ser Val Leu Ser Phe Ile Met Tyr Glu
305                 310                 315                 320

Leu Ala Thr His Pro Asp Val Gln Gln Lys Leu Gln Glu Glu Ile Asp
                325                 330                 335

Ala Val Leu Pro Asn Lys Ala Pro Thr Tyr Asp Thr Val Leu Gln
            340                 345                 350

Met Glu Tyr Leu Asp Met Val Val Asn Glu Thr Leu Arg Leu Phe Pro
        355                 360                 365

Ile Ala Met Arg Leu Glu Arg Val Cys Lys Lys Asp Val Glu Ile Asn
370                 375                 380

Gly Met Phe Ile Pro Lys Gly Val Val Met Ile Pro Ser Tyr Ala
385                 390                 395                 400

Leu His Arg Asp Pro Lys Tyr Trp Thr Glu Pro Glu Lys Phe Leu Pro
                405                 410                 415

Glu Arg Phe Ser Lys Lys Asn Lys Asp Asn Ile Asp Pro Tyr Ile Tyr
            420                 425                 430

Thr Pro Phe Gly Ser Gly Pro Arg Asn Cys Ile Gly Met Arg Phe Ala
        435                 440                 445

Leu Met Asn Met Lys Leu Ala Leu Ile Arg Val Leu Gln Asn Phe Ser
450                 455                 460

Phe Lys Pro Cys Lys Glu Thr Gln Ile Pro Leu Lys Leu Ser Leu Gly
465                 470                 475                 480

Gly Leu Leu Gln Pro Glu Lys Pro Val Val Leu Lys Val Glu Ser Arg
                485                 490                 495

Asp Gly Thr Val Ser Gly Ala
            500

<210> SEQ ID NO 28
<211> LENGTH: 2040
<212> TYPE: DNA
<213> ORGANISM: Human

<400> SEQUENCE: 28
atgattaata tgggagattc acatgttgat acttcatcaa ctgtttcaga agctgttgct    60
gaagaagttt cattgttttc aatgactgat atgattttgt tttcattgat tgttggattg   120
ttgacttatt ggttttgtt tagaaaaaaa aagaagaag ttcctgaatt tactaaaatt    180
caaactttga cttcatcagt tagagaatca tcatttgttg aaaaaatgaa aaaactgga    240 agaaatatta ttgtttttta tggatcacaa actggaactg ctgaagaatt tgctaataga   300
ttgtcaaaag atgctcatag atatggaatg agaggaatgt cagctgatcc tgaagaatat   360
gatttggctg atttgtcatc attgcctgaa attgataatg ctttggttgt tttttgcatg   420
gctacttatg agaaggaga tcctactgat aatgctcaag atttttatga ttggttgcaa    480
gaaactgatg ttgatttgtc aggagttaaa tttgctgttt ttggattggg aaataaaact   540
tatgaacatt ttaatgctat gggaaaatat gttgataaaa gattgaaca attgggagct   600 caagaatttt tgaattggg attgggagat gatgatggaa attttgaaga gattttatt    660 acttggagag aacaattttg gttggctgtt tgcgaacatt ttggagttga agctactgga   720
gaagaatcat caattagaca atatgaattg gttgttcata ctgatattga tgctgctaaa   780
```

-continued

```
gtttatatgg gagaaatggg aagattgaaa tcatatgaaa atcaaaaacc tccttttgat    840
gctaaaaatc cttttttggc tgctgttact actaatagaa aattgaatca aggaactgaa    900
agacatttga tgcatttgga attggatatt tcagattcaa aaattagata tgaatcagga    960
gatcatgttg ctgtttatcc tgctaatgat tcagctttgg ttaatcaatt gggaaaaatt   1020
ttgggagctg atttggatgt tgttatgtca ttgaataatt tggatgaaga atcaaataaa   1080
aaacatcctt ttccttgccc tacttcatat agaactgctt tgacttatta tttggatatt   1140
actaatcctc ctagaactaa tgttttgtat gaattggctc aatatgcttc agaaccttca   1200
gaacaagaat tgttgagaaa atggcttca tcatcaggag aaggaaaaga attgtatttg   1260 tcatggggttg ttgaagctag aagacatatt ttggctattt tgcaagattg cccttcattg   1320
agacctccta ttgatcattt gtgcgaattg ttgcctagat gcaagctag atattattca   1380 attgcttcat catcaaaagt tcatcctaat tcagttcata tttgcgctgt tgttgttgaa   1440
tatgaaacta aagctggaag aattaataaa ggagttgcta ctaattggtt gagagctaaa   1500
gaacctgttg gagaaaatgg aggaagagct ttggttccta tgtttgttag aaaatcacaa   1560
tttagattgc cttttaaagc tactactcct gttattatgg ttggacctgg aactggagtt   1620 gctccttta ttggatttat tcaagaaaga gcttggttga caacaagg aaaagaagtt   1680 ggagaaactt tgttgtatta tggatgcaga agatcagatg aagattattt gtatagagaa   1740
gaattggctc aatttcatag agatggagct ttgactcaat tgaatgttgc tttttcaaga   1800
gaacaatcac ataaagttta tgttcaacat ttgttgaaac aagatagaga acatttgtgg   1860
aaattgattg aaggaggagc tcatatttat gtttgcggag atgctagaaa tatggctaga   1920
gatgttcaaa atacttttta tgatattgtt gctgaattgg gagctatgga acatgctcaa   1980
gctgttgatt atattaaaaa attgatgact aaaggaagat attcattgga tgtttggtca   2040
```

<210> SEQ ID NO 29
<211> LENGTH: 680
<212> TYPE: PRT
<213> ORGANISM: Human

<400> SEQUENCE: 29

```
Met Ile Asn Met Gly Asp Ser His Val Asp Thr Ser Ser Thr Val Ser
1               5                   10                  15

Glu Ala Val Ala Glu Glu Val Ser Leu Phe Ser Met Thr Asp Met Ile
            20                  25                  30

Leu Phe Ser Leu Ile Val Gly Leu Leu Thr Tyr Trp Phe Leu Phe Arg
        35                  40                  45

Lys Lys Lys Glu Glu Val Pro Glu Phe Thr Lys Ile Gln Thr Leu Thr
    50                  55                  60

Ser Ser Val Arg Glu Ser Phe Val Glu Lys Met Lys Lys Thr Gly
65                  70                  75                  80

Arg Asn Ile Ile Val Phe Tyr Gly Ser Gln Thr Gly Thr Ala Glu Glu
                85                  90                  95

Phe Ala Asn Arg Leu Ser Lys Asp Ala His Arg Tyr Gly Met Arg Gly
            100                 105                 110

Met Ser Ala Asp Pro Glu Glu Tyr Asp Leu Ala Asp Leu Ser Ser Leu
        115                 120                 125

Pro Glu Ile Asp Asn Ala Leu Val Val Phe Cys Met Ala Thr Tyr Gly
    130                 135                 140

Glu Gly Asp Pro Thr Asp Asn Ala Gln Asp Phe Tyr Asp Trp Leu Gln
145                 150                 155                 160
```

```
Glu Thr Asp Val Asp Leu Ser Gly Val Lys Phe Ala Val Phe Gly Leu
                165                 170                 175
Gly Asn Lys Thr Tyr Glu His Phe Asn Ala Met Gly Lys Tyr Val Asp
            180                 185                 190
Lys Arg Leu Glu Gln Leu Gly Ala Gln Arg Ile Phe Glu Leu Gly Leu
        195                 200                 205
Gly Asp Asp Asp Gly Asn Leu Glu Glu Asp Phe Ile Thr Trp Arg Glu
    210                 215                 220
Gln Phe Trp Leu Ala Val Cys Glu His Phe Gly Val Glu Ala Thr Gly
225                 230                 235                 240
Glu Glu Ser Ser Ile Arg Gln Tyr Glu Leu Val Val His Thr Asp Ile
                245                 250                 255
Asp Ala Ala Lys Val Tyr Met Gly Glu Met Gly Arg Leu Lys Ser Tyr
            260                 265                 270
Glu Asn Gln Lys Pro Pro Phe Asp Ala Lys Asn Pro Phe Leu Ala Ala
        275                 280                 285
Val Thr Thr Asn Arg Lys Leu Asn Gln Gly Thr Glu Arg His Leu Met
    290                 295                 300
His Leu Glu Leu Asp Ile Ser Asp Ser Lys Ile Arg Tyr Glu Ser Gly
305                 310                 315                 320
Asp His Val Ala Val Tyr Pro Ala Asn Asp Ser Ala Leu Val Asn Gln
                325                 330                 335
Leu Gly Lys Ile Leu Gly Ala Asp Leu Asp Val Val Met Ser Leu Asn
            340                 345                 350
Asn Leu Asp Glu Glu Ser Asn Lys Lys His Pro Phe Pro Cys Pro Thr
        355                 360                 365
Ser Tyr Arg Thr Ala Leu Thr Tyr Tyr Leu Asp Ile Thr Asn Pro Pro
    370                 375                 380
Arg Thr Asn Val Leu Tyr Glu Leu Ala Gln Tyr Ala Ser Glu Pro Ser
385                 390                 395                 400
Glu Gln Glu Leu Leu Arg Lys Met Ala Ser Ser Ser Gly Glu Gly Lys
                405                 410                 415
Glu Leu Tyr Leu Ser Trp Val Val Glu Ala Arg Arg His Ile Leu Ala
            420                 425                 430
Ile Leu Gln Asp Cys Pro Ser Leu Arg Pro Pro Ile Asp His Leu Cys
        435                 440                 445
Glu Leu Leu Pro Arg Leu Gln Ala Arg Tyr Tyr Ser Ile Ala Ser Ser
    450                 455                 460
Ser Lys Val His Pro Asn Ser Val His Ile Cys Ala Val Val Val Glu
465                 470                 475                 480
Tyr Glu Thr Lys Ala Gly Arg Ile Asn Lys Gly Val Ala Thr Asn Trp
                485                 490                 495
Leu Arg Ala Lys Glu Pro Val Gly Glu Asn Gly Gly Arg Ala Leu Val
            500                 505                 510
Pro Met Phe Val Arg Lys Ser Gln Phe Arg Leu Pro Phe Lys Ala Thr
        515                 520                 525
Thr Pro Val Ile Met Val Gly Pro Gly Thr Gly Val Ala Pro Phe Ile
    530                 535                 540
Gly Phe Ile Gln Glu Arg Ala Trp Leu Arg Gln Gln Gly Lys Glu Val
545                 550                 555                 560
Gly Glu Thr Leu Leu Tyr Tyr Gly Cys Arg Arg Ser Asp Glu Asp Tyr
                565                 570                 575
```

| | | | | | | | | | | | |
|---|---|---|---|---|---|---|---|---|---|---|---|
|Leu|Tyr|Arg|Glu|Glu|Leu|Ala|Gln|Phe|His|Arg|Asp|Gly|Ala|Leu|Thr|
| | | |580| | | |585| | | |590|

Gln Leu Asn Val Ala Phe Ser Arg Glu Gln Ser His Lys Val Tyr Val
　　　595　　　　　　　　600　　　　　　　605

Gln His Leu Leu Lys Gln Asp Arg Glu His Leu Trp Lys Leu Ile Glu
610　　　　　　　615　　　　　　　620

Gly Gly Ala His Ile Tyr Val Cys Gly Asp Ala Arg Asn Met Ala Arg
625　　　　　　　630　　　　　　　635　　　　　　　640

Asp Val Gln Asn Thr Phe Tyr Asp Ile Val Ala Glu Leu Gly Ala Met
　　　　　　645　　　　　　　650　　　　　　　655

Glu His Ala Gln Ala Val Asp Tyr Ile Lys Lys Leu Met Thr Lys Gly
　　　660　　　　　　　665　　　　　　　670

Arg Tyr Ser Leu Asp Val Trp Ser
　　　675　　　　　　　680

<210> SEQ ID NO 30
<211> LENGTH: 1554
<212> TYPE: DNA
<213> ORGANISM: Cannabis sativa

<400> SEQUENCE: 30

```
atgaatcctc gagaaaactt ccttaaatgc ttctcgcaat atattcccaa taatgcaaca      60
aatctaaaac tcgtatacac tcaaaacaac ccattgtata tgtctgtcct aaattcgaca     120
atacacaatc ttagattcac ctctgacaca accccaaaac cacttgttat cgtcactcct     180
tcacatgtct ctcatatcca aggcactatt ctatgctcca agaaagttgg cttgcagatt     240
cgaactcgaa gtggtggtca tgattctgag ggcatgtcct acatatctca gtcccattt      300
gttatagtag acttgagaaa catgcgttca atcaaaatag atgttcatag ccaaactgca     360
tgggttgaag ccggagctac ccttggagaa gtttattatt gggttaatga aaaaatgag      420
aatcttagtt tggcggctgg gtattgccct actgtttgcg caggtggaca ctttggtgga     480
ggaggctatg gaccattgat gagaaactat ggcctcgcgg ctgataatat cattgatgca     540
cacttagtca acgttcatgg aaaagtgcta gatcgaaaat ctatggggga agatctcttt     600
tgggctttac gtggtggtgg agcagaaagc ttcggaatca ttgtagcatg gaaaattaga     660
ctggttgctg tcccaaagtc tactatgttt agtgttaaaa agatcatgga gatacatgag     720
cttgtcaagt tagttaacaa atggcaaaat attgcttaca gtatgacaa agatttatta     780
ctcatgactc acttcataac taggaacatt acagataatc aagggaagaa taagacagca     840
atacacactt acttctcttc agttttcctt ggtggagtgg atagtctagt cgacttgatg     900
aacaagagtt tcctgagtt gggtattaaa aaaacggatt gcagacaatt gagctggatt     960
gatactatca tcttctatag tggtgttgta aattacgaca ctgataattt taacaaggaa    1020
attttgcttg atagatccgc tgggcagaac ggtgctttca gattaagtt agactacgtt    1080
aagaaaccaa ttccagaatc tgtatttgtc caaattttgg aaaaattata tgaagaagat    1140
ataggagctg gatgtatgc gttgtaccct tacggtggta atggatga gatttcagaa    1200
tcagcaattc cattccctca tcgagctgga atcttgtatg agttatggta catatgtagt    1260
tgggagaagc aagaagataa cgaaaagcat ctaaactgga ttagaaatat ttataacttc    1320
atgactcctt atgtgtccaa aaattcaaga ttggcatatc tcaattatag agaccttgat    1380
ataggaataa atgatcccaa gaatccaaat aattacacac aagcacgtat ttggggtgag    1440
aagtattttg gtaaaaattt tgacaggcta gtaaaagtga aaaccctggt tgatcccaat    1500
```
aactttttta gaaacgaaca aagcatccca cctcaaccac ggcatcgtca ttaa    1554

<210> SEQ ID NO 31
<211> LENGTH: 517
<212> TYPE: PRT
<213> ORGANISM: Cannabis sativa

<400> SEQUENCE: 31

```
Met Asn Pro Arg Glu Asn Phe Leu Lys Cys Phe Ser Gln Tyr Ile Pro
1               5                   10                  15

Asn Asn Ala Thr Asn Leu Lys Leu Val Tyr Thr Gln Asn Asn Pro Leu
            20                  25                  30

Tyr Met Ser Val Leu Asn Ser Thr Ile His Asn Leu Arg Phe Thr Ser
        35                  40                  45

Asp Thr Thr Pro Lys Pro Leu Val Ile Val Thr Pro Ser His Val Ser
    50                  55                  60

His Ile Gln Gly Thr Ile Leu Cys Ser Lys Lys Val Gly Leu Gln Ile
65                  70                  75                  80

Arg Thr Arg Ser Gly Gly His Asp Ser Glu Gly Met Ser Tyr Ile Ser
                85                  90                  95

Gln Val Pro Phe Val Ile Val Asp Leu Arg Asn Met Arg Ser Ile Lys
            100                 105                 110

Ile Asp Val His Ser Gln Thr Ala Trp Val Glu Ala Gly Ala Thr Leu
        115                 120                 125

Gly Glu Val Tyr Tyr Trp Val Asn Glu Lys Asn Glu Asn Leu Ser Leu
    130                 135                 140

Ala Ala Gly Tyr Cys Pro Thr Val Cys Ala Gly Gly His Phe Gly Gly
145                 150                 155                 160

Gly Gly Tyr Gly Pro Leu Met Arg Asn Tyr Gly Leu Ala Ala Asp Asn
                165                 170                 175

Ile Ile Asp Ala His Leu Val Asn Val His Gly Lys Val Leu Asp Arg
            180                 185                 190

Lys Ser Met Gly Glu Asp Leu Phe Trp Ala Leu Arg Gly Gly Gly Ala
        195                 200                 205

Glu Ser Phe Gly Ile Ile Val Ala Trp Lys Ile Arg Leu Val Ala Val
    210                 215                 220

Pro Lys Ser Thr Met Phe Ser Val Lys Lys Ile Met Glu Ile His Glu
225                 230                 235                 240

Leu Val Lys Leu Val Asn Lys Trp Gln Asn Ile Ala Tyr Lys Tyr Asp
                245                 250                 255

Lys Asp Leu Leu Leu Met Thr His Phe Ile Thr Arg Asn Ile Thr Asp
            260                 265                 270

Asn Gln Gly Lys Asn Lys Thr Ala Ile His Thr Tyr Phe Ser Ser Val
        275                 280                 285

Phe Leu Gly Gly Val Asp Ser Leu Val Asp Leu Met Asn Lys Ser Phe
    290                 295                 300

Pro Glu Leu Gly Ile Lys Lys Thr Asp Cys Arg Gln Leu Ser Trp Ile
305                 310                 315                 320

Asp Thr Ile Ile Phe Tyr Ser Gly Val Val Asn Tyr Asp Thr Asp Asn
                325                 330                 335

Phe Asn Lys Glu Ile Leu Leu Asp Arg Ser Ala Gly Gln Asn Gly Ala
            340                 345                 350

Phe Lys Ile Lys Leu Asp Tyr Val Lys Lys Pro Ile Pro Glu Ser Val
        355                 360                 365
```

```
Phe Val Gln Ile Leu Glu Lys Leu Tyr Glu Glu Asp Ile Gly Ala Gly
    370             375             380
Met Tyr Ala Leu Tyr Pro Tyr Gly Gly Ile Met Asp Glu Ile Ser Glu
385             390             395                 400
Ser Ala Ile Pro Phe Pro His Arg Ala Gly Ile Leu Tyr Glu Leu Trp
                405             410                 415
Tyr Ile Cys Ser Trp Glu Lys Gln Glu Asp Asn Glu Lys His Leu Asn
                420             425             430
Trp Ile Arg Asn Ile Tyr Asn Phe Met Thr Pro Tyr Val Ser Lys Asn
            435             440             445
Ser Arg Leu Ala Tyr Leu Asn Tyr Arg Asp Leu Asp Ile Gly Ile Asn
450             455             460
Asp Pro Lys Asn Pro Asn Asn Tyr Thr Gln Ala Arg Ile Trp Gly Glu
465             470             475                 480
Lys Tyr Phe Gly Lys Asn Phe Asp Arg Leu Val Lys Val Lys Thr Leu
                485             490             495
Val Asp Pro Asn Asn Phe Phe Arg Asn Glu Gln Ser Ile Pro Pro Gln
            500             505             510
Pro Arg His Arg His
        515

<210> SEQ ID NO 32
<211> LENGTH: 1374
<212> TYPE: DNA
<213> ORGANISM: Stevia rebaudiana

<400> SEQUENCE: 32
atggaaaata aaactgaaac tactgttaga agaagaagaa gaattatttt gtttcctgtt      60
ccttttcaag acatattaa tcctattttg caattggcta atgttttgta ttcaaaagga     120
ttttcaatta ctattttca tactaatttt aataaaccta aaacttcaaa ttatcctcat     180
tttactttta gatttatttt ggataatgat cctcaagatg aaagaatttc aaatttgcct     240
actcatggac ctttggctgg aatgagaatt cctattatta tgaacatgg agctgatgaa      300 ttgagaagag aattggaatt gttgatgttg gcttcagaag aagatgaaga gtttcatgc      360 ttgattactg atgctttgtg gtattttgct caatcagttg ctgattcatt gaatttgaga     420
agattggttt tgatgacttc atcattgttt aattttcatg ctcatgtttc attgcctcaa     480
tttgatgaat tgggatattt ggatcctgat gataaaacta gattggaaga caagcttca     540 ggatttccta tgttgaaagt taaagatatt aaatcagctt attcaaattg gcaaattttg     600
aaagaaattt tgggaaaaat gattaaacaa actagagctt catcaggagt tatttggaat     660 tcattaaag aattggaaga atcagaattg gaaactgtta ttagagaaat tcctgctcct     720 tcattttga ttcctttgcc taaacatttg actgcttcat catcatcatt gttggatcat     780
gatagaactg ttttcaatg gttggatcaa caacctcctt catcagtttt gtatgtttca     840
tttggatcaa cttcagaagt tgatgaaaaa gattttttgg aaattgctag aggattggtt     900
gattcaaaac aatcattttt gtgggttgtt agacctggat tgttaaagg atcaacttgg     960 gttgaaccct tgcctgatgg attttttggga gaaagaggaa gaattgttaa atgggttcct    1020
caacaagaag ttttggctca tggagctatt ggagcttttt ggactcattc aggatggaat    1080
tcaactttgg aatcagtttg cgaaggagtt cctatgattt tttcagattt tggattggat    1140 caaccctttga atgctagata tatgtcagat gttttgaaag ttggagtta tttgaaaaat    1200 ggatgggaaa gaggagaaat tgctaatgct attagaagag ttatggttga tgaagaagga    1260
```

```
gaatatatta gacaaaatgc tagagttttg aaacaaaaag ctgatgtttc attgatgaaa    1320
ggaggatcat catatgaatc attggaatca ttggtttcat atatttcatc attg          1374
```

<210> SEQ ID NO 33
<211> LENGTH: 458
<212> TYPE: PRT
<213> ORGANISM: Stevia rebaudiana

<400> SEQUENCE: 33

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Arg Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350
```

```
Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
                420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
        450                 455

<210> SEQ ID NO 34
<211> LENGTH: 485
<212> TYPE: PRT
<213> ORGANISM: Nicotiana tabacum

<400> SEQUENCE: 34

Met Gly Ser Ile Gly Ala Glu Leu Thr Lys Pro His Ala Val Cys Ile
1               5                   10                  15

Pro Tyr Pro Ala Gln Gly His Ile Asn Pro Met Leu Lys Leu Ala Lys
            20                  25                  30

Ile Leu His His Lys Gly Phe His Ile Thr Phe Val Asn Thr Glu Phe
        35                  40                  45

Asn His Arg Arg Leu Leu Lys Ser Arg Gly Pro Asp Ser Leu Lys Gly
    50                  55                  60

Leu Ser Ser Phe Arg Phe Glu Thr Ile Pro Asp Gly Leu Pro Pro Cys
65                  70                  75                  80

Glu Ala Asp Ala Thr Gln Asp Ile Pro Ser Leu Cys Glu Ser Thr Thr
                85                  90                  95

Asn Thr Cys Leu Ala Pro Phe Arg Asp Leu Leu Ala Lys Leu Asn Asp
            100                 105                 110

Thr Asn Thr Ser Asn Val Pro Pro Val Ser Cys Ile Val Ser Asp Gly
        115                 120                 125

Val Met Ser Phe Thr Leu Ala Ala Ala Gln Glu Leu Gly Val Pro Glu
    130                 135                 140

Val Leu Phe Trp Thr Thr Ser Ala Cys Gly Phe Leu Gly Tyr Met His
145                 150                 155                 160

Tyr Cys Lys Val Ile Glu Lys Gly Tyr Ala Pro Leu Lys Asp Ala Ser
                165                 170                 175

Asp Leu Thr Asn Gly Tyr Leu Glu Thr Thr Leu Asp Phe Ile Pro Gly
            180                 185                 190

Met Lys Asp Val Arg Leu Arg Asp Leu Pro Ser Phe Leu Arg Thr Thr
        195                 200                 205

Asn Pro Asp Glu Phe Met Ile Lys Phe Val Leu Gln Glu Thr Glu Arg
    210                 215                 220

Ala Arg Lys Ala Ser Ala Ile Ile Leu Asn Thr Phe Gly Thr Leu Glu
225                 230                 235                 240

Ala Glu Val Leu Glu Ser Leu Arg Asn Leu Leu Pro Pro Val Tyr Pro
                245                 250                 255

Ile Gly Pro Leu His Phe Leu Val Lys His Val Asp Asp Glu Asn Leu
            260                 265                 270
```

```
Lys Gly Leu Arg Ser Ser Leu Trp Lys Glu Glu Pro Glu Cys Ile Gln
        275                 280                 285

Trp Leu Asp Thr Lys Glu Pro Asn Ser Val Val Tyr Val Asn Phe Gly
        290                 295                 300

Ser Ile Thr Val Met Thr Pro Asn Gln Leu Ile Glu Phe Ala Trp Gly
305                 310                 315                 320

Leu Ala Asn Ser Gln Gln Thr Phe Leu Trp Ile Ile Arg Pro Asp Ile
                325                 330                 335

Val Ser Gly Asp Ala Ser Ile Leu Pro Pro Glu Phe Val Glu Glu Thr
            340                 345                 350

Lys Asn Arg Gly Met Leu Ala Ser Trp Cys Ser Gln Glu Glu Val Leu
        355                 360                 365

Ser His Pro Ala Ile Val Gly Phe Leu Thr His Ser Gly Trp Asn Ser
    370                 375                 380

Thr Leu Glu Ser Ile Ser Ser Gly Val Pro Met Ile Cys Trp Pro Phe
385                 390                 395                 400

Phe Ala Glu Gln Gln Thr Asn Cys Trp Phe Ser Val Thr Lys Trp Asp
                405                 410                 415

Val Gly Met Glu Ile Asp Ser Asp Val Lys Arg Asp Glu Val Glu Ser
            420                 425                 430

Leu Val Arg Glu Leu Met Val Gly Gly Lys Gly Lys Lys Met Lys Lys
        435                 440                 445

Lys Ala Met Glu Trp Lys Glu Leu Ala Glu Ala Ser Ala Lys Glu His
    450                 455                 460

Ser Gly Ser Ser Tyr Val Asn Ile Glu Lys Leu Val Asn Asp Ile Leu
465                 470                 475                 480

Leu Ser Ser Lys His
                485

<210> SEQ ID NO 35
<211> LENGTH: 1458
<212> TYPE: DNA
<213> ORGANISM: Nicotiana tabacum

<400> SEQUENCE: 35
atgggttcca ttggtgctga attaacaaag ccacatgcag tttgcatacc atatcccgcc     60
caaggccata ttaaccccat gttaaagcta gccaaaatcc ttcatcacaa aggctttcac    120
atcacttttg tcaatactga atttaaccac cgacgtctcc ttaaatctcg tggccctgat    180
tctctcaagg gtctttcttc tttccgtttt gagaccattc ctgatggact tccgccatgt    240
gaggcagatg ccacacaaga tatccttct ttgtgtgaat ctacaaccaa tacttgcttg    300
gctcctttta gggatcttct tgcgaaactc aatgatacta acacatctaa cgtgccaccc    360
gtttcgtgca tcgtctcgga tggtgtcatg agcttcacct tagccgctgc acaagaattg    420
ggagtccctg aagttctgtt ttggaccact agtgcttgtg gtttcttagg ttacatgcat    480
tactgcaagg ttattgaaaa aggatatgct ccacttaaag atgcgagtga cttgacaaat    540
ggatacctag agacaacatt ggattttata ccaggcatga agacgtacg tttaagggat    600 cttccaagtt tcttgagaac tacaaatcca gatgaattca tgatcaaatt tgtcctccaa    660
gaaacagaga gagcaagaaa ggcttctgca attatcctca acacatttga aacactagag    720
gctgaagttc ttgaatcgct ccgaaatctt cttcctccag tctacccat agggcccttg    780 catttctag tgaaacatgt tgatgatgag aatttgaagg gacttagatc cagcctttgg    840
```

```
aaagaggaac cagagtgtat acaatggctt gataccaaag aaccaaattc tgttgtttat    900
gttaactttg gaagcattac tgttatgact cctaatcagc ttattgagtt tgcttgggga    960
cttgcaaaca gccagcaaac attcttatgg atcataagac ctgatattgt ttcaggtgat   1020
gcatcgattc ttccacccga attcgtggaa gaaacgaaga acagaggtat gcttgctagt   1080
tggtgttcac aagaagaagt acttagtcac cctgcaatag taggattctt gactcacagt   1140
ggatggaatt cgacactcga agtataagc agtggggtgc ctatgatttg ctggccattt   1200
ttcgctgaac agcaaacaaa ttgttggttt tccgtcacta aatgggatgt tggaatggag   1260
attgacagtg atgtgaagag agatgaagtg gaaagccttg taagggaatt gatggttggg   1320
ggaaaaggca aaaagatgaa gaaaaaggca atggaatgga aggaattggc tgaagcatct   1380
gctaaagaac attcagggtc atcttatgtg aacattgaaa agttggtcaa tgatattctt   1440
ctttcatcca acattaa                                                 1458
```

<210> SEQ ID NO 36
<211> LENGTH: 485
<212> TYPE: PRT
<213> ORGANISM: Nicotiana tabacum

<400> SEQUENCE: 36

```
Met Gly Ser Ile Gly Ala Glu Phe Thr Lys Pro His Ala Val Cys Ile
1               5                   10                  15

Pro Tyr Pro Ala Gln Gly His Ile Asn Pro Met Leu Lys Leu Ala Lys
            20                  25                  30

Ile Leu His His Lys Gly Phe His Ile Thr Phe Val Asn Thr Glu Phe
        35                  40                  45

Asn His Arg Arg Leu Leu Lys Ser Arg Gly Pro Asp Ser Leu Lys Gly
    50                  55                  60

Leu Ser Ser Phe Arg Phe Glu Thr Ile Pro Asp Gly Leu Pro Pro Cys
65                  70                  75                  80

Asp Ala Asp Ala Thr Gln Asp Ile Pro Ser Leu Cys Glu Ser Thr Thr
                85                  90                  95

Asn Thr Cys Leu Gly Pro Phe Arg Asp Leu Leu Ala Lys Leu Asn Asp
            100                 105                 110

Thr Asn Thr Ser Asn Val Pro Pro Val Ser Cys Ile Ile Ser Asp Gly
        115                 120                 125

Val Met Ser Phe Thr Leu Ala Ala Ala Gln Glu Leu Gly Val Pro Glu
    130                 135                 140

Val Leu Phe Trp Thr Thr Ser Ala Cys Gly Phe Leu Gly Tyr Met His
145                 150                 155                 160

Tyr Tyr Lys Val Ile Glu Lys Gly Tyr Ala Pro Leu Lys Asp Ala Ser
                165                 170                 175

Asp Leu Thr Asn Gly Tyr Leu Glu Thr Thr Leu Asp Phe Ile Pro Cys
            180                 185                 190

Met Lys Asp Val Arg Leu Arg Asp Leu Pro Ser Phe Leu Arg Thr Thr
        195                 200                 205

Asn Pro Asp Glu Phe Met Ile Lys Phe Val Leu Gln Glu Thr Glu Arg
    210                 215                 220

Ala Arg Lys Ala Ser Ala Ile Ile Leu Asn Thr Tyr Glu Thr Leu Glu
225                 230                 235                 240

Ala Glu Val Leu Glu Ser Leu Arg Asn Leu Pro Pro Val Tyr Pro
                245                 250                 255

Ile Gly Pro Leu His Phe Leu Val Lys His Val Asp Asp Glu Asn Leu
```

```
                260              265              270
Lys Gly Leu Arg Ser Ser Leu Trp Lys Glu Glu Pro Glu Cys Ile Gln
            275                  280                  285

Trp Leu Asp Thr Lys Glu Pro Asn Ser Val Val Tyr Val Asn Phe Gly
            290                  295                  300

Ser Ile Thr Val Met Thr Pro Asn Gln Leu Ile Glu Phe Ala Trp Gly
305                  310                  315                  320

Leu Ala Asn Ser Gln Gln Ser Phe Leu Trp Ile Ile Arg Pro Asp Ile
            325                  330                  335

Val Ser Gly Asp Ala Ser Ile Leu Pro Pro Glu Phe Val Glu Glu Thr
                340                  345                  350

Lys Lys Arg Gly Met Leu Ala Ser Trp Cys Ser Gln Glu Glu Val Leu
            355                  360                  365

Ser His Pro Ala Ile Gly Gly Phe Leu Thr His Ser Gly Trp Asn Ser
            370                  375                  380

Thr Leu Glu Ser Ile Ser Ser Gly Val Pro Met Ile Cys Trp Pro Phe
385                  390                  395                  400

Phe Ala Glu Gln Gln Thr Asn Cys Trp Phe Ser Val Thr Lys Trp Asp
                405                  410                  415

Val Gly Met Glu Ile Asp Cys Asp Val Lys Arg Asp Glu Val Glu Ser
                420                  425                  430

Leu Val Arg Glu Leu Met Val Gly Gly Lys Gly Lys Lys Met Lys Lys
            435                  440                  445

Lys Ala Met Glu Trp Lys Glu Leu Ala Glu Ala Ser Ala Lys Glu His
            450                  455                  460

Ser Gly Ser Ser Tyr Val Asn Ile Glu Lys Val Val Asn Asp Ile Leu
465                  470                  475                  480

Leu Ser Ser Lys His
                485

<210> SEQ ID NO 37
<211> LENGTH: 1458
<212> TYPE: DNA
<213> ORGANISM: Nicotiana tabacum

<400> SEQUENCE: 37
atgggttcca ttggtgctga atttacaaag ccacatgcag tttgcatacc atatcccgcc      60
caaggccata ttaaccccat gttaaagcta gccaaaatcc ttcatcacaa aggctttcac     120
atcacttttg tcaatactga atttaaccac agacgtctgc ttaaatctcg tggccctgat     180
tctctcaagg gtctttcttc tttccgtttt gagacaattc ctgatggact tccgccatgt     240
gatgcagatg ccacacaaga tataccttct ttgtgtgaat ctacaaccaa tacttgcttg     300
ggtccttttc gggatcttct tgcgaaactc aatgatacta acacatctaa cgtgccaccc     360
gtttcgtgca tcatctcaga tggtgtcatg agcttcacct tagccgctgc acaagaattg     420
ggagtccctg aagttctgtt ttggaccact agtgcttgtg gtttcttagg ttacatgcat     480
tattacaagg ttattgaaaa aggatacgct ccacttaaag atgcgagtga cttgacaaat     540
ggatacctag agacaacatt ggattttata ccatgcatga agacgtacg tttaagggat     600 cttccaagtt tcttgagaac tacaaatcca gatgaattca tgatcaaatt tgtcctccaa     660
gaaacagaga gagcaagaaa ggcttctgca attatcctca acacatatga aacactagag     720
gctgaagttc ttgaatcgct ccgaaatctt cttcctccag tctacccat tgggcccttg     780 catttttctag tgaaacatgt tgatgatgag aatttgaagg gacttagatc cagcctttgg     840
```

-continued

```
aaagaggaac cagagtgtat acaatggctt gataccaaag aaccaaattc tgttgtttat    900
gttaactttg gaagcattac tgttatgact cctaatcaac ttattgaatt tgcttgggga    960
cttgcaaaca gccaacaatc attcttatgg atcataagac ctgatattgt ttcaggtgat   1020
gcatcgattc ttcccccccga attcgtggaa gaaacgaaga agagaggtat gcttgctagt   1080
tggtgttcac aagaagaagt acttagtcac cctgcaatag gaggattctt gactcacagt   1140
ggatggaatt cgacactcga agtataagc agtggggtgc ctatgatttg ctggccattt   1200
ttcgctgaac agcaaacaaa ttgttggttt tccgtcacta atgggatgt tggaatggag   1260 attgactgtg atgtgaagag ggatgaagtg gaaagccttg taagggaatt gatggttggg   1320
ggaaaaggca aaaagatgaa gaaaaaggca atggaatgga aggaattggc tgaagcatct   1380
gctaaagaac attcagggtc atcttatgtg aacattgaga aggtggtcaa tgatattctt   1440
ctttcgtcca aacattaa                                                 1458
```

<210> SEQ ID NO 38
<211> LENGTH: 496
<212> TYPE: PRT
<213> ORGANISM: Nicotiana tabacum

<400> SEQUENCE: 38

```
Met Ala Thr Gln Val His Lys Leu His Phe Ile Leu Phe Pro Leu Met
1               5                   10                  15

Ala Pro Gly His Met Ile Pro Met Ile Asp Ile Ala Lys Leu Leu Ala
            20                  25                  30

Asn Arg Gly Val Ile Thr Thr Ile Thr Thr Pro Val Asn Ala Asn
        35                  40                  45

Arg Phe Ser Ser Thr Ile Thr Arg Ala Ile Lys Ser Gly Leu Arg Ile
    50                  55                  60

Gln Ile Leu Thr Leu Lys Phe Pro Ser Val Glu Val Gly Leu Pro Glu
65                  70                  75                  80

Gly Cys Glu Asn Ile Asp Met Leu Pro Ser Leu Asp Leu Ala Ser Lys
                85                  90                  95

Phe Phe Ala Ala Ile Ser Met Leu Lys Gln Gln Val Glu Asn Leu Leu
            100                 105                 110

Glu Gly Ile Asn Pro Ser Pro Ser Cys Val Ile Ser Asp Met Gly Phe
        115                 120                 125

Pro Trp Thr Thr Gln Ile Ala Gln Asn Phe Asn Ile Pro Arg Ile Val
    130                 135                 140

Phe His Gly Thr Cys Cys Phe Ser Leu Leu Cys Ser Tyr Lys Ile Leu
145                 150                 155                 160

Ser Ser Asn Ile Leu Glu Asn Ile Thr Ser Asp Ser Glu Tyr Phe Val
                165                 170                 175

Val Pro Asp Leu Pro Asp Arg Val Glu Leu Thr Lys Ala Gln Val Ser
            180                 185                 190

Gly Ser Thr Lys Asn Thr Thr Ser Val Ser Ser Val Leu Lys Glu
        195                 200                 205

Val Thr Glu Gln Ile Arg Leu Ala Glu Glu Ser Tyr Gly Val Ile
    210                 215                 220

Val Asn Ser Phe Glu Glu Leu Glu Gln Val Tyr Lys Glu Tyr Arg
225                 230                 235                 240

Lys Ala Arg Gly Lys Lys Val Trp Cys Val Gly Pro Val Ser Leu Cys
                245                 250                 255
```

```
Asn Lys Glu Ile Glu Asp Leu Val Thr Arg Gly Asn Lys Thr Ala Ile
                260                 265                 270
Asp Asn Gln Asp Cys Leu Lys Trp Leu Asp Asn Phe Glu Thr Glu Ser
            275                 280                 285
Val Val Tyr Ala Ser Leu Gly Ser Leu Ser Arg Leu Thr Leu Leu Gln
        290                 295                 300
Met Val Glu Leu Gly Leu Gly Leu Glu Glu Ser Asn Arg Pro Phe Val
305                 310                 315                 320
Trp Val Leu Gly Gly Asp Lys Leu Asn Asp Leu Glu Lys Trp Ile
                325                 330                 335
Leu Glu Asn Gly Phe Glu Gln Arg Ile Lys Glu Arg Gly Val Leu Ile
                340                 345                 350
Arg Gly Trp Ala Pro Gln Val Leu Ile Leu Ser His Pro Ala Ile Gly
                355                 360                 365
Gly Val Leu Thr His Cys Gly Trp Asn Ser Thr Leu Glu Gly Ile Ser
            370                 375                 380
Ala Gly Leu Pro Met Val Thr Trp Pro Leu Phe Ala Glu Gln Phe Cys
385                 390                 395                 400
Asn Glu Lys Leu Val Val Gln Val Leu Lys Ile Gly Val Ser Leu Gly
                405                 410                 415
Val Lys Val Pro Val Lys Trp Gly Asp Glu Glu Asn Val Gly Val Leu
                420                 425                 430
Val Lys Lys Asp Asp Val Lys Lys Ala Leu Asp Lys Leu Met Asp Glu
            435                 440                 445
Gly Glu Glu Gly Gln Val Arg Arg Thr Lys Ala Lys Glu Leu Gly Glu
450                 455                 460
Leu Ala Lys Lys Ala Phe Gly Glu Gly Gly Ser Ser Tyr Val Asn Leu
465                 470                 475                 480
Thr Ser Leu Ile Glu Asp Ile Ile Glu Gln Gln Asn His Lys Glu Lys
                485                 490                 495

<210> SEQ ID NO 39
<211> LENGTH: 1491
<212> TYPE: DNA
<213> ORGANISM: Nicotiana tabacum

<400> SEQUENCE: 39
atggcaactc aagtgcacaa acttcatttc atactattcc ctttaatggc tccaggccac    60
atgattccta tgatagacat agctaaactt ctagcaaatc gcggtgtcat taccactatc   120
atcaccactc cagtaaacgc caatcgtttc agttcaacaa ttactcgtgc cataaaatcc   180
ggtctaagaa tccaaattct tacactcaaa tttccaagtg tagaagtagg attaccagaa   240
ggttgcgaaa atattgacat gcttccttct cttgacttgg cttcaaagtt ttttgctgca   300
attagtatgc tgaaacaaca agttgaaaat ctcttagaag aataaatcc aagtccaagt   360 tgtgttattt cagatatggg atttccttgg actactcaaa ttgcacaaaa ttttaatatc   420
ccaagaattg ttttttcatgg tacttgttgt ttctcacttt tatgttccta taaaatactt   480
tcctccaaca ttcttgaaaa tataacctca gattcagagt attttgttgt tcctgattta   540
cccgatagag ttgaactaac gaaagctcag gtttcaggat cgacgaaaaa tactacttct   600
gttagttctt ctgtattgaa agaagttact gagcaaatca gattagccga ggaatcatca   660
tatggtgtaa ttgttaatag ttttgaggag tggagcaagt gtatgagaa agaatatagg   720 aaagctagag ggaaaaaagt ttggtgtgtt ggtcctgttt ctttgtgtaa taaggaaatt   780
```

```
gaagatttgg ttacaagggg taataaaact gcaattgata atcaagattg cttgaaatgg    840
ttagataatt ttgaaacaga atctgtggtt tatgcaagtc ttggaagttt atctcgtttg    900
acattattgc aaatggtgga acttggtctt ggtttagaag agtcaaatag gccttttgta    960
tgggtattag gaggaggtga taaattaaat gatttagaga aatggattct tgagaatgga   1020
tttgagcaaa gaattaaaga aagaggagtt ttgattagag gatgggctcc tcaagtgctt   1080
atactttcac accctgcaat tggtggagta ttgactcatt gcggatggaa ttctacattg   1140
gaaggtattt cagcaggatt accaatggta acatggccac tatttgctga gcaattttgc   1200
aatgagaagt tagtagtcca agtgctaaaa attggagtga gcctaggtgt gaaggtgcct   1260
gtcaaatggg gagatgagga aaatgttgga gttttggtaa aaaaggatga tgttaagaaa   1320
gcattagaca aactaatgga tgaaggagaa gaaggacaag taagaagaac aaaagcaaaa   1380
gagttaggag aattggctaa aaaggcattt ggagaaggtg gttcttctta tgttaactta   1440
acatctctga ttgaagacat cattgagcaa caaaatcaca aggaaaaata g            1491
```

<210> SEQ ID NO 40
<211> LENGTH: 479
<212> TYPE: PRT
<213> ORGANISM: Nicotiana tabacum

<400> SEQUENCE: 40

```
Met Lys Thr Ala Glu Leu Val Phe Ile Pro Ala Pro Gly Met Gly His
1               5                   10                  15

Leu Val Pro Thr Val Glu Val Ala Lys Gln Leu Val Asp Arg His Glu
            20                  25                  30

Gln Leu Ser Ile Thr Val Leu Ile Met Thr Ile Pro Leu Glu Thr Asn
        35                  40                  45

Ile Pro Ser Tyr Thr Lys Ser Leu Ser Ser Asp Tyr Ser Ser Arg Ile
    50                  55                  60

Thr Leu Leu Pro Leu Ser Gln Pro Glu Thr Ser Val Thr Met Ser Ser
65                  70                  75                  80

Phe Asn Ala Ile Asn Phe Phe Glu Tyr Ile Ser Ser Tyr Lys Gly Arg
                85                  90                  95

Val Lys Asp Ala Val Ser Glu Thr Ser Phe Ser Ser Ser Asn Ser Val
            100                 105                 110

Lys Leu Ala Gly Phe Val Ile Asp Met Phe Cys Thr Ala Met Ile Asp
        115                 120                 125

Val Ala Asn Glu Phe Gly Ile Pro Ser Tyr Val Phe Tyr Thr Ser Ser
    130                 135                 140

Ala Ala Met Leu Gly Leu Gln Leu His Phe Gln Ser Leu Ser Ile Glu
145                 150                 155                 160

Cys Ser Pro Lys Val His Asn Tyr Val Glu Pro Glu Ser Glu Val Leu
                165                 170                 175

Ile Ser Thr Tyr Met Asn Pro Val Pro Val Lys Cys Leu Pro Gly Ile
            180                 185                 190

Ile Leu Val Asn Asp Glu Ser Ser Thr Met Phe Val Asn His Ala Arg
        195                 200                 205

Arg Phe Arg Glu Thr Lys Gly Ile Met Val Asn Thr Phe Thr Glu Leu
    210                 215                 220

Glu Ser His Ala Leu Lys Ala Leu Ser Asp Asp Glu Lys Ile Pro Pro
225                 230                 235                 240

Ile Tyr Pro Val Gly Pro Ile Leu Asn Leu Glu Asn Gly Asn Glu Asp
                245                 250                 255
```

```
His Asn Gln Glu Tyr Asp Ala Ile Met Lys Trp Leu Asp Glu Lys Pro
                260                 265                 270

Asn Ser Ser Val Val Phe Leu Cys Phe Gly Ser Lys Gly Ser Phe Glu
            275                 280                 285

Glu Asp Gln Val Lys Glu Ile Ala Asn Ala Leu Glu Ser Ser Gly Tyr
        290                 295                 300

His Phe Leu Trp Ser Leu Arg Arg Pro Pro Lys Asp Lys Leu Gln
305                 310                 315                 320

Phe Pro Ser Glu Phe Glu Asn Pro Glu Glu Val Leu Pro Glu Gly Phe
                325                 330                 335

Phe Gln Arg Thr Lys Gly Arg Gly Lys Val Ile Gly Trp Ala Pro Gln
            340                 345                 350

Leu Ala Ile Leu Ser His Pro Ser Val Gly Gly Phe Val Ser His Cys
        355                 360                 365

Gly Trp Asn Ser Thr Leu Glu Ser Val Arg Ser Gly Val Pro Ile Ala
    370                 375                 380

Thr Trp Pro Leu Tyr Ala Glu Gln Gln Ser Asn Ala Phe Gln Leu Val
385                 390                 395                 400

Lys Asp Leu Gly Met Ala Val Glu Ile Lys Met Asp Tyr Arg Glu Asp
                405                 410                 415

Phe Asn Thr Arg Asn Pro Pro Leu Val Lys Ala Glu Glu Ile Glu Asp
            420                 425                 430

Gly Ile Arg Lys Leu Met Asp Ser Glu Asn Lys Ile Arg Ala Lys Val
        435                 440                 445

Thr Glu Met Lys Asp Lys Ser Arg Ala Ala Leu Leu Glu Gly Gly Ser
    450                 455                 460

Ser Tyr Val Ala Leu Gly His Phe Val Glu Thr Val Met Lys Asn
465                 470                 475

<210> SEQ ID NO 41
<211> LENGTH: 1440
<212> TYPE: DNA
<213> ORGANISM: Nicotiana tabacum

<400> SEQUENCE: 41
atgaagacag cagagttagt attcattcct gctcctggga tgggtcacct tgtaccaact      60
gtggaggtgg caaagcaact agtcgacaga cacgagcagc tttcgatcac agttctaatc     120
atgacaattc ctttggaaac aaatattcca tcatatacta atcactgtc ctcagactac     180
agttctcgta taacgctgct tccactctct caacctgaga cctctgttac tatgagcagt     240
tttaatgcca tcaattttttt tgagtacatc tccagctaca agggtcgtgt caaagatgct     300
gttagtgaaa cctcctttag ttcgtcaaat tctgtgaaac ttgcaggatt tgtaatagac     360
atgttctgca ctgcgatgat tgatgtagcg aacgagtttg gaatcccaag ttatgtgttc     420
tacacttcta gtgcagctat gcttggacta caactgcatt tcaaagtct tagcattgaa     480
tgcagtccga aagttcataa ctacgttgaa cctgaatcag aagttctgat ctcaacttac     540
atgaatccgg ttccagtcaa atgtttgccc ggaattatac tagtaaatga tgaaagtagc     600
accatgtttg tcaatcatgc acgaagattc agggagacga aaggaattat ggtgaacacg     660
ttcactgagc ttgaatcaca cgctttgaaa gccctttccg atgatgaaaa aatcccacca     720
atctacccag ttggacctat acttaacctt gaaatgggaa tgaagatca caatcaagaa     780
tatgatgcga ttatgaagtg gcttgacgag aagcctaatt catcagtggt gttcttatgc     840
```

-continued

```
tttggaagca aggggtctttt cgaagaagat caggtgaagg aaatagcaaa tgctctagag      900
agcagtggct accacttctt gtggtcgcta aggcgaccgc caccaaaaga caagctacaa      960
ttcccaagcg aattcgagaa tccagaggaa gtcttaccag agggattctt tcaaaggact     1020
aaaggaagag gaaaggtgat aggatgggca ccccagttgg ctattttgtc tcatccttca     1080
gtaggaggat tcgtgtcgca ttgtgggtgg aattcaactc tggagagcgt tcgaagtgga     1140
gtgccgatag caacatggcc attgtatgca gagcaacaga gcaatgcatt tcaactggtg     1200
aaggatttgg gtatggcagt agagattaag atggattaca gggaagattt taatacgaga     1260
aatccaccac tggttaaagc tgaggagata gaagatggaa ttaggaagct gatggattca     1320
gagaataaaa tcagggctaa ggtgacggag atgaaggaca aaagtagagc agcactgctg     1380
gagggcggat catcatatgt agctcttggg cattttgttg agactgtcat gaaaaactag     1440
```

<210> SEQ ID NO 42
<211> LENGTH: 478
<212> TYPE: PRT
<213> ORGANISM: Nicotiana tabacum

<400> SEQUENCE: 42

```
Met Lys Thr Thr Glu Leu Val Phe Ile Pro Ala Pro Gly Met Gly His
1               5                   10                  15

Leu Val Pro Thr Val Glu Val Ala Lys Gln Leu Val Asp Arg Asp Glu
            20                  25                  30

Gln Leu Ser Ile Thr Val Leu Ile Met Thr Leu Pro Leu Glu Thr Asn
        35                  40                  45

Ile Pro Ser Tyr Thr Lys Ser Leu Ser Ser Asp Tyr Ser Ser Arg Ile
    50                  55                  60

Thr Leu Leu Gln Leu Ser Gln Pro Glu Thr Ser Val Ser Met Ser Ser
65                  70                  75                  80

Phe Asn Ala Ile Asn Phe Phe Glu Tyr Ile Ser Ser Tyr Lys Asp Arg
                85                  90                  95

Val Lys Asp Ala Val Asn Glu Thr Phe Ser Ser Ser Ser Val Lys
            100                 105                 110

Leu Lys Gly Phe Val Ile Asp Met Phe Cys Thr Ala Met Ile Asp Val
        115                 120                 125

Ala Asn Glu Phe Gly Ile Pro Ser Tyr Val Phe Tyr Thr Ser Asn Ala
    130                 135                 140

Ala Met Leu Gly Leu Gln Leu His Phe Gln Ser Leu Ser Ile Glu Tyr
145                 150                 155                 160

Ser Pro Lys Val His Asn Tyr Leu Asp Pro Glu Ser Glu Val Ala Ile
                165                 170                 175

Ser Thr Tyr Ile Asn Pro Ile Pro Val Lys Cys Leu Pro Gly Ile Ile
            180                 185                 190

Leu Asp Asn Asp Lys Ser Gly Thr Met Phe Val Asn His Ala Arg Arg
        195                 200                 205

Phe Arg Glu Thr Lys Gly Ile Met Val Asn Thr Phe Ala Glu Leu Glu
    210                 215                 220

Ser His Ala Leu Lys Ala Leu Ser Asp Glu Lys Ile Pro Pro Ile
225                 230                 235                 240

Tyr Pro Val Gly Pro Ile Leu Asn Leu Gly Asp Gly Asn Glu Asp His
                245                 250                 255

Asn Gln Glu Tyr Asp Met Ile Met Lys Trp Leu Asp Glu Gln Pro His
            260                 265                 270
```

```
Ser Ser Val Val Phe Leu Cys Phe Gly Ser Lys Gly Ser Phe Glu Glu
        275                 280                 285

Asp Gln Val Lys Glu Ile Ala Asn Ala Leu Glu Arg Ser Gly Asn Arg
    290                 295                 300

Phe Leu Trp Ser Leu Arg Arg Pro Pro Lys Asp Thr Leu Gln Phe
305                 310                 315                 320

Pro Ser Glu Phe Glu Asn Pro Glu Glu Val Leu Pro Val Gly Phe Phe
                325                 330                 335

Gln Arg Thr Lys Gly Arg Gly Lys Val Ile Gly Trp Ala Pro Gln Leu
            340                 345                 350

Ala Ile Leu Ser His Pro Ala Val Gly Gly Phe Val Ser His Cys Gly
            355                 360                 365

Trp Asn Ser Thr Leu Glu Ser Val Arg Ser Gly Val Pro Ile Ala Thr
370                 375                 380

Trp Pro Leu Tyr Ala Glu Gln Gln Ser Asn Ala Phe Gln Leu Val Lys
385                 390                 395                 400

Asp Leu Gly Met Ala Val Glu Ile Lys Met Asp Tyr Arg Glu Asp Phe
                405                 410                 415

Asn Lys Thr Asn Pro Pro Leu Val Lys Ala Glu Glu Ile Glu Asp Gly
            420                 425                 430

Ile Arg Lys Leu Met Asp Ser Glu Asn Lys Ile Arg Ala Lys Val Met
            435                 440                 445

Glu Met Lys Asp Lys Ser Arg Ala Ala Leu Leu Glu Gly Gly Ser Ser
        450                 455                 460

Tyr Val Ala Leu Gly His Phe Val Glu Thr Val Met Lys Asn
465                 470                 475

<210> SEQ ID NO 43
<211> LENGTH: 1437
<212> TYPE: DNA
<213> ORGANISM: Nicotiana tabacum

<400> SEQUENCE: 43
atgaagacaa cagagttagt attcattcct gctcctggca tgggtcacct tgtacccact    60
gtggaggtgg caaagcaact agtcgacaga gacgaacagc tttcaatcac agttctcatc   120
atgacgcttc ctttggaaac aaatattcca tcatatacta aatcactgtc ctcagactac   180
agttctcgta taacgctgct tcaactttct caacctgaga cctctgttag tatgagcagt   240
tttaatgcca tcaattttttt tgagtacatc tccagctaca aggatcgtgt caaagatgct   300
gttaatgaaa cctttagttc gtcaagttct gtgaaactca aaggatttgt aatagacatg   360
ttctgcactg cgatgattga tgtggcgaac gagtttggaa tcccaagtta tgtcttctac   420
acttctaatg cagctatgct tggactccaa ctccattttc aaagtcttag tattgaatac   480
agtccgaaag ttcataatta cctagaccct gaatcagaag tagcgatctc aacttacatt   540
aatccgattc cagtcaaatg tttgcccggg attatactag acaatgataa agtggcacc    600 atgttcgtca atcatgcacg aagattcagg gagacgaaag gaattatggt gaacacattc   660
gctgagcttg aatcacacgc tttgaaagcc ctttccgatg atgagaaaat cccaccaatc   720
tacccagttg ggcctatact taaccttgga gatgggaatg aagatcacaa tcaagaatat   780
gatatgatta tgaagtggct cgacgagcag cctcattcat cagtggtgtt cctatgcttt   840
ggaagcaagg gatcttttcga agaagatcaa gtgaaggaaa tagcaaatgc tctagagaga   900
agtggtaacc ggttcttgtg gtcgctaaga cgaccgccac caaaagacac gctacaattc   960
```

```
ccaagcgaat tcgagaatcc agaggaagtc ttgccggtgg gattctttca aaggactaaa    1020
ggaagaggaa aggtgatagg atgggcaccc cagttggcta ttttgtctca tcctgcagta    1080
ggaggattcg tgtcgcattg tgggtggaat tcaactttgg agagtgttcg tagtggagta    1140
ccgatagcaa catggccatt gtatgcagag caacagagca atgcatttca actggtgaag    1200
gatttgggga tggcagtgga gattaagatg gattacaggg aagattttaa taagacaaat    1260
ccaccactgg ttaaagctga ggagatagaa gatggaatta ggaagctgat ggattcagag    1320
aataaaatca gggctaaggt gatggagatg aaggacaaaa gtagagcagc gttattagaa    1380
ggcggatcat catatgtagc tctcgggcat tttgttgaga ctgtcatgaa aaactaa      1437
```

<210> SEQ ID NO 44
<211> LENGTH: 482
<212> TYPE: PRT
<213> ORGANISM: Nicotiana tabacum

<400> SEQUENCE: 44

```
Met Lys Glu Thr Lys Lys Ile Glu Leu Val Phe Ile Pro Ser Pro Gly
1               5                   10                  15

Ile Gly His Leu Val Ser Thr Val Glu Met Ala Lys Leu Leu Ile Ala
            20                  25                  30

Arg Glu Glu Gln Leu Ser Ile Thr Val Leu Ile Ile Gln Trp Pro Asn
        35                  40                  45

Asp Lys Lys Leu Asp Ser Tyr Ile Gln Ser Val Ala Asn Phe Ser Ser
    50                  55                  60

Arg Leu Lys Phe Ile Arg Leu Pro Gln Asp Asp Ser Ile Met Gln Leu
65                  70                  75                  80

Leu Lys Ser Asn Ile Phe Thr Thr Phe Ile Ala Ser His Lys Pro Ala
                85                  90                  95

Val Arg Asp Ala Val Ala Asp Ile Leu Lys Ser Glu Ser Asn Asn Thr
            100                 105                 110

Leu Ala Gly Ile Val Ile Asp Leu Phe Cys Thr Ser Met Ile Asp Val
        115                 120                 125

Ala Asn Glu Phe Glu Leu Pro Thr Tyr Val Phe Tyr Thr Ser Gly Ala
    130                 135                 140

Ala Thr Leu Gly Leu His Tyr His Ile Gln Asn Leu Arg Asp Glu Phe
145                 150                 155                 160

Asn Lys Asp Ile Thr Lys Tyr Lys Asp Glu Pro Glu Glu Lys Leu Ser
                165                 170                 175

Ile Ala Thr Tyr Leu Asn Pro Phe Pro Ala Lys Cys Leu Pro Ser Val
            180                 185                 190

Ala Leu Asp Lys Glu Gly Gly Ser Thr Met Phe Leu Asp Leu Ala Lys
        195                 200                 205

Arg Phe Arg Glu Thr Lys Gly Ile Met Ile Asn Thr Phe Leu Glu Leu
    210                 215                 220

Glu Ser Tyr Ala Leu Asn Ser Leu Ser Arg Asp Lys Asn Leu Pro Pro
225                 230                 235                 240

Ile Tyr Pro Val Gly Pro Val Leu Asn Leu Asn Asn Val Glu Gly Asp
                245                 250                 255

Asn Leu Gly Ser Ser Asp Gln Asn Thr Met Lys Trp Leu Asp Asp Gln
            260                 265                 270

Pro Ala Ser Ser Val Val Phe Leu Cys Phe Gly Ser Gly Gly Ser Phe
        275                 280                 285

Glu Lys His Gln Val Lys Glu Ile Ala Tyr Ala Leu Glu Ser Ser Gly
```

```
                290             295             300
Cys Arg Phe Leu Trp Ser Leu Arg Arg Pro Thr Glu Asp Ala Arg
305             310             315             320

Phe Pro Ser Asn Tyr Glu Asn Leu Glu Glu Ile Leu Pro Glu Gly Phe
                325             330             335

Leu Glu Arg Thr Lys Gly Ile Gly Lys Val Ile Gly Trp Ala Pro Gln
                340             345             350

Leu Ala Ile Leu Ser His Lys Ser Thr Gly Gly Phe Val Ser His Cys
            355             360             365

Gly Trp Asn Ser Thr Leu Glu Ser Thr Tyr Phe Gly Val Pro Ile Ala
            370             375             380

Thr Trp Pro Met Tyr Ala Glu Gln Gln Ala Asn Ala Phe Gln Leu Val
385             390             395             400

Lys Asp Leu Arg Met Gly Val Glu Ile Lys Met Asp Tyr Arg Lys Asp
                405             410             415

Met Lys Val Met Gly Lys Glu Val Ile Val Lys Ala Glu Glu Ile Glu
                420             425             430

Lys Ala Ile Arg Glu Ile Met Asp Ser Glu Ser Glu Ile Arg Val Lys
            435             440             445

Val Lys Glu Met Lys Glu Lys Ser Arg Ala Ala Gln Met Glu Gly Gly
            450             455             460

Ser Ser Tyr Thr Ser Ile Gly Gly Phe Ile Gln Ile Ile Met Glu Asn
465             470             475             480

Ser Gln

<210> SEQ ID NO 45
<211> LENGTH: 1449
<212> TYPE: DNA
<213> ORGANISM: Nicotiana tabacum

<400> SEQUENCE: 45
atgaaagaaa ccaagaaaat agagttagtc ttcattcctt caccaggaat tggccattta      60
gtatccacag ttgaaatggc aaagcttctt atagctagag aagagcagct atctatcaca     120
gtcctcatca tccaatggcc taacgacaag aagctcgatt cttatatcca atcagtcgcc     180
aatttcagct cgcgtttgaa attcattcga ctccctcagg atgattccat tatgcagcta     240
ctcaaaagca catttttcac cacgtttatt gccagtcata agcctgcagt tagagatgct     300
gttgctgata ttctcaagtc agaatcaaat aatacgctag caggtattgt tatcgacttg     360
ttctgcacct caatgataga cgtggccaat gagttcgagc taccaaccta tgttttctac     420
acgtctggtg cagcaaccct tggtcttcat tatcatatac agaatctcag ggatgaattt     480
aacaaagata ttaccaagta caagacgaa cctgaagaaa aactctctat agcaacatat      540
ctcaatccat ttccagcaaa atgtttgccg tctgtagcct tagacaaaga aggtggttca     600
acaatgtttc ttgatctcgc aaaaaggttt cgagaaccaa aagtattat gataaacaca      660 tttctagagc tcgaatccta tgcattaaac tcgctctcac gagacaagaa tcttccacct     720 atatacctg tcggaccagt attgaacctt aacaatgttg aaggtgacaa cttaggttca     780
tctgaccaga atactatgaa atggttagat gatcagcccg cttcatctgt agtgttcctt     840
tgttttggta gtggtggaag ctttgaaaaa catcaagtta aggaaatagc ctatgctctg     900
gagagcagtg ggtgtcggtt tttgtggtcg ttaaggcgac caccaaccga agatgcaaga     960
tttccaagca actatgaaaa tcttgaagaa attttgccag aaggattctt ggaaagaaca    1020
```

```
aaagggattg gaaaagtgat aggatgggca cctcagttgg cgattttgtc acataaatcg    1080 acgggggat ttgtgtcgca ctgtggatgg aattcgactt tggaaagtac atattttgga    1140
gtgccaatag caacctggcc aatgtacgcg gagcaacaag cgaatgcatt tcaattggtt    1200
aaggatttga gaatgggagt tgagattaag atggattata ggaaggatat gaaagtgatg    1260
ggcaaagaag ttatagtgaa agctgaggag attgagaaag caataagaga aattatggat    1320
tccgagagtg aaattcgggt gaaggtgaaa gagatgaagg agaagagcag agcagcacaa    1380
atggaaggtg gctcttctta cacttctatt ggaggtttca tccaaattat catggagaat    1440
tctcaataa                                                              1449
```

<210> SEQ ID NO 46
<211> LENGTH: 470
<212> TYPE: PRT
<213> ORGANISM: Nicotiana tabacum

<400> SEQUENCE: 46

```
Met Val Gln Pro His Val Leu Leu Val Thr Phe Pro Ala Gln Gly His
1               5                   10                  15

Ile Asn Pro Cys Leu Gln Phe Ala Lys Arg Leu Ile Arg Met Gly Ile
            20                  25                  30

Glu Val Thr Phe Ala Thr Ser Val Phe Ala His Arg Arg Met Ala Lys
        35                  40                  45

Thr Thr Thr Ser Thr Leu Ser Lys Gly Leu Asn Phe Ala Ala Phe Ser
    50                  55                  60

Asp Gly Tyr Asp Asp Gly Phe Lys Ala Asp Glu His Asp Ser Gln His
65                  70                  75                  80

Tyr Met Ser Glu Ile Lys Ser Arg Gly Ser Lys Thr Leu Lys Asp Ile
                85                  90                  95

Ile Leu Lys Ser Ser Asp Glu Gly Arg Pro Val Thr Ser Leu Val Tyr
            100                 105                 110

Ser Leu Leu Leu Pro Trp Ala Ala Lys Val Ala Arg Glu Phe His Ile
        115                 120                 125

Pro Cys Ala Leu Leu Trp Ile Gln Pro Ala Thr Val Leu Asp Ile Tyr
    130                 135                 140

Tyr Tyr Tyr Phe Asn Gly Tyr Glu Asp Ala Ile Lys Gly Ser Thr Asn
145                 150                 155                 160

Asp Pro Asn Trp Cys Ile Gln Leu Pro Arg Leu Pro Leu Leu Lys Ser
                165                 170                 175

Gln Asp Leu Pro Ser Phe Leu Ser Ser Asn Glu Glu Lys Tyr
            180                 185                 190

Ser Phe Ala Leu Pro Thr Phe Lys Glu Gln Leu Asp Thr Leu Asp Val
        195                 200                 205

Glu Glu Asn Pro Lys Val Leu Val Asn Thr Phe Asp Ala Leu Glu Pro
    210                 215                 220

Lys Glu Leu Lys Ala Ile Glu Leu Tyr Asn Leu Ile Gly Ile Gly Pro
225                 230                 235                 240

Leu Ile Pro Ser Thr Phe Leu Asp Gly Lys Asp Pro Leu Asp Ser Ser
                245                 250                 255

Phe Gly Gly Asp Leu Phe Gln Lys Ser Asn Asp Tyr Ile Glu Trp Leu
            260                 265                 270

Asn Ser Lys Ala Asn Ser Ser Val Val Tyr Ile Ser Phe Gly Ser Leu
        275                 280                 285

Leu Asn Leu Ser Lys Asn Gln Lys Glu Glu Ile Ala Lys Gly Leu Ile
```

```
              290             295             300
Glu Ile Lys Lys Pro Phe Leu Trp Val Ile Arg Asp Gln Glu Asn Gly
305             310             315             320

Lys Gly Asp Glu Lys Glu Lys Leu Ser Cys Met Met Glu Leu Glu
            325             330             335

Lys Gln Gly Lys Ile Val Pro Trp Cys Ser Gln Leu Glu Val Leu Thr
            340             345             350

His Pro Ser Ile Gly Cys Phe Val Ser His Cys Gly Trp Asn Ser Thr
            355             360             365

Leu Glu Ser Leu Ser Ser Gly Val Ser Val Val Ala Phe Pro His Trp
            370             375             380

Thr Asp Gln Gly Thr Asn Ala Lys Leu Ile Glu Asp Val Trp Lys Thr
385             390             395             400

Gly Val Arg Leu Lys Lys Asn Glu Asp Gly Val Val Glu Ser Glu Glu
            405             410             415

Ile Lys Arg Cys Ile Glu Met Val Met Asp Gly Gly Glu Lys Gly Glu
            420             425             430

Glu Met Arg Arg Asn Ala Gln Lys Trp Lys Glu Leu Ala Arg Glu Ala
            435             440             445

Val Lys Glu Gly Gly Ser Ser Glu Met Asn Leu Lys Ala Phe Val Gln
            450             455             460

Glu Val Gly Lys Gly Cys
465             470

<210> SEQ ID NO 47
<211> LENGTH: 1413
<212> TYPE: DNA
<213> ORGANISM: Nicotiana tabacum

<400> SEQUENCE: 47
atggtgcaac cccatgtcct cttggtgact tttccagcac aaggccatat taatccatgt      60
ctccaatttg ccaagaggct aattagaatg ggcattgagg taacttttgc cacgagcgtt     120
ttcgcccatc gtcgtatggc aaaaactacg acttccactc tatccaaggg cttaaatttt     180
gcggcattct ctgatgggta cgacgatggt ttcaaggccg atgagcatga ttctcaacat     240
tacatgtcgg agataaaaag tcgcggttct aaaaccctaa agatatcatt tttgaagagc     300
tcagacgagg acgtcctgtg acatccctcg tctattctct ttttgcttcc atgggctgca     360
aaggtagcgc gtgaatttca cataccgtgc gcgttactat ggattcaacc agcaactgtg     420
ctagacatat attattatta cttcaatggc tatgaggatg ccataaaagg tagcaccaat     480
gatccaaatt ggtgtattca attgcctagg cttccactac taaaaagcca agatcttcct     540
tcttttttac tttcttctag taatgaagaa aaatatagct ttgctctacc aacatttaaa     600
gagcaacttg acacattaga tgttgaagaa atcctaaagt acttgtgaa cacatttgat      660
gcattagagc caaaggaact caaagctatt gaaaagtaca atttaattgg gattggacca     720
ttgattcctt caacattttt ggacggaaaa gacccttttgg attcttcctt tggtggtgat     780
cttttttcaaa agtctaatga ctatattgaa tggttgaact caaaggctaa ctcatctgtg     840
gtttatatct catttgggag tctcttgaat ttgtcaaaaa atcaaaagga ggagattgca     900
aaagggttga tagagattaa aaagccattc ttgtgggtaa taagagatca agaaaatggt     960
aagggagatg aaaagaagaa gaaattaagt tgtatgatgg agttgaaaaa gcaagggaaa    1020
atagtaccat ggtgttcaca acttgaagtc ttaacacatc catctatagg atgtttcgtg    1080
```

```
tcacattgtg gatggaattc gactctggaa agtttatcgt caggcgtgtc agtagtggca    1140
tttcctcatt ggacggatca agggacaaat gctaaactaa ttgaagatgt ttggaagaca    1200
ggtgtaaggt tgaaaagaa tgaagatggt gtggttgaga gtgaagagat aaaaaggtgc    1260
atagaaatgg taatgatgg tggagagaaa ggagaagaaa tgaagagaaa tgctcaaaaa    1320
tggaaagaat tggcaaggga agctgtaaaa gaaggcggat cttcggaaat gaatctaaaa    1380
gcttttgttc aagaagttgg caaaggttgc tga                                 1413
```

<210> SEQ ID NO 48
<211> LENGTH: 545
<212> TYPE: PRT
<213> ORGANISM: Cannabis

<400> SEQUENCE: 48

```
Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
            20                  25                  30

Asn Phe Leu Lys Cys Phe Ser Lys His Ile Pro Asn Asn Val Ala Asn
        35                  40                  45

Pro Lys Leu Val Tyr Thr Gln His Asp Gln Leu Tyr Met Ser Ile Leu
    50                  55                  60

Asn Ser Thr Ile Gln Asn Leu Arg Phe Ile Ser Asp Thr Thr Pro Lys
65                  70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
    210                 215                 220

Asp Leu Phe Trp Ala Ile Arg Gly Gly Gly Gly Glu Asn Phe Gly Ile
225                 230                 235                 240

Ile Ala Ala Trp Lys Ile Lys Leu Val Asp Val Pro Ser Lys Ser Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
    290                 295                 300

Asn Lys Thr Thr Val His Gly Tyr Phe Ser Ser Ile Phe His Gly Gly
305                 310                 315                 320
```

```
Val Asp Ser Leu Val Asp Leu Met Asn Lys Ser Phe Pro Glu Leu Gly
            325                 330                 335

Ile Lys Lys Thr Asp Cys Lys Glu Phe Ser Trp Ile Asp Thr Thr Ile
            340                 345                 350

Phe Tyr Ser Gly Val Val Asn Phe Asn Thr Ala Asn Phe Lys Lys Glu
            355                 360                 365

Ile Leu Leu Asp Arg Ser Ala Gly Lys Lys Thr Ala Phe Ser Ile Lys
            370                 375                 380

Leu Asp Tyr Val Lys Lys Pro Ile Pro Glu Thr Ala Met Val Lys Ile
385                 390                 395                 400

Leu Glu Lys Leu Tyr Glu Glu Asp Val Gly Ala Gly Met Tyr Val Leu
            405                 410                 415

Tyr Pro Tyr Gly Gly Ile Met Glu Glu Ile Ser Glu Ser Ala Ile Pro
            420                 425                 430

Phe Pro His Arg Ala Gly Ile Met Tyr Glu Leu Trp Tyr Thr Ala Ser
            435                 440                 445

Trp Glu Lys Gln Glu Asp Asn Glu Lys His Ile Asn Trp Val Arg Ser
            450                 455                 460

Val Tyr Asn Phe Thr Thr Pro Tyr Val Ser Gln Asn Pro Arg Leu Ala
465                 470                 475                 480

Tyr Leu Asn Tyr Arg Asp Leu Asp Leu Gly Lys Thr Asn His Ala Ser
            485                 490                 495

Pro Asn Asn Tyr Thr Gln Ala Arg Ile Trp Gly Glu Lys Tyr Phe Gly
            500                 505                 510

Lys Asn Phe Asn Arg Leu Val Lys Val Lys Thr Lys Val Asp Pro Asn
            515                 520                 525

Asn Phe Phe Arg Asn Glu Gln Ser Ile Pro Pro Leu Pro Pro His His
            530                 535                 540

His
545

<210> SEQ ID NO 49
<211> LENGTH: 1437
<212> TYPE: DNA
<213> ORGANISM: Nicotiana tabacum

<400> SEQUENCE: 49
atgaaaacaa cagaacttgt cttcataccc gccccggta tgggtcacct tgtacccaca      60
gtcgaagtcg ccaaacaact agttgataga gacgaacagt tgtctattac cgtcttgata     120
atgacgttac ccctggagac taatatccca agttacacca agagtttgtc ctctgactat     180
tcatcccgta tcacgttgtt acaactaagt caacctgaga cgagtgtctc aatgagtagt     240
tttaacgcca taacttcttc gaatacatt agttcctata aggatcgtgt taaagatgcc      300
gtaaacgaga cattctcctc ttcatcctcc gtcaaactta aggatttgt aatcgacatg      360 ttttgcacgg caatgataga cgtggccaac gagttcggta ttccatctta tgtattctac     420
acgtccaacg ctgccatgct aggcctacaa cttcacttcc aatccttgtc catcgaatat     480
tcacctaagg ttcataatta tttagaccct gaatctgagg tagctatatc aacgtacatt     540
aacccaatac cagtaaaatg cttacccggt ataattcttg acaatgataa gagtggcact     600
atgttcgtaa accatgccag gagattccgt gaaacaaagg gtataatggt aaatactttt     660
gcagaattag aaagtcacgc cctaaaggca cttagtgacg atgagaaaat tcctccaatc     720
tatcccgtcg gacccattct aaacttgggt gatggtaatg aggatcataa ccaagagtac     780
```

```
gacatgataa tgaaatggct ggatgaacaa ccacacagtt cagtggtttt cctgtgcttc      840
ggttccaaag gttcatttga agaagaccag gttaaagaga tagcaaatgc tttagagaga      900
tcaggcaata ggttcctgtg gagtttaaga cgtccccctc ccaaggatac tcttcaattc      960
ccttccgaat ttgaaaaccc cgaggaagtg ctacctgtag gatttttca aagaaccaaa      1020 ggcagaggaa aagtcatcgg atgggcacca cagcttgcaa ttctatctca ccctgccgtc      1080
ggtggattcg tttcccactg cggctggaat agtactttgg aatcagttag atcaggtgta      1140
cccatagcaa catggcctct ttatgcagag cagcagtcca atgcatttca attggtcaag      1200
gatctaggta tggccgtcga aattaaaatg gattaccgtg aggactttaa caagactaat      1260
cctccattgg taaaggcaga ggaaatagaa gacggcatta ggaagttgat ggactccgag      1320
aataagatta gggcaaaggt gatggaaatg aaagataagt ccagagctgc attactggaa      1380
ggaggatcct cctatgttgc actgggtcac ttcgtggaga ccgtaatgaa gaactaa        1437
```

<210> SEQ ID NO 50
<211> LENGTH: 478
<212> TYPE: PRT
<213> ORGANISM: Nicotiana tabacum

<400> SEQUENCE: 50

```
Met Lys Thr Thr Glu Leu Val Phe Ile Pro Ala Pro Gly Met Gly His
1               5                   10                  15

Leu Val Pro Thr Val Glu Val Ala Lys Gln Leu Val Asp Arg Asp Glu
                20                  25                  30

Gln Leu Ser Ile Thr Val Leu Ile Met Thr Leu Pro Leu Glu Thr Asn
            35                  40                  45

Ile Pro Ser Tyr Thr Lys Ser Leu Ser Ser Asp Tyr Ser Ser Arg Ile
        50                  55                  60

Thr Leu Leu Gln Leu Ser Gln Pro Glu Thr Ser Val Ser Met Ser Ser
65                  70                  75                  80

Phe Asn Ala Ile Asn Phe Glu Tyr Ile Ser Ser Tyr Lys Asp Arg
                85                  90                  95

Val Lys Asp Ala Val Asn Glu Thr Phe Ser Ser Ser Ser Val Lys
                100                 105                 110

Leu Lys Gly Phe Val Ile Asp Met Phe Cys Thr Ala Met Ile Asp Val
            115                 120                 125

Ala Asn Glu Phe Gly Ile Pro Ser Tyr Val Phe Tyr Thr Ser Asn Ala
        130                 135                 140

Ala Met Leu Gly Leu Gln Leu His Phe Gln Ser Leu Ser Ile Glu Tyr
145                 150                 155                 160

Ser Pro Lys Val His Asn Tyr Leu Asp Pro Glu Ser Glu Val Ala Ile
                165                 170                 175

Ser Thr Tyr Ile Asn Pro Ile Pro Val Lys Cys Leu Pro Gly Ile Ile
            180                 185                 190

Leu Asp Asn Asp Lys Ser Gly Thr Met Phe Val Asn His Ala Arg Arg
        195                 200                 205

Phe Arg Glu Thr Lys Gly Ile Met Val Asn Thr Phe Ala Glu Leu Glu
    210                 215                 220

Ser His Ala Leu Lys Ala Leu Ser Asp Asp Glu Lys Ile Pro Pro Ile
225                 230                 235                 240

Tyr Pro Val Gly Pro Ile Leu Asn Leu Gly Asp Gly Asn Glu Asp His
                245                 250                 255
```

```
Asn Gln Glu Tyr Asp Met Ile Met Lys Trp Leu Asp Glu Gln Pro His
            260                 265                 270

Ser Ser Val Val Phe Leu Cys Phe Gly Ser Lys Gly Ser Phe Glu Glu
        275                 280                 285

Asp Gln Val Lys Glu Ile Ala Asn Ala Leu Glu Arg Ser Gly Asn Arg
        290                 295                 300

Phe Leu Trp Ser Leu Arg Arg Pro Pro Lys Asp Thr Leu Gln Phe
305                 310                 315                 320

Pro Ser Glu Phe Glu Asn Pro Glu Glu Val Leu Pro Val Gly Phe Phe
                325                 330                 335

Gln Arg Thr Lys Gly Arg Gly Lys Val Ile Gly Trp Ala Pro Gln Leu
            340                 345                 350

Ala Ile Leu Ser His Pro Ala Val Gly Gly Phe Val Ser His Cys Gly
            355                 360                 365

Trp Asn Ser Thr Leu Glu Ser Val Arg Ser Gly Val Pro Ile Ala Thr
            370                 375                 380

Trp Pro Leu Tyr Ala Glu Gln Gln Ser Asn Ala Phe Gln Leu Val Lys
385                 390                 395                 400

Asp Leu Gly Met Ala Val Glu Ile Lys Met Asp Tyr Arg Glu Asp Phe
                405                 410                 415

Asn Lys Thr Asn Pro Pro Leu Val Lys Ala Glu Glu Ile Glu Asp Gly
            420                 425                 430

Ile Arg Lys Leu Met Asp Ser Glu Asn Lys Ile Arg Ala Lys Val Met
            435                 440                 445

Glu Met Lys Asp Lys Ser Arg Ala Ala Leu Leu Glu Gly Gly Ser Ser
        450                 455                 460

Tyr Val Ala Leu Gly His Phe Val Glu Thr Val Met Lys Asn
465                 470                 475

<210> SEQ ID NO 51
<211> LENGTH: 1413
<212> TYPE: DNA
<213> ORGANISM: Nicotiana tabacum

<400> SEQUENCE: 51
atggttcaac cacacgtctt actggttact tttccagcac aaggccatat caacccttgc      60
ctacaattcg ccaaaagact aataaggatg ggcatcgaag taacttttgc acgagtgta     120 ttcgcacata ggcgtatggc taaaactacg acatcaactt tgtccaaagg actaaacttc    180
gccgccttca gtgatggcta tgacgatgga ttcaaagccg acgaacatga cagtcaacac    240
tacatgagtg aaataaagtc ccgtggatct aaaacactta aggatattat acttaaatcc    300
tccgatgagg gaagacccgt tacctcttta gttattcac tgttactgcc ctgggctgca     360
aaagtcgcca gagagtttca tattccttgc gctttattgt ggatccaacc agctacggta    420
ttagacatct actattacta cttcaatgga tacgaggatg caataaaggg atcaacaaac    480
gaccccaact ggtgtattca actgcctaga cttcctctat aaaaagtca ggacttacct     540 agttttttac tgtcatccag taacgaagaa aaatattcat tcgctttacc caccttcaaa    600
gagcagcttg acactttgga tgttgaagag aaccccaagg ttttggtcaa tactttgac    660 gctttggagc caaaagagct aaaggctatt gaaaaatata accttatcgg cataggacct    720
taatccccct ctacttcctt agatggcaaa gaccctctag attcaagttt cggaggtgat    780
ttgtttcaaa agagtaacga ttatatcgag tggctaaata gtaaagccaa ctccagtgtg    840
gtctacattt ctttcggaag tcttctgaat ttatcaaaa accaaaagga agagatcgca    900
```

```
aaaggactga tagagataaa aaaacctttc ttatgggtga tcagagacca ggaaaacggt    960
aaaggcgatg agaaggagga aaaactgtcc tgtatgatgg agctagagaa acaaggaaaa   1020
atcgttccct ggtgttcaca gttagaagtg ttaacccatc catccatagg ttgcttcgta   1080
tcacattgtg gttggaatag tacacttgaa agtctttcat caggcgtctc tgtcgtcgca   1140
ttccccacct ggacggacca gggcacaaac gccaaactga tcgaagatgt atggaagacg   1200
ggcgtcaggc taaaaaaaaa tgaggatggc gtggtagaga gtgaagagat aaagcgttgc   1260
atagaaatgg tcatggatgg cggtgaaaag ggagaggaaa tgaggcgtaa cgcacaaaag   1320
tggaaggaac tagcccgtga agcagtgaaa gaaggaggtt ctagtgagat gaatttaaaa   1380
gctttcgtgc aggaagttgg aaaaggctgc tga                               1413
```

<210> SEQ ID NO 52
<211> LENGTH: 470
<212> TYPE: PRT
<213> ORGANISM: Nicotiana tabacum

<400> SEQUENCE: 52

```
Met Val Gln Pro His Val Leu Leu Val Thr Phe Pro Ala Gln Gly His
1               5                   10                  15

Ile Asn Pro Cys Leu Gln Phe Ala Lys Arg Leu Ile Arg Met Gly Ile
            20                  25                  30

Glu Val Thr Phe Ala Thr Ser Val Phe Ala His Arg Arg Met Ala Lys
        35                  40                  45

Thr Thr Thr Ser Thr Leu Ser Lys Gly Leu Asn Phe Ala Ala Phe Ser
    50                  55                  60

Asp Gly Tyr Asp Asp Gly Phe Lys Ala Asp Glu His Asp Ser Gln His
65                  70                  75                  80

Tyr Met Ser Glu Ile Lys Ser Arg Gly Ser Lys Thr Leu Lys Asp Ile
                85                  90                  95

Ile Leu Lys Ser Ser Asp Glu Gly Arg Pro Val Thr Ser Leu Val Tyr
            100                 105                 110

Ser Leu Leu Leu Pro Trp Ala Ala Lys Val Ala Arg Glu Phe His Ile
        115                 120                 125

Pro Cys Ala Leu Leu Trp Ile Gln Pro Ala Thr Val Leu Asp Ile Tyr
    130                 135                 140

Tyr Tyr Tyr Phe Asn Gly Tyr Glu Asp Ala Ile Lys Gly Ser Thr Asn
145                 150                 155                 160

Asp Pro Asn Trp Cys Ile Gln Leu Pro Arg Leu Pro Leu Leu Lys Ser
                165                 170                 175

Gln Asp Leu Pro Ser Phe Leu Ser Ser Ser Asn Glu Glu Lys Tyr
            180                 185                 190

Ser Phe Ala Leu Pro Thr Phe Lys Glu Gln Leu Asp Thr Leu Asp Val
        195                 200                 205

Glu Glu Asn Pro Lys Val Leu Val Asn Thr Phe Asp Ala Leu Glu Pro
    210                 215                 220

Lys Glu Leu Lys Ala Ile Glu Lys Tyr Asn Leu Ile Gly Ile Gly Pro
225                 230                 235                 240

Leu Ile Pro Ser Thr Phe Leu Asp Gly Lys Asp Pro Leu Asp Ser Ser
                245                 250                 255

Phe Gly Gly Asp Leu Phe Gln Lys Ser Asn Asp Tyr Ile Glu Trp Leu
            260                 265                 270

Asn Ser Lys Ala Asn Ser Ser Val Val Tyr Ile Ser Phe Gly Ser Leu
```

-continued

|  |  | 275 |  |  | 280 |  |  | 285 |  |  |  |
|---|---|---|---|---|---|---|---|---|---|---|---|

Leu Asn Leu Ser Lys Asn Gln Lys Glu Glu Ile Ala Lys Gly Leu Ile
                290                 295                 300

Glu Ile Lys Lys Pro Phe Leu Trp Val Ile Arg Asp Gln Glu Asn Gly
305                 310                 315                 320

Lys Gly Asp Glu Lys Glu Lys Leu Ser Cys Met Met Glu Leu Glu
                325                 330                 335

Lys Gln Gly Lys Ile Val Pro Trp Cys Ser Gln Leu Glu Val Leu Thr
                340                 345                 350

His Pro Ser Ile Gly Cys Phe Val Ser His Cys Gly Trp Asn Ser Thr
                355                 360                 365

Leu Glu Ser Leu Ser Ser Gly Val Ser Val Val Ala Phe Pro His Trp
                370                 375                 380

Thr Asp Gln Gly Thr Asn Ala Lys Leu Ile Glu Asp Val Trp Lys Thr
385                 390                 395                 400

Gly Val Arg Leu Lys Lys Asn Glu Asp Gly Val Val Glu Ser Glu Glu
                405                 410                 415

Ile Lys Arg Cys Ile Glu Met Val Met Asp Gly Gly Glu Lys Gly Glu
                420                 425                 430

Glu Met Arg Arg Asn Ala Gln Lys Trp Lys Glu Leu Ala Arg Glu Ala
                435                 440                 445

Val Lys Glu Gly Gly Ser Ser Glu Met Asn Leu Lys Ala Phe Val Gln
                450                 455                 460

Glu Val Gly Lys Gly Cys
465                 470

<210> SEQ ID NO 53
<211> LENGTH: 1449
<212> TYPE: DNA
<213> ORGANISM: Nicotiana tabacum

<400> SEQUENCE: 53
atgaaagaga ctaaaaaaat tgagttagtt tttatcccca gtcctggtat aggacactta    60
gtctcaactg tggagatggc caaactgttg atagcccgtg aagagcaact ttctattact   120
gtcctgatta caatggcc taatgataaa aagctagaca gttatatcca gtccgtcgca    180
aactttagtt ctagactgaa gtttatacgt ctgccccaag atgactcaat catgcaactt   240
ttgaaatcaa acattttcac gacattcatc gcctctcaca agccagctgt aagagacgcc   300
gttgctgaca tactaaagag tgaaagtaat aacacattgg caggcattgt aatcgatctt   360
ttctgcacat ccatgatcga tgtagccaat gagtttgagc tgcctactta tgtgttttac   420
actagtggcg cagccacgtt gggtctgcac taccatattc aaaatctgcg tgatgagttt   480
aataaagaca ttaccaaata taaggatgag ccagaagaaa aattaagtat agccacgtac   540
cttaacccat tccctgctaa gtgtctaccc tccgtggcat tggataagga aggaggatca   600
acgatgttcc tagacttagc taagaggttc agggagacca aagcataat gattaacact   660 tttcttgagc tggaatcata cgctctaaac tcattgtcta gagataaaaa cttgccccct   720
atataccctg taggccctgt tttgaacttg aacaacgttg agggtgataa cttgggctct   780
agtgatcaaa ataccatgaa atggctggac gaccagccag cttcttccgt tgtgttccta   840
tgttttggct caggaggaag tttcgaaaaa caccaagtca agaaatagc ttatgcctta   900 gaatcttccg gatgcaggtt cttgtggagt ttgcgtagac cccccacgga agatgctagg   960 ttccccttcta attacgaaaa cttagaggaa atttttaccag agggatttct ggaaagaacg  1020

```
aaaggcattg gtaaggtcat tggatgggcc ccacagttag caatcttgtc tcaacaagtcc    1080 acaggaggat tcgtgtctca ttgcggatgg aactctaccc ttgaaagtac ctatttcggc    1140
gttcctattg ctacttggcc aatgtatgct gaacaacagg ccaacgcttt tcaacttgtt    1200
aaagatttga ggatgggtgt tgagatcaaa atggattata ggaaggatat gaaggtaatg    1260
ggcaaggagg ttatcgttaa ggcagaagaa attgaaaagg ccataaggga aatcatggac    1320
tcagaatcag aaatcagggt caaggtcaaa gagatgaagg agaaaagtcg tgcagcccaa    1380
atggaaggag gatcatcata tacctctatc ggcggcttca ttcaaataat catggagaac    1440
tcacagtaa                                                             1449

<210> SEQ ID NO 54
<211> LENGTH: 482
<212> TYPE: PRT
<213> ORGANISM: Nicotiana tabacum

<400> SEQUENCE: 54
```

| Met<br>1 | Lys | Glu | Thr | Lys<br>5 | Ile | Glu | Leu | Val | Phe<br>10 | Ile | Pro | Ser | Pro | Gly<br>15 |
|---|---|---|---|---|---|---|---|---|---|---|---|---|---|---|
| Ile | Gly | His | Leu<br>20 | Val | Ser | Thr | Val | Glu<br>25 | Met | Ala | Lys | Leu | Leu<br>30 | Ile Ala |

Ile Gly His Leu Val Ser Thr Val Glu Met Ala Lys Leu Leu Ile Ala
              20                  25                  30

Arg Glu Glu Gln Leu Ser Ile Thr Val Leu Ile Ile Gln Trp Pro Asn
         35                  40                  45

Asp Lys Lys Leu Asp Ser Tyr Ile Gln Ser Val Ala Asn Phe Ser Ser
     50                  55                  60

Arg Leu Lys Phe Ile Arg Leu Pro Gln Asp Asp Ser Ile Met Gln Leu
 65                  70                  75                  80

Leu Lys Ser Asn Ile Phe Thr Thr Phe Ile Ala Ser His Lys Pro Ala
                 85                  90                  95

Val Arg Asp Ala Val Ala Asp Ile Leu Lys Ser Glu Ser Asn Asn Thr
            100                 105                 110

Leu Ala Gly Ile Val Ile Asp Leu Phe Cys Thr Ser Met Ile Asp Val
        115                 120                 125

Ala Asn Glu Phe Glu Leu Pro Thr Tyr Val Phe Tyr Thr Ser Gly Ala
    130                 135                 140

Ala Thr Leu Gly Leu His Tyr His Ile Gln Asn Leu Arg Asp Glu Phe
145                 150                 155                 160

Asn Lys Asp Ile Thr Lys Tyr Lys Asp Glu Pro Glu Glu Lys Leu Ser
                165                 170                 175

Ile Ala Thr Tyr Leu Asn Pro Phe Pro Ala Lys Cys Leu Pro Ser Val
            180                 185                 190

Ala Leu Asp Lys Glu Gly Gly Ser Thr Met Phe Leu Asp Leu Ala Lys
        195                 200                 205

Arg Phe Arg Glu Thr Lys Gly Ile Met Ile Asn Thr Phe Leu Glu Leu
    210                 215                 220

Glu Ser Tyr Ala Leu Asn Ser Leu Ser Arg Asp Lys Asn Leu Pro Pro
225                 230                 235                 240

Ile Tyr Pro Val Gly Pro Val Leu Asn Leu Asn Asn Val Glu Gly Asp
                245                 250                 255

Asn Leu Gly Ser Ser Asp Gln Asn Thr Met Lys Trp Leu Asp Asp Gln
            260                 265                 270

Pro Ala Ser Ser Val Val Phe Leu Cys Phe Gly Ser Gly Gly Ser Phe
        275                 280                 285

```
Glu Lys His Gln Val Lys Glu Ile Ala Tyr Ala Leu Glu Ser Ser Gly
        290                 295                 300

Cys Arg Phe Leu Trp Ser Leu Arg Arg Pro Pro Thr Glu Asp Ala Arg
305                 310                 315                 320

Phe Pro Ser Asn Tyr Glu Asn Leu Glu Glu Ile Leu Pro Glu Gly Phe
                325                 330                 335

Leu Glu Arg Thr Lys Gly Ile Gly Lys Val Ile Gly Trp Ala Pro Gln
            340                 345                 350

Leu Ala Ile Leu Ser His Lys Ser Thr Gly Gly Phe Val Ser His Cys
                355                 360                 365

Gly Trp Asn Ser Thr Leu Glu Ser Thr Tyr Phe Gly Val Pro Ile Ala
370                 375                 380

Thr Trp Pro Met Tyr Ala Glu Gln Gln Ala Asn Ala Phe Gln Leu Val
385                 390                 395                 400

Lys Asp Leu Arg Met Gly Val Glu Ile Lys Met Asp Tyr Arg Lys Asp
                405                 410                 415

Met Lys Val Met Gly Lys Glu Val Ile Val Lys Ala Glu Glu Ile Glu
            420                 425                 430

Lys Ala Ile Arg Glu Ile Met Asp Ser Glu Ser Glu Ile Arg Val Lys
                435                 440                 445

Val Lys Glu Met Lys Glu Lys Ser Arg Ala Ala Gln Met Glu Gly Gly
        450                 455                 460

Ser Ser Tyr Thr Ser Ile Gly Gly Phe Ile Gln Ile Ile Met Glu Asn
465                 470                 475                 480

Ser Gln

<210> SEQ ID NO 55
<211> LENGTH: 1491
<212> TYPE: DNA
<213> ORGANISM: Nicotiana tabacum

<400> SEQUENCE: 55
atggctactc aggtgcataa attgcatttc attctgttcc cactgatggc tcccggtcac      60
atgatcccta tgatagacat cgcaaaacta ttggctaacc gtggcgtgat aactaccata     120
ataactacgc ccgttaacgc caatcgtttt tcctctacga tcactagggc cattaaatca     180
ggcctaagaa tccagatttt aaccttaaaa ttcccatcag ttgaggtagg cctgcctgaa     240
ggatgtgaaa acatcgacat gttgccatct ttggacttag cctctaaatt ctttgctgct     300
atttctatgc ttaaacaaca agtggagaac ttgctagagg gtattaaccc tagtccctca     360
tgcgttattt ctgacatggg cttcccatgg acgacacaga tcgctcaaaa tttcaatatt     420
cctcgtatcg tatttcatgg cacgtgttgc ttttctcttc tttgttctta caaaatcctg     480
tcatccaata tcttagagaa cattactagt gactcagagt attttgtcgt gccagatctg     540
ccagaccgtg tcgagctaac taaggcccaa gtctctggat ctacaaagaa tactacatca     600
gtaagtagtt cagtactgaa ggaggttaca gagcagatca ggcttgcaga ggaatcatcc     660
tacggtgtga tagttaattc cttcgaagaa ctggaacagg tgtatgaaaa agagtacaga     720
aaagccaggg gcaaaaaggt ctggtgcgtg ggtcctgtct ctttgtgcaa caggagatt     780 gaagatcttg ttactagagg aaacaaaacc gctatagaca tcaggattg tcttaagtgg     840 ttagacaact cgagactga atccgtcgtc tatgcaagtt aggctcact aagtaggctt     900 acgttactgc aaatggttga gctgggattg ggactgagg agagtaatag gccatttgta     960
tgggttctgg gaggaggaga caaactaaat gatcttgaga atggatatt ggagaatggc    1020
```

```
tttgaacagc gtataaagga gagaggtgtc ctgatacgtg gctgggcacc tcaagtattg   1080
attttaagtc accccgcaat tggaggagtt ttaacgcatt gtggatggaa ctctacatta   1140
gagggcattt cagccggact acccatggtc acctggccac tatttgccga acagttctgt   1200
aacgaaaaat tagtagtgca ggttcttaaa atcggtgtct cacttggagt gaaggtccct   1260
gttaagtggg gtgacgaaga gaacgtaggt gtcttagtga aaaaggatga cgttaaaaaa   1320
gcactggata agctaatgga tgagggtgag gagggccagg ttaggaggac caaagccaaa   1380
gagcttggtg agttagctaa aaaagccttt ggagagggcg gatcatccta cgtgaaccta   1440
acgtccctaa ttgaagatat aatcgagcag cagaaccata aggagaagta g           1491
```

<210> SEQ ID NO 56
<211> LENGTH: 496
<212> TYPE: PRT
<213> ORGANISM: Nicotiana tabacum

<400> SEQUENCE: 56

```
Met Ala Thr Gln Val His Lys Leu His Phe Ile Leu Phe Pro Leu Met
1               5                   10                  15

Ala Pro Gly His Met Ile Pro Met Ile Asp Ile Ala Lys Leu Leu Ala
            20                  25                  30

Asn Arg Gly Val Ile Thr Thr Ile Ile Thr Pro Val Asn Ala Asn
        35                  40                  45

Arg Phe Ser Ser Thr Ile Thr Arg Ala Ile Lys Ser Gly Leu Arg Ile
    50                  55                  60

Gln Ile Leu Thr Leu Lys Phe Pro Ser Val Glu Val Gly Leu Pro Glu
65                  70                  75                  80

Gly Cys Glu Asn Ile Asp Met Leu Pro Ser Leu Asp Leu Ala Ser Lys
                85                  90                  95

Phe Phe Ala Ala Ile Ser Met Leu Lys Gln Gln Val Glu Asn Leu Leu
            100                 105                 110

Glu Gly Ile Asn Pro Ser Pro Ser Cys Val Ile Ser Asp Met Gly Phe
        115                 120                 125

Pro Trp Thr Thr Gln Ile Ala Gln Asn Phe Asn Ile Pro Arg Ile Val
    130                 135                 140

Phe His Gly Thr Cys Cys Phe Ser Leu Leu Cys Ser Tyr Lys Ile Leu
145                 150                 155                 160

Ser Ser Asn Ile Leu Glu Asn Ile Thr Ser Asp Ser Glu Tyr Phe Val
                165                 170                 175

Val Pro Asp Leu Pro Asp Arg Val Glu Leu Thr Lys Ala Gln Val Ser
            180                 185                 190

Gly Ser Thr Lys Asn Thr Thr Ser Val Ser Ser Val Leu Lys Glu
        195                 200                 205

Val Thr Glu Gln Ile Arg Leu Ala Glu Glu Ser Ser Tyr Gly Val Ile
    210                 215                 220

Val Asn Ser Phe Glu Glu Leu Glu Gln Val Tyr Glu Lys Glu Tyr Arg
225                 230                 235                 240

Lys Ala Arg Gly Lys Lys Val Trp Cys Val Gly Pro Val Ser Leu Cys
                245                 250                 255

Asn Lys Glu Ile Glu Asp Leu Val Thr Arg Gly Asn Lys Thr Ala Ile
            260                 265                 270

Asp Asn Gln Asp Cys Leu Lys Trp Leu Asp Asn Phe Glu Thr Glu Ser
        275                 280                 285
```

```
Val Val Tyr Ala Ser Leu Gly Ser Leu Ser Arg Leu Thr Leu Leu Gln
        290                 295                 300

Met Val Glu Leu Gly Leu Gly Leu Glu Glu Ser Asn Arg Pro Phe Val
305                 310                 315                 320

Trp Val Leu Gly Gly Asp Lys Leu Asn Asp Leu Glu Lys Trp Ile
                325                 330                 335

Leu Glu Asn Gly Phe Glu Gln Arg Ile Lys Glu Arg Gly Val Leu Ile
                340                 345                 350

Arg Gly Trp Ala Pro Gln Val Leu Ile Leu Ser His Pro Ala Ile Gly
                355                 360                 365

Gly Val Leu Thr His Cys Gly Trp Asn Ser Thr Leu Glu Gly Ile Ser
        370                 375                 380

Ala Gly Leu Pro Met Val Thr Trp Pro Leu Phe Ala Glu Gln Phe Cys
385                 390                 395                 400

Asn Glu Lys Leu Val Val Gln Val Leu Lys Ile Gly Val Ser Leu Gly
                405                 410                 415

Val Lys Val Pro Val Lys Trp Gly Asp Glu Asn Val Gly Val Leu
                420                 425                 430

Val Lys Lys Asp Asp Val Lys Lys Ala Leu Asp Lys Leu Met Asp Glu
                435                 440                 445

Gly Glu Glu Gly Gln Val Arg Arg Thr Lys Ala Lys Glu Leu Gly Glu
        450                 455                 460

Leu Ala Lys Lys Ala Phe Gly Glu Gly Gly Ser Ser Tyr Val Asn Leu
465                 470                 475                 480

Thr Ser Leu Ile Glu Asp Ile Ile Glu Gln Gln Asn His Lys Glu Lys
                485                 490                 495

<210> SEQ ID NO 57
<211> LENGTH: 1458
<212> TYPE: DNA
<213> ORGANISM: Nicotiana tabacum

<400> SEQUENCE: 57
atgggctcta tcggtgcaga actaaccaag ccacacgccg tatgcattcc ctatcccgcc      60
cagggacaca taaatcctat gctgaagtta gctaagatac tgcatcacaa gggcttccat     120
ataaccttcg taaatacgga atttaatcac aggcgtctgc tgaagtccag aggtcctgac     180
tccctgaaag gtctttcaag tttcaggttc gagacgatac tgacggact gcccccatgc      240 gaagctgacg ctacacagga cattccttca ctgtgtgaat ccacgactaa tacatgtcta     300
gctcctttta gagacctact tgctaagcta aatgatacga atacttctaa cgtccctccc     360
gtaagttgta ttgtcagtga cggagtgatg tcatttaccc ttgcagctgc acaggaactg     420
ggtgtcccag aggttttatt ttggactaca tctgcttgtg gattcttagg ttacatgcac     480
tattgcaaag tcattgaaaa aggatatgct ccattaaaag acgcatcaga cctgacgaat     540
ggctatcttg agacaacctt ggacttcatc cccggcatga aggacgtcag gctgagagac     600
ttaccttcct ttcttaggac caccaatcca gacgaattta tgattaagtt tgtactacag     660
gaaactgagc gtgctcgtaa ggccagtgcc ataatactta atacctttga aaccttagag     720
gcagaggtat tagaatcatt aaggaacctt ctaccccccg tctatccaat cggcccttg      780 catttccttg tcaaacacgt agacgatgag aacctaaaag gtctacgttc ctcactttgg     840
aaggaggaac tgaatgtgtat tcaatggtta gacaccaaag aacctaactc tgtcgtgtac     900
gtgaatttcg gatccattac tgtgatgact cccaatcaat aatagagtt cgcttgggga     960
```

-continued

```
ctggcaaact ctcaacagac cttcctttgg atcataaggc ctgacatcgt aagtggtgat    1020
gcttccatat tacctcccga gtttgttgag gagactaaga acagaggcat gcttgcctcc    1080
tggtgctctc aggaggaggt actatcccat cccgcaatag tgggattttt gacgcactct    1140
ggttggaact caactttaga atcaatttct agtggcgtcc ccatgatctg ttggcctttc    1200
tttgctgagc agcaaacgaa ctgctggttt tcagtgacga agtgggacgt tggaatggaa    1260
attgattcag atgtgaagag agatgaagta gagagtttag taagagagtt aatggtgggt    1320
ggtaaaggca agaagatgaa gaagaaggca atggagtgga aggaactggc cgaggcttca    1380
gcaaaagaac actctggctc ctcttacgtc aatatcgaga agttggttaa cgatatatta    1440
ctatctagta agcactaa                                                  1458
```

<210> SEQ ID NO 58
<211> LENGTH: 485
<212> TYPE: PRT
<213> ORGANISM: Nicotiana tabacum

<400> SEQUENCE: 58

```
Met Gly Ser Ile Gly Ala Glu Leu Thr Lys Pro His Ala Val Cys Ile
1               5                   10                  15

Pro Tyr Pro Ala Gln Gly His Ile Asn Pro Met Leu Lys Leu Ala Lys
                20                  25                  30

Ile Leu His His Lys Gly Phe His Ile Thr Phe Val Asn Thr Glu Phe
            35                  40                  45

Asn His Arg Arg Leu Leu Lys Ser Arg Gly Pro Asp Ser Leu Lys Gly
        50                  55                  60

Leu Ser Ser Phe Arg Phe Glu Thr Ile Pro Asp Gly Leu Pro Pro Cys
65                  70                  75                  80

Glu Ala Asp Ala Thr Gln Asp Ile Pro Ser Leu Cys Glu Ser Thr Thr
                85                  90                  95

Asn Thr Cys Leu Ala Pro Phe Arg Asp Leu Leu Ala Lys Leu Asn Asp
            100                 105                 110

Thr Asn Thr Ser Asn Val Pro Pro Val Ser Cys Ile Val Ser Asp Gly
        115                 120                 125

Val Met Ser Phe Thr Leu Ala Ala Ala Gln Glu Leu Gly Val Pro Glu
130                 135                 140

Val Leu Phe Trp Thr Thr Ser Ala Cys Gly Phe Leu Gly Tyr Met His
145                 150                 155                 160

Tyr Cys Lys Val Ile Glu Lys Gly Tyr Ala Pro Leu Lys Asp Ala Ser
                165                 170                 175

Asp Leu Thr Asn Gly Tyr Leu Glu Thr Thr Leu Asp Phe Ile Pro Gly
            180                 185                 190

Met Lys Asp Val Arg Leu Arg Asp Leu Pro Ser Phe Leu Arg Thr Thr
        195                 200                 205

Asn Pro Asp Glu Phe Met Ile Lys Phe Val Leu Gln Glu Thr Glu Arg
    210                 215                 220

Ala Arg Lys Ala Ser Ala Ile Ile Leu Asn Thr Phe Glu Thr Leu Glu
225                 230                 235                 240

Ala Glu Val Leu Glu Ser Leu Arg Asn Leu Pro Pro Val Tyr Pro
                245                 250                 255

Ile Gly Pro Leu His Phe Leu Val Lys His Val Asp Asp Glu Asn Leu
            260                 265                 270

Lys Gly Leu Arg Ser Ser Leu Trp Lys Glu Glu Pro Glu Cys Ile Gln
        275                 280                 285
```

| Trp | Leu | Asp | Thr | Lys | Glu | Pro | Asn | Ser | Val | Val | Tyr | Val | Asn | Phe | Gly |
| | 290 | | | | 295 | | | | 300 | | | | | | |

| Ser | Ile | Thr | Val | Met | Thr | Pro | Asn | Gln | Leu | Ile | Glu | Phe | Ala | Trp | Gly |
| 305 | | | | 310 | | | | | 315 | | | | | 320 | |

| Leu | Ala | Asn | Ser | Gln | Gln | Thr | Phe | Leu | Trp | Ile | Ile | Arg | Pro | Asp | Ile |
| | | | 325 | | | | | 330 | | | | | 335 | | |

| Val | Ser | Gly | Asp | Ala | Ser | Ile | Leu | Pro | Pro | Glu | Phe | Val | Glu | Glu | Thr |
| | | | 340 | | | | | 345 | | | | | 350 | | |

| Lys | Asn | Arg | Gly | Met | Leu | Ala | Ser | Trp | Cys | Ser | Gln | Glu | Glu | Val | Leu |
| | | 355 | | | | | 360 | | | | | 365 | | | |

| Ser | His | Pro | Ala | Ile | Val | Gly | Phe | Leu | Thr | His | Ser | Gly | Trp | Asn | Ser |
| | 370 | | | | | 375 | | | | | 380 | | | | |

| Thr | Leu | Glu | Ser | Ile | Ser | Ser | Gly | Val | Pro | Met | Ile | Cys | Trp | Pro | Phe |
| 385 | | | | | 390 | | | | | 395 | | | | | 400 |

| Phe | Ala | Glu | Gln | Gln | Thr | Asn | Cys | Trp | Phe | Ser | Val | Thr | Lys | Trp | Asp |
| | | | | 405 | | | | | 410 | | | | | 415 | |

| Val | Gly | Met | Glu | Ile | Asp | Ser | Asp | Val | Lys | Arg | Asp | Glu | Val | Glu | Ser |
| | | | 420 | | | | | 425 | | | | | 430 | | |

| Leu | Val | Arg | Glu | Leu | Met | Val | Gly | Gly | Lys | Gly | Lys | Lys | Met | Lys | Lys |
| | | 435 | | | | | 440 | | | | | 445 | | | |

| Lys | Ala | Met | Glu | Trp | Lys | Glu | Leu | Ala | Glu | Ala | Ser | Ala | Lys | Glu | His |
| | 450 | | | | | 455 | | | | | 460 | | | | |

| Ser | Gly | Ser | Ser | Tyr | Val | Asn | Ile | Glu | Lys | Leu | Val | Asn | Asp | Ile | Leu |
| 465 | | | | 470 | | | | | 475 | | | | | 480 | |

| Leu | Ser | Ser | Lys | His |
| | | | 485 | |

<210> SEQ ID NO 59
<211> LENGTH: 1377
<212> TYPE: DNA
<213> ORGANISM: Stevia rebaudiana

<400> SEQUENCE: 59

| atggagaaca | aaaccgagac | aaccgttagg | cgtagacgta | ggataatatt | gtttcccgtg | 60 |
| cccttttcaag | gccatataaa | cccaatcctg | cagctagcca | acgtattgta | ctcaaagggc | 120 |
| ttcagtataa | cgatcttcca | caccaacttt | aataagccaa | aaacgtctaa | ttatccacac | 180 |
| ttcacattta | gatttatact | tgataacgac | ccacaggatg | aaagaatatc | aaacttgccc | 240 |
| acgcacggcc | cactagccgg | aatgagaata | ccaataatca | atgagcatgg | cgccgacgag | 300 |
| ttgcgtagag | agctggaatt | gttgatgcta | gccagtgagg | aagacgaaga | ggtgtcctgc | 360 |
| ttaataacgg | atgcactttg | gtattttgct | caatctgtgg | ccgactccct | taacctgagg | 420 |
| cgtcttgtcc | ttatgaccct | cagtctattc | aactttcatg | cccatgtctc | attgccccaa | 480 |
| tttgatgagc | ttggctattt | ggatcctgat | gacaaaacta | ggctggagga | acaggcttcc | 540 |
| ggttttccca | tgctaaaggt | taaggacatc | aaatccgcct | actcaaactg | gcagatcctt | 600 |
| aaggaaattc | ttggcaaaat | gatcaaacag | acgagggcat | ccagtggcgt | catctggaac | 660 |
| tcctttaagg | aacttgaaga | atcagaactt | gaaacagtaa | tcagagaaat | acctgcccca | 720 |
| agtttcttga | tccctctacc | taagcacctt | acggcttcta | gttcttcttt | gttggaccac | 780 |
| gatcgtactg | tctttcaatg | gttagatcag | caaccccccct | catcagtgct | atatgtgtca | 840 |
| ttcggtagta | catcagaagt | ggacgaaaag | gattccttg | agatagcccg | tggattggtg | 900 |
| gactctaaac | agtccttttt | atgggttgtg | agacctggat | ttgtaaaggg | atccacgtgg | 960 |

-continued

```
gtcgaaccct tgcccgatgg tttcctgggt gaaagaggaa ggatagtgaa gtgggtccct    1020
cagcaagagg tactggccca tggtgctata ggtgctttct ggacccactc cggctggaat    1080
agtacactag aatccgtttg cgagggtgtc cctatgattt tttctgattt tggtttagat    1140 caaccectga atgctaggta catgtcagac gtccttaaag tcggcgtcta cctagaaaat    1200
ggctgggaga ggggtgagat agcaaacgct atcagacgtg ttatggtaga cgaagaggga    1260
gagtacataa ggcaaaacgc cagggtcctg aaacaaaaag ccgatgtgtc cttgatgaag    1320
ggcggctctt catacgaaag tctagaaagt cttgtttctt atatttcctc actataa      1377
```

<210> SEQ ID NO 60
<211> LENGTH: 458
<212> TYPE: PRT
<213> ORGANISM: Stevia rebaudiana

<400> SEQUENCE: 60

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Lys Thr Arg Leu Glu
                165                 170                 175

Glu Gln Ala Ser Gly Phe Pro Met Leu Lys Val Lys Asp Ile Lys Ser
        180                 185                 190

Ala Tyr Ser Asn Trp Gln Ile Leu Lys Glu Ile Leu Gly Lys Met Ile
    195                 200                 205

Lys Gln Thr Arg Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300
```

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
            325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
            405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
    450                 455

<210> SEQ ID NO 61
<211> LENGTH: 1434
<212> TYPE: DNA
<213> ORGANISM: Lycium barbarum

<400> SEQUENCE: 61
atgggtcaat tgcatttttt tttgtttcca atgatggctc aaggtcatat gattccaact      60
ttggatatgg ctaagttgat tgcttctaga ggtgttaagg ctactattat tactactcca     120
ttgaacgaat ctgttttttc taaggctatt caaagaaaca agcaattggg tattgaaatt     180
gaaattgaaa ttagattgat taagtttcca gctttggaaa acgatttgcc agaagattgt     240
gaaagattgg atttgattcc aactgaagct catttgccaa acttttttaa ggctgctgct     300
atgatgcaag aaccattgga acaattgatt caagaatgta gaccagattg tttggttttct    360
gatatgtttt tgccatggac tactgatact gctgctaagt ttaacattcc aagaattgtt     420
tttcatggta ctaactactt tgctttgtgt gttggtgatt ctatgagaag aaacaagcca     480
tttaagaacg tttcttctga ttctgaaact tttgttgttc caaacttgcc acatgaaatt     540
aagttgacta gaactcaagt ttctccattt gaacaatctg atgaagaatc tgttatgtct     600
agagttttga aggaagttag agaatctgat ttgaagtctt acggtgttat ttttaactct     660
ttttacgaat tggaaccaga ttacgttgaa cattacacta ggttatggg tagaaagtct     720
tgggctattg gtccattgtc tttgtgtaac agagatgttg aagataaggc tgaaagaggt     780
aagaagtctt ctattgataa gcatgaatgt tggaatggt tggattctaa gaagccatct     840
tctattgttt acgtttgttt tggttctgtt gctaacttta ctgttactca atgagagaa     900
ttggctttgg gtttggaagc ttctggtttg attttatttt gggctgttag agctgataac     960
gaagattggt tgccagaagg ttttgaagaa agaactaagg aaaagggttt gattattaga    1020
ggttgggctc acaagttttt gattttggat catgaatctg ttggtgcttt tgttactcat    1080
tgtggttgga actctacttt ggaaggtatt tctgctggtg ttccaatggt tacttggcca    1140
gtttttgctg aacaattttt taacgaaaag ttggttactc aagttatgag aactggtgct    1200

```
ggtgttggtt ctgttcaatg gaagagatct gcttctgaag gtgttgaaaa ggaagctatt    1260
gctaaggcta ttaagagagt tatggtttct gaagaagctg aaggttttag aaacagagct    1320
agagcttaca aggaaatggc tagacaagct attgaagaag gtggttcttc ttacactggt    1380
ttgactactt tgttggaaga tatttcttct tacgaatctt tgtcttctga ttaa          1434
```

<210> SEQ ID NO 62
<211> LENGTH: 477
<212> TYPE: PRT
<213> ORGANISM: Lycium barbarum

<400> SEQUENCE: 62

```
Met Gly Gln Leu His Phe Phe Leu Phe Pro Met Met Ala Gln Gly His
1               5                   10                  15

Met Ile Pro Thr Leu Asp Met Ala Lys Leu Ile Ala Ser Arg Gly Val
            20                  25                  30

Lys Ala Thr Ile Ile Thr Thr Pro Leu Asn Glu Ser Val Phe Ser Lys
        35                  40                  45

Ala Ile Gln Arg Asn Lys Gln Leu Gly Ile Glu Ile Glu Ile
    50                  55                  60

Arg Leu Ile Lys Phe Pro Ala Leu Glu Asn Asp Leu Pro Glu Asp Cys
65                  70                  75                  80

Glu Arg Leu Asp Leu Ile Pro Thr Glu Ala His Leu Pro Asn Phe Phe
                85                  90                  95

Lys Ala Ala Ala Met Met Gln Glu Pro Leu Glu Gln Leu Ile Gln Glu
            100                 105                 110

Cys Arg Pro Asp Cys Leu Val Ser Asp Met Phe Leu Pro Trp Thr Thr
        115                 120                 125

Asp Thr Ala Ala Lys Phe Asn Ile Pro Arg Ile Val Phe His Gly Thr
    130                 135                 140

Asn Tyr Phe Ala Leu Cys Val Gly Asp Ser Met Arg Arg Asn Lys Pro
145                 150                 155                 160

Phe Lys Asn Val Ser Ser Asp Ser Glu Thr Phe Val Val Pro Asn Leu
                165                 170                 175

Pro His Glu Ile Lys Leu Thr Arg Thr Gln Val Ser Pro Phe Glu Gln
            180                 185                 190

Ser Asp Glu Glu Ser Val Met Ser Arg Val Leu Lys Glu Val Arg Glu
        195                 200                 205

Ser Asp Leu Lys Ser Tyr Gly Val Ile Phe Asn Ser Phe Tyr Glu Leu
    210                 215                 220

Glu Pro Asp Tyr Val Glu His Tyr Thr Lys Val Met Gly Arg Lys Ser
225                 230                 235                 240

Trp Ala Ile Gly Pro Leu Ser Leu Cys Asn Arg Asp Val Glu Asp Lys
                245                 250                 255

Ala Glu Arg Gly Lys Lys Ser Ser Ile Asp Lys His Glu Cys Leu Glu
            260                 265                 270

Trp Leu Asp Ser Lys Lys Pro Ser Ser Ile Val Tyr Val Cys Phe Gly
        275                 280                 285

Ser Val Ala Asn Phe Thr Val Thr Gln Met Arg Glu Leu Ala Leu Gly
    290                 295                 300

Leu Glu Ala Ser Gly Leu Asp Phe Ile Trp Ala Val Arg Ala Asp Asn
305                 310                 315                 320

Glu Asp Trp Leu Pro Glu Gly Phe Glu Glu Arg Thr Lys Glu Lys Gly
                325                 330                 335
```

| | | | | | | | | | | | |
|---|---|---|---|---|---|---|---|---|---|---|---|
|Leu|Ile|Ile|Arg|Gly|Trp|Ala|Pro|Gln|Val|Leu|Ile|Leu|Asp|His|Glu|
| | |340| | | |345| | | |350| |

Ser Val Gly Ala Phe Val Thr His Cys Gly Trp Asn Ser Thr Leu Glu
        355                 360                 365

Gly Ile Ser Ala Gly Val Pro Met Val Thr Trp Pro Val Phe Ala Glu
370                 375                 380

Gln Phe Phe Asn Glu Lys Leu Val Thr Gln Val Met Arg Thr Gly Ala
385                 390                 395                 400

Gly Val Gly Ser Val Gln Trp Lys Arg Ser Ala Ser Glu Gly Val Glu
                405                 410                 415

Lys Glu Ala Ile Ala Lys Ala Ile Lys Arg Val Met Val Ser Glu Glu
            420                 425                 430

Ala Glu Gly Phe Arg Asn Arg Ala Arg Ala Tyr Lys Glu Met Ala Arg
            435                 440                 445

Gln Ala Ile Glu Glu Gly Gly Ser Ser Tyr Thr Gly Leu Thr Thr Leu
    450                 455                 460

Leu Glu Asp Ile Ser Ser Tyr Glu Ser Leu Ser Ser Asp
465                 470                 475

<210> SEQ ID NO 63
<211> LENGTH: 1377
<212> TYPE: DNA
<213> ORGANISM: Stevia rebaudiana

<400> SEQUENCE: 63

```
atggaaaata aaaccgaaac caccgtccgc cgtcgtcgcc gtatcattct gttcccggtc      60
ccgttccagg gccacatcaa cccgattctg caactggcga acgtgctgta ttcgaaaggt     120
ttcagcatca ccatcttcca tacgaacttc aacaagccga agaccagcaa ttacccgcac     180
tttacgttcc gttttattct ggataacgac ccgcaggatg aacgcatctc taatctgccg     240
acccacggcc cgctggcggg tatgcgtatt ccgattatca acgaacacgg cgcagatgaa     300
ctgcgtcgcg aactggaact gctgatgctg gccagcgaag aagatgaaga gtttcttgc      360
ctgatcaccg acgcactgtg gtattttgcc cagtctgttg cagatagtct gaacctgcgt     420
cgcctggtcc tgatgaccag cagcctgttc aattttcatg cccacgttag tctgccgcag     480
ttcgatgaac tgggttatct ggacccggat gacaaaaccc gcctggaaga acaggcgagc     540
ggcttttccga tgctgaaagt caaggatatt aagtcagcgt actcgaactg gcagattctg     600
aaagaaatcc tgggtaaaat gattaagcaa accaaagcaa gttccggcgt catctggaat     660
agtttcaaag aactggaaga tccgaactg gaaacggtga ttcgtgaaat cccggctccg     720
agtttttctga ttccgctgcc gaagcatctg accgcgagca gcagcagcct gctggatcac     780
gaccgcacgg tgtttcagtg gctggatcag caaccgccga ttccgtgct gtatgttagc     840
ttcggtagta cctcggaagt ggatgaaaag gactttctgg aaatcgctcg tggcctggtt     900
gatagcaaaa atcttttcct gtgggtggtt cgcccgggtt ttgtgaaggg ctctacgtgg     960
gttgaaccgc tgccggacgg cttcctgggt gaacgtggcc gcattgtcaa atgggtgccg    1020
cagcaagaag tgctggcgca tggcgcgatt ggcgcgtttt ggacccactc cggttggaac    1080
tcaacgctgg aatcggtttg tgaaggtgtc ccgatgattt tctcagattt tggcctggac    1140
cagccgctga atgcacgtta tatgtcggat gttctgaaag tcggtgtgta cctggaaaac    1200
ggttgggaac gcggcgaaat tgcgaatgcc atccgtcgcg ttatggtcga tgaagaaggc    1260
gaatacattc gtcagaatgc tcgcgtcctg aaacaaaagg cggacgtgag cctgatgaaa    1320
```
ggcggttcat cgtatgaaag tctggaatcc ctggtttcat acatcagctc tctgtaa    1377

<210> SEQ ID NO 64
<211> LENGTH: 458
<212> TYPE: PRT
<213> ORGANISM: Stevia rebaudiana

<400> SEQUENCE: 64

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Lys Gly Ser Thr Trp
305                 310                 315                 320

Val Glu Pro Leu Pro Asp Gly Phe Leu Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365
```

Gly Val Pro Met Ile Phe Ser Asp Phe Gly Leu Asp Gln Pro Leu Asn
          370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
            435                 440                 445

Glu Ser Leu Val Ser Tyr Ile Ser Ser Leu
        450                 455

<210> SEQ ID NO 65
<211> LENGTH: 88
<212> TYPE: PRT
<213> ORGANISM: S. cerevisiae

<400> SEQUENCE: 65

Met Arg Gln Val Trp Phe Ser Trp Ile Val Gly Leu Phe Leu Cys Phe
1               5                   10                  15

Phe Asn Val Ser Ser Ala Ala Pro Val Asn Thr Thr Thr Glu Asp Glu
            20                  25                  30

Thr Ala Gln Ile Pro Ala Glu Ala Val Ile Gly Tyr Ser Asp Leu Glu
        35                  40                  45

Gly Asp Phe Asp Val Ala Val Leu Pro Phe Ser Asn Ser Thr Asn Asn
    50                  55                  60

Gly Leu Leu Phe Ile Asn Thr Thr Ile Ala Ser Ile Ala Ala Lys Glu
65                  70                  75                  80

Glu Gly Val Ser Leu Glu Lys Arg
                85

<210> SEQ ID NO 66
<211> LENGTH: 22
<212> TYPE: PRT
<213> ORGANISM: S. cerevisiae

<400> SEQUENCE: 66

Met Arg Gln Val Trp Phe Ser Trp Ile Val Gly Leu Phe Leu Cys Phe
1               5                   10                  15

Phe Asn Val Ser Ser Ala
            20

<210> SEQ ID NO 67
<211> LENGTH: 215
<212> TYPE: PRT
<213> ORGANISM: Mus musculus

<400> SEQUENCE: 67

Met Arg Gln Val Trp Phe Ser Trp Ile Val Gly Leu Phe Leu Cys Phe
1               5                   10                  15

Phe Asn Val Ser Ser Ala Ala Pro Val Asn Thr Thr Thr Glu Asp Glu
            20                  25                  30

Thr Ala Gln Ile Pro Ala Glu Ala Val Ile Gly Tyr Ser Asp Leu Glu
        35                  40                  45

Gly Asp Phe Asp Val Ala Val Leu Pro Phe Ser Asn Ser Thr Asn Asn
    50                  55                  60

Gly Leu Leu Phe Ile Asn Thr Thr Ile Ala Ser Ile Ala Ala Lys Glu

```
                65                  70                  75                  80
Glu Gly Val Ser Leu Glu Lys Arg Met Asn Phe Ser Gly Lys Tyr Gln
                    85                  90                  95

Leu Gln Ser Gln Glu Asn Phe Glu Pro Phe Met Lys Ala Ile Gly Leu
                100                 105                 110

Pro Glu Asp Leu Ile Gln Lys Gly Lys Asp Ile Lys Gly Val Ser Glu
                115                 120                 125

Ile Val His Glu Gly Lys Lys Ile Lys Leu Thr Ile Thr Tyr Gly Pro
            130                 135                 140

Lys Val Val Arg Asn Glu Phe Thr Leu Gly Glu Cys Glu Leu Glu
145                 150                 155                 160

Thr Met Thr Gly Glu Lys Val Lys Ala Val Val Lys Leu Glu Gly Asp
                165                 170                 175

Asn Lys Met Val Thr Thr Phe Lys Gly Ile Lys Ser Val Thr Glu Leu
            180                 185                 190

Asn Gly Asp Thr Ile Thr Asn Thr Met Thr Leu Gly Asp Ile Val Tyr
            195                 200                 205

Lys Arg Val Ser Lys Arg Ile
            210                 215

<210> SEQ ID NO 68
<211> LENGTH: 215
<212> TYPE: PRT
<213> ORGANISM: Bos taurus

<400> SEQUENCE: 68

Met Arg Gln Val Trp Phe Ser Trp Ile Val Gly Leu Phe Leu Cys Phe
1               5                   10                  15

Phe Asn Val Ser Ser Ala Ala Pro Val Asn Thr Thr Thr Glu Asp Glu
                20                  25                  30

Thr Ala Gln Ile Pro Ala Glu Ala Val Ile Gly Tyr Ser Asp Leu Glu
            35                  40                  45

Gly Asp Phe Asp Val Ala Val Leu Pro Phe Ser Asn Ser Thr Asn Asn
        50                  55                  60

Gly Leu Leu Phe Ile Asn Thr Thr Ile Ala Ser Ile Ala Ala Lys Glu
65                  70                  75                  80

Glu Gly Val Ser Leu Glu Lys Arg Met Asn Phe Ser Gly Lys Tyr Gln
                85                  90                  95

Val Gln Thr Gln Glu Asn Tyr Glu Ala Phe Met Lys Ala Val Gly Met
                100                 105                 110

Pro Asp Asp Ile Ile Gln Lys Gly Lys Asp Ile Lys Gly Val Ser Glu
            115                 120                 125

Ile Val Gln Asn Gly Lys His Phe Lys Phe Ile Thr Ala Gly Ser
            130                 135                 140

Lys Val Ile Gln Asn Glu Phe Thr Leu Gly Glu Glu Cys Glu Met Glu
145                 150                 155                 160

Phe Met Thr Gly Glu Lys Ile Lys Ala Val Val Gln Gln Glu Gly Asp
                165                 170                 175

Asn Lys Leu Val Thr Thr Phe Lys Gly Ile Lys Ser Val Thr Glu Phe
            180                 185                 190

Asn Gly Asp Thr Val Thr Ser Thr Met Thr Lys Gly Asp Val Val Phe
            195                 200                 205

Lys Arg Val Ser Lys Arg Ile
            210                 215
```

<210> SEQ ID NO 69
<211> LENGTH: 22
<212> TYPE: PRT
<213> ORGANISM: E. Coli

<400> SEQUENCE: 69

Met Glu Phe Phe Lys Lys Thr Ala Leu Ala Ala Leu Val Met Gly Phe
1               5                   10                  15

Ser Gly Ala Ala Leu Ala
            20

<210> SEQ ID NO 70
<211> LENGTH: 36
<212> TYPE: PRT
<213> ORGANISM: E. Coli

<400> SEQUENCE: 70

Met Lys Leu Ser Arg Arg Ser Phe Met Lys Ala Asn Ala Val Ala Ala
1               5                   10                  15

Ala Ala Ala Ala Ala Gly Leu Ser Val Pro Gly Val Ala Arg Ala Val
            20                  25                  30

Val Gly Gln Gln
        35

<210> SEQ ID NO 71
<211> LENGTH: 25
<212> TYPE: PRT
<213> ORGANISM: Arabidopsis thalinia

<400> SEQUENCE: 71

Met Ser Ser Ser Phe Leu Ser Ser Thr Ala Phe Phe Leu Leu Leu Cys
1               5                   10                  15

Leu Gly Phe Cys His Val Ser Ser Ser
            20                  25

<210> SEQ ID NO 72
<211> LENGTH: 23
<212> TYPE: PRT
<213> ORGANISM: barley (Hordeum vulgare)

<400> SEQUENCE: 72

Met Gly Lys Lys Ser His Ile Cys Cys Phe Ser Leu Leu Leu Leu Leu
1               5                   10                  15

Phe Ala Gly Leu Ala Ser Gly
            20

<210> SEQ ID NO 73
<211> LENGTH: 28
<212> TYPE: PRT
<213> ORGANISM: rice

<400> SEQUENCE: 73

Met Lys Asn Thr Ser Ser Leu Cys Leu Leu Leu Val Val Leu Cys
1               5                   10                  15

Ser Leu Thr Cys Asn Ser Gly Gln Ala Ala Gln Val
            20                  25

<210> SEQ ID NO 74
<211> LENGTH: 132
<212> TYPE: PRT
<213> ORGANISM: Gallus gallus

```
<400> SEQUENCE: 74

Met Val Glu Ala Phe Cys Ala Thr Trp Lys Leu Ala Asp Ser His Asn
1               5                   10                  15

Phe Asp Glu Tyr Met Lys Ala Leu Gly Val Gly Phe Ala Met Arg Gln
                20                  25                  30

Val Gly Asn Val Thr Lys Pro Thr Val Ile Ile Ser Ser Glu Gly Asp
            35                  40                  45

Lys Val Val Ile Arg Thr Gln Ser Thr Phe Lys Asn Thr Glu Ile Ser
    50                  55                  60

Phe Lys Leu Gly Glu Glu Phe Asp Glu Thr Thr Pro Asp Asp Arg Asn
65                  70                  75                  80

Cys Lys Ser Val Val Thr Leu Asp Gly Asp Lys Leu Val His Val Gln
                85                  90                  95

Lys Trp Asp Gly Lys Glu Thr Asn Phe Val Arg Glu Ile Lys Asp Gly
                100                 105                 110

Arg Met Val Met Thr Leu Thr Phe Gly Asp Val Val Ala Val Arg His
                115                 120                 125

Tyr Glu Lys Ala
                130

<210> SEQ ID NO 75
<211> LENGTH: 127
<212> TYPE: PRT
<213> ORGANISM: Sus scrofa

<400> SEQUENCE: 75

Met Asn Phe Ser Gly Lys Tyr Gln Val Gln Ser Gln Glu Asn Phe Glu
1               5                   10                  15

Ala Phe Met Lys Ala Val Gly Leu Pro Asp Glu Leu Ile Gln Lys Gly
                20                  25                  30

Lys Asp Ile Lys Gly Thr Ser Glu Ile Val Gln Asn Gly Lys His Phe
            35                  40                  45

Lys Leu Thr Ile Thr Thr Gly Ser Lys Val Val Gln Asn Glu Phe Thr
    50                  55                  60

Leu Gly Glu Glu Cys Glu Met Glu Thr Leu Thr Gly Glu Lys Val Lys
65                  70                  75                  80

Thr Val Val Gln Leu Glu Gly Asp Asn Lys Leu Val Thr Thr Phe Lys
                85                  90                  95

Gly Ile Lys Ser Val Thr Glu Leu Asn Gly Asp Ile Ile Thr Ser Thr
                100                 105                 110

Met Thr Leu Gly Asp Ile Val Phe Lys Arg Ile Ser Lys Arg Ile
                115                 120                 125

<210> SEQ ID NO 76
<211> LENGTH: 155
<212> TYPE: PRT
<213> ORGANISM: Equus caballus

<400> SEQUENCE: 76

Met Asn Phe Ser Gly Lys Tyr Gln Leu Gln Ser Gln Glu Asn Phe Glu
1               5                   10                  15

Pro Phe Met Lys Ala Val Gly Met Ser Asp Asp Leu Ile Gln Lys Gly
                20                  25                  30

Lys Asp Leu Lys Glu Thr Ser Glu Ile Val His Asn Gly Asn His Phe
            35                  40                  45

Lys Ile Thr Ile Thr Thr Gly Pro Lys Val Val His His Glu Phe Thr
```

```
                    50                  55                  60
Leu Gly Glu Glu Phe Glu Leu Glu Ser Phe Thr Gly Glu Lys Val Lys
 65                  70                  75                  80

Ala Ile Thr His Met Glu Gly Asp Lys Leu Val Ser Thr Ile Lys Gly
                 85                  90                  95

Ile Lys Ser Val Thr Glu Leu Lys Gly Asp Ile Ile Thr Asn Gln Leu
                100                 105                 110

Ser Val Trp His Thr Pro Val Val Cys Ala Thr Ser Ala Leu Val Pro
            115                 120                 125

Ala Cys Arg Pro Gly Pro Val Leu Asp Leu Gly Thr Met Thr Leu Gly
130                 135                 140

Asp Ile Val Phe Lys Arg Val Ser Lys Arg Ile
145                 150                 155

<210> SEQ ID NO 77
<211> LENGTH: 135
<212> TYPE: PRT
<213> ORGANISM: Rhodamnia argentea

<400> SEQUENCE: 77

Met Thr Glu Phe Ala Gly Val Tyr Glu Phe Val Lys Asp Asp Gly Lys
 1               5                  10                  15

Phe Glu Glu Ile Leu Lys Ala Met Asp Val Asn Phe Leu Ile Arg Lys
                20                  25                  30

Val Ala Gly Lys Met Asn Pro Asn Thr Ala Ile Asp Val Leu Asp Asp
             35                  40                  45

Gly Lys Met Ala Phe Lys Thr Ile Thr Pro Leu Lys Thr Val Glu Ile
         50                  55                  60

His Phe Glu Leu Gly Lys Glu Tyr Glu Asn Lys Arg Leu Asp Gly Thr
 65                  70                  75                  80

Val Val Lys Gly Ile Val Thr Arg Asp Gly Asn Lys Leu Ile Gln Glu
                 85                  90                  95

Gln Met Ser Glu Pro Lys Phe Lys Val Ile Arg Glu Leu Asp Gly Pro
                100                 105                 110

Glu Lys Leu Ile Val Thr Trp Met Cys Lys Asp Ile Val Cys Val Arg
            115                 120                 125

Glu Tyr Lys Arg Ile Gln Thr
130                 135

<210> SEQ ID NO 78
<211> LENGTH: 127
<212> TYPE: PRT
<213> ORGANISM: Mus musculus

<400> SEQUENCE: 78

Met Asn Phe Ser Gly Lys Tyr Gln Leu Gln Ser Gln Glu Asn Phe Glu
 1               5                  10                  15

Pro Phe Met Lys Ala Ile Gly Leu Pro Glu Asp Leu Ile Gln Lys Gly
                20                  25                  30

Lys Asp Ile Lys Gly Val Ser Glu Ile Val His Glu Gly Lys Lys Ile
             35                  40                  45

Lys Leu Thr Ile Thr Tyr Gly Pro Lys Val Val Arg Asn Glu Phe Thr
         50                  55                  60

Leu Gly Glu Glu Cys Glu Leu Glu Thr Met Thr Gly Glu Lys Val Lys
 65                  70                  75                  80

Ala Val Val Lys Leu Glu Gly Asp Asn Lys Met Val Thr Thr Phe Lys
```

```
                    85                  90                  95
Gly Ile Lys Ser Val Thr Glu Leu Asn Gly Asp Thr Ile Thr Asn Thr
                100                 105                 110

Met Thr Leu Gly Asp Ile Val Tyr Lys Arg Val Ser Lys Arg Ile
            115                 120                 125

<210> SEQ ID NO 79
<211> LENGTH: 132
<212> TYPE: PRT
<213> ORGANISM: Gallus gallus

<400> SEQUENCE: 79

Met Val Glu Ala Phe Cys Ala Thr Trp Lys Leu Ala Asp Ser His Asn
1               5                   10                  15

Met Asp Glu Ala Leu Lys Ala Trp Gly Val Gly Phe Ala Ile Arg Gln
            20                  25                  30

Val Ala Asn Val Thr Lys Pro Thr Val Ile Ile Ser Ser Glu Gly Asp
        35                  40                  45

Lys Val Val Ile Arg Met Gln Ser Thr Phe Lys Asn Thr Glu Ile Ser
    50                  55                  60

Phe Lys Leu Gly Glu Glu Phe Asp Glu Thr Thr Ala Asp Asp Arg Asn
65                  70                  75                  80

Cys Lys Ser Val Val Thr Leu Asp Gly Asp Lys Leu Val His Val Gln
                85                  90                  95

Lys Trp Asp Gly Lys Glu Thr Asn Val Val Arg Glu Ile Lys Asp Gly
                100                 105                 110

Arg Met Val Met Thr Val Thr Phe Gly Asp Val Val Ala Val Arg His
            115                 120                 125

Tyr Glu Lys Ala
    130

<210> SEQ ID NO 80
<211> LENGTH: 132
<212> TYPE: PRT
<213> ORGANISM: Gallus gallus

<400> SEQUENCE: 80

Met Val Glu Ala Phe Cys Ala Thr Trp Lys Leu Ala Asp Ser His Asn
1               5                   10                  15

Gln Asp Glu Gly Leu Lys Ala Leu Gly Val Gly Phe Ala Met Arg Gln
            20                  25                  30

Leu Phe Asn Val Asp Lys Pro Thr Val Ile Ile Ser Ser Glu Gly Asp
        35                  40                  45

Lys Val Val Ile Arg Ile Glu Gly Thr Val Lys Asn Thr Glu Ile Ser
    50                  55                  60

Phe Lys Leu Gly Glu Glu Phe Asp Glu Thr Thr Ala Asp Asp Arg Asn
65                  70                  75                  80

Cys Lys Ser Val Val Thr Leu Asp Gly Asp Lys Leu Val His Val Gln
                85                  90                  95

Lys Trp Asp Gly Lys Glu Thr Asn Val Val Arg Glu Ile Lys Asp Gly
                100                 105                 110

Arg Met Val Ala Thr Phe Thr Phe Gly Asp Val Val Ala Val Ala His
            115                 120                 125

Tyr Glu Lys Ala
    130
```

```
<210> SEQ ID NO 81
<211> LENGTH: 126
<212> TYPE: PRT
<213> ORGANISM: Sus scrofa

<400> SEQUENCE: 81

Met Asn Phe Ser Gly Lys Tyr Gln Val Gln Ser Gln Glu Asn Phe Glu
1               5                   10                  15

Ala Phe Met Lys Ala Val Gly Gln Pro Asp Glu Leu Ile Gln Lys Gly
            20                  25                  30

Lys Asp Ile Lys Gly Thr Ser Glu Ile Val Gln Asn Gly Lys His Phe
        35                  40                  45

Lys Val Thr Ile Thr Thr Gly Ser Lys Val Val Gln Ala Glu Phe Thr
    50                  55                  60

Leu Gly Glu Glu Cys Glu Ala Glu Thr Asp Thr Gly Glu Lys Val Lys
65                  70                  75                  80

Val Val Val Gln Leu Glu Gly Asp Asn Lys Ala Val Val Thr Ala Lys
                85                  90                  95

Gly Ile Lys Ala Val Phe Glu Leu Asn Gly Asp Ile Ile Thr Ala Thr
            100                 105                 110

Ala Thr Leu Gly Asp Ile Val Phe Lys Arg Ile Ser Lys Arg
        115                 120                 125

<210> SEQ ID NO 82
<211> LENGTH: 126
<212> TYPE: PRT
<213> ORGANISM: Sus scrofa

<400> SEQUENCE: 82

Met Asn Phe Ser Gly Lys Tyr Gln Val Gln Ser Gln Glu Asn Phe Glu
1               5                   10                  15

Ala Ala Ala Lys Ala Ala Gly Val Pro Asp Glu Glu Ile Gln Lys Gly
            20                  25                  30

Lys Asp Ile Lys Gly Thr Leu Glu Ile Val Gln Asn Gly Lys His Phe
        35                  40                  45

Lys Leu Thr Leu Thr Thr Gly Ser Lys Val Val Gln Asn Glu Phe Thr
    50                  55                  60

Leu Gly Glu Glu Cys Glu Met Glu Thr Leu Gly Gly Glu Lys Ala Lys
65                  70                  75                  80

Thr Val Val Gln Leu Glu Gly Asp Asn Lys Ala Val Trp Thr Phe Lys
                85                  90                  95

Gly Ile Lys Ala Val Ile Glu Leu Asn Gly Asp Ile Ile Thr Leu Thr
            100                 105                 110

Val Thr Leu Gly Asp Ile Val Phe Lys Arg Ile Ser Lys Arg
        115                 120                 125

<210> SEQ ID NO 83
<211> LENGTH: 155
<212> TYPE: PRT
<213> ORGANISM: Equus caballus

<400> SEQUENCE: 83

Met Asn Phe Ser Gly Lys Tyr Gln Leu Gln Ser Gln Glu Asn Ala Glu
1               5                   10                  15

Pro Phe Phe Lys Ala Val Gly Met Ser Asp Asp Leu Ile Gln Leu Ala
            20                  25                  30

Lys Asp Leu Lys Val Thr Gly Glu Ile Val His Asn Gly Asn His Phe
        35                  40                  45
```

```
Lys Ile Thr His Thr Ser Gly Ala Ala Val His His Glu Phe Thr
 50                  55                  60

Leu Gly Glu Glu Phe Glu Leu Ser Leu Thr Gly Glu Lys Val Lys
 65                  70                  75                  80

Ala Ile Thr His Met Glu Gly Asp Lys Leu Val Ser Thr Ile Lys Gly
                 85                  90                  95

Ile Lys Ser Val Thr Glu Leu Lys Gly Asp Ile Ile Thr Asn Gln Leu
                100                 105                 110

Ser Val Trp His Thr Pro Val Val Cys Ala Thr Ser Ala Leu Val Pro
            115                 120                 125

Ala Cys Arg Pro Gly Pro Val Leu Asp Leu Gly Thr Met Thr Leu Gly
        130                 135                 140

Asp Ile Val Met Lys Phe Val Ser Lys Arg Ile
145                 150                 155

<210> SEQ ID NO 84
<211> LENGTH: 155
<212> TYPE: PRT
<213> ORGANISM: Equus caballus

<400> SEQUENCE: 84

Met Asn Phe Ser Gly Lys Tyr Gln Leu Gln Ser Ser Glu Asn Val Glu
  1               5                  10                  15

Pro Phe Asn Lys Ala Val Gly Met Ser Asp Asp Leu Ile Gln Lys Ala
                 20                  25                  30

Lys Asp Leu Lys Phe Thr Gly Glu Ile Val His Asn Gly Asn His Phe
             35                  40                  45

Lys Ile Thr Ile Thr Thr Gly Pro Lys Val Val His His Glu Phe Thr
 50                  55                  60

Leu Gly Glu Glu Phe Glu Leu Glu His Phe Thr Gly Glu Lys Val Lys
 65                  70                  75                  80

Ala Ile Thr His Met Glu Gly Asp Lys Leu Val Met Thr Val Lys Gly
                 85                  90                  95

Ile Lys Ser Val Met Val Trp Lys Gly Asp Ile Ile Thr Asn Gln Leu
                100                 105                 110

Ser Val Trp His Thr Pro Val Val Cys Ala Thr Ser Ala Leu Val Pro
            115                 120                 125

Ala Cys Arg Pro Gly Pro Val Leu Asp Leu Gly Thr Gly Val Leu Gly
        130                 135                 140

Asp Ile Val Met Lys His Val Ser Lys Arg Ile
145                 150                 155

<210> SEQ ID NO 85
<211> LENGTH: 135
<212> TYPE: PRT
<213> ORGANISM: Rhodamnia argentea

<400> SEQUENCE: 85

Met Thr Glu Phe Ala Gly Val Tyr Glu Phe Val Lys Asp Asp Gly Lys
  1               5                  10                  15

Phe Glu Glu Ile Leu Lys Ala Met Asp Val Asn Phe Leu Ile Arg Lys
                 20                  25                  30

Val Gly Met Lys Met Asn Ala Asn Val Ala Ile Asp Val Leu Asp Asp
             35                  40                  45

Gly Lys Met Ala Ile Lys Val Ile Thr Pro Leu Lys Thr Val Glu Ile
 50                  55                  60
```

```
His Phe Glu Leu Gly Lys Glu Tyr Glu Asn Lys Arg Phe Asp Gly Thr
 65                  70                  75                  80

Val Val Lys Gly Ile Val Thr Arg Asp Gly Asn Lys Leu Ile Ile Glu
                 85                  90                  95

Gln Met Ser Glu Pro Lys Phe Lys Val Ile Ala Glu Leu Asp Gly Pro
            100                 105                 110

Glu Lys Leu Ile Phe Thr Glu Met Cys Lys Asp Ile Val Cys Val Ala
            115                 120                 125

Glu Tyr Lys Arg Ile Gln Thr
            130                 135

<210> SEQ ID NO 86
<211> LENGTH: 135
<212> TYPE: PRT
<213> ORGANISM: Rhodamnia argentea

<400> SEQUENCE: 86

Met Thr Glu Phe Ala Gly Val Tyr Glu Phe Val Lys Asp Asp Gly Lys
 1               5                  10                  15

Phe Glu Glu Ile Leu Lys Ala Met Asp Val Asn Phe Leu Ile Arg Lys
                 20                  25                  30

Val Ala Gly Lys Met Asn Pro Asn Ile Ala Ile Asp Val Leu Asp Asp
             35                  40                  45

Gly Lys Met Ala Ile Lys Met Ile Thr Pro Leu Lys Thr Val Glu Val
         50                  55                  60

His Phe Glu Leu Gly Lys Glu Tyr Glu Ala Lys Ala Leu Asp Gly Thr
 65                  70                  75                  80

Val Val Lys Ala Ile Val Thr Arg Asp Gly Asn Lys Leu Ile Ile Glu
                 85                  90                  95

Asn Met Ser Glu Pro Lys Phe Thr Val Ile Arg Glu Leu Asp Gly Pro
            100                 105                 110

Glu Lys Leu Ile Val Thr Trp Met Cys Lys Asp Ile Val Cys Val Ala
            115                 120                 125

Glu Tyr Lys Arg Ile Gln Thr
            130                 135
```